United States Patent
Muraoka et al.

(10) Patent No.: US 9,073,897 B2
(45) Date of Patent: Jul. 7, 2015

(54) CYCLIC SULFONIUM SALT, PROCESS FOR PRODUCTION OF SAME, AND α-GLUCOSIDASE INHIBITOR COMPRISING SAME

(75) Inventors: Osamu Muraoka, Higashiosaka (JP); Genzoh Tanabe, Higashiosaka (JP)

(73) Assignees: KINKI UNIVERSITY, Higashiosaka-Shi (JP); DIABETYM CO., LTD., Osaka-Shi (JP)

( * ) Notice: Subject to any disclaimer, the term of this patent is extended or adjusted under 35 U.S.C. 154(b) by 0 days.

(21) Appl. No.: 13/982,715

(22) PCT Filed: Jan. 31, 2012

(86) PCT No.: PCT/JP2012/052174
§ 371 (c)(1),
(2), (4) Date: Oct. 8, 2013

(87) PCT Pub. No.: WO2012/105573
PCT Pub. Date: Aug. 9, 2012

(65) Prior Publication Data
US 2014/0031394 A1      Jan. 30, 2014

(30) Foreign Application Priority Data
Jan. 31, 2011   (JP) .................................. 2011-018442

(51) Int. Cl.
*C07D 409/12* (2006.01)
*A23L 1/30* (2006.01)
*C07D 333/46* (2006.01)

(52) U.S. Cl.
CPC ................. *C07D 409/12* (2013.01); *A23L 1/30* (2013.01); *C07D 333/46* (2013.01)

(58) Field of Classification Search
CPC .............................. A23L 1/30; C07D 409/12
USPC .................... 549/336, 66; 546/280.4
See application file for complete search history.

(56) References Cited

U.S. PATENT DOCUMENTS

| | | |
|---|---|---|
| 2003/0191104 A1 | 10/2003 | Pinto et al. |
| 2007/0037870 A1 | 2/2007 | Asada et al. |
| 2007/0135486 A1 | 6/2007 | Muraoka et al. |

FOREIGN PATENT DOCUMENTS

| | | |
|---|---|---|
| EP | 1 645 557 A1 | 4/2006 |
| JP | 2002-179679 A | 6/2002 |
| JP | 2004-323420 A | 11/2004 |
| JP | 2005-2051 A | 1/2005 |
| WO | WO 2004/113289 A2 | 12/2004 |

OTHER PUBLICATIONS

Eskandari et al., "Probing the active-site requirements of human intestinal N-terminal maltase glucoamylase: The effect of replacing the sulfate moiety by a methyl ether in ponkoranol, a naturally occuring . . .", Bioorganic & Medicinal Chemistry Letters, 2010, vol. 20, pp. 5686-5689.

Yoshikawa et al., "Absolute Stereostructure of Potent α-Glucosidase Inhibitor, Salacinol, with Unique Thiosugar Sulfonium Sulfate Inner Salt Structure from *Salacia reticulata*", Bioorganic & Medicinal Chemistry, 2002, vol. 10, pp. 1547-1554.

Yoshikawa et al., "Kotalanol, a Potent α-Glucosidase Inhibitor with Thiosugar Sulfonium Sulfate Structure, from Antidiabetic Ayurvedic Medicine *Salacia reticulata*", Chem. Pharm. Bull., Aug. 1998, vol. 46, No. 8, pp. 1339-1340.

Yoshikawa et al., "Salacinol, Potent Antidiabetic Principle with Unique Thiosugar Sulfonium Sulfate Structure from the Ayurvedic Traditional Medicine *Salacia reticulata* in Sri Lanka and India", Tetrahedron Letters, 1997, vol. 38, No. 48, pp. 8367-8370.

Yoshikawa et al., "Salaprinol and Ponkoranol with Thiosugar Sulfonium Sulfate Structure from *Salacia prinoides* and α-Glucosidase Inhibitory Activity of Ponkoranol and Kotalanol Desulfate", Heterocycles, 2008 (published online Feb. 12, 2008), vol. 75, No. 6, pp. 1397-1405.

Eskandari et al., "Probing the active-site requirements of human intestinal N-terminal maltase glucoamylase: The effect of replacing the sulfate moiety by a methyl ether in ponkoranol, a naturally occuring alpha-glucosidase inhibitor", Bioorganic & Medicinal Chemistry Letters, vol. 20, 2010, pp. 5686-5689.

Eskandari et al., "Selectivity of 3'-O-methylponkoranol for inhibition of N- and C-terminal maltase glucoamylase and sucrase isomaltase, potential therapeutics for digestive disorders or their sequelae", Bioorganic & Medicinal Chemistry Letters, vol. 21, 2011, pp. 6491-6494.

International Search Report for PCT/JP2012/052174 dated Feb. 28, 2012.

Tanabe et al., "Biological evaluation of 3'-O-alkylated analogs of salacinol, the role of hydrophobic alkyl groupat 3' position in the side chain on the alpha-glucosidase inhibitory activity", Bioorganic & Medicinal Chemistry Letters, vol. 21, 2011, pp. 3159-3162.

Chinese Office Action, dated Mar. 17, 2014, for Chinese Application No. 201280014788.0.

*Primary Examiner* — Taofiq A Solola
(74) *Attorney, Agent, or Firm* — Birch, Stewart, Kolasch & Birch, LLP

(57) ABSTRACT

Provided is a novel cyclic sulfonium salt compound which is useful for the prevention or treatment of diabetes and the like. The present invention relates to a novel cyclic sulfonium salt compound represented by general formula (I) or (II), an isomer or solvate of the compound, or a pharmaceutically acceptable salt of the compound or the isomer or solvate. The present invention also relates to an α-glucosidase inhibitor, a pharmaceutical composition for preventing or treating diabetes, and an anti-diabetes food, each of which comprises the compound represented by general formula (I) or (II) and the like.

4 Claims, No Drawings

CYCLIC SULFONIUM SALT, PROCESS FOR PRODUCTION OF SAME, AND α-GLUCOSIDASE INHIBITOR COMPRISING SAME

TECHNICAL FIELD

The present invention relates to novel cyclic sulfonium salt compounds and their medical use. More particularly, the present invention relates to novel cyclic sulfonium salt compounds having an α-glucosidase inhibitory activity, or isomers, solvates or pharmaceutically acceptable salts thereof, medical compositions for inhibition of α-glucosidase containing the compounds, and medical compositions for prevention or treatment of diabetes, and anti-diabetic foods.

BACKGROUND ART

Diabetes is a group of the diseases characterized by an abnormal glucose homeostasis causing an increased blood glucose and may be divided mainly into two types, i.e., type 1 diabetes mellitus (insulin-dependent diabetes mellitus) and type 2 diabetes mellitus (noninsulin-dependent diabetes mellitus). Among the diabetes, the type 2 diabetes mellitus accounts for the great majority of the diabetes.

Glucosidase as a carbohydrate degrading enzyme (particularly α-glucosidase) is involved in several significant biological processes (including, for example, digestion, biosynthesis of glycoproteins, and lysosomal catabolic reaction of conjugated carbohydrates). Therefore, by using a glucosidase inhibitor such a substance inhibiting the carbohydrate degrading action of such an α-glucosidase, the digestion and absorption of carbohydrates in the intestines and so on can be suppressed. This is expected to be useful for a glucosidase inhibitor as an agent for treating or preventing diabetes.

In the latter half of the 1990s, salacinol having the chemical formula as will be described below has been discovered as a pharmacologically essential substance from a medicinal plant (*Salacia reticulate*) which has been used in a traditional medicine (ayur veda) of India. Salacinol is reported as having an α-glucosidase inhibitory activity (Patent Document No. 1, Non-Patent Literature Documents 1 and 2).

[Chem. 1]

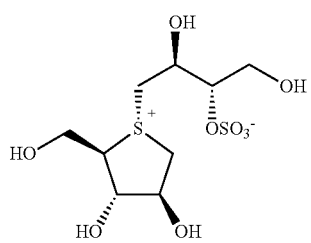

In addition to salacinol as described above, kotalanol, ponkoranol and so on were discovered as salacinol analogs. These analogs are reported, too, as having a α-glucosidase inhibitory activity (Patent Document 2, Non-Patent Literature Documents 3 and 4). These naturally occurring substances including salacinol have the characteristics that an erythritol-like carbon side chain is connected to the endocyclic sulfur atom at the thiosugar moiety portion forming a sulfonium ion and further the sulfonium ion forms an intramolecular bond with a sulfate anion on the carbon side chain, thereby forming a specific structure with a spiro framework.

Moreover, from a viewpoint of readiness of production or improvements in pharmacological activities, there have been reported cyclic onium compounds which are desulfate esters having no sulfate anion on the carbon side chain of salacinol, including a desulfate ester of salacinol (hereinafter called neosalcinol), as will be described by the following chemical formula (Patent Document 3). These desulfate esters have α-glucosidase inhibitory activities equal to or higher than the naturally occurring substances and are superior in terms of readiness in production such as stability and so on.

[Chem. 2]

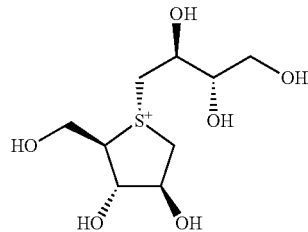

Further, recently, 3'-O-methylneoponkoranol (n=0) was reported (Non-Patent Literature Document 5). In this document, it was reported that the methyl derivative have little contributed to improvements in the α-glucosidase inhibitory activity compared with the naturally occurring salacinol. This implies that the introduction of an alkyl group or the like into the hydroxyl group at the 3'-position cannot improve the α-glucosidase inhibitory activity.

[Patent Document 1] Japanese Patent Publication No. 2002-179673.

[Patent Document 2] Japanese Patent Publication No. 2004-323420.

[Patent Document 3] Japanese Patent Publication No. 2005-002051.

[Non-Patent Literature Document 1] Yoshikawa, M., Muraoka, O., et al., Tetrahedron Lett., 1997, 38, 8367.

[Non-Patent Literature Document 2] Yoshikawa, M., Muraoka, O., et al., Bioorg. Med. Chem., 2002, 10, 1547.

[Non-Patent Literature Document 3] Yoshikawa, M., et al., Chem. Pharm. Bull., 1998, 46, 1339.

[Non-Patent Literature Document 4] Yoshikawa, M., Muraoka, O., Heterocycles, 2008, 75, 1397.

[Non-Patent Literature Document 5] Eskandari, R., et al., Bioorg. Med. Chem. Lett., 2010, 20, 5686.

SUMMARY OF THE INVENTION

Problems to be Solved by the Invention

As a result of extensive studies, regardless of a negative implication on the above Non-Patent Literature Document regarding the introduction of methyl group into the 3'-hydroxy group, the present inventors have found, surprisingly, that the α-glucosidase inhibitory activity was increased remarkably by the introduction of alkyl groups having larger carbon atoms, such as alkyl groups including ethyl group, cycloalkyl groups, aralkyl groups, heteroaralkyl groups, or the like.

More specifically, the present inventors have found that the 3'-O-alkylated analogs of salacinol and so on, that is, the cyclic sulfonium salt compounds as represented by chemical formula (I) below can function as an α-glucosidase inhibitory agent and they are useful as medicine for preventing or treating diabetes mellitus. The present invention has been completed on the basis of these findings.

Therefore, the present invention has the object to provide a cyclic sulfonium salt compound, an isomer or a solvate thereof or a pharmaceutically acceptable salt thereof. The present invention has another object to provide a medical composition for inhibition of α-glucosidase, a medical composition for prevention or treatment of diabetes mellitus, and foods for diabetes mellitus.

Means for Solving the Problems

In order to achieve the objects of the present invention, the present invention in a major aspect provides a cyclic sulfonium salt compound as represented by chemical formula (I):

[Chem. 3]

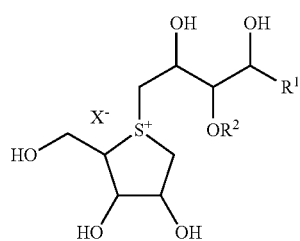

(I)

[in which $R^1$ means hydrogen atom or a chemical formula as represented by —(CH(OH))n-$CH_2OH$ (wherein n is 0 or an integer of 1 or 2), $R^2$ means a hydrophobic group selected from:
(i) an unsubstituted or substituted $C_1$-$C_{16}$ alkyl group (provided that methyl is removed when n is 1),
(ii) an unsubstituted or substituted $C_3$-$C_6$ cycloalkyl group,
(iii) an unsubstituted or substituted aralkyl group as represented by chemical formula (Ia): —$R_1$-$R_2$ (wherein $R_1$ means a $C_1$-$C_4$ alkylene group and $R_2$ means a monovalent arom. cyclic group), or
(iv) an unsubstituted or substituted heteroaralkyl group as represented by chemical formula (Ib): —$R_3$-$R_4$ (wherein $R_3$ means a $C_1$-$C_4$ alkylene group and $R_4$ means a monovalent heterocyclic group), $X^-$ means a conjugated basic ion of a Broensted acid], an isomer or a solvate thereof or a pharmaceutically acceptable salt thereof.

The present invention in a preferred aspect provides a cyclic sulfonium salt compound as represented by chemical formula (II):

[Chem. 4]

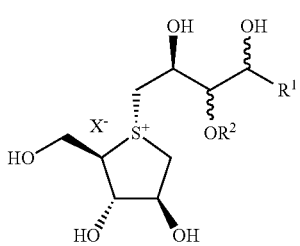

(II)

(wherein $R^1$, $R^2$ and $X^-$ have the same meanings as above), an isomer or a solvate thereof or a pharmaceutically acceptable salt thereof.

In the description, the term "cyclic sulfonium salt compound, an isomer or a solvate thereof or a pharmaceutically acceptable salt thereo" may be abbreviated simply as "cyclic sulfonium salt compound" in some cases. It is to be noted, however, that this abbreviation is intended to be used solely for brevity of explanation and that, unless otherwise stated herein, it is understood to mean and encompass all or either of other isomers or solvates thereof and/or pharmaceutically acceptable salts thereof.

The present invention in a preferred embodiment provides the cyclic sulfonium salt compound (I) or (II) in which $R^1$ means hydrogen atom or —$CH_2OH$, —$(CH_2)_2$—$CH_2OH$ or —$(CH_2)_3$—$CH_2OH$.

The present invention in a preferred embodiment provides the cyclic sulfonium salt compound (I) or (II), in which $R^2$ means a $C_1$-$C_{13}$ alkyl group, benzyl group, o-, m- or p-halobenzyl, o-, m- or p-nitrobenzyl, o-, m- or p-methylbenzyl, o-, m- or p-trifluoromethylbenzyl, hydroxymethylbenzyl, naphthylmethyl or pyridylmethyl.

The present invention in a preferred embodiment provides the cyclic sulfonium salt compound (1) or (II) in which $X^-$ means a halogen ion, a sulfonate ion as represented by $R^3SO_3^-$ (wherein $R^3$ means an unsubstituted or halogen-substituted alkyl group or an unsubstituted aryl group or a halogen- or alkyl-substituted aryl group), a carboxylate ion as represented by $R^4COO^-$ (wherein $R^4$ means hydrogen atom, an unsubstituted or halogen-substituted alkyl group or an unsubstituted or a halogen- or alkyl-substituted aryl group), a sulfate ion, an alkylsulfate ion, a hydrogen sulfate ion, a perchlorate ion, or a conjugated basic ion of a Broensted acid as a conjugated basic ion between a Lewis acid and a hydrogen halide.

The present invention in a more preferred embodiment provides the cyclic sulfonium salt compound (I) or (II), in which $X^-$ means $Cl^-$ or $BF4^-$.

The present invention in another mode provides a medical composition for the inhibition of α-glucosidase, which contains the cyclic sulfonium salt compound (I) or (II) as defined above, and a pharmaceutically acceptable carrier.

The present invention in another aspect provides a medical composition comprising the cyclic sulfonium salt compound (I) or (II) and a pharmaceutically acceptable carrier, which prevents or treats diseases such as diabetes mellitus including type 2 diabetes mellitus, diabetic complication, obesity, dyslipidemia, hypertension, and so on.

The present invention in a further aspect provides a method for inhibiting an α-glucosidase inhibitory activity in mammals, comprising administering a therapeutically effective amount of the cyclic sulfonium salt compound (I) or (II) to the mammals of interest.

The present invention in a still further aspect provides a method for preventing or treating diabetes, diabetic complication, obesity, dyslipidemia or hypertension in mammals, comprising administering a therapeutically effective amount of the cyclic sulfonium salt compound (I) or (II) to the mammals of interest.

The present invention in another mode provides a diabetic food containing the above-defined cyclic sulfonium salt compound (I) or (II).

Effects of the Invention

The cyclic sulfonium salt compounds (I) and (II) according to the present invention are useful as medicine for inhibiting the α-glucosidase inhibitory activity or medicine for preventing or treating diabetes, diabetic complication, obesity, dyslipidemia or hypertension in mammals.

MODES FOR CARRYING OUT THE INVENTION

The cyclic sulfonium salt compound according to the present invention may be represented by general formula (I):

[Chem. 5]

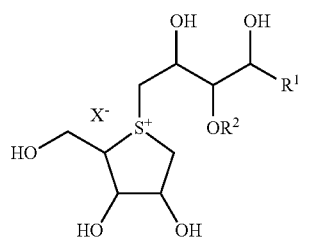

(I)

[in which $R^1$ means hydrogen atom or a chemical formula as represented by —(CH(OH))n—CH$_2$OH (wherein n means 0 or an integer 1 or 2), $R^2$ means a hydrophobic group selected from:
(i) an unsubstituted or substituted $C_1$-$C_{16}$ alkyl group (provided that methyl is removed when n is 1),
(ii) an unsubstituted or substituted $C_3$-$C_6$ cycloalkyl group,
(iii) an unsubstituted or substituted aralkyl group as represented by chemical formula (Ia): —$R_1$-$R_2$ (wherein $R_1$ means a $C_1$-$C_4$ alkylene group and $R_2$ means a monovalent arom. cyclic group), or
(iv) an unsubstituted or substituted heteroaralkyl group as represented by chemical formula (Ib): —$R_3$-$R_4$ (wherein $R_3$ means a $C_1$-$C_4$ alkylene group and $R_4$ means a monovalent heterocyclic group), $X^-$ means a conjugated basic ion of a Broensted acid].

The cyclic sulfonium salt compound in a preferred embodiment may be represented by general formula (II):

[Chem. 6]

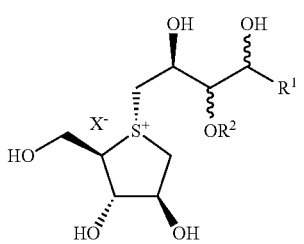

(II)

(wherein $R^1$, $R^2$ and $X^-$ have the same meanings as above).

In general formulas (I) and (II), the term "alkyl group" as represented by $R^2$(i) is intended to mean a straight-chained or branched, monovalent saturated aliphatic hydrocarbon residue having 1-16 carbon atoms, preferably 1-14 carbon atoms. The alkyl group may include, for example, methyl, ethyl, n-propyl, isopropyl, n-butyl, isobutyl, sec-butyl, tert-butyl, n-pentyl, neopentyl, hexyl, heptyl, octyl, nonyl, decyl, undecyl, dodecyl, tridecyl, tetradecyl, and the like, although it is not limited to those described above.

The above alkyl group may have a substituent, and the substituent may include, for example, a halogen atom such as chlorine atom, fluorine atom or the like, hydroxyl group, amino group, nitro group and so on, although it is not limited to those as described above. The number of the substituents is not limited to a particular one, although it is preferred to be 1 to 3, and the kind of the substituents may be different from each other.

In the above general formulas (I) and (II), the term "cycloalkyl group" as represented by $R^2$(ii) is intended to mean a monovalent, cyclic, saturated aliphatic hydrocarbon residue having 3-6 carbon atoms, preferably 3-5 carbon atoms, and they may specifically include, for example, cyclopropyl, cyclobutyl, cyclopentyl, cyclohexyl, and so on, although it is not limited to those as described above.

The above cycloalkyl group may have a substituent, and the substituent may be the same as the substituents for the alkyl group in the above general formula (I), including, for example, a halogen atom such as chlorine atom, fluorine atom, or the like, hydroxyl group, amino group, nitro group, and so on, although it is not limited to those as described above. The number of the substituents is not limited to a particular one, although it is preferred to be 1 to 3, and the kind of the substituents may be different from each other.

In the term "aralkyl group" as represented by the above general formula $R^2$(iii), the term "$C_1$-$C_4$ alkylene group" as represented by $R_1$ refers to a straight-chained or branch-chained, divalent, saturated aliphatic hydrocarbon residue having 1-4 carbon atoms, and may include, for example, methylene, ethylene, propylene, butylene, methylethylene and so on. The term "aryl group" as represented by $R_2$ refers to a monovalent arom. cyclic group and may include, for example, phenyl, naphthyl and so on. The aryl group may have one substituent or more, preferably one to three substituents, identical to or different from each other, at an optional position or positions. The substituent may include, for example, a halogen atom such as chlorine atom, bromine atom or fluorine atom, hydroxyl group, nitro group, a $C_1$-$C_3$ alkyl group such as methyl or ethyl, a $C_1$-$C_3$ haloalkyl group such as trifluoromethyl, or a $C_1$-$C_3$ hydroxylalkyl group such as hydroxymethyl.

Therefore, the aralkyl group may include, for example, benzyl, a halobenzyl group such as o-, m- or p-chlorobenzyl or o-, m- or p-bromobenzyl, a nitrobenzyl group such as o-, m- or p-nitrobenzyl, an alkylbenzyl group such as o-, m- or p-methylbenzyl, a trifluorobenzyl group such as o-, m- or p-trifluorobenzyl, a hydroxylalkylbenzyl group such as o-, m- or p-hydroxymethylbenzyl, and so on.

In the term "heteroaralkyl group" as represented by the above general formula $R^2$(iv), the term "$C_1$-$C_4$ alkylene group" as represented by $R_3$ has the same meaning as the term "$C_1$-$C_4$ alkylene group" as represented by $R_1$ as described above.

In the above general formula $R^2$(iv), the term "heteroaryl group" as represented by $R_4$ refers to a monovalent heterocyclic group which may be a five- or six-membered monocyclic group having at least one, preferably 1-3 heteroatoms selected from nitrogen atom, oxygen atom or sulfur atom as a ring-structuring atom in the ring, or a ring-condensed polycyclic group (for example, dicyclic group) thereof, or a hydroheterocyclic group thereof, such as a dihydro-, tetrahydro- or hexahydro-heterocyclic group. The heteroatoms of the heteroaryl group may be identical to or different from each other. The heteroaryl group may include, for example, a monocyclic heteroaryl group such as pyrrolyl group, pyrazolyl group, imidazolyl, oxazolyl, isoxazolyl, thiazolyl, thiadiazolyl, isothiazolyl, pyridyl, furyl, thienyl, oxadiazolyl, oxazepinyl, azepinyl, pyrazinyl, pyrimidinyl, pyridazinyl, triazinyl, triazolyl and so on; and a dicyclic heteroaryl group such as benzothiazolyl, benzoxazolyl, benzothienyl, benzofuryl, quinolinyl, quinolinyl-N-oxide, isoquinolinyl, isoquinolinyl-N-oxide, benzimidazolyl, benzopyranyl, indolizinyl, cinnolinyl, quinoxalinyl, indazolyl, pyrrolopyridyl, furopyridinyl, benzisothiazolyl, benzisoxazolyl, benzodiazinyl, benzothiopyranyl, benzotriazolyl, benzopyrazolyl, naphthylidinyl, phthalaziny, purinyl, pyridopyridyl, quinazolinyl, thienofuryl, thienopyridyl, thienothienyl and so on, as well as dihyroheteroaryl, tetrahydroheteroaryl group thereof, and so on. They are not limited to those as described above, and they may have one or more substituents, preferably one to three substituents, identical to or different from each other, at an optional position or positions. The substituents may include, for example, a halogen atom such as chlorine atom, bromine atom, fluorine atom or the like, hydroxyl group, nitro group, a $C_1$-$C_3$ alkyl group such as methyl or ethyl, a $C_1$-$C_3$ haloalkyl group such as trifluoromethyl, a $C_1$-$C_3$ hydroxylalkyl group such as hydroxymethyl, or the like.

In the above general formulas (I) and (II), a counter anion as represented by $X^-$ is intended to mean an anion playing a role as a counter ion to a sulfonium ion and specifically means a conjugated base of a Broensted acid. As the Broensted acid as used herein, there may be illustrated, for example, a Broensted acid having a high acidity, including, for example, a hydrogen halide such as hydrogen chloride, hydrogen bromide, etc.; sulfuric acid or a monoalkyl ester of sulfuric acid such as monomethyl sulfate or monoethyl sulfate, etc.; a sulfonic acid such as methanesulfonic acid, ethanesulfonic acid, chlorosulfonic acid, fluorosulfonic acid, benzenesulfonic acid, to luenesu lfon ic acid, nitrobenzenesulfonic acid, dinitrobenzenesulfonic acid, trifluoromethanesulfonic acid, trichloromethanesulfonic acid, perfluorobutanesulfonic acid, trifluoroethanesulfonic acid, etc.; a trihalocarboxylic acid such as trifluoroacetic acid, trichloroacetic acid, etc.; a compound of a Lewis acid such as $HBF_4$, $HPF_6$, $HSbF_4$, $HSbF_6$, $HAsF_6$, $HBCl_4$, $HBCl_3F$, $HSbCl_6$, $HSbCl_5$, etc., with hydrogen halide, and so on.

Therefore, as examples of the conjugated bases of the Broensted acid, there may be mentioned, for example, a halogen ion, a sulfate ion, a hydrogen sulfate ion, an alkylsulfate ion, a perchlorate ion, a sulfonate ion as represented by $R^3SO_3^-$ (wherein $R^3$ means an unsubstituted or halogen-substituted alkyl group or an unsubstituted aryl group or a halogen- or alkyl-substituted aryl group), an alkylsulfate ion as represented by $R^4OSO_3^-$ (wherein $R^4$ means an unsubstituted or halogen-substituted alkyl group or an unsubstituted or a halogen- or alkyl-substituted aryl group), a carboxylate ion as represented by $R^5COO^-$ (wherein $R^5$ means a hydrogen atom, an unsubstituted or a halogen-substituted alkyl group, or an unsubstituted or an alkyl- or halogen-substituted aryl group), or an ion such as a conjugated base of a compound of the above Lewis acid with hydrogen halide.

Moreover, as specific examples, there may be illustrated, for example, a halogen ion (e.g., $F^-$, $Cl^-$, $Br^-$, etc.); a sulfonate ion (e.g., $CH_3SO_3^-$, $C_2H_5SO_3^-$, $CF_3SO_3^-$, p-$CH_3C_6H_4SO_3^-$, etc.); an alkylsulfate ion (e.g., $CH_3OSO_3^-$, $C_2H_5OSO_3^-$, $CF_3OSO_3^-$, p-$CH_3C_6H_4OSO_3^-$, etc.); a carboxylate ion (e.g., $HCOO^-$, $CH_3COO^-$, $CF_3COO^-$, $C_6H_5COO^-$, etc.); a phosphate ion, a hydrogen phosphate ion or a dihydrogen phosphate ion; $ClO_4^-$ ion; a conjugated base of the Lewis acid with the hydrogen halide (e.g., $BF_4^-$, $PF_6^-$, etc.); and so on, although they are not limited to particular ones. Among these represented by $X^-$, $Cl^-$ and $BF_4$— are particularly preferred.

In the definition of the conjugated base of the above Broensted acid, the term "halogen-substituted alkyl group" is intended to mean the above alkyl group substituted by one or plural halogen atoms (e.g., chlorine atom, bromine atom, fluorine atom, etc.). Similarly, the term "halogen- or alkyl-substituted aryl group" is intended to mean the above aryl group substituted by one or plural halogen atoms (e.g., chlorine atom, bromine atom, fluorine atom, etc.) and/or substituted by the above alkyl group.

The definitions of the above terms are similarly applied to the following description unless otherwise defined.

In accordance with the present invention, the cyclic sulfonium salt compound is characterized by the structure as represented by the general formula (I):

[Chem. 7]

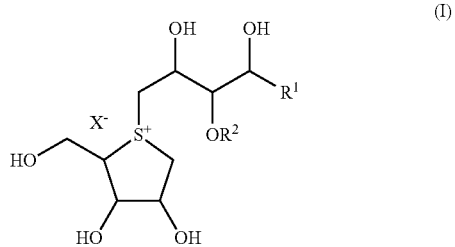

(wherein $R^1$, $R^2$ and $X^-$ have the same meanings as above), in which a polyhydroxyhydrocarbon chain is connected to the endocyclic sulfur atom of the 5-membered thiosugar moiety and the sulfonium ion: $S^-$ on the endocyclic sulfur atom of the 5-membered thiosugar forms a salt with the counter anion $X^-$.

Further, the cyclic sulfonium salt compound according to the present invention as represented by the general formula (II):

[Chem. 8]

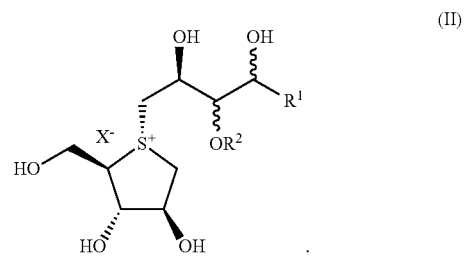

(wherein $R^1$, $R^2$ and $X^-$ have the same meanings as above), may be characterized in that each of the substituents on the 5-membered thiosugar moiety and on the polyhydroxycarbohydrate chain on sulfur atom is located in a steric configuration.

More specifically, in the above general formula (II), the $OR^2$ group at the 3'-position may assume either (R)- or (S)-configuration. The hydrocarbon chain moiety as represented by $R^1$ group at 4'-6'-position may be substituted by the hydroxyl group, In this case, the 4'-hydroxyl substituent may be located in a (R)-configuration while each of the 5'- and 6'-hydroxyl substituents may be located in either of (R)- or (S)-configuration. Therefore, a variety of stereoisomers may be present in combination of the steric configuration of each carbon atom. As the stereoisomer, a diastereomer may be present, and all of these isomers and the mixture thereof are understood to be encompassed within the scope of the present invention.

Further, a specific description will be made regarding the steric configuration of each substituent of the cyclic sulfonium salt compound (II). When $R^1$ means —(CH(OH))n-CH$_2$OH and n means 0, the steric configuration of each substituent may be represented by general formula (IIa):

[Chem. 9]

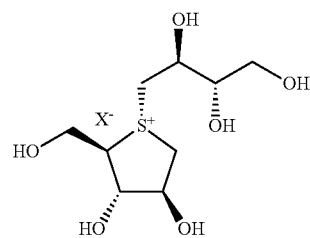

(IIa)

This compound is generally called neosalacinol. For reference, a derivative of the compound of general formula (IIa) wherein OH at the 3'-position is converted to —OSO$_3^-$ is called salacinol.

Moreover, the configuration of the connection position of each hydroxyl substituent of the cyclic sulfonium salt compound wherein $R^1$ is —(CH(OH))$_2$—CH$_2$OH may be represented by general formula (IIb):

[Chem. 10]

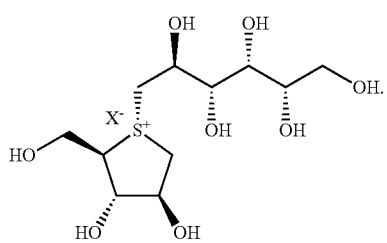

(IIb)

This compound is generally called neoponkoranol. For reference, a derivative of the compound of general formula (IIb) wherein —OH at the 3'-position is converted to —OSO$_3^-$ is generally called ponkoranol.

In addition, the configuration of the connection position of each hydroxyl substituent of the cyclic sulfonium salt compound wherein $R^1$ means —(CH(OH))$_3$—CH$_2$OH may be represented by general formula (IIc):

[Chem. 11]

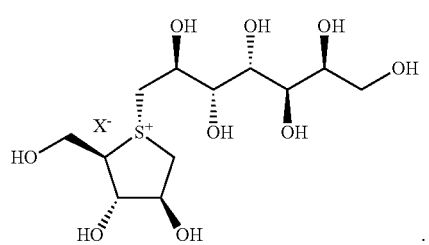

(IIc)

This compound is generally called neokotalanol. For reference, a derivative of the compound of general formula (IIb) wherein —OH at the 3'-position is converted to —OSO$_3^-$ is generally called kotalanol.

The cyclic sulfonium salt compound (I, II) according the present invention (hereinafter referred to as "compound of the invention", too) may contain a solvate. The term "solvate" as used herein is intended to mean a compound in which a molecule of a pharmaceutically acceptable solvent is configured in the compound of the invention. Such a solvate may include, for example, a hydrate, an alcoholic solvate, a solvate of a nonprotonic polar organic type, and so on, and a solvate such as the hydrate, a solvate of ethanol or a solvate of dimethylsulfoxide is preferred. The solvates may be prepared by conventional procedures.

The compound of the invention may also be used as a pharmaceutically acceptable salt. As such a pharmaceutically acceptable salt, there may be used any pharmaceutically acceptable salt that is produced from the compound of the invention, and it may include, for example, a salt with an inorganic acid, an organic acid, an amino acid, or the like. The pharmaceutically acceptable salt may be produced by conventional procedures by a reaction of the compound of the invention with an inorganic base, organic base, inorganic acid, organic acid or amino acid.

The inorganic acid may include, for example, hydrochloric acid, nitric acid, sulfuric acid, phosphoric acid, hydrobromic acid, or hydroiodic acid. The organic acid may include, for example, oxalic acid, maleic acid, citric acid, fumaric acid, lactic acid, malic acid, succinic acid, tartaric acid, acetic acid, trifluoroacetic acid, gluconic acid, glucuronic acid, ascorbic acid, methanesulfonic acid, benzenesulfonic acid, or p-toluenesulfonic acid. The amino acid may include, for example, lysine, arginine or glutamic acid.

The following is a brief description regarding the processes of the production of the cyclic sulfonium salt compounds (I) and (II) according to the present invention, but it is to be understood that the processes are not limited to those as will be described below.

The cyclic sulfonium salt compounds (I) and (II) according to the present invention may be prepared in a conventional way, for example, in accordance with the reaction schemes as will be described below. The compounds to be used therefor may be used by protecting their functional groups with protective groups, as needed, and deprotecting the protected groups in subsequent steps, or by using functional groups as precursors to convert them to objective functional groups. The isolation or purification of the products may be made, as needed, by appropriately choosing conventional procedures such as crystallization, recrystallization, liquid separation, silica gel chromatography, or fractionating HPLC. The products may be treated by next steps without isolation or purification.

In accordance with the present invention, a general process for the production of the cyclic sulfonium salt compound wherein $R^1$ is —(CH)n-CH$_2$OH (wherein n is 0) will be shown below.

(REACTION SCHEME 1)

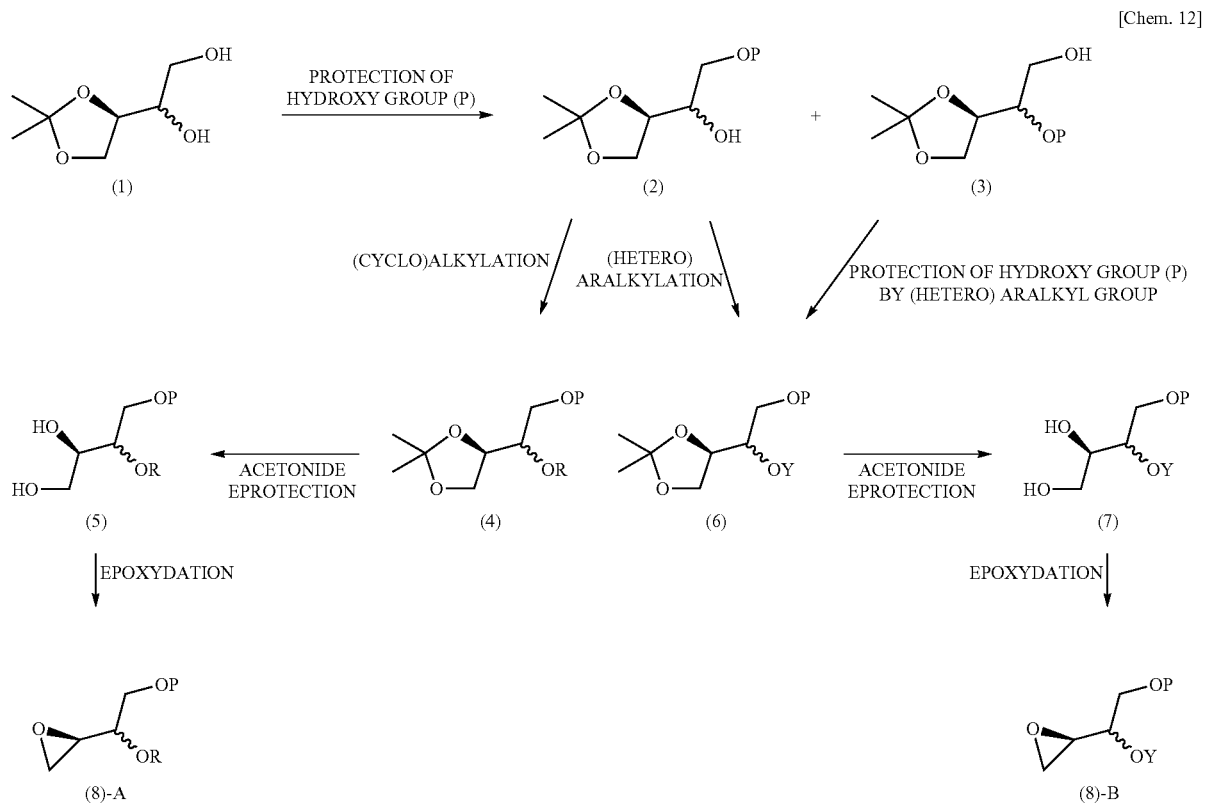

R: (CYCLO)ALKYL GROUP
P: HYDROXY PROTECTIVE GROUP
Y: (HETERO)ARALKYL GROUP

First, one of the hydroxyl groups of a diol compound (1) as a starting material is protected with a (cyclo)alkylating agent or a (hetero)aralkylating agent to yield two compounds, i.e., a terminal O-protected compound (2) and an intermediate O-protected compound (3).

The resulting terminal O-protected compound (2) may be reacted with a (cyclo)alkylating agent such as a (cyclo)alkyl halide or the like to (cyclo)alkylate the hydroxyl group, yielding a corresponding ether compound (4) which may be in turn subjected to de-acetonidation to give a compound (5). The resulting compound (5) may then be epoxidated to yield an epoxy compound (8)-A (wherein R means an alkyl group or a cycloalkyl group).

On the other hand, the resulting compound (3) may be reacted with a (hetero)aralkylating agent such as a (hetero) aralkyl halide or the like to (hetero)aralkylate the hydroxyl group, yielding a corresponding compound (6) which is then subjected to de-acetonidation to give a compound (7) that is in turn epoxidated to yield an epoxy compound (8)-B (wherein OY means a (hetero)aralkyl group).

The epoxy compounds (8)-A and (8)-B obtained in the Reaction Scheme 1 above are subjected to coupling reaction with a thiosugar compound (9)-A in accordance with Reaction Scheme 2-A below, yielding a 5-allylated cyclic sulfonium salt compound (10)-A. The de-protection of the protected group of the resulting compound (10)-A yields an objective compound (I)-A.

(REACTION SCHEME 2-A)

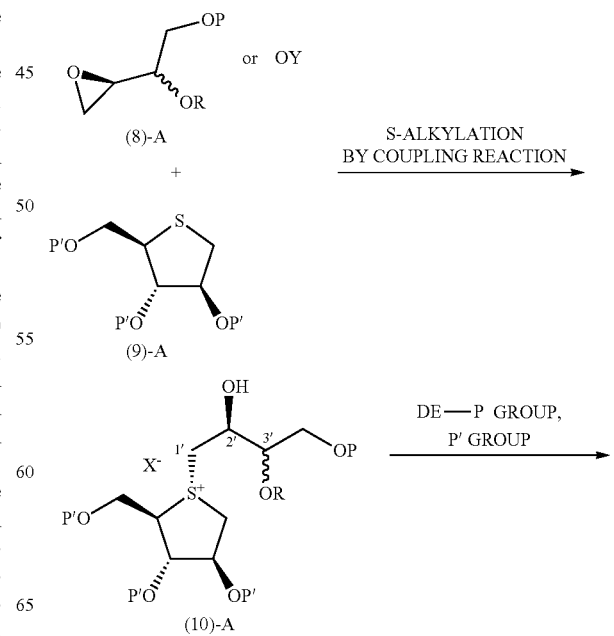

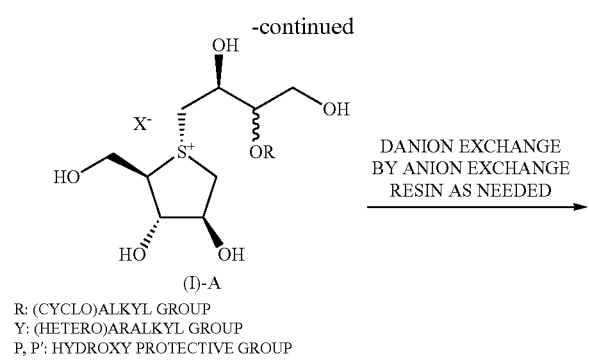

(I)-A

R: (CYCLO)ALKYL GROUP
Y: (HETERO)ARALKYL GROUP
P, P': HYDROXY PROTECTIVE GROUP

As is shown in the Reaction Scheme 2-A above, the epoxy compound (8)-A obtained by the Reaction Scheme 1 is S-alkylated by the coupling reaction with the thiosugar compound (9)-A to yield the cyclic sulfonium salt compound (10)-A. By eliminating the protected groups (P and P'), there is obtained the compound of the invention, i.e., the cyclic sulfonium salt compound as represented by formula (I)-A (wherein R means a (cyclo)alkyl group or a (cyclo)aralkyl group). The resulting compounds may be subjected to anion exchange reaction with an anion exchange resin, as needed, to convert $X^-$, after either of the steps of the above Reaction Scheme.

Next, the following is a description regarding a general process for the production of the cyclic sulfonium salt compound in which $R^1$ means $—(CH(OH))n-CH_2OH$ (n is 1 to 3, inclusive).

(REACTION SCHEME 3)

[Chem. 14]

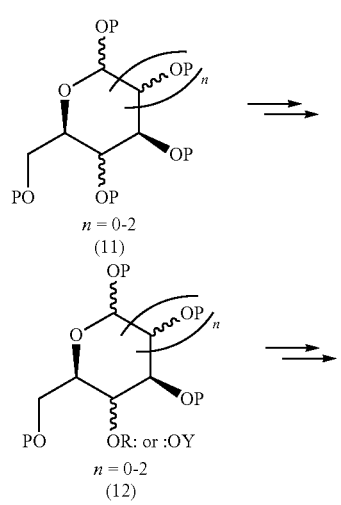

R: (CYCLO)ALKYL GROUP
P: HYDROXY PROTECTIVE GROUP
P': DEPROTECTIVE GROUP
Y: (HETERO)ARALKYL GROUP

As shown in Reaction Scheme 3 above, one protected hydroxyl group (P) of the sugar derivative (11) of the starting substance was converted to a compound (12) having a (cyclo)alkyl group (R) or a (cyclo)aralkyl group (Y). The terminal O-protected group (P) is removed to a deprotected group (P') to give a sugar derivative (13).

Next, the sugar derivative (13) obtained by the Reaction Scheme 3 above is then subjected to coupling reaction with a thiosugar compound by the Reaction Scheme 2-B above, followed by a step of deprotection of the protected group and a step of reduction, yielding the cyclic sulfonium salt compound as an objective compound.

(REACTION SCHEME 2-B)

[Chem. 15]

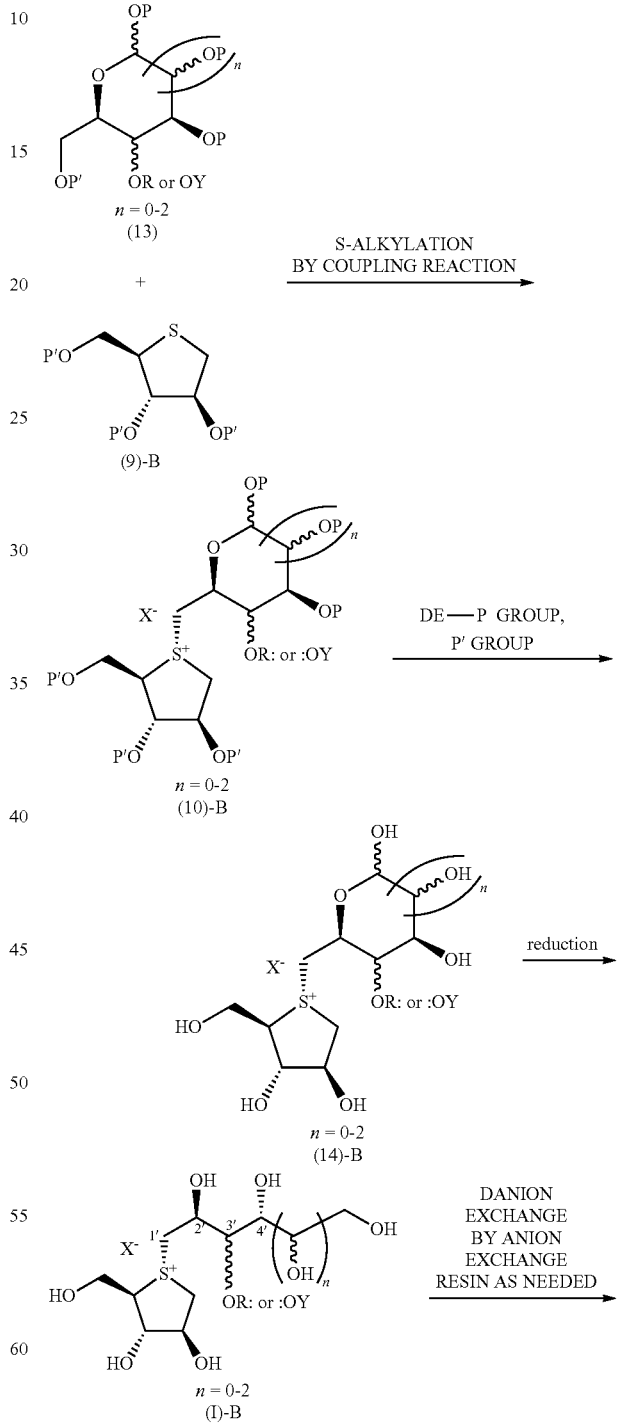

More specifically, the sugar derivative (13) obtained by the Reaction Scheme 3 is subjected to coupling reaction with the thiosugar compound (9)-B in a manner as shown in the Reaction Scheme 2-B above, thereby S-alkylating and yielding a cyclic sulfonium salt compound (10)-B. The protected groups (P and P') are then removed to give a cyclic sulfonium salt compound (14)-B which is in turn reduced to give a cyclic sulfonium salt compound ((I)-B) of the present invention. In this formula, the group corresponding to R is a (cyclo)alkyl group and the group corresponding to Y is a (cyclo)aralkyl group. After either step of the reaction scheme above, the resulting compound may be subjected to anion exchange reaction with an anion exchange resin, as needed.

The kind of the conjugated base of the Broensted acid as represented by $X^-$ is not limited to a particular one from a viewpoint of pharmacokinetics and production. The anion exchange may be readily conducted using an anion exchange resin or an acid reagent which is conventionally used in the field of organic syntheses.

The cyclic sulfonium salt compounds (I, II) or their isomers, solvates or pharmaceutically acceptable salts may inhibit the action of α-glucosidase, so that they may delay a digestion and absorption of carbohydrates and improve or suppress a rise of blood sugar after meal. Therefore, the cyclic sulfonium salt compounds according to the present invention are useful for the prevention or treatment of diseases associated with α-glucosidase.

The diseases associated with α-glucosidase may include metabolic diseases and disorders associated with metabolism, such as, for example, diabetes and/or diabetic complications. More specifically, such diseases may include, for example, type 1 diabetes mellitus, type 2 diabetes mellitus, dyslipidemia, postprandial hyperglycemia, impaired glucose tolerance (IGT), fasting plasma glucose disorders, obesity, diabetic retinopathy, cataract, diabetic nephropathy, hypertension, diabetic neuropathy, insulin resistance, and so on, although they are not limited to those as described above. Among those, diabetes, obesity and dyslipidemia are typical, and type 2 diabetes mellitus are most typical.

The compound of the invention may be formulated with a pharmaceutically acceptable carrier to give a medical composition by conventional procedures known per se in the technical field of medical preparations. The composition of the invention may be administered orally or parenterally. The medical composition for oral administration may include, for example, tablets, capsules, granules, dispersants, troches, syrups, emulsions, suspensions, and so on. The medical composition for parenteral administration may include, for example, external preparations, suppositories, injections, eye drops, nasal preparations, and so on. Although the amount of the ingredient of the medical composition according to the present invention may vary according to dosage forms, amounts of administration or the like, it may be preferred to be 0.1 to 100% by weight, preferably 0.1 to 70% by weight, relative to the total amount of the composition.

As the pharmaceutically acceptable carriers to be contained in the medical composition of the present invention, there may be used any organic or inorganic carrier substance which has been conventionally used as a raw material for use with medical preparations. They may include, for example, excipients, disintegrators, binders, plasticizers or lubricants for solid preparations, and solvents, solubilizers, suspensions, isotonizing agents, buffers or pH-adjusting agents or soothing agents for liquid preparations. Additives such as preservatives, anti-oxidants, coloring agents, sweetening agents, cooling agents or correctives, antifoaming agents or thickening agents may also be added as needed.

The excipients may include, for example, lactose, white sugar, D-mannitol, D-sorbitol, corn starch, dextrin, fine crystalline cellulose, crystalline cellulose, carmellose, carmellose calcium, carboxymethylstarch sodium, low substituted hydroxypropylcellulose, gum Arabic, and so on. The disintegrators may include, for example, carmellose, carmellose calcium, carmellose sodium, carboxymethylstarch sodium, croscarmellose sodium, crospovidone, low substituted hydroxypropylcellulose, hydroxypropylmethylcellulose, crystalline cellulose, and so on. The binders may include, for example, hydroxypropylcellulose, hydroxypropylmethylcellulose, povidone, crystalline cellulose, white sugar, dextrin, starch, gelatin, carmellose sodium, gum arabic, and so on. The plasticizers may include, for example, light anhydrous silicic acid, magnesium stearate, and so on. The lubricants may include, for example, magnesium stearate, calcium stearate, talc, and so on.

The solvents may include, for example, purified water, ethanol, propylene glycol, macrogol, sesame oil, corn oil, olive oil, and so on. The solubilizers may include, for example, propylene glycol, D-mannitol, benzylbenzoate, ethanol, triethanolamine, sodium carbonate, sodium citrate, and so on. The suspensions may include, for example, benzalkonium chloride, carmellose, hydroxypropylcellulose, propylene glycol, povidone, methylcellulose, glyceryl monostearate, and so on. The isotonizing agents may include, for example, glucose, D-sorbitol, sodium chloride, D-mannitol, and so on. The buffers or pH-adjusting agents may include, for example, dibasic sodium phosphate, sodium acetate, sodium carbonate, sodium citrate, and so on. The soothing agents may include, for example, benzylalcohol, and so on.

The preservatives may include, for example, methyl parahydroxybenzoate, ethyl parahydroxybenzoate, propyl parahydroxybenzoate, chloroethanol, benzylalcohol, sodium dehydroacetate, sorbic acid, and so on. The anti-oxidants may include, for example, sodium sulfite, ascorbic acid, and so on. The coloring agents may include, for example, food colorings (e.g., Food Red 2 or 3, Food Yellow 4 or 5, etc), □-carotene, and so on. The sweetening agents may include, for example, saccharin sodium, dipotassium glycyrrhizate, aspartame, and so on. The cooling agents or correctives may include, for example, 1-menthol, peppermint water, and so on. The antifoaming agents may include, for example, dimethylpolysiloxane, silicone antifoaming agent, and so on. The thickening agents may include, for example, xanthan gum, tragacanth, methylcellulose, dextrin, and so on.

The medical compositions according to the present invention may be administered to human patients as well as pet animals such as dogs and cats. The doses may vary with objects of administration, diseases, dosage forms, administration routes and so on, and may be usually in the range of approximately 1 mg to 1 gram of the ingredients with respect to an adult patient with diabetes mellitus (body weight: 60 kg) when orally administered. The dose may be administered once or several times.

The medical composition according to the present invention may be used as a medical composition in combination with one or plural other agents (hereinafter referred to as "combined agent") in a conventional manner as used in the medical field. The combined medical composition may be administered as a combination medicine containing the medical composition of the present invention and the combined agent together in the same preparation or in such a manner that each of the agents may be administered simultaneously or separately at a given interval. The doses of the combined agents may be proportionate to the doses to be used clinically and may be appropriately chosen depending upon the objects of administration, diseases, symptoms, dosage forms, routes of administration routes, time of administration, combinations, and so on. The type of administration of the combined agents is not limited to a particular one as long as the compound of the invention or its salt can be combined with the combined agent.

As the combined agents to be used for the combined medical composition according to the present invention, there may be mentioned, for example, anti-diabetes agents, anti-obesity agents, anti-dyslipidemia agent, anti-hypertension agents, and so on.

The anti-diabetes agents may include, for example, hypoglycemic agent, anti-diabetic complication agent, and so on. As the anti-diabetes agents, there may be mentioned, for example, insulin preparations (injections), fructose-1,6-bisphosphatase (FBPase) inhibitor, glucagon receptor antagonist, glucocorticoid receptor antagonist, glucokinase activator, glutamine fructose-6-phosphate aminotransferase (GFAT) inhibitor, glycogen phosphorylase (GP) inhibitor, glycogen synthase kinase 3 (GSK-3) inhibitor, GPR 40 agonist, phosphoenol pyruvate carboxylase (PEPCK) inhibitor, protein tyrosine phosphatase 1B (PTPase 1B) inhibitor, pyruvate dehydroxygenase kinase (PDHK) inhibitor, SGLUT inhibitor, SH2 domain-containing inositol phosphatase 2 (SHIP2) inhibitor, dipeptidyl aminopeptidase IV (DPP-IV) inhibitor, tGLP-1 peptide analogue, α-glucosidase inhibitor, insulin sensitivity enhancer, sulfonylurea receptor agonist (SU agent), instantaneous insulin secretion stimulant (nateglinide), low-molecular tGLP-1 receptor agonist, low-molecular insulin oral agent, biguanide agent, 11β-HSD-1 inhibitor, adiponectin receptor agonist, AMP-activation protein kinase (AMPK) activator, PPARγ receptor agonist-antagonist, β3 adrenalin receptor agonist, and so on. As the anti-diabetic complication agents, there may be mentioned, for example, agent for suppressing the production of advanced glycation endproduct (AGE), aldose reductase inhibitor, angiotensin II receptor antagonist, angiotensin converting enzyme (ACE) inhibitor, protein kinase C8 (PKC8) inhibitor, and so on.

As the anti-obesity agents, there may be mentioned, for example, acetyl-coA carboxylase 1 (ACC1) inhibitor, acetyl-CoA carboxylase 2 (ACC2) inhibitor, bombesin receptor subtype 3 (BRS-3) agonist, diacylglycerol acyltransferase (DGAT) inhibitor, glucose-dependent insulin secretion-promoting polypeptide (GIP) receptor antagonist, leptin receptor agonist, melanocortin (MC) receptor agonist, neuropeptide Y5 (NPY5) receptor antagonist, perilipin inhibitor, uncoupling protein (UCP) inducing-activation agent, 11β-HSD-1 inhibitor, adiponectin receptor agonist, AMP activation protein kinase (AMPK) activator, PPARγ receptor agonist-antagonist, β3 adrenalin receptor agonist, and so on.

As the anti-dyslipidemia agents, there may be mentioned, for example, apolipoprotein A1 (Apo-A1) inducing agent, cholesteryl ester transfer protein (CETP) inhibitor, endothelial lipase inhibitor, HMG-CoA reductasd inhibitor, lipoprotein lipase (LPL) activator, microsome triglyceride transfer protein (MTP) inhibitor, PPARα receptor agonist, PPARδ agonist, and so on.

As the anti-hypertension agents, there may be mentioned, for example, α blocker, β blocker, angiotensin converting enzyme inhibitor (ACE inhibitor), calcium antagonist, renin inhibitor, and so on.

The cyclic sulfonium salt compounds (I and II) or the isomer or solvate thereof or the pharmaceutically acceptable salt thereof according to the present invention may be used as food for preventing or treating diabetes, diabetic complication, obesity, dyslipidemia or hypertension, particularly as anti-diabetic foods, anti-obesity foods, and so on. Therefore, the foods of the present invention are useful as health foods such as functional foods.

The food according to the present invention may contain conventional additives depending upon the kinds of the food. The additives may include, for example, the excipients, pH-adjusting agents, cooling agents, suspensions, antifoaming agents, thickening agents, solubilizers, disintegrators, binders, lubricants, coloring agents, or correctives, as those illustrated above. The food of the present invention may be admixed with other biologically active constituents, minerals, vitamins, hormones, nutritive constituents, flavors, and so on.

The food of the present invention may be processed by conventional procedures, for example, into the form of solutions, capsules such as hard capsules or soft capsules, tablets, pills, granules, and so on, and they may be eaten as confectionery such as snack foods, biscuits, cookies, etc., or drunken as soft drink, juices, etc.

EXAMPLES

The present invention will be described in more detail by reference to examples that will be described below, but it is to be understood that the present invention is not limited thereto.

Examples of the specific methods for the productions of the compound of the invention will be indicated by Reaction Schemes 4 and 5.

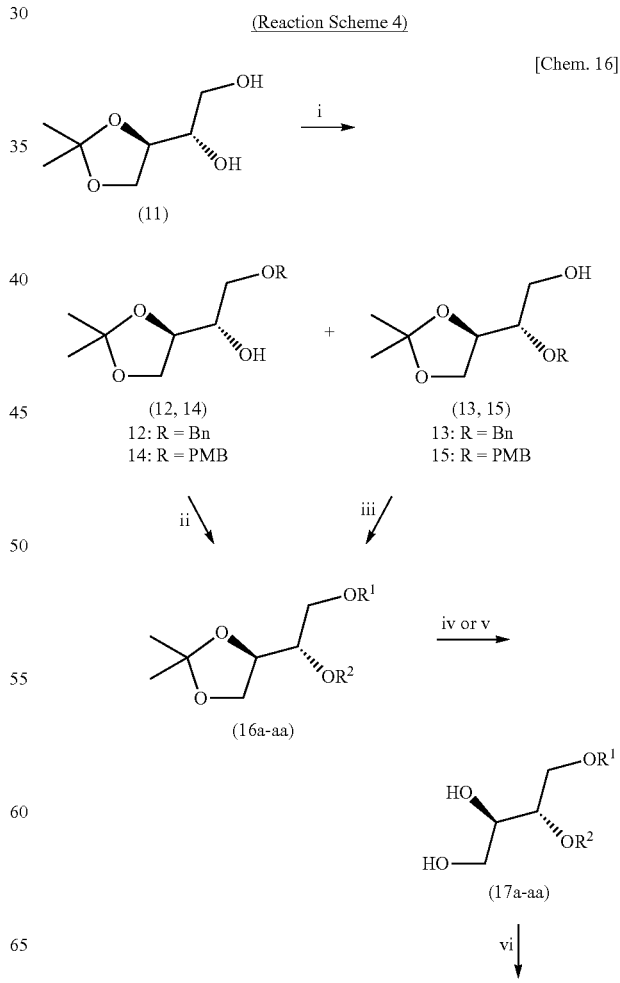

(Reaction Scheme 4)

[Chem. 16]

19
-continued

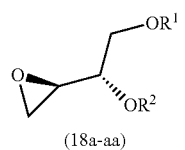
(18a-aa)

a: R¹ = Bn, R² = CH₃
b: R¹ = Bn, R² = C₂H₅
c: R¹ = Bn, R² = C₇H₁₁
d: R¹ = Bn, R² = C₇H₁₅
e: R¹ = Bn, R² = C₁₃H₂₇
f: R¹ = Bn, R² = neopentyl
g: R¹ = PMB, R² = Bn
h: R¹ = PMB, R² = CH₂C₆H₄(o-CH₃)
i: R¹ = PMB, R² = CH₂C₆H₄(m-CH₃)
j: R¹ = PMB, CH₂C₆H₄(p-CH₃)
k: R¹ = PMB, R² = CH₂C₆H₄(o-Cl)
l: R¹ = PMB, R² = CH₂C₆H₄(m-Cl)
m: R¹ = PMB, R² = CH₂C₆H₄(p-Cl)
n: R¹ = PMB, R² = (o-Br)C₆H₄
o: R¹ = PMB, R² = (m-Br)C₆H₄
p: R¹ = PMB, R² = (p-Br)C₆H₄
q: R¹ = PMB, R² = (o-CF₃)C₆H₄
r: R¹ = PMB, R² = (m-CF₃)C₆H₄
s: R¹ = PMB, R² = (p-CF₃)C₆H₄
t: R¹ = PMB, R² = (o-NH₂)C₆H₄
u: R¹ = PMB, R² = (m-NO₂)C₆H₄
v: R¹ = PMB, R² = (p-NO₂)C₆H₄
w: R¹ = PMB, R² = (p-HOCH₂)C₆H₄
x: R¹ = PMB, R² = napthalene-1-ylmethyl
y: R¹ = PMB, R² = naphthalene-2-ylmethyl
z: R¹ = PMB, R² = pyridine-3-ylmethyl
aa: R¹ = PMB, R² = pyridine-4-ylmethyl (Reaction Scheme 5)

[Chem. 17]

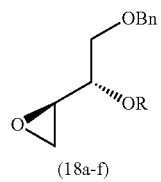
(18a-f)

+

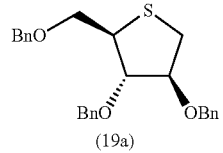
(19a)

↓ vii

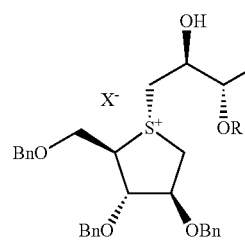
(20a-20f)

viii ⎡ X = BF₄
     ⎣ → X = Cl

20
-continued

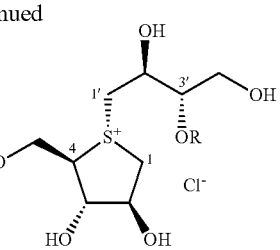

compound Ia: R = CH₃,
compound Ib: R = C₂H₅,
compound Ic: R = C₅H₁₁
compound Id: R = C₇H₁₅
compound Ie: R = C₁₃H₂₇
compound If: R = neopentyl

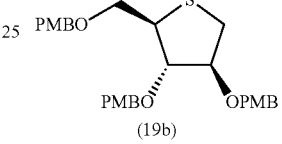
(18g-aa)

+

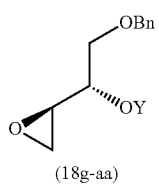
(19b)

↓ vii

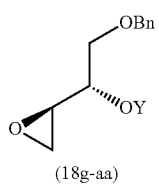
(20g-20aa)

→ x

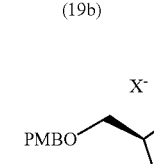

viii ⎡ X = BF₄
     ⎣ → X = Cl compound Ig: Y = Bn, X⁻ = BF₄⁻ or Cl⁻
compound Ih: Y = CH₂C₆H₄(o-CH₃), X⁻ = Cl⁻
compound Ii: Y = CH₂C₆H₄(m-CH₃), X⁻ = Cl⁻
compound Ij: Y = CH₂C₆H₄(p-CH₃), X⁻ = Cl⁻
compound Ik: Y = CH₂C₆H₄(o-Cl), X⁻ = Cl⁻
compound Il: Y = CH₂C₆H₄(m-Cl), X⁻ = Cl⁻
compound Im: Y = CH₂C₆H₄(p-Cl), X⁻ = Cl⁻
compound In: Y = CH₂C₆H₄(o-Br), X⁻ = Cl⁻
compound Io: Y = CH₂C₆H₄(m-Br), X⁻ = Cl⁻
compound Ip: Y = CH₂C₆H₄(p-Br), X⁻ = Cl⁻
compound Iq: Y = CH₂C₆H₄(o-CF₃), X⁻ = Cl⁻
compound Ir: Y = CH₂C₆H₄(m-CF₃), X⁻ = Cl⁻
compound Is: Y = CH₂C₆H₄(p-CF₃), X⁻ = Cl⁻
compound It: Y = CH₂C₆H₄(o-NO₂), X⁻ = Cl⁻
compound Iu: Y = CH₂C₆H₄(m-NO₂), X⁻ = Cl⁻
compound Iv: Y = CH₂C₆H₄(p-NO₂), X⁻ = Cl⁻
compound Iw: Y = CH₂C₆H₄(p-CH₂OH), X⁻ = Cl⁻
compound IX: Y = naphthalene-1-ylmethyl, X⁻ = Cl⁻
compound IY: Y = napthalene-2-ylmethyl, X⁻ = Cl⁻
compound Iz: Y = pyridine-3-ylmethyl, X⁻ = Cl⁻
compound Iaa: Y = pyridine-4-ylmethyl, X⁻ = Cl⁻

In the above reaction schemes and the examples below, abbreviations have meanings as will be described below.

Me is intended to mean methyl group, Et to ethyl group, Bn to benzyl group, AcOH to acetic acid, DMF to N,N-dimethylformamide, DEAD to diethylazodicarboxylate, PMBCl to paramethoxybezyl chloride, and aq. to aqueous solution or aqueous.

The verification of the compounds was conducted by an analysis of various spectroscopies, including, specifically, one-dimensional or two-dimensional proton or $H^{13}$ nuclear magnetic resonance spectrum ($^1$H NMR or $^{13}$C NMR), infrared absorption spectrum (IR), mass spectrum (MS) (e.g., fast atom bombardment mass spectrometry (FABMS), or fast atom bombardment high-resolution mass spectrometry (FABHRMS)) or by an analysis of specific rotation. For proton nuclear magnetic resonance spectrum using heavy chloroform, tetramethylsilane was used as internal standard. For $^{13}$C NMR, the following signals were used as standards: 77.0 ppm in heavy chloroform, and 49.0 ppm in heavy methanol.

Example 1

1-O-benzyl-3,4-O-isopropylidene-D-erythritol compound (12) and 2-O-benzyl-3,4-O-isopropylidene-D-erythritol compound (13) (Reaction Scheme 4)

First, a diol compound (3,4-O-isopropylidene-D-erythritol) (11) was obtained from D-isoascorbic acid by a method known per se (Abushanab E.; Vemishetti P.; Leiby R. W.; Singh H. K.; Mikkilineni A. B.; Wu D. C.-J.; Saibaba R.; Panzica, R. P. J. Org. Chem. 1988, 53, 2598), and the resulting compound (11) (6 g, 37.0 mmol) was then refluxed with a mixture of Bu$_2$Sn(IV)O (11.1 g, 44.6 mmol) and toluene (60 ml) by heating for 1 hour, followed by concentrating the reaction mixture in an egg-plant shaped flask with a Dean-Stark cooler under reduced pressure. To the residue were added DMF (60 ml), cesium fluoride (8.5 g, 55.9 mmol) and benzyl bromide (6.6 ml, 55.6 mmol), and the resulting suspension was heated at 60° C. for 1 hour. After cooling, the reaction mixture was diluted with ethyl ether (200 ml), followed by filtering the undissolved material off and washing with diethyl ether. After the filtrate was combined with the washings, the mixture was made alkaline by adding 10% aqueous sodium hydroxide solution (100 ml). Then, the precipitated gel was filtered off with celite, and the solution was washed with diethyl ether. The separated organic layer was washed with saturated saline water and then concentrated yielding a pale yellow oily substance (11.3 g) which was in turn purified by column chromatography (n-hexane:AcOEt; 10:1→5:1→1:1) yielding the compound (12) (8.5 g, 91%) and the compound (13) (651 mg, 7%).

[Chem. 18]

Compound (12): colorless oily substance: $[\alpha]_D^{24}$ −0.50 (c=0.32, CHCl$_3$). IR (neat): 3417, 1454, 1373, 1246, 1211, 1153, 1107, 1065 cm$^{-1}$. $^1$H-NMR (500 MHz, CDCl$_3$) δ: 1.35/1.41 [each 3H, s, (CH$_3$)$_2$C], 2.44 (1H, d, J=4.3 Hz, OH), 3.55 (1H, dd, J=9.8, 6.3 Hz, H-1a), 3.67 (1H, dd, J=9.8, 3.5 Hz, H-1b), 3.79 (1H, dddd-like, J=ca. 6.3, 6.3, 4.3, 3.5 Hz, H-2), 3.98 (1H, dd-like, J=11.2, 8.6 Hz, H-4a), 4.06 (1H, dd-like, J=11.2, 6.3 Hz, H-1b), 4.07 (1H, ddd, J=8.6, 6.3, 6.3 Hz, H-3), 4.56/4.58 (each 1H, d, J=12.0 Hz, CH$_2$Ph), 7.28-7.38 (5H, m, arom.). $^{13}$C-NMR (125 MHz, CDCl$_3$) δ: 25.3/26.7 [(CH$_3$)$_2$C], 66.5 (C-4), 71.15 (C-1), 71.19 (C-2), 73.5 (OCH$_2$Ph), 75.9 (C-3), 109.2 [(CH$_3$)$_2$C], 127.7/127.8/128.5 (d, arom.), 137.8 (s, arom.).

[Chem. 19]

Compound (13): colorless oily substance. $[\alpha]_D^{25}$ +20.6 (c=1.26, CHCl$_3$), IR (neat): 3418, 1456, 1381, 1371, 1256, 1213, 1072 cm$^{-1}$. $^1$H NMR (500 MHz, CDCl$_3$) δ: 1.35/1.42 [each 3H, s, (CH$_3$)$_2$C], 2.07 (1H, dd-like, J=ca. 7.2, 4.3 Hz, OH), 3.53 (1H, ddd, J=6.6, 4.3, 4.3 Hz, H-2), 3.71 (1H, ddd, J=11.8, 7.2, 4.3 Hz, H-1a), 3.83 (1H, ddd, J=11.8, 4.3, 4.3 Hz, H-1b), 3.88 (1H, dd, J=8.3, 6.0 Hz, H-4-a), 4.08 (1H, dd, J=8.3, 6.3 Hz, H-4b), 4.19 (1H, ddd, J=6.6, 6.3, 6.0 Hz, H-3), 4.64/4.67 (each 1H, d, J=11.5 Hz, OCH$_2$Ph), 7.28-7.38 (5H, m, arom.). $^{13}$C NMR (125 MHz, CDCl$_3$) δ: 25.3/26.7 [(CH$_3$)$_2$C], 61.9 (C-1), 67.0 (C-4), 72.8 (OCH$_2$Ph), 76.0 (C-3), 79.7 (C-2), 109.4 [(CH$_3$)$_2$C], 128.0/128.1/128.7 (d, arom.), 138.0 (s, arom.).

Example 2

3,4-O-isopropylidene-1-O-paramethoxybenzyl-D-erythritol compound (14) and 3,4-O-isopropylidene-2-O-paramethoxybenzyl-D-erythritol compound (15) (Reaction Scheme 4)

By following substantially the same processes as for the synthesis of the compounds (12) and (13) in Example 1, a mixture of 3,4-O-isopropylidene-D-erythritol compound (11) (500 mg, 3.1 mmol) and Bu$_2$SnO (920 mg, 3.7 mmol) with toluene (5 ml) was refluxed by heating for 1 hour, and the reaction mixture was concentrated under reduced pressure. To the residue was added DMF (60 ml), cesium fluoride (8.5 g, 55.9 mmol) and paramethoxybenzyl chloride (0.63 ml, 4.6 mmol) in order, and the resulting suspension was in turn heated at 60° C. for 12 hour. After diluting the reaction mixture with diethyl ether (40 ml), the reaction mixture was treated with 10% aqueous sodium hydroxide solution (pH>11). The precipitated gel was filtered off with celite and then washed with diethyl ether. The filtrate and the washings were combined, and the separated organic layer separated from the combined solution of the filtrate and the washings was washed with saturated saline water, followed by concentrating to yield a pale yellow oily substance (1.22 g). The product was then purified by column chromatography (n-hexane: AcOEt; 10:1→5:1→1:1) yielding the compound (14) (730 mg, 89%) and the compound (15) (53 mg, 6.5%), respectively.

[Chem. 20]

Compound (14): colorless waxy solid. Mp 46-48° C. $[\alpha]_D^{28}$ −1.47 (c=1.43, CHCl$_3$). IR (nujol): 3406, 1612, 1512, 1303, 1249, 1211, 1172, 1153, 1064 cm$^{-1}$. $^1$H-NMR (500 MHz, CDCl$_3$) δ: 1.35/1.40 [each 3H, s, C(CH$_3$)$_2$], 2.43 (1H, d, J=4.0 Hz, OH), 3.53 (1H, dd, J=9.8, 6.3, H-1a), 3.64 (1H, dd, J=9.8, 3.5, H-1b), 3.74-3.80 (1H, br m, J, H-2), 3.80 (3H, s, OCH$_3$), 3.94-4.00 (1H, m, H-4a), 4.02-4.07 (2H, m, H-3 and H-4b), 4.48/4.51 (each 1H, d, J=11.5, OCH$_2$Ar), 7.28-7.38 (5H, m, arom.). $^{13}$C-NMR (125 MHz, CDCl$_3$) δ: 25.3/26.7 [C(CH$_3$)$_2$], 55.3 (OCH$_3$), 66.4 (C-4), 70.9 (C-1), 71.2 (C-2), 73.2 (OCH$_2$Ar), 75.9 (C-3), 109.2 [C(CH$_3$)$_2$], 113.8/129.4 (d, arom.), 129.9/159.3 (s, arom.). FABMS (pos.) m/z: 305 [M+Na]$^+$.

[Chem. 21]

Compound (15): colorless oily substance. $[\alpha]_D^{26}$ +25.3 (c=0.58, CHCl$_3$). IR (neat): 3456, 1612, 1516, 1462, 1373, 1300, 1250, 1216, 1157, 1111, 1072, 1038 cm$^{-1}$. $^1$H NMR (500 MHz, CDCl$_3$) δ: 1.35/1.42 [each 3H, s, C(CH$_3$)$_2$], 2.07 (1H, br dd-like, J=ca. 6.5, 5.0, OH), 3.50 (1H, ddd, J=6.9, 4.3, 4.3 Hz, H-2), 3.69 (1H, ddd, J=11.0, 6.5, 4.3 Hz, H-1a), 3.77-3.84 (1H, br m, H-1 b), 3.80 (3H, s, OCH$_3$), 3.85 (1H, dd, J=8.3, 6.0, H-4a), 4.07 (1H, dd, J=8.3, 6.3, H-4b), 4.17

(1H, ddd, J=6.9, 6.3, 6.0 Hz, H-3), 4.57/4.59 (each 1H, d, J=11.5, OCH$_2$Ar), 6.89/7.26 (each 2H, d-like, J=8.6 Hz, arom.). $^{13}$C NMR (125 MHz, CDCl$_3$) δ: 25.1/26.6 [C(CH$_3$)$_2$], 55.3 (OCH$_3$), 61.8 (C-1), 66.9 (C-4), 72.3 (OCH$_2$Ar), 75.9 (C-3), 79.3 (C-2), 109.3 [C(CH$_3$)$_2$], 114.0/129.5 (d, arom.), 130.0/159.4 (s, arom.). FABMS (pos.) m/z: 305 [M+Na]+.

Example 3

1-O-benzyl-2-O-methyl-3,4-O-isopropylidene-D-erythritol compound (16a) (Reaction Scheme 4)

A DMF solution (10 ml) of the compound (12) (2.0 g, 7.94 mmol) was added dropwise in a mixture of sodium hydride (476 mg, 11.9 mmol, 60% in liquid paraffin), methyl iodide (1 ml, 16 mmol) at 0° C., followed by stirring at 0° C. for 1 hour. The resulting reaction mixture was then poured into an ice water (100 ml) and extracted with a mixture of n-hexane with diethyl ether (v/v, 1/1). The resulting extract was washed with saturated saline water and concentrated yielding colorless oily substance, 1-O-benzyl-2-O-methyl-3,4-O-isopropylidene-D-erythritol compound (16a) (2.31 g). The resulting compound was then purified by column chromatography (n-hexane:AcOEt; 10:1) yielding the titled compound (16a) (2.0 g, 97%).
[Chem. 22]
Compound (16a): colorless oily substance. $[α]_D^{20}$ +13.5 (c=1.10, CHCl$_3$). IR (neat): 1454, 1370, 1253, 1211, 1153, 1100, 1053 cm$^{-1}$. $^1$H-NMR (500 MHz, CDCl$_3$) δ: 1.35/1.41 [each 3H, s, C(CH$_3$)$_2$], 3.38 (1H, ddd, J=6.6, 4.9, 2.9 Hz, H-2), 3.48 (3H, s, OCH$_3$), 3.55 (1H, dd, J=10.6, 4.9 Hz, H-1a), 3.71 (1H, dd, J=10.6, 2.9 Hz, H-1b), 3.93 (1H, dd, J=8.3, 6.1 Hz, H-4a), 4.05 (1H, dd, J=8.3, 6.3 Hz, H-4b), 4.14 (1H, ddd, J=6.6, 6.3, 6.1 Hz, H-3), 4.56/4.58 (each 1H, d, J=12.1 Hz, CH$_2$Ph), 7.26-7.36 (5H, m, arom.). $^{13}$C-NMR (125 MHz, CDCl$_3$) δ: 25.3/26.6 [C(CH$_3$)$_2$], 58.7 (OCH$_3$), 66.5 (C-4), 69.3 (C-1), 73.5 (OCH$_2$Ph), 75.3 (C-3), 80.9 (C-2), 109.1 [C(CH$_3$)$_2$], 127.6/128.3 (d, arom.), 138.2 (s, arom.). FABMS (pos.) m/z C: 289 [M+Na]$^+$.

Example 4

1-O-benzyl-2-O-ethyl-3,4-O-isopropylidene-D-erythritol compound (16b) (Reaction Scheme 4)

By following substantially the same procedures as for the synthesis of the compound (16a), the compound (12) (2.0 g, 7.94 mmol) was reacted with ethyl iodide (1.27 ml, 15.9 mmol) to give 1-O-benzyl-2-O-ethyl-3,4-O-isopropylidene-1-D-erythritol compound (16b) as colorless oily substance (2.13 g, 96%).
[Chem. 23]
Compound (16b): colorless oily substance. $[α]_D^{24}$ +10.4 (c=0.85, CHCl$_3$). IR (neat): 1456, 1371, 1260, 1213, 1099, 1074 cm$^{-1}$. $^1$H-NMR (500 MHz, CDCl$_3$) δ: 1.19 (3H, t, J=7.2 Hz, OCH$_2$CH$_3$), 1.35/1.40 [each 3H, s, C(CH$_3$)$_2$], 3.48 (1H, ddd, J=6.6, 5.2, 3.2 Hz, H-2), 3.54 (1H, dd, J=10.3, 5.2 Hz, H-1a), 3.57/3.75 (each 1H, dq, J=9.5, 7.2 Hz, OCH$_2$CH$_3$), 3.68 (1H, dd, J=10.3, 3.2 Hz, H-1b), 3.93 (1H, dd, J=8.3, 6.1 Hz, H-4a), 4.05 (1H, dd, J=8.3, 6.3 Hz, H-4b), 4.14 (1H, ddd, J=6.6, 6.3, 6.1 Hz, H-3), 4.55/4.57 (each 1H, d, J=12.3 Hz, OCH$_2$Ph), 7.26-7.36 (5H, m, arom.). $^{13}$C-NMR (125 MHz, CDCl$_3$) δ: 15.6 (OCH$_2$CH$_3$), 25.4/26.6 [C(CH$_3$)$_2$], 66.5 (OCH$_2$CH$_3$), 66.6 (C-4), 70.1 (C-1), 73.4 (OCH$_2$Ph), 75.5 (C-3), 79.3 (C-2), 109.1 [C(CH$_3$)$_2$], 127.5/1278.3 (d, arom.), 138.3 (s, arom.). FABMS (pos.) m/z: 303 [M+Na]$^+$.

Example 5

1-O-benzyl-2-O-pentyl-3,4-O-isopropylidene-D-erythritol compound (16c) (Reaction Scheme 4)

By following substantially the same procedures as for the synthesis of the compound (16a), 1-O-benzyl-2-O-pentyl-3,4-O-isopropylidene-D-erythritol compound (16c) (1.1 g, 96%) was obtained from the compound (12) (900 mg, 3.57 mmol) and 1-bromopentane.
[Chem. 24]
Compound (16c): colorless oily substance. $[α]_D^{23}$ +16.0 (c=0.91, CHCl$_3$). IR (neat): 1454, 1370, 1258, 1211, 1099, 1072 cm$^{-1}$. $^1$H NMR (500 Hz, CDCl$_3$) δ: 0.89 [3H, t, J=7.1 Hz, O(CH$_2$)$_4$CH$_3$], 1.28-1.34 [4H, m, OCH$_2$CH$_2$(CH$_2$)$_2$CH$_3$], 1.35/1.40 [each 3H, s, C(CH$_3$)$_2$], 1.52-1.59 [2H, m, OCH$_2$CH$_2$(CH$_2$)$_2$CH$_3$], 3.46 (1H, ddd, J=6.6, 5.2, 3.1 Hz, H-2), 3.48/3.68 [each 1H, dt, J=9.0, 6.9 Hz, OCH$_2$(CH$_2$)$_3$CH$_3$], 3.54 (1H, dd, J=10.3, 5.2 Hz, H-1a), 3.69 (1H, dd, J=10.3, 3.1 Hz, H-1b), 3.93 (1H, dd, J=8.3, 6.0 Hz, H-4a), 4.05 (1H, dd, J=8.3, 6.6 Hz, H-4b), 4.15 (1H, ddd, J=6.6, 6.6, 6.0 Hz, H-3), 4.55/4.57 (each 1H, d, J=12.3 Hz, OCH$_2$Ph), 7.26-7.36 (5H, m, arom.). $^{13}$C NMR (125 Hz, CDCl$_3$) δ: 14.0 [O(CH$_2$)$_4$CH$_3$], 22.5 [O(CH$_2$)$_3$CH$_2$CH$_3$], 25.4/26.6 [C(CH$_3$)$_2$], 28.3 [O(CH$_2$)$_2$CH$_2$CH$_2$CH$_3$], 29.8 [OCH$_2$CH$_2$(CH$_2$)$_2$CH$_3$], 66.7 (C-4), 70.0 (C-1), 71.2 [OCH$_2$(CH$_2$)$_3$CH$_3$], 73.4 (OCH$_2$Ph), 75.4 (C-3), 79.5 (C-2), 109.0 [C(CH$_3$)$_2$], 127.5/128.3 (d, arom.), 138.3 (s, arom.). FABMS (pos.) m/z: 345 [M+Na]$^+$.

Example 6

1-O-benzyl-2-O-heptyl-3,4-O-isopropylidene-D-erythritol compound (16d) (Reaction Scheme 4)

By following substantially the same procedures as for the synthesis of the compound (16a), the compound (12) (500 mg, 1.98 mmol) was reacted with 1-bromoheptane to give 1-O-benzyl-2-O-pentyl-3,4-O-isopropylidene-D-erythritol compound (16d) (673 mg, 97%).
[Chem. 25]
Compound (16d): colorless oily substance. $[α]_D^{23}$ +13.3 (c=0.97, CHCl$_3$). IR (neat): 1454, 1369, 1346, 1273, 1253, 1215, 1099, 1076 cm$^{-1}$. $^1$H NMR (500 MHz, CDCl$_3$) δ: 0.88 [3H, t, J=7.0 Hz, O(CH$_2$)$_6$CH$_3$], 1.22-1.34 [8H, m O(CH$_2$)$_2$(CH$_2$)$_4$CH$_3$], 1.35/1.40 [each 3H, s, C(CH$_3$)$_2$], 1.52-1.59 [2H, m OCH$_2$CH$_2$(CH$_2$)$_4$CH$_3$], 3.46 (1H, ddd, J=6.6, 5.2, 3.1 Hz, H-2), 3.47/3.68 [each 1H, dt, J=9.2, 7.0 Hz, OCH$_2$(CH$_2$)$_5$CH$_3$], 3.54 (1H, dd, J=10.3, 5.2 Hz, H-1a), 3.69 (1H, dd J=10.6, 3.1 Hz, H-1b), 3.93 (1H, dd, J=8.3, 6.0 Hz, H-4a), 4.05 (1H, dd, J=8.3, 6.3 Hz, H-4b), 4.14 (1H, ddd, J=6.6, 6.3, 6.0 Hz, H-3), 4.58/4.54 (each 1H, d, J=12.0 Hz, OCH$_2$Ph) 7.25-7.35 (5H, m, arom.). $^{13}$C NMR (125 MHz, CDCl$_3$) δ: 14.1 [O(CH$_2$)$_6$CH$_3$], 22.6 [O(CH$_2$)$_5$CH$_2$CH$_3$], 25.4/26.6 [C(CH$_3$)$_2$], 25.4 [O(CH$_2$)$_2$CH$_2$(CH$_2$)$_3$CH$_3$], 29.1 [O(CH$_2$)$_3$CH$_2$CH$_2$CH$_3$], 30.1 [OCH$_2$CH$_2$(CH$_2$)$_4$CH$_3$], 31.8 [O(CH$_2$)$_4$CH$_2$CH$_2$CH$_3$], 66.7 (C-4), 70.0 (C-1), 71.3 [OCH$_2$(CH$_2$)$_5$CH$_3$], 73.4 (OCH$_2$Ph), 75.4 (C-3), 79.5 (C-2), 109.0 [C(CH$_3$)$_2$], 127.5/128.3 (d, arom.), 138.3 (s, arom). FABMS (pos.) m/z: 373 [M+Na]$^+$.

Example 7

1-O-benzyl-2-O-tridecyl-3,4-O-isopropylidene-D-erythritol compound (16e) (Reaction Scheme 4)

By following substantially the same procedures as for the synthesis of the compound (16a), the compound (12) (800 mg, 3.17 mmol) was reacted with 1-bromotridecane (2.4 ml, 9.4 mmol) to give 1-O-benzyl-1-O-tridecyl-3,4-isopropylidene-D-erythritol compound (16e) (16e, 1.19 g, 86%).
[Chem. 26]

Compound (16e): colorless oily substance. $[\alpha]_D^{24}$ +10.7 (c=1.03, CHCl$_3$). IR (neat): 1456, 1377, 1369, 1256, 1213, 1099, 1076 cm$^{-1}$. $^1$H NMR (500 MHz, CDCl$_3$) δ: 0.88 [3H, t, J=6.9 Hz, O(CH$_2$)$_{12}$CH$_3$], 1.22-1.33 [20H, O(CH$_2$)$_2$(CH$_2$)$_{10}$CH$_3$], 1.35/1.40 [each 3H, s, C(CH$_3$)$_2$], 1.51-1.59 [2H, m, OCH$_2$CH$_2$(CH$_2$)$_{10}$CH$_3$], 3.45 (1H, ddd, J=6.6, 5.2, 3.2 Hz, H-2), 3.48/3.68 [each 1H, dd, J=9.2, 6.9 Hz, OCH$_2$(CH$_2$)$_{11}$CH$_3$], 3.54 (1H, dd, J=10.3, 5.2 Hz, H-1a), 3.69 (1H, dd, J=10.3, 3.2 Hz, H-1b), 3.93 (1H, dd, J=8.3, 6.3 Hz, H-4a), 4.05 (1H, dd, J=8.3, 6.6 Hz, H-4b), 4.15 (1H, ddd, J=6.6, 6.6, 6.3 Hz, H-3), 4.55/4.58 (each 1H, d, 12.1 Hz, OCH$_2$Ph), 7.25-7.36 (5H, m, arom.). $^{13}$C NMR (125 MHz, CDCl$_3$) δ: 14.1 [O(CH$_2$)$_{12}$CH$_3$], 22.7 [O(CH$_2$)$_{11}$CH$_2$CH$_3$], 25.4/26.6 [C(CH$_3$)$_2$], 26.1 [O(CH$_2$)$_{10}$CH$_2$CH$_2$CH$_3$], 29.3/29.5/29.61/29.64/29.7 [O(CH$_2$)$_3$(CH$_2$)$_7$(CH$_2$)$_2$CH$_3$], 30.1 [OCH$_2$CH$_2$(CH$_2$)$_{10}$CH$_3$], 31.9 [O(CH$_2$)$_2$CH$_2$(CH$_2$)$_9$CH$_3$], 66.7 (C-4), 70.0 (C-1), 71.3 [OCH$_2$(CH$_2$)$_{11}$CH$_3$], 73.4 (OCH$_2$Ph), 75.4 (C-3), 79.5 (C-2), 109.0 [C(CH$_3$)$_2$], 127.5/128.3 (d, arom.), 138.3 (s, arom.). FABMS m/z: 457 [M+Na]$^+$.

Example 8

1-O-benzyl-2-O-neopentyl-3,4-O-isopropylidene-D-erythritol compound (16f) (Reaction Scheme 4)

By following substantially the same procedures as for the synthesis of the compound (16a), the compound (12) (800 mg, 3.17 mmol) was reacted with 1-bromoneopentane to give the title compound (16d) (16f, 409 mg, 40%).
[Chem. 27]

Compound (16f): colorless oily substance. $[\alpha]^{23}_D$ +15.0 (c=1.05, CHCl$_3$). IR (neat): 1477, 1454, 1369, 1253, 1215, 1084, 1061, 1030 cm$^{-1}$. $^1$H NMR (500 MHz, CDCl$_3$) δ: 0.90 [9H, s, OCH$_2$C(CH$_3$)$_3$], 1.35/1.41 [each 3H, s, C(CH$_3$)$_2$], 3.13/3.35 [each 1H, d, J=8.3 Hz, OCH$_2$C(CH$_3$)$_3$], 3.46 (1H, ddd, J=6.3, 4.9, 3.2 Hz, H-2), 3.55 (1H, dd, J=10.6, 4.9 Hz, H-1a), 3.68 (1H, dd, J=10.6, 3.2 Hz, H-1b), 3.95 (1H, dd, J=8.3, 6.3 Hz, H-4a), 4.05 (1H, dd, J=8.3, 6.3 Hz, H-4b), 4.16 (1H, ddd, J=6.3, 6.3, 6.3 Hz, H-3), 4.56 (2H, s, CH$_2$Ph), 7.25-7.36 (5H, m, arom.). $^{13}$C NMR (125 MHz, CDCl$_3$) δ. 25.4/26.7 [C(CH$_3$)$_2$], 26.7 OCH$_2$C(CH$_3$)$_3$], 32.2 [OCH$_2$C(CH$_3$)$_3$], 66.7 (C-4), 70.0 (C-1), 73.4 (CH$_2$Ph), 75.6 (C-3), 80.0 (C-2), 81.5 [OCH$_2$C(CH$_3$)$_3$], 108.9 [C(CH$_3$)$_2$], 127.5/128.3 (d, arom.), 138.4 (s, arom.). FABMS (pos.) m/z: 345 [M+Na]$^+$.

Example 9

Process A: 2-O-benzyl-3,4-O-isopropylidene-1-O-(p-methoxybenzyl)-D-erythritol compound (16g) (Reaction Scheme 4)

By following substantially the same procedures as for the synthesis of the compound (16a), the compound (13) (300 mg, 1.19 mmol) was reacted with p-methoxybenzyl bromide to yield the title compound (16 g, 425 mg, 96%) as colorless oily substance.
[Chem. 28]

Compound (16g): colorless oily substance. $[\alpha]_D^{27}$+22.4 (c=1.16, CHCl$_3$). IR (neat): 1612, 1585, 1512, 1454, 1369, 1300, 1249, 1211, 1072, 1037 cm$^{-1}$. $^1$H NMR (500 MHz, CDCl$_3$) δ: 1.34/1.40 [each 3H, s, C(CH$_3$)$_2$], 3.57 (1H, dd, J=10.3, 5.2 Hz, H-1a), 3.64 (1H, ddd, J=6.3, 5.2, 3.2 Hz, H-2), 3.70 (1H, dd, J=10.3, 3.2 Hz, H-1b), 3.80 (3H, s, OCH$_3$), 3.91 (1H, dd, J=8.3, 6.3 Hz, H-4a), 4.04 (1H, dd, J=8.3, 6.3 Hz, H-4b), 4.17 (1H, ddd, J=6.3, 6.3, 6.3 Hz, H-3), 4.49 (2H, s-like, OCH$_2$Ar), 4.62/4.75 (each 1H, d, J=11.7 Hz, OCH$_2$Ar), 6.87 (2H, d-like, J=8.6 Hz, arom.), 7.23-7.35 (7H, m, arom.). $^{13}$C NMR (125 MHz, CDCl$_3$) δ: δ.25.3/26.6 [C(CH$_3$)$_2$], 55.3 (OCH$_3$), 66.6 (C-4), 70.0 (C-1), 72.9/73.1 (OCH$_2$Ar), 75.6 (C-3), 78.7 (C-2), 109.1 [C(CH$_3$)$_2$], 113.7/127.6/127.8/128.3/129.2 (d, arom.), 130.3/138.4/159.2 (s, arom.). FABMS (pos.) m/z: 395 [M+Na]$^+$.

Example 10

Process B: 2-O-benzyl-3,4-O-isopropylidene-1-O-(p-methoxybenzyl)-D-erythritol compound (16g) (Reaction Scheme 4)

By following substantially the same procedures as for the synthesis of the compound (16a), the compound (14) (300 mg, 1.06 mmol) was reacted with p-methoxybenzyl bromide to yield the title compound (16 g, 387 mg, 98%) as colorless oily substance. The resulting compound was confirmed to show the results of $^1$H NMR and $^{13}$C NMR identical to those of the compound obtained by Example 9.

Example 11

3,4-O-isopropylidene-2-O-(o-methylbenzyl)-1-O-(p-methoxybenzyl)-D-erythritol compound (16h) (Reaction Scheme 4)

By following substantially the same procedures as for the synthesis of the compound (16a), the compound (14) (150 mg, 0.53 mmol) was o-methylbenzylated yielding the title compound (16h, 176 mg, 86%) as colorless oily substance.
[Chem. 29]

Compound (16h): colorless oily substance. $[\alpha]^{25}_D$ +26.3 (c=1.02, CHCl$_3$). IR (neat): 1612, 1512, 1462, 1369, 1300, 1250, 1219, 1076, 1038 cm$^{-1}$. $^1$H NMR (700 MHz, CDCl$_3$) δ: 1.34/1.39 [each 3H, s, C(CH$_3$)$_2$], 2.31 (3H, s, C$_6$H$_4$CH$_3$), 3.57 (1H, dd, J=10.4, 5.4, H-1a), 3.64 (1H, ddd, J=6.4, 5.4, 3.0, H-2), 3.72 (1H, dd, J=10.4, 3.0, H-1b), 3.80 (3H, s, OCH$_3$), 3.88 (1H, dd, J=8.4, 6.4, H-4a), 4.03 (1H, dd, J=8.4, 6.4, H-4b), 4.15 (1H, ddd, J=6.4, 6.4, 6.4, H-3), 4.48/4.50 (each 1H, d, J=11.8, OCH$_2$Ar), 4.59/4.77 (each 1H, d, J=11.6, OCH$_2$Ar), 6.87/7.26 (each 2H, d-like, J=8.6, arom.), 7.15 (1H, br J=ca. 7.8, arom.), 7.16 (1H, br td-like, J=ca. 7.8, 1.5, arom), 7.19 (1H, td-like, J=7.8, 1.5, arom.), 7.30 (1H, br dd-like, J=7.8, 1.5, arom.). $^{13}$C NMR (175 MHz, CDCl$_3$) δ: 18.8 (C$_6$H$_4$CH$_3$), 25.3/26.6 [C(CH$_3$)$_2$], 55.3 (OCH$_3$), 66.7 (C-4), 70.2 (C-1), 71.2/73.1 (OCH$_2$Ar), 75.5 (C-3), 78.8 (C-2), 109.1 [(CH$_3$)$_2$C], 113.7/125.7/127.8/128.8/129.2/130.2 (d, arom.), 130.3/136.3/136.6/159.2 (s, arom.). FABMS (pos.) m/z: 409 [M+Na]$^+$.

Example 12

3,4-O-isopropylidene-2-O-(m-methylbenzyl)-1-O-(p-methoxybenzyl)-D-erythritol compound (16i) (Reaction Scheme 4)

By following substantially the same procedures as for the synthesis of the compound (14) (150 mg, 0.53 mmol) was m-methylbenzylated yielding the title compound (16i, 200 mg, 98%) as colorless oily substance.

[Chem. 30]

Compound (16i): colorless oily substance., [α]$^{25}_D$ +19.9 (c=2.26, CHCl$_3$). IR (neat): 1612, 1512, 1458, 1369, 1300, 1250, 1157, 1076, 1038 cm$^{-1}$. $^1$H NMR (700 MHz, CDCl$_3$) δ: 1.34/1.40 [each 3H, s, C(CH$_3$)$_2$], 2.33 (3H, s, C$_6$H$_4$CH$_3$), 3.57 (1H, dd, J=10.4, 5.5, H-1a), 3.63 (1H, ddd, J=6.4, 5.5, 3.2, H-2), 3.70 (1H, dd, J=10.4, 3.2, H-1b), 3.80 (3H, s, OCH$_3$), 3.91 (1H, dd, J=8.4, 6.2, H-4a), 4.04 (1H, dd, J=8.4, 6.4, H-4b), 4.16 (1H, ddd, J=6.4, 6.4, 6.2, H-3), 4.49 (2H, s-like, OCH$_2$Ar), 4.58/4.71 (each 1H, d, J=11.6, OCH$_2$Ar), 6.87/7.26 (each 2H, d-like, J=8.6, arom.), 7.08/7.11 (each 1H, br, d, J=7.6 Hz, arom), 7.13 (1H, br s-like, arom.), 7.21 (1H, t, J=7.6, arom.). $^{13}$C NMR (175 MHz, CDCl$_3$) δ: 21.4 (C$_6$H$_4$CH$_3$), 25.3/26.6 [C(CH$_3$)$_2$], 55.2 (OCH$_3$), 66.6 (C-4), 70.0 (C-1), 72.9/73.1 (OCH$_2$Ar), 75.6 (C-3), 78.7 (C-2), 109.1 [C(CH$_3$)$_2$], 113.7/124.9/128.2/128.3/128.6/129.2 (d, arom.), 130.3/137.9/138.3/159.1 (s, arom.). FABMS (pos.) m/z: 409 [M+Na]$^+$.

Example 13

3,4-O-isopropylidene-2-O-(p-methylbenzyl)-1-O-(p-methoxybenzyl)-D-erythritol compound (16j) (Reaction Scheme 4)

By following substantially the same procedures as for the synthesis of the compound (16a), the compound (14) (150 mg, 0.53 mmol) was p-methylbenzylated yielding the title compound (16j, 200 mg, 98%) as colorless oily substance.
[Chem. 31]

Compound (16j): colorless oily substance. [c]$^{25}_D$ +14.5 (c=1.91, CHCl$_3$). IR (neat): 1612, 1512, 1458, 1369, 1300, 1250, 1076, 1038 cm$^{-1}$. $^1$H NMR (700 MHz, CDCl$_3$) δ: 1.34/1.39 [each 3H, s, C(CH$_3$)$_2$], 2.33 (3H, s, C$_6$H$_4$CH$_3$), 3.56 (1H, dd, J=10.4, 5.3, H-1a), 3.62 (1H, ddd, J=6.4, 5.3, 3.2, H-2), 3.69 (1H, dd, J=10.4, 3.2, H-1b), 3.80 (3H, s, OCH$_3$), 3.89 (1H, dd, J=8.3, 6.2, H-4a), 4.03 (1H, dd, J=8.3, 6.4, H-4b), 4.15 (1H, ddd, J=6.4, 6.4, 6.2, H-3), 4.48/4.50 (each 1H, d, J=11.8, OCH$_2$Ar), 4.57/4.70 (each 1H, d, J=11.4, OCH$_2$Ar), 6.87/7.26 (each 2H, d-like, J=8.6, arom.), 7.13/7.20 (each 2H, br d-like, J=8.0, arom.). $^{13}$C NMR (175 MHz, CDCl$_3$) δ: 21.2 (C$_6$H$_4$CH$_3$), 25.3/26.6 [C(CH$_3$)$_2$], 55.2 (OCH$_3$), 66.6 (C-4), 70.0 (C-1), 72.7/73.1 (ArCH$_2$), 75.6 (C-3), 78.5 (C-2), 109.1 [C(CH$_3$)$_2$], 113.7/128.0/129.0/129.2 (d, 130.3/135.3/137.3/159.1 (s, arom.). FABMS (pos.) m/z: 409 [M+Na]$^+$.

Example 14

3,4-O-isopropylidene-2-O-(o-chlorobenzyl)-1-O-(p-methoxybenzyl)-D-erythritol compound (16k) (Reaction Scheme 4)

By following substantially the same procedures as for the synthesis of the compound (16a), the compound (14) (300 mg, 1.06=01) was o-chlorobenzylated yielding the title compound (16k, 397 mg, 92%) as colorless oily substance.
[Chem. 32]

Compound (16k): colorless oily substance. [α]$^{24}_D$ +26.5 (c=0.62, CHCl$_3$). IR (neat): 1612, 1512, 1458, 1442, 1300, 1250, 1211, 1084, 1037 cm$^{-1}$. $^1$H NMR (500 MHz, CDCl$_3$) δ: 1.35/1.40 [each 3H, s, C(CH$_3$)$_2$], 3.60 (1H, dd, J=10.3, 5.2, H-1a), 3.69 (1H, ddd, J=6.3, 5.2, 2.9, 14-2), 3.75 (1H, dd, J=10.3, 2.9, H-1b), 3.80 (3H, s, OCH$_3$), 3.96 (1H, dd, J=8.3, 6.3, H-4a), 4.06 (1H, dd, J=8.3, 6.3, H-4b), 4.19 (1H, ddd, J=6.3, 6.3, 6.3, H-3), 4.50 (2H, s-like, OCH$_2$Ar), 4.71/4.84 (each 1H, d, J=12.6, OCH$_2$Ar), 6.87/7.26 (each 2H, d-like, J=8.6, arom.), 7.21 (1H, td, J=7.2, 2.0, arom.), 7.24 (1H, td, J=7.2, 2.0, arom.), 7.34 (1H, dd, J=7.2, 1.5, arom.), 7.48 (1H, dd, J=7.2, 2.0, arom.). $^{13}$C NMR (125 MHz, CDCl$_3$) δ: 25.3/26.6 [C(CH$_3$)$_2$], 55.3 (OCH$_3$), 66.6 (C-4), 69.9 (C-1), 66.9/73.1 (OCH$_2$Ar), 75.5 (C-3), 79.4 (C-2), 109.1 [C(CH$_3$)$_2$], 113.8/126.7/128.7/129.18/129.22/129.3 (d, arom.), 130.3/132.8/136.2/159.2 (s, arom.). FABMS (pos.) m/z: 429 [M+Na]$^+$.

Example 15

3,4-O-isopropylidene-2-O-(m-chlorobenzyl)-1-O-(p-methoxybenzyl)-D-erythritol compound (161) (Reaction Scheme 4)

By following substantially the same procedures as for the synthesis of the compound (16a), the compound (14) (400 mg, 1.42 mmol) was m-chlorobenzylated yielding the title compound (161, 518 mg, 90%) as colorless oily substance.
[Chem. 33]

Compound (161): colorless oily substance. [α]$_D^{23}$+18.5 (c=0.88, CHCl$_3$). IR (neat): 1612, 1581, 1512, 1462, 1369, 1300, 1250, 1211, 1076, 1038 cm$^{-1}$. $^1$H NMR (500 MHz, CDCl$_3$) δ: 1.35/1.41 [each 3H, s, C(CH$_3$)$_2$], 3.56, (1H, dd, J=10.3, 5.5, H-1a), 3.65 (1H, ddd, J=6.3, 5.5, 3.2, H-2), 3.69 (1H, dd, J=10.3, 3.2, H-1b), 3.81 (3H, s, OCH$_3$), 3.92 (1H, dd, J=8.3, 6.3, H-4a), 4.05 (1H, dd, J=8.3, 6.6, H-4b), 4.16 (ddd, J=6.6, 6.3, 6.3, H-3), 4.48 (2H, s-like, OCH$_2$Ar), 4.60/4.72 (each 1H, d, J=12.1, OCH$_2$Ar), 6.88 (2H, d-like, J=8.6, arom.), 7.15-7.27 (5H, m, arom.), 7.33 (1H, br s-like, arom.). $^{13}$C NMR (125 MHz, CDCl$_3$) δ: 25.3/26.6 [C(CH$_3$)$_2$], 55.3 (OCH$_3$), 66.5 (C-4), 70.0 (C-1), 72.1/73.1 (OCH$_2$Ar), 75.6 (C-3), 79.0 (C-2), 109.1 [C(CH$_3$)$_2$], 113.8/125.6/127.66/127.72/129.3/129.6 (d. arom.), 130.2/134.2/140.6/159.2 (s, arom.). FABMS (pos.) m/z: 429 [M+Na]$^+$.

Example 16

3,4-O-isopropylidene-2-O-(p-chlorobenzyl)-1-O-(p-methoxybenzyl)-D-erythritol compound (16m) (Reaction Scheme 4)

By following substantially the same procedures as for the synthesis of the compound (16a), the compound (14) (257 mg, 0.91 mmol) was p-chlorobenzylated yielding the title compound (16m, 336 mg, 91%) as colorless oily substance.
[Chem. 34]

Compound (16m): colorless oily substance. [α]$_D^{23}$ +13.9 (c=1.32, CHCl$_3$). IR (neat): 1612, 1512, 1493, 1458, 1370, 1300, 1246, 1211, 1080, 1037 cm$^{-1}$. NMR (500 MHz, CDCl$_3$) δ: 1.34/1.40 [each 3H, s, (CH$_3$)$_2$C], 3.55 (1H, dd, J=10.3, 5.2, H-1a), 3.63 (1H, ddd, J=6.3, 5.2, 3.2, H-2), 3.68 (1H, dd, J=10.3, 3.2, H-1b), 3.81 (3H, s, OCH$_3$), 3.91 (1H, dd, J=8.3, 6.3, H-4a), 4.04 (1H, dd, J=8.3, 6.3, H-4b), 4.15 (1H, ddd, J=6.3, 6.3, 6.3, H-3), 4.47 (2H, s-like, OCH$_2$Ar), 4.59/4.70 (each 1H, d, J=12.0, OCH$_2$Ar), 6.87 (2H, d-like, J=8.6, arom.), 7.24 (4H, br d-like, J=ca. 8.6, arom.), 7.29 (2H, d-like, J=8.6, arom.). $^{13}$C NMR (125 MHz, CDCl$_3$) δ: 25.3/26.6 [(CH$_3$)$_2$C], 55.3 (OCH$_3$), 66.5 (C-4), 70.0 (C-1), 72.1/73.1 (OCH$_2$Ar), 75.6 (C-3), 78.8 (C-2), 109.1 [(CH$_3$)$_2$C], 113.8/128.4/129.1/129.3 (d, arom.), 130.2/133.3/137.0/159.2 (s, arom.). FABMS (pos.) m/z: 429 [M+Na]$^+$.

Example 17

3,4-O-isopropylidene-2-O-(o-bromobenzyl)-1-O-(p-methoxybenzyl)-D-erythritol compound (16n) (Reaction Scheme 4)

By following substantially the same procedures as for the synthesis of the compound (16a), the compound (14) (282 mg, 1.0 mmol) was o-bromobenzylated yielding the title compound (16n, 432 mg, 96%) as colorless oily substance.
[Chem. 35]

Compound (16n): colorless oily substance. $[\alpha]^{25}_D$ +32.3 (c=0.57, CHCl$_3$). IR (neat): 1612, 1516, 1443, 1369, 1339, 1300, 1250, 1211, 1173, 1080, 1038 cm$^{-1}$. $^1$H NMR (500 MHz, CDCl$_3$) δ: 1.35/1.40 [each 3H, s, C(CH$_3$)$_2$], 3.61 (1H, dd, J=10.3, 5.2 Hz, H-1a), 3.70 (1H, ddd, J=6.3, 5.2, 3.2, H-2), 3.75 (1H, dd, J=10.3, 3.2, H-1b), 3.80 (3H, s, OCH$_3$), 3.98 (1H, dd, J=8.3, 6.0, H-4a), 4.07 (1H, dd, J=8.3, 6.3, H-4b), 4.20 (1H, ddd, J=6.3, 6.3, 6.0, H-3), 4.50 (2H, s-like, OCH$_2$Ar), 4.68/4.82 (each 1H, d, J=12.6, OCH$_2$Ar), 6.86 (2H, d-like, J=8.6, arom.) 7.14 (1H, td, J=7.7, 1.5, arom.), 7.26 (2H, d-like, J=8.6, arom.), 7.29 (1H, td, J=7.7, 0.9, arom.), 7.48 (1H, dd, J=7.7, 1.5 Hz, arom.), 7.52 (1H, dd, J=7.7, 0.9, arom.). $^{13}$C NMR (125 MHz, CDCl$_3$) δ: 25.3/26.6 [C(CH$_3$)$_2$], 55.3 (OCH$_3$), 66.6 (C-4), 69.9 (C-1), 72.1/73.1 (CH$_2$Ph), 75.5 (C-3), 79.4 (C-2), 109.1 [C(CH$_3$)$_2$], 113.7/127.3/128.9/129.2/129.4/132.4 (d, arom.), 122.6/130.2/137.8/159.2 (s, arom). FABMS (pos.) m/z: 473 and 475 [M+Na]$^+$.

Example 18

3,4-O-isopropylidene-2-O-(m-bromobenzyl)-1-O-(p-methoxybenzyl)-D-erythritol compound (16o) (Reaction Scheme 4)

By following substantially the same procedures as for the synthesis of the compound (16a), the compound (14) (275 mg, 0.98 mmol) was m-bromobenzylated yielding the title compound (16o, 430 mg, 98%) as colorless oily substance.
[Chem. 36]

Compound (16o): colorless oily substance. $[\alpha]^{24}_D$ +7.2 (c=0.25, CHCl$_3$). IR (neat): 1612, 1585, 1512, 1462, 1369, 1300, 1250, 1215, 1157, 1065, 1038 cm$^{-1}$. $^1$H NMR (500 MHz, CDCl$_3$) δ: 1.35/1.41 [each 3H, s, C(CH$_3$)$_2$], 3.55 (1H, dd, J=10.3, 5.5, H-1a), 3.64 (1H, ddd, J=6.0, 5.5, 3.2, H-2), 3.68 (1H, dd, J=10.3, 3.2, H-1b) 3.81 (3H, s, OCH$_3$), 3.92 (2H, dd, J=8.3, 6.3, H-4a), 4.05 (1H, dd, J=8.3, 6.3, H-4b), 4.16 (1H, ddd, J=6.3, 6.3, 6.0, H-3), 4.48 (2H, s-like, OCH$_2$Ar), 4.59/4.71 (each 1H, d, J=12.0, OCH$_2$Ar), 6.88/7.25 (each 2H, d-like, J=8.6, arom.), 7.19 (1H, t, J=7.8, arom.), 7.23 (1H, br, d-like, J=7.8, arom.), 7.40 (1H, dt-like, J=7.8, 1.5, arom.), 7.49 (1H, t-like, J=1.5, arom.). $^{13}$C NMR (125 MHz, CDCl$_3$) δ: 25.3/26.6 [C(CH$_3$)$_2$], 55.3 (OCH$_3$), 66.5 (C-4), 70.0 (C-1), 72.0/73.1 (OCH$_2$Ar), 75.6 (C-3), 79.0 (C-2), 109.1 [C(CH$_3$)$_2$], 113.8/126.1/129.3/129.9/130.60/130.63 (d, arom.), 122.4/130.1/140.9/159.2 (s, arom.). FABMS (pos.) m/z: 473 and 475 [M+Na]$^+$.

Example 19

3,4-O-isopropylidene-2-O-(p-bromobenzyl)-1-O-(p-methoxybenzyl)-D-erythritol compound (16p) (Reaction Scheme 4)

By following substantially the same procedures as for the synthesis of the compound (16a), the compound (14) (314 mg, 1.11 mmol) was p-bromobenzylated yielding the title compound (16p, 492 mg, 98%) as colorless oily substance.
[Chem. 37]

Compound (16p): colorless oily substance. $[\alpha]^{25}_D$ +15.2 (c=0.82, CHCl$_3$). IR (neat): 1612, 1589, 1512, 1489, 1454, 1369, 1300, 1250, 1211, 1076, 1038, 1011 cm$^{-1}$. $^1$H NMR (500 MHz, CDCl$_3$) δ: 1.34/1.40 [each 3H, s, C(CH$_3$)$_2$], 3.54 (1H, dd, J=10.4, 5.2, H-1a), 3.64 (1H, ddd, J=6.3, 5.2, 3.2, H-2), 3.67 (1H, dd, J=10.4, 3.2, H-1b), 3.81 (3H, s, OCH$_3$), 3.91 (1H, dd, J=8.3, 6.3, H-4a), 4.04 (1H, dd, J=8.3, 6.3, H-4b), 4.15 (1H, ddd, J=6.3, 6.3, 6.3, H-3), 4.46/4.49 (each 1H, J=11.8, OCH$_2$Ar), 4.58/4.69 (each 1H, d, J=12.1, OCH$_2$Ar), 6.87/7.19/7.24/7.44 (each 2H, d-like, J=ca. 8.6, arom.). $^{13}$C NMR (125 MHz, CDCl$_3$) δ: 25.3/26.6 [C(CH$_3$)$_2$], 55.3 (OCH$_3$), 66.5 (C-4), 70.0 (C-1), 72.1/73.1 (OCH$_2$Ar), 75.6 (C-3), 78.8 (C-2), 109.1 [C(CH$_3$)$_2$], 113.8/129.3/129.4/131.4 (d, arom.), 121.4/130.2/137.5/159.2 (s, arom.). FABMS (pos.) m/z: 473 and 475 [M+Na]$^+$.

Example 20

3,4-O-isopropylidene-1-O-(p-methoxybenzyl)-2-O-(o-trifluorobenzyl)-D-erythritol compound (16q) (Reaction Scheme 4)

By following substantially the same procedures as for the synthesis of the compound (16a), the compound (14) (400 mg, 1.42 mmol) was o-trifluoromethylbenzylated yielding the title compound (16q, 600 mg, 96%) as colorless oily substance.
[Chem. 38]

Compound (16q): colorless oily substance. $[\alpha]^{22}_D$ +15.2 (c=1.91, CHCl$_3$). IR (neat): 1651, 1616, 1589, 1539, 1516, 1454, 1373, 1315, 1257, 1211, 1161, 1107, 1072, 1037 cm$^{-1}$. $^1$H NMR (500 MHz, CDCl$_3$) δ: 1.35/1.41 [each 3H, s, (CH$_3$)$_2$C], 3.60 (1H, dd-like, J=9.0, 6.0, H-1a), 3.72 (1H, ddd, J=6.0, 6.0, 2.9, H-2), 3.73 (1H, dd, J=9.0, 2.9, H-1b), 3.80 (3H, s, OCH$_3$), 3.97 (1H, dd, J=8.3, 6.3, H-4a), 4.06 (1H, dd, J=8.3, 6.6, H-4b), 4.21 (1H, ddd, J=6.6, 6.3, 6.0, H-3), 4.49 (1H, s-like, OCH$_2$Ar), 4.82/4.96 (each 1H, d, J=12.9, CH$_2$Ar), 6.86/7.25 (each 2H, d, J=8.9, arom.), 7.36/7.52 (each 1H, br d, J=7.5, arom.), 7.62/7.71 (each 1H, d, J=7.7, arom.). $^{13}$C NMR (125 MHz, CDCl$_3$) δ. 25.3/26.5 [(CH$_3$)$_2$C], 55.2 (OCH$_3$), 66.4 (C-4), 68.5 [q, J=2.3 Hz, CH$_2$C$_6$H$_4$-(o-CF$_3$)], 68.7 (C-1), 73.1 [CH$_2$C$_6$H$_4$-(p-OCH$_3$)], 75.6 (C-3), 79.5 (C-2), 109.1 [(CH$_3$)$_2$C], 113.7/127.22/129.1/129.2/131.8 (d, arom), 124.3 [q, J=273 Hz, CF$_3$], 125.5 [q, J=6.0 Hz, C$_{ortho}$—CF$_3$,], 127.219 [q, J=31.7 Hz, C$_{ipso}$—CF$_3$], 130.2/137.3/159.2 (d, arom.). FABMS (pos.) m/z: 463 [M+Na]$^+$.

Example 21

3,4-O-isopropylidene-1-O-(p-methoxybenzyl)-2-O-(m-trifluorobenzyl)-D-erythritol compound (16r) (Reaction Scheme 4)

By following substantially the same procedures as for the synthesis of the compound (16a), the compound (14) (275 mg, 0.97 mmol) was m-trifluoromethylbenzylated yielding the title compound (16r, 412 mg, 96%) as colorless oily substance.
[Chem. 39]

Compound (16r): colorless oily substance. $[\alpha]^{25}_D$ +12.5 (c=0.57, CHCl$_3$). IR (neat): 1612, 1589, 1512, 1462, 1369, 1330, 1249, 1203, 1165, 1126, 1072, 1038 cm$^{-1}$. $^1$H NMR (500 MHz, CDCl$_3$) δ: 1.35/1.41 [each 3H, s, C(CH$_3$)$_2$], 3.57 (1H, dd-like, J=10.0, 5.2, H-1a), 3.67 (1H, ddd, J=6.3, 5.2, 2.9, H-2), 3.70 (1H, dd, J=10.0, 2.9, H-1b), 3.81 (3H, s, OCH$_3$), 3.93 (1H, dd, J=8.3, 6.3, H-4a), 4.05 (1H, dd, J=8.3, 6.3, H-4b), 4.17 (1H, ddd, J=6.3, 6.3, 6.3, H-3), 4.48 (2H, s-like, OCH$_2$Ar), 4.68/4.80 (each 1H, d, 12.0, OCH$_2$Ar), 6.87 (2H, d-like, J=8.6, arom.), 7.25 (2H, d, J=8.6, arom.), 7.44 (1H, t, J=7.8, arom.), 7.49 (1H, br d, J=7.8, arom.), 7.53 (1H, br d, J=7.8, arom.), 7.59 (1H, br s, arom.). $^{13}$C NMR (125 MHz, CDCl$_3$) δ: 25.3/26.5 [C(CH$_3$)$_2$], 55.3 (OCH$_3$), 66.4

(C-4), 70.0 (C-1), 72.1/73.1 (OCH$_2$Ar), 75.6 (C-3), 79.1 (C-2), 109.1 [C(CH$_3$)$_2$], 113.8/128.7/129.3/130.8 [d, arom.], 124.1 (q, J=271 Hz, CF$_3$), 124.26/124.32 [each q, J=3.6 Hz, C$_{ortho}$—CF$_3$,], 130.1/139.6/159.2 [s, arom.], 130.6 [q, J=31.0 Hz, C$_{ipso}$—CF$_3$]. FABMS (pos.) m/z: 463 [M+Na]$^+$.

Example 22

3,4-O-isopropylidene-1-O-(p-methoxybenzyl)-2-O-(p-trifluoromethylbenzyl)-D-erythritol compound (16s) (Reaction Scheme 4)

By following substantially the same procedures as for the synthesis of the compound (16a), the compound (14) (200 mg, 0.71 mmol) was p-trifluoromethylbenzylated yielding the title compound (16s, 302 mg, 97%) as colorless oily substance.
[Chem. 40]
Compound (16s): colorless oily substance. [α]$_D^{24}$ +17.5 (c=1.00, CHCl$_3$). IR (neat): 1612, 1516, 1462, 1369, 1327, 1249, 1211, 1165, 1126, 1064 cm$^{-1}$. $^1$H NMR (500 MHz, CDCl$_3$) δ: 1.35/1.40 [each 3H, s, C(CH$_3$)$_2$], 3.57 (1H, dd-like, J=10.0, 5.2, H-1a), 3.67 (1H, ddd, J=6.3, 5.2, 3.2, H-2), 3.69 (1H, dd, J=10.0, 3.2, H-1b), 3.80 (3H, s, OCH$_3$), 3.94 (1H, dd, J=8.3, 6.3, H-4a), 4.05 (1H, dd, J=8.3, 6.3, H-4b), 4.17 (1H, ddd, J=6.3, 6.3, 6.3, H-3), 4.47/4.49 (each 1H, d, J=12.0, OCH$_2$Ar), 4.69/4.80 (each 1H, d, J=12.3, OCH$_2$Ar), 6.75/6.89 (each 2H, d-like, J=8.9, arom.), 7.43/7.57 (each 1H, br d-like, J=8.0, arom.). $^{13}$C NMR (125 MHz, CDCl$_3$) δ: 25.2/26.6 [C(CH$_3$)$_2$], 55.3 (OCH$_3$), 66.4 (C-4), 70.1 (C-1), 72.1/73.1 (OCH$_2$Ar), 75.6 (C-3), 79.2 (C-2), 109.2 [C(CH$_3$)$_2$], 113.8/127.6/129.3 (d, arom.), 124.1 (q, J=271, CF$_3$), 125.2 [q, J=3.6, C$_{ortho}$—CF$_3$], 129.7 [q, J=32.2, C$_{ipso}$—CF$_3$], 130.1/142.5/159.3 (s, arom.). FABMS (pos.) m/z: 463 [M+Na]$^+$.

Example 23

3,4-O-isopropylidene-1-O-(p-methoxybenzyl)-2-O-(o-nitrobenzyl)-D-erythritol compound (16t) (Reaction Scheme 4)

A mixture of the compound (14) (450 mg, 1.59 mmol), sodium hydroxide (750 mg, 18.8 mmol), water (4 ml) and dichloromethane (6 ml) was ultrasonicated at 25° C. for 30 minutes and then stirred under argon atmosphere for 24 hours at room temperature after the addition of o-nitrobenzyl bromide (1.72 g, 0.8 mmol) and n-BuN$^+$I$^-$ (589 mg, 1.59 mmol). The resulting reaction mixture was then diluted with 5 ml of water and extracted with dichloromethane. The extract was washed with saline water and concentrated to give 2.17 g of a pale yellow oily substance which was then purified by column chromatograph using chloroform yielding the title compound (16t, 585 mg, 88%) as pale yellow oily substance.
[Chem. 41]
Compound (16t): pale yellow oily substance. [α]$^{24}_D$ +12.5 (c=1.52, CHCl$_3$). IR (neat): 1612, 1585, 1531, 1516, 1465, 1454, 1369, 1346, 1303, 1249, 1099, 1076 cm$^{-1}$. $^1$H NMR (500 MHz, CDCl$_3$) δ: 1.35/1.40 [each 3H, s, C(CH$_3$)$_2$)], 3.60 (1H, dd, J=10.3, 5.2, H-1a), 3.72 (1H, dd, J=10.3, 3.2, H-1b), 3.75 (1H, ddd, J=6.3, 5.2, 3.2, H-2), 3.80 (3H, s. OCH$_3$), 3.98 (1H, dd, J=8.3, 6.3, H-4a), 4.07 (1H, dd, J=8.3, 6.3, H-4b), 4.22 (1H, ddd, J=6.3, 6.3, 6.3, H-3), 4.47 (2H, s-like, OCH$_2$Ar), 5.02/5.11 (each 1H, d-like, J=14.9, OCH$_2$Ar), 6.85/7.23 (each 2H, d-like, J=8.6, arom.), 7.42 (1H, ddd, J=8.0, 7.8, 1.0, arom.), 7.61 (1H, ddd, J=8.0, 7.8, 1.2, arom.), 7.83 (1H, dd, J=8.0, 1.0, arom.), 8.05 (1H, dd, J=8.0, 1.2, arom.). $^{13}$C NMR (125 MHz, CDCl$_3$) δ: 25.2/26.5 [C(CH$_3$)$_2$], 55.3 (OCH$_3$), 66.3 (C-4), 69.3 (C-1), 69.6/73.1 (OCH$_2$Ar), 75.6 (C-3), 79.8 (C-2), 109.1 [C(CH$_3$)$_2$], 113.8/124.5/127.8/129.0/129.2/133.5 (d, arom.), 130.1/135.3/147.1/159.2 (s, arom.). FABMS (pos.) m/z: 440 [M+Na]$^+$.

Example 24

3,4-O-isopropylidene-1-O-(p-methoxybenzyl)-2-O-(m-nitrobenzyl)-D-erythritol compound (16u) (Reaction Scheme 4)

By following substantially the same procedures as for the synthesis of the compound (16t), the compound (14) (500 mg, 1.77 mmol) was m-nitrobenzylated yielding the title compound (16u, 640 mg, 87%) as pale yellow oily substance.
[Chem. 42]
Compound (16u): pale yellow oily substance. [α]$^{25}_D$ +11.8 (c=1.20, CHCl$_3$). IR (neat): 1612, 1585, 1535, 1516, 1454, 1350, 1303, 1249, 1211, 1076, 1037 cm$^{-1}$ $^1$H NMR (500 MHz, CDCl$_3$) δ: 1.35/1.41 [each 3H, s. C(CH$_3$)$_2$], 3.57 (1H, dd, J=10.9, 6.3, H-1a), 3.70 (2H, dd, J=10.9, 3.2, H-1b and ddd, J=6.3, 6.3, 3.2, H-2), 3.80 (3H, s. OCH$_3$), 3.94 (1H, dd, J=8.3, 6.3, H-4a), 4.06 (1H, dd, J=8.3, 6.3, H-4b), 4.18 (1H, ddd, J=6.3, 6.3, 6.3, H-3), 4.48 (2H, s-like, OCH$_2$Ar), 4.73/4.84 (each 1H, d, J=12.3, OCH$_2$Ar), 6.87/7.24 (each 2H, d-like, J=8.6, arom.), 7.49 (1H, t, J=8.0, arom.), 7.64, (1H, br d-like, J=ca. 8.0, arom.), 8.13 (1H, br dd-like, J=ca. 8.0, 1.5, arom.), 8.20 (1H, br t-like, J=ca. 1.5, arom.). $^{13}$C NMR (125 MHz, CDCl$_3$) δ: 25.2/26.6 [C(CH$_3$)$_2$], 55.3 (OCH$_3$), 66.3 (C-4), 70.0 (C-1), 71.6/73.2 (OCH$_2$Ar), 75.6 (C-3), 79.3 (C-2), 109.2 [C(CH$_3$)$_2$], 113.8/122.3/122.5/129.2/129.3/133.3 (d, arom.), 130.0/140.8/148.3/159.2 (s, arom.). FABMS (pos.) m/z: 440 [M+Na]$^+$.

Example 25

3,4-O-isopropylidene-1-O-(p-methoxybenzyl)-2-O-(p-nitrobenzyl)-D-erythritol compound (16v) (Reaction Scheme 4)

By following substantially the same procedures as for the synthesis of the compound (16t), the compound (14) (300 mg, 1.06 mmol) was p-nitrobenzylated yielding the title compound (16v, 386 mg, 87%) as pale yellow oily substance.
[Chem. 43]
Compound (16v): pale yellow oily substance. [α]$_D^{24}$ +3.4 (c=1.25, CHCl$_3$). IR (neat): 1608, 1516, 1346, 1250, 1084, 1033 cm$^{-1}$. $^1$H NMR (500 MHz, CDCl$_3$) δ: 1.35/1.41 [each 3H, s, C(CH$_3$)$_2$], 3.57 (1H, dd, J=11.2, 6.6, H-1a), 3.69 (1H, dd, J=11.2, 3.2, H-1b), 3.70 (1H, ddd, J=6.6, 6.3, 3.2, H-2), 3.81 (3H, s, OCH$_3$), 3.95 (1H, dd, J=8.3, 6.3, H-4a), 4.06 (1H, dd, J=8.3, 6.6, H-4b), 4.18 (1H, ddd, J=6.6, 6.3, 6.3, H-3), 4.49 (2H, s-like, OCH$_2$Ar), 4.75/4.85 (each 1H, d, J=13.2, OCH$_2$Ar), 6.87/7.23 (each 1H, d-like, J=8.9, arom.), 7.47/8.17 (each 1H, d-like, J=8.6, arom.). $^{13}$C NMR (125 MHz, CDCl$_3$) δ: 25.2/26.6 [C(CH$_3$)$_2$], 55.3 (OCH$_3$), 66.2 (C-4), 70.1 (C-1), 71.7/73.2 (OCH$_2$Ar), 75.6 (C-3), 79.5 (C-2), 109.2 [C(CH$_3$)$_2$], 113.8/123.5/127.7/129.3 (d, arom.), 130.0/146.2/147.3/159.3 (s, arom.). FABMS (pos.) m/z: 440 [M+Na]$^+$.

Example 26

3,4-O-isopropyldene-1-O-(p-methoxybenzyl)-2-O-(p-(p-methoxybenzyloxymethyl)benzyl)-D-erythritol compound (16w) (Reaction Scheme 4)

By following substantially the same procedures as for the synthesis of the compound (16t), the compound (14) (300 mg, 1.06 mmol) was benzylated yielding the title compound (16w, 521 mg, 94%) as colorless oily substance.
[Chem. 44]

Compound (16w): colorless oil, $[\alpha]^{24}_D$ +18.4 (c=1.18, CHCl$_3$). IR (neat): 1612, 1558, 1512, 1462, 1369, 1300, 1246, 1215, 1173, 1076, 1034 cm$^{-1}$. $^1$H NMR (500 MHz, CDCl$_3$) δ: 1.34/1.40 [each 3H, s, C(CH$_3$)$_2$], 3.56 (1H, dd, J=10.3, 5.2, H-1a), 3.63 (1H, ddd, J=6.3, 5.2, 3.2, H-2), 3.69 (1H, dd, J=10.3, 3.2, H-1b), 3.80/3.81 (each 3H, s, OCH$_3$), 3.91 (1H, dd, J=8.4, 6.3, H-4a), 4.04 (1H, dd, J=8.4, 6.6, H-4b), 4.16 (1H, ddd, J=6.6, 6.3, 6.3, H-3), 4.47/4.49/4.52 (each 2H, s-like, OCH$_2$Ar), 4.62/4.74 (each 1H, d-like, J=11.8, ArCH$_2$), 6.85-6.91 (4H, m, arom.), 7.24-7.34 (8H, m, arom.). $^{13}$C NMR (125 MHz, CDCl$_3$) δ: 25.3/26.6 [C(CH$_3$)$_2$], 55.3 (OCH$_3$), 66.6 (C-4), 70.0 (C-1), 71.5/71.7/72.6/73.1 (OCH$_2$Ar), 75.6 (C-3), 78.7 (C-2), 109.1 [C(CH$_3$)$_2$], 113.7/113.8/127.8/127.9/129.2/129.4 (d, arom.), 130.30/130.31/137.76/137.80/159.16/159.19 (s, arom.). FABMS (pos.) m/z: 545 [M+Na]$^+$.

Example 27

3,4-O-isopropyl idene-1-O-(p-methoxybenzyl)-2-O-(naphthalen-1-yl)methyl)-D-erythritol compound (16x) (Reaction Scheme 4)

By following substantially the same procedures as for the synthesis of the compound (16a), the compound (14) (200 mg, 0.71 mmol) was naphthalen-1-ylmethylated yielding the title compound (16x, 291 mg, 97%) as colorless oily substance.
[Chem. 45]

Compound (16×): colorless oily substance. $[\alpha]^{23}_D$ +33.5 (c=0.60, CHCl$_3$). IR (neat): 3055, 2931, 2870, 1612, 1585, 1512, 1462, 1369, 1303, 1249, 1172, 1087, 1033 cm$^{-1}$. $^1$H NMR (500 MHz, CDCl$_3$) δ: 1.32/1.38 [each 3H, s, C(CH$_3$)$_2$], 3.60 (1H, dd, J=10.0, 5.5 Hz, H-1a), 3.73 (1H, ddd, J=6.5, 5.5, 3.0 Hz, H-2), 3.75 (1H, dd, J=10.0, 3.0 Hz, H-1b), 3.79 (1H, dd, J=8.3, 6.3 Hz, H-4a), 3.80 (3H, s, OCH$_3$), 3.96 (1H, dd, J=8.3, 6.5 Hz, H-4b), 4.14 (1H, ddd, J=6.5, 6.5, 6.3 Hz, H-3), 4.49/4.52 (each 1H, d, J=11.8 Hz, CH$_2$Ar), 5.02/5.24 (each 1H, d, J=11.8 Hz, OCH$_2$Ar), 6.87/7.27 (each 2H, d-like, J=8.6 Hz, arom.), 7.39-8.15 (7H, m, arom.). $^{13}$C NMR (125 MHz, CDCl$_3$) δ: 25.3/26.6 [C(CH$_3$)$_2$], 55.3 (OCH$_3$), 66.7 (C-4), 70.2 (C-1), 72.1/73.2 (OCH$_2$Ar), 75.5 (C-3), 78.6 (C-2), 109.1 [C(CH$_3$)$_2$], 113.8/124.2/125.2/125.7/126.1/126.8/128.5/128.7/129.3 (d, arom.), 130.3/131.8/133.7/133.8/159.2 (s, arom.). FABMS (pos.) m/z: 445 [M+Na]$^+$.

Example 28

3,4-O-isopropylidene-1-O-(p-methoxybenzyl)-2-O-(naphthalen-2-ylmethyl)-D-erythritol compound (16y) (Reaction Scheme 4)

By following substantially the same procedures as for the synthesis of the compound (16a), the compound (14) (200 mg, 0.71 mmol) was naphthalen-2-ylmethylated yielding the title compound (16y, 275 mg, 92%) as colorless oily substance.
[Chem. 46]

Compound (16y): colorless oily substance. $[\alpha]^{23}_D$ +31.6 (c=0.50, CHCl$_3$). IR (neat): 3367, 2932, 2878, 1612, 1512, 1462, 1358, 1300, 1246, 1172, 1099, 1068, 1033, 1002 cm$^{-1}$. $^1$H NMR (500 MHz, CDCl$_3$) δ: 1.35/1.41 [each 3H, s, C(CH$_3$)$_2$], 3.59 (1H, dd-like, J=10.0, 5.2 Hz, H-1a), 3.69 (1H, ddd, J=6.3, 5.2, 3.2 Hz, H-2), 3.72 (1H, dd, J=10.0, 3.2 Hz, H-1b), 3.80 (3H, s, OCH$_3$), 3.95 (1H, dd, J=8.3, 6.3 Hz, H-4a), 4.07 (1H, dd, J=8.3, 6.3 Hz, H-4b), 4.20 (1H, dt, J=6.3, 6.3 Hz, H-3), 4.48/4.51/4.79/4.90 (each 1H, d, J=12.0 Hz, OCH$_2$Ar), 6.87 (2H, d-like, J=8.9 Hz, arom.), 7.23-7.85 (9H, m, arom.). $^{13}$C NMR (125 MHz, CDCl$_3$) δ: 25.3/26.6 [C(CH$_3$)$_2$], 55.3 (OCH$_3$), 66.6 (C-4), 70.0 (C-1), 72.9/73.1 (OCH$_2$Ar), 75.6 (C-3), 78.7 (C-2), 109.1 [C(CH$_3$)$_2$], 113.7/125.8/125.9/126.0/126.5/127.7/127.9/128.1/129.2 (d, arom.), 130.3/133.0/133.2/135.9/159.2 (s, arom.). FABMS (pos.) m/z: 445 [M+Na]$^+$.

Example 29

3,4-O-isopropyl idene-1-O-(p-methoxybenzyl)-2-O-(pyridin-3-ylmethyl)-D-erythritol compound (16z) (Reaction Scheme 4)

By following substantially the same procedures as for the synthesis of the compound (16a), the compound (14) (500 mg, 1.77 mmol) was pyridin-3-ylmethylated yielding the title compound (16z, 615 mg, 93%) as colorless oily substance.
[Chem. 47]

Compound (16z): colorless oily substance., $[\alpha]^{25}_D$ +15.5 (c=1.46, CHCl$_3$). IR (neat): 1713, 1605, 1512, 1458, 1423, 1373, 1254, 1219, 1169, 1080, 1030 cm$^{-1}$. $^1$H NMR (500 MHz, CDCl$_3$) δ: 1.35/1.40 [each 3H, s, (CH$_3$)$_2$C], 3.57 (1H, dd-like, J=10.0, 5.2 Hz, H-1a), 3.67 (1H, ddd, J=5.2, 5.2, 2.9 Hz, H-2), 3.70 (1H, dd, J=10.0, 2.9 Hz, H-1b), 3.81 (3H, s, OCH$_3$), 3.92 (1H, dd, J=8.3, 6.3 Hz, H-4a), 4.04 (1H, dd, J=8.3, 6.3 Hz, H-4b), 4.16 (1H, td, J=6.3, 5.2 Hz, H-3), 4.47/4.49 (each 1H, d-like, J=12.4 Hz, CH$_2$Ar), 4.65/4.77 (each 1H, d-like, J=12.1 Hz, CH$_2$Ar), 6.88/7.25 (each 2H, d-like, J=8.9 Hz, arom.), 7.24-7.28 (1H, m, pyridine H-5), 7.66 (1H, dt-like, J=7.7, 2.0 Hz, pyridine H-4), 8.53 (1H, br d-like, J=ca. 5.0 Hz, pyridine H-6), 8.55 (1H, br s-like, pyridine H-2). $^{13}$C NMR (125 MHz, CDCl$_3$) δ: 25.2/26.6 [(CH$_3$)$_2$C], 55.3 (OCH$_3$), 66.4 (C-4), 70.0 (C-1), 70.4/73.1 (CH$_2$Ar), 75.5 (C-3), 79.1 (C-2), 109.1 [(CH$_3$)$_2$C], 113.8/123.3/129.3/135.5/149.0/149.1 (d, arom.), 130.1/133.9/159.2 (s, arom.). FABMS (pos.) m/z: 374 [M+H]$^+$.

Example 30

3,4-O-isopropylidene-1-O-(p-methoxybenzyl)-2-O-(pyridin-4-ylmethyl)-D-erythritol compound (16aa) (Reaction Scheme 4)

By following substantially the same procedures as for the synthesis of the compound (16a), the compound (14) (400 mg, 1.42 mmol) was pyridin-4-ylmethylated yielding the title compound (16aa, 500 mg, 95%) as colorless oily substance.
[Chem. 48]

Compound (16aa): colorless oily substance., $[\alpha]^{25}_D$ +14.1 (c=1.10, CHCl$_3$). IR (neat): 1712, 1605, 1512, 1458, 1416, 1373, 1319, 1258, 1219, 1169, 1103, 1080, 1065, 1034 cm$^{-1}$. $^1$H NMR (500 MHz, CDCl$_3$) δ:1.35/1.40 [each 3H, s, (CH$_3$)$_2$C], 3.55-3.59 (1H, m, H-1a), 3.65-3.71 (2H, m, H-1b and H-2), 3.80 (3H, s, OCH$_3$), 3.96 (1H, dd, J=8.3, 6.3 Hz, H-4a), 4.07 (1H, dd, J=8.3, 6.6 Hz, H-4b), 4.19 (1H, ddd, J=6.6, 6.3, 6.3 Hz, H-3), 4.47 (2H, s-like, CH$_2$Ar), 4.66/4.77 (each 1H, d-like, J=13.2 Hz, CH$_2$Ar), 6.86/7.23 (each 2H, d-like, J=8.9 Hz, arom.), 7.24 (2H, d. J=5.5 Hz, Pyridine H-3 and H-5), 8.55 (2H, br s, pyridine H-2 and 4). $^{13}$C NMR (125 MHz, CDCl$_3$) δ: 25.2/26.5 [(CH$_3$)$_2$C], 55.3 (OCH$_3$), 66.3 (C-4), 70.0 (C-1), 71.2/73.1 (CH$_2$Ar), 75.6 (C-3), 79.4 (C-2), 109.2 [(CH$_3$)$_2$C], 113.8/121.7/129.3/149.7 (d, arom.), 130.0/147.7/159.2 (s, arom.). FABMS (pos.) m/z: 374 [M+H]$^+$.

Example 31

1-O-benzyl-2-O-methyl-D-erythritol compound (17a) (Reaction Scheme 4)

A mixture of the compound (16a, 2.0 g, 7.5 mmol), 4 ml of 1% hydrochloric acid and 6 ml of ethanol was heated under reflux for 30 minutes and, after removal of the solvent, the residue was dissolved in 20 ml of ethanol. The resulting mixture was neutralized with ion exchange resin (IRA67). After the ion ion exchange resin was filtered off, the filtrate was concentrated yielding a pale yellow oily substance (2.0 g) which was in turn smashed with n-hexane yielding the title compound (17a) as almost pure, colorless oily substance. This substance was used at the next step without purification.
[Chem. 49]
Compound (17a): colorless oily substance. $^1$H NMR (500 MHz, CDCl$_3$) δ: 2.27 (2H, br s, OH), 3.446 (3H, s, OCH$_3$), 3.448 (1H, ddd, J=5.2, 5.2, 4.6 Hz, H-2), 3.66 (1H, dd, J=10.3, 4.6 Hz, H-1a), 3.69 (1H, dd, J=10.3, 5.2 Hz, H-1b), 3.71 (2H, d-like, J=ca. 4.6 Hz, H-4a and H-4b), 3.83 (1H, dt, J=5.2, 4.6 Hz, H-3), 4.55/4.58 (each 1H, d, J=12.0 Hz, OCH$_2$Ph), 7.28-7.38 (5H, m, arom.). $^{13}$C NMR (125 MHz, CDCl$_3$) δ: 58.4 (OCH$_3$), 63.5 (C-4), 69.0 (C-1), 71.9 (C-3), 73.7 (OCH$_2$Ph), 80.6 (C-2), 127.8/127.9/128.6 (d, arom.), 137.5 (s, arom.).

Example 32

1-O-benzyl-2-O-ethyl-D-erythritol compound (17b) (Reaction Scheme 4)

By following substantially the same procedures as for the synthesis of the compound (17a), the compound (16b) (2.1 g, 8.1 mmol) was hydrolyzed with 1% hydrochloric acid, yielding the title compound (17b) quantitatively as an almost pure substance. This compound was used at the next step without purification.
[Chem. 50]
Compound (17b): colorless oily substance. $^1$H NMR (500 MHz, CDCl$_3$) δ: 1.19 (3H, t, J=7.2 Hz, OCH$_2$CH$_3$), 2.37/2.90 (each 1H, br s, OH), 3.55/3.70 (each 1H, dq, J=9.5, 7.2 Hz, OCH$_2$CH$_3$), 3.56 (1H, ddd-like, J=ca. 5.2, 5.2, 5.2 Hz, H-2), 3.64 (1H, dd, J=10.0, 5.2 Hz, H-1a), 3.67 (1H, dd, J=10.0, 5.2 Hz, H-1b), 3.72 (2H, d-like, J=ca. 4.3 Hz, H-4a and H-4b), 3.83 (1H, dt-like, J=ca. 5.2, 4.3 Hz, H-3), 4.55/4.58 (each 1H, d, J=12.0 Hz, OCH$_2$Ph), 7.28-7.38 (5H, m, arom.). $^{13}$C NMR (125 MHz, CDCl$_3$) δ: 15.5 (OCH$_2$CH$_3$), 63.5 (C-4), 66.3 (OCH$_2$CH$_3$), 69.7 (C-1), 72.1 (C-3), 73.7 (OCH$_2$Ph), 78.9 (C-2), 127.7/127.9/128.5 (d, arom.), 137.6 (s, arom.).

Example 33

1-O-benzyl-2-O-(1-pentyl)-D-erythritol compound (17c) (Reaction Scheme 4)

By following substantially the same procedures as for the synthesis of the compound (17a), the compound (16c) (798 mg, 2.5 mmol) was hydrolyzed with 1% hydrochloric acid. After cooling, the resulting mixture was diluted with water, and the resulting mixture was neutralized with sodium hydrogen carbonate and then extracted with diethyl ether. The filtrate was washed with saline water and then concentrated under reduced pressure yielding the title compound (17c) quantitatively as an almost pure, colorless oily substance. This compound was used at the next step without purification.
[Chem. 51]
Compound (17c): colorless oily substance. $^1$H NMR (500 Mz, CDCl$_3$) δ: 0.89 (3H, t, J=6.9 Hz, O(CH$_2$)$_4$CH$_3$], 1.27-1.35 [4H, m, OCH$_2$CH$_2$(CH$_2$)$_2$CH$_3$], 1.52-1.59 [2H, m, OCH$_2$CH$_2$(CH$_2$)$_2$CH$_3$], 2.42 (1H, t, J=6.0 Hz, OH), 2.93 (1H, d, J=5.2 Hz, OH), 3.47/3.62 (each 1H, dt, J=9.2, 6.9 Hz, OCH$_2$(CH$_2$)$_3$CH$_3$], 3.54 (1H, ddd, J=5.5, 5.2, 5.2 Hz, H-2), 3.64 (1H, dd, J=10.0, 5.5 Hz, H-1a), 3.66 (1H, dd, J=10.0, 5.2 Hz, H-1b), 3.72 (2H, dd-like, J=ca. 6.0, 4.5 Hz, I-1-4a and H-4b), 3.81 (1H, ddt, J=5.2, 5.2, 4.5 Hz, H-3), 4.55/4.57 (each 1H, d, J=11.8 Hz, CH$_2$Ph), 7.28-7.38 (5H, m, arom.). $^{13}$C NMR (125 Mz, CDCl$_3$) δ. 14.0 [O(CH$_2$)$_4$CH$_3$], 22.5 [O(CH$_2$)$_3$CH$_2$CH$_3$], 28.2 [O(CH$_2$)$_2$CH$_2$CH$_3$], 29.7 [OCH$_2$CH$_2$(CH$_2$)$_2$CH$_3$], 63.5 (C-4), 69.6 (C-1), 71.1 [OCH$_2$(CH$_2$)$_3$CH$_3$], 72.1 (C-3), 73.6 (CH$_2$Ph), 79.1 (C-2), 127.7/127.9/128.5 (d, arom.), 137.6 (s, arom.).

Example 34

1-O-benzyl-2-O-(1-heptyl)-D-erythritol compound (17d) (Reaction Scheme 4)

By following substantially the same procedures as for the synthesis of the compound (17a), the compound (16c) (637 mg, 1.8 mmol) was hydrolyzed with 1% hydrochloric acid, yielding the title compound (17d) quantitatively as an almost pure, colorless oily substance. This compound was used at the next step without purification.
[Chem. 52]
Compound (17d): colorless oily substance. $^1$H NMR (700 MHz, CDCl$_3$) δ: 0.88 (3H, t, J=7.0 Hz, O(CH$_2$)$_6$CH$_3$], 1.22-1.34 [8H m O(CH$_2$)$_2$(CH$_2$)$_4$CH$_3$], 1.51-1.58 [2H, m OCH$_2$CH$_2$(CH$_2$)$_4$CH$_3$], 2.38 (1H, t, J=6.2 Hz, OH), 2.90 (1H, d, J=5.4 Hz, OH), 3.46/3.62 (each 1H, dt, J=9.2, 7.0 Hz, OCH$_2$(CH$_2$)$_5$CH$_3$], 3.54 (1H, ddd, J=5.4, 5.3, 4.8 Hz, H-2), 3.64 (1H, dd, J=10.0, 5.4 Hz, H-1a), 3.66 (1H, dd, J=10.0, 4.8 Hz, H-1b), 3.72 (2H, dd-like, J=ca. 6.2, 4.5 Hz, H-4a and H-4b), 3.81 (1H, ddt, J=5.4, 5.4, 4.5 Hz, H-3), 4.55/4.57 (each 1H, d, J=12.0 Hz, CH$_2$Ph), 7.28-7.37 (5H, m, arom.). $^{13}$C NMR (175 MHz, CDCl$_3$) δ. 14.1 [O(CH$_2$)$_6$CH$_3$], 22.6 [O(CH$_2$)$_5$CH$_2$CH$_3$], 26.0 [O(CH$_2$)$_2$CH$_2$(CH$_2$)$_3$CH$_3$], 29.1 [O(CH$_2$)$_3$CH$_2$(CH$_2$)$_2$CH$_3$], 30.0 [OCH$_2$CH$_2$(CH$_2$)$_4$CH$_3$], 31.8 [O(CH$_2$)$_4$CH$_2$CH$_2$CH$_3$], 63.5 (C-4), 69.7 (C-1), 71.1 [OCH$_2$(CH$_2$)$_5$CH$_3$], 72.2 (C-3), 73.7 (CH$_2$Ph), 79.2 (C-2), 127.7/127.9/128.5 (d, arom.), 137.6 (s, arom.).

Example 35

1-O-benzyl-2-O-(1-tridecyl)-D-erythritol compound (17e) (Reaction Scheme 4)

By following substantially the same procedures as for the synthesis of the compound (17a), the compound (16e) (1.15 g, 2.65 mmol) was hydrolyzed with 1% hydrochloric acid, yielding the title compound (17e) quantitatively as an almost pure, colorless oily substance. This compound was used at the next step without purification.
[Chem. 53]
Compound (17e): colorless oily substance. $^1$H NMR (500 MHz, CDCl$_3$) δ: 0.88 (3H, t; J=7.0 Hz, O(CH$_2$)$_{12}$CH$_3$], 1.22-1.34 [20H m O(CH$_2$)$_2$(CH$_2$)$_{10}$CH$_3$], 1.50-1.59 [2H, m OCH$_2$CH$_2$(CH$_2$)$_{10}$CH$_3$], 2.37 (1H, br t, J=5.2 Hz, OH), 2.89 (1H, d, J=5.2 Hz, OH), 3.46/3.62 (each 1H, dt, J=9.2, 7.0 Hz, OCH$_2$(CH$_2$)$_{11}$CH$_3$], 3.54 (1H, ddd, J=5.5, 5.2, 5.2 Hz, H-2), 3.64 (1H, dd, J=10.0, 5.5 Hz, H-1a), 3.66 (1H, dd, J=10.0, 5.2

Hz, H-1b), 3.72 (2H, dd-like, J=ca. 5.2, 5.2 Hz, H-4a and H-4b), 3.81 (1H, ddt, J=5.2, 5.2, 5.2 Hz, H-3), 4.54/4.57 (each 1H, d, J=12.0 Hz, CH$_2$Ph), 7.28-7.37 (5H, m, arom.). $^{13}$C NMR (125 MHz, CDCl$_3$) δ. 14.1 [O(CH$_2$)$_{12}$CH$_3$], 22.6 [O(CH$_2$)$_{11}$CH$_2$CH$_3$], 26.1 [O(CH$_2$)$_2$CH$_2$(CH$_2$)$_9$CH$_3$], 29.3/29.4/29.56/29.59/29.64/29.7 [O(CH$_2$)$_3$(CH$_2$)$_7$(CH$_2$)$_2$CH$_3$], 30.0 [OCH$_2$CH$_2$(CH$_2$)$_{10}$CH$_3$], 31.9 [O(CH$_2$)$_{10}$CH$_2$CH$_2$CH$_3$], 63.5 (C-4), 69.7 (C-1), 71.1 [OCH$_2$(CH$_2$)$_{11}$CH$_3$], 72.1 (C-3), 73.7 (OCH$_2$Ph), 79.1 (C-2), 127.7/127.9/128.5 (d, arom.), 137.6 (s, arom.).

Example 36

1-O-benzyl-2-O-neopentyl-D-erythritol compound (17f) (Reaction Scheme 4)

By following substantially the same procedures as for the synthesis of the compound (17a), the compound (16f) (161 mg, 0.5 mmol) was hydrolyzed with 0.5 ml of 1% hydrochloric acid, yielding the title compound (17f) quantitatively as an almost pure, colorless oily substance. This compound was used at the next step without purification.
[Chem. 54]
Compound (17f): colorless oily substance. $^1$H NMR (500 MHz, CDCl$_3$) δ: 0.90 [9H, s, OCH$_2$C(CH$_3$)$_3$], 2.40/2.39 (each 1H, br s, OH), 3.13/3.30 [each 1H, d, J=8.3 Hz, OCH$_2$C(CH$_3$)$_3$], 3.54 (1H, ddd, J=5.8, 5.8, 4.6 Hz H-2), 3.64 (1H, dd, J=10.1, 5.8 Hz H-1a), 3.67 (1H, dd, J=10.1, 4.6 Hz, H-1b), 3.74 (2H, d-like, J=ca. 4.6 Hz, H-4a and H-4b), 3.83 (1H, dt, J=5.8, 4.6 Hz, H-3), 4.56 (2H, s-like, OCH$_2$Ph), 7.28-7.38 (5H, m, arom.). $^{13}$C NMR (125 MHz, CDCl$_3$) δ: 26.6 [OCH$_2$C(CH$_3$)$_3$], 32.1 [OCH$_2$C(CH$_3$)$_3$], 63.5 (C-4), 69.6 (C-1), 72.3 (C-3), 73.7 (OCH$_2$Ph), 79.6 (C-2), 81.4 [OCH$_2$C(CH$_3$)$_3$], 127.7/127.9/128.5 (d, arom.), 137.6 (s, arom).

Example 37

2-O-benzyl-1-O-(o-methoxybenzyl)-D-erythritol compound (17g) (Reaction Scheme 4)

A mixture of the compound (16g) (360 mg, 0.97 mmol) in 3.0 ml of acetic acid and 1.5 ml of water was hydrolyzed at room temperature for 7 hours. The resulting reaction mixture was diluted with 50 ml of water and then neutralized with sodium hydrogen carbonate, followed by extraction with diethyl ether. The resulting extract was washed with saline water and concentrated under reduced pressure yielding the title compound (17g) quantitatively as an almost pure, colorless oily substance. This compound was used at the next step without purification.
[Chem. 55]
Compound (17g): colorless oily substance. $^1$H NMR (700 MHz, CDCl$_3$) δ: 2.26 (1H, br t-like, J=ca. 5.8, OH), 2.89 (1H, d, J=5.3, OH), 3.64-3.70 (3H, m, H-1a, H-1b and H-2), 3.71 (2H, br dd-like, J=ca. 5.8, 5.8, H-4a and H-4b), 3.80 (3H, s, OCH$_3$), 3.81-3.86 (1H, br m, H-3), 4.47/4.50 (each 1H, d, H=11.6 Hz, OCH$_2$Ar), 4.57/4.68 (each 1H, d, J=11.6, OCH$_2$Ar), 6.88/7.24 (each 2H, d-like, J=8.6, arom.), 7.28-7.36 (5H, m, arom.). $^{13}$C NMR (175 MHz, CDCl$_3$) δ: 55.3 (OCH$_3$), 63.4 (C-4), 69.4 (C-1), 72.3 (C-3), 72.7/73.3 (OCH$_2$Ar), 78.2 (C-2), 113.9/127.9/128.5/129.4 (d, arom.), 129.6/137.9/159.4 (s, arom.).

Example 38

2-O-(o-methylbenzyl)-1-O-(p-methoxybenzyl)-D-erythritol compound (17h) (Reaction Scheme 4)

By following substantially the same procedures as for the synthesis of the compound (17g), the compound (16h) (160 mg, 0.41 mmol) was hydrolyzed with acetic acid aqueous solution yielding the title compound (17h) quantitatively as an almost pure, colorless oily substance. This compound was used at the next step without purification.
[Chem. 56]
Compound (17h): colorless oily substance. $^1$H NMR (500 MHz, CDCl$_3$) δ: 2.20 (1H, br t-like, J=ca. 6.0, OH), 2.33 (3H, s, C$_6$H$_4$CH$_3$), 2.85 (1H, d, J=5.5, OH), 3.63-3.72 (5H, m, H-1a, H-1b, H-2, H-4a and H-4b), 3.81 (3H, s, OCH$_3$), 3.81-3.86 (1H, br m, H-3), 4.47/4.50 (each 1H, d, J=11.6, OCH$_2$Ar), 4.56/4.69 (each 1H, d, J=11.5, OCH$_2$Ar), 6.88/7.24 (each 2H, d-like, J=8.6, arom.), 7.14-7.23 (3H, m, arom.), 7.26-7.30 (1H, m, arom.). $^{13}$C NMR (125 MHz, CDCl$_a$) δ: 18.8 (C$_6$H$_4$CH$_3$), 55.3 (OCH$_3$), 63.4 (C-4), 69.4 (C-1), 71.0/73.3 (OCH$_2$Ar), 72.3 (C-3), 78.1 (C-2), 113.9/125.9/128.1/128.9/129.4/130.3 (d, arom.), 129.6/135.7/136.7/159.4 (s, arom.).

Example 39

2-O-(m-methylbenzyl)-1-O-(p-methoxybenzyl)-D-erythritol compound (17i) (Reaction Scheme 4)

By following substantially the same procedures as for the synthesis of the compound (17g), the compound (16i) (200 mg, 0.52 mmol) was hydrolyzed with acetic acid aqueous solution yielding the title compound (17i) quantitatively as an almost pure, colorless oily substance. This compound was used at the next step without purification.
[Chem. 57]
Compound (17i): colorless oily substance. $^1$H NMR (700 MHz, CDCl$_3$) δ: 2.28 (1H, br s, OH), 2.34 (3H, s, C$_6$H$_4$CH$_3$), 2.90 (1H, br s, OH), 3.64-3.69 (3H, m, H-1a, H-1b and H-2), 3.70 (2H, d-like, J=ca. 4.2, H-4a and H-4b), 3.81 (3H, s, OCH$_3$), 3.81-3.86 (1H, br m, H-3), 4.47/4.50 (each 1H, d, J=11.6, OCH$_2$Ar), 4.53/4.64 (each 1H, d, J=11.5, OCH$_2$Ar), 6.88/7.25 (each 2H, d-like, J=8.6, arom.), 7.11 (2H, br d-like, J=ca. 7.2, arom.), 7.12 (1H, br s-like, arom.), 7.23 (1H, t, J=7.2, arom.). $^{13}$C NMR (175 MHz, CDCl$_3$) δ: 21.3 (C$_6$H$_4$CH$_3$), 55.3 (OCH$_3$), 63.4 (C-4), 69.4 (C-1), 72.3 (C-3), 72.7/73.3 (OCH$_2$Ar), 78.1 (C-2), 113.9/125.0/128.4/128.66/128.68/129.4 (d, arom.), 129.6/137.8/138.1/159.4 (s, arom.).

Example 40

2-O-(p-methylbenzyl)-1-O-(p-methoxybenzyl)-D-erythritol compound (17j) (Reaction Scheme 4)

By following substantially the same procedures as for the synthesis of the compound (17g), the compound (16j) (190 mg, 0.49 mmol) was hydrolyzed with an aqueous acetic acid solution yielding the title compound (17j) quantitatively as an almost pure, colorless oily substance. This compound was used at the next step without purification.
[Chem. 58]
Compound (17j): colorless oily substance. $^1$H NMR (700 MHz, CDCl$_3$) δ: 2.26 (1H, br s, OH), 2.34 (3H, s, C$_6$H$_4$CH$_3$), 2.87 (1H, d, J=5.0, OH), 3.63-3.68 (3H, m, H-1a, H-1b and H-2), 3.69 (2H, d-like, J=ca. 4.0, H-4a and H-4b), 3.81 (3H, s, OCH$_3$), 3.80-3.85 (1H, br m, H-3), 4.47/4.50 (each 1H, d, J=11.5, OCH$_2$Ar), 4.52/4.64 (each 1H, d, J=11.4, OCH$_2$Ar), 6.88/7.25 (each 2H, d-like, J=8.6, arom.), 7.14/7.20 (each 2H, br d-like, J=ca. 8.0, arom.). $^{13}$C NMR (175 MHz, CDCl$_3$) δ: 21.2 (C$_6$H$_4$CH$_3$), 55.3 (OCH$_3$), 63.4 (C-4), 69.4 (C-1), 72.3 (C-3), 72.5/73.3 (OCH$_2$Ar), 78.0 (C-2), 113.9/128.0/129.2/129.4 (d, arom.), 129.6/134.5/137.7/159.4 (s, arom.).

Example 41

2-O-(o-chlorobenzyl)-1-O-(p-methoxybenzyl)-D-erythritol compound (17k) (Reaction Scheme 4)

By following substantially the same procedures as for the synthesis of the compound (17g), the compound (16k) (144 mg, 0.35 mmol) was hydrolyzed with an aqueous acetic acid solution yielding the title compound (17k) quantitatively as an almost pure, colorless oily substance. This compound was used at the next step without purification.
[Chem. 59]

Compound (17k): colorless oily substance. $^1$H NMR (700 MHz, CDCl$_3$) δ: 2.26 (1H, br t-like, J=ca. 5.0, OH), 2.89 (1H, d, J=5.4, OH), 3.68-3.75 (5H, m, H-1a, H-1b, H-2 H-4a and H-4b), 3.81 (3H, s, OCH$_3$), 3.84-3.89 (1H, br m, H-3), 4.49/4.51 (each 1H, d, J=11.6, OCH$_2$Ar), 4.67/4.77 (each 1H, d, J=12.0, OCH$_2$Ar), 6.88 (2H, d-like, J=8.6, arom.), 7.22-7.27 (4H, m, arom.), 7.34-7.37 (1H, m, arom.), 7.71-7.44 (1H, m, arom.). $^{13}$C NMR (175 MHz, CDCl$_3$) δ: 55.3 (OCH$_3$), 63.4 (C-4), 69.3 (C-1), 69.8/73.3 (OCH$_2$Ar), 72.2 (C-3), 78.8 (C-2), 113.9/126.8/129.1/129.4/129.5/129.7 (d, arom.), 129.6/133.2/135.6/159.4 (s, arom.).

Example 42

2-O-(m-chlorobenzyl)-1-O-(p-methoxybenzyl)-D-erythritol compound (17l) (Reaction Scheme 4)

By following substantially the same procedures as for the synthesis of the compound (17g), the compound (16l) (470 mg, 1.16 mmol) was hydrolyzed with an aqueous acetic acid solution yielding the title compound (17l) quantitatively as an almost pure, colorless oily substance. This compound was used at the next step without purification.
[Chem. 60]

Compound (17l): colorless oily substance. $^1$H NMR (500 MHz, CDCl$_3$) δ: 2.25/2.88 (each 1H, br s, OH), 3.62-3.68 (3H, m, H-1a, H-1b and H-2), 3.70 (1H, dd, J=11.5, 4.9, H-4a), 3.73 (1H, dd, J=11.5, 4.1, H-4b), 3.81 (3H, s, OCH$_3$), 3.82-3.87 (1H, br m, H-3), 4.47/4.50 (each 1H, d, J=11.8, OCH$_2$Ar), 4.55/4.64 (each 1H, d, J=12.0, OCH$_2$Ar), 6.89/7.24 (each 2H, d-like, J=8.6, arom.), 7.16-7.20 (1H, m, arom.), 7.24-7.27 (2H, m, arom.), 7.31 (1H, br s-like, arom.). $^{13}$C NMR (125 MHz, CDCl$_3$) δ: 55.3 (OCH$_3$), 63.3 (C-4), 69.4 (C-1), 71.8/73.3 (OCH$_2$Ar), 72.3 (C-3), 78.4 (C-2), 113.9/125.7/127.8/127.9/129.46/129.7 (d, arom.), 129.50/134.3/140.1/159.4 (s, arom.).

Example 43

2-O-(p-chlorobenzyl)-1-O-(p-methoxybenzyl)-D-erythritol compound (17m) (Reaction Scheme 4)

By following substantially the same procedures as for the synthesis of the compound (17g), the compound (16m) (277 mg, 0.681 mmol) was hydrolyzed with an aqueous acetic acid solution yielding the title compound (17m) quantitatively as an almost pure, colorless oily substance. This compound was used at the next step without purification.
[Chem. 61]

Compound (17m): colorless oily substance. $^1$H NMR (500 MHz, CDCl$_3$) δ: 2.38/2.96 (each 1H, br s, OH), 3.61-3.66 (3H, m, H-1a, H-1b and H-2), 3.68 (1H, dd, J=11.5, 4.6, H-4a), 3.71 (1H, dd, J=11.5, 4.0, H-4b), 3.79-3.84 (1H, br m, H-3), 3.80 (3H, s, OCH$_3$), 4.46/4.49 (each 1H, d, J=11.5, OCH$_2$Ar), 4.54/4.63 (each 1H, d, J=12.0, OCH$_2$Ar), 6.88/7.30 (each 2H, d-like, J=8.6, arom.), 7.23 (4H, br d-like, J=ca. 8.6, arom.). $^{13}$C NMR (125 MHz, CDCl$_3$) δ: 55.3 (OCH$_3$), 63.3 (C-4), 69.4 (C-1), 71.8/73.3 (OCH$_2$Ar), 72.2 (C-3), 78.4 (C-2), 113.9/128.6/129.1/129.4 (d, arom.), 129.5/133.6/136.5/159.4 (s, arom.).

Example 44

2-O-(o-bromobenzyl-1-O-(p-methoxybenzyl)-D-erythritol compound (17n) (Reaction Scheme 4)

By following substantially the same procedures as for the synthesis of the compound (17g), the compound (16n) (404 mg, 0.90 mmol) was hydrolyzed with an aqueous acetic acid solution yielding the title compound (17n) quantitatively as an almost pure, colorless oily substance. This compound was used at the next step without purification.
[Chem. 62]

Compound (17n): colorless oily substance. $^1$H NMR (500 MHz, CDCl$_3$) δ: 2.27 (1H, br t-like, J=ca. 6.0, OH), 2.90 (1H, d, J=5.8, OH), 3.70-3.75 (5H, m, H-1a, H-1b, H-2a, H-4a and H-4b), 3.80 (3H, s, OCH$_3$), 3.88 (1H, br, m, H-3), 4.49/4.52 (each 1H, d, J=11.8, CH$_2$Ph), 4.64/4.74 (each 1H, d, J=12.3, OCH$_2$Ar), 6.88/7.26 (each 2H, J=8.6, arom.) 7.16 (1H, dd, J=7.7, 1.7, arom.), 7.30 (1H, td, J=7.7, 1.2, arom.), 7.43 (1H, dd, J=7.7, 1.7, arom.), 7.54 (1H, dd, J=7.7, 1.2, arom.). $^{13}$C NMR (125 MHz, CDCl$_3$) δ: 55.2 (OCH$_3$), 63.4 (C-4), 69.2 (C-1), 71.9/73.3 (OCH$_2$Ar), 72.2 (C-3), 78.8 (C-2) 113.9/127.5/129.3/129.5/129.8/132.7 (d, arom.), 123.1/129.6/137.2/159.4 (s, arom.).

Example 45

2-O-(o-bromobenzyl)-1-O-(p-methoxybenzyl)-D-erythritol compound (17o) (Reaction Scheme 4)

By following substantially the same procedures as for the synthesis of the compound (17g), the compound (16o) (422 mg, 0.94 mmol) was hydrolyzed with an aqueous acetic acid solution yielding the title compound (17o) quantitatively as an almost pure, colorless oily substance. This compound was used at the next step without purification.
[Chem. 63]

Compound (17o): colorless oily substance. $^1$H NMR (500 MHz, CDCl$_3$) δ: 2.27 (1H, br t-like, J=ca. 6.3, OH), 2.90 (1H, br d-like, J=ca. 5.2, OH), 3.63-3.74 (5H, in, H-1a. H-1b, H-2, H-4a and H-4b), 3.81 (3H, s, OCH$_3$), 3.84 (1H, br, m, H-3), 4.46/4.50 (each 1H, d, J=11.5, OCH$_2$Ar), 4.55/4.64 (each 1H, d, J=11.8, OCH$_2$Ar), 6.89/7.25 (each 2H, d-like, J=8.6, arom.), 7.20 (1H, t, J=7.7, arom.), 7.23 (1H, br, d-like, J=7.7, arom.), 7.42 (1H, dt, J=7.7, 1.5, arom.), 7.47 (1H, t-like, J=1.5, arom.). $^{13}$C NMR (125 MHz, CDCl$_3$) δ: 55.3 (OCH$_3$), 63.3 (C-4), 69.3 (C-1), 71.8 (C-3), 72.2/73.3 (OCH$_2$Ar), 78.4 (C-2), 113.9/126.2/129.5/130.0/130.7/130.9 (d, arom.), 122.5/140.4/159.4 (s, arom.).

Example 46

2-O-(p-bromobenzyl)-1-O-(p-methoxybenzyl)-D-erythritol compound (17p) (Reaction Scheme 4)

By following substantially the same procedures as for the synthesis of the compound (17g), the compound (16p) (485 mg, 1.08 mmol) was hydrolyzed with an aqueous acetic acid solution yielding the title compound (17p) quantitatively as an almost pure, colorless oily substance. This compound was used at the next step without purification.

[Chem. 64]

Compound (17p): colorless oily substance. $^1$H NMR (500 MHz, CDCl$_3$) δ: 2.23 (1H, br, t-like, J=ca. 5.7, OH), 2.86 (1H, d, J=5.2, OH), 3.63-3.72 (5H, m, H-1a, H-1b, H-2a, H-4a and H-4b), 3.82 (3H, s, OCH$_3$), 3.84 (1H, m, H-3), 4.47/4.50 (each 1H, d, J=11.5, OCH$_2$Ar), 4.53/4.63 (each 1H, d, J=11.8, OCH$_2$Ar), 6.89/7.19/7.24/7.46 (each 21-1, d-like, J=ca. 8.6, arom.). $^{13}$C NMR (125 MHz, CDCl$_3$) δ: 55.3 (OCH$_3$), 63.3 (C-4), 69.4 (C-1), 71.9 (C-3), 72.3/73.3 (OCH$_2$Ar), 78.3 (C-2), 113.9/129.5/131.6 (d, arom.), 121.7/137.0/159.4 (s, arom.).

Example 47

1-O-(p-methoxybenzyl)-2-O-(o-trifluoromethylbenzyl)-D-erythritol compound (17q) (Reaction Scheme 4)

By following substantially the same procedures as for the synthesis of the compound (17g), the compound (16q) (531 mg, 1.21 mmol) was hydrolyzed with an aqueous acetic acid solution yielding the title compound (17q) quantitatively as an almost pure, colorless oily substance. This compound was used at the next step without purification.

[Chem. 65]

Compound (17q): colorless oily substance. $^1$H NMR (500 MHz, CDCl$_3$) δ: 3.68-3.77 (5H, m, H-1a, H-1b, H-2, H-4a and H-4b), 3.81 (3H, s, OCH$_3$), 3.89 (1H, m, H-3), 4.48/4.51 (each 1H, d, J=11.5, CH$_2$Ar), 4.75/4.87 (each 1H, d, J=12.6, CH$_2$Ar), 6.88/7.25 (each 2H, d, J=8.6, arom.), 7.39/7.53 (each 1H, t, J=7.7, arom.), 7.63/7.65 (1H, d, J=3.5, arom.). $^{13}$C NMR (125 MHz, CDCl$_3$) δ: 55.2 (OCH$_3$), 63.3 (C-4), 68.5 [q, J=2.3, CH$_2$C$_6$H$_4$-(o-CF$_3$)], 69.0 (C-1), 72.3 (C-3), 73.3 [CH$_2$C$_6$H$_4$-(p-OCH$_3$)], 79.0 (C-2), 113.9/127.6/129.4/129.5/132.0 (d, arom.), 124.3 [q, J=272, CF$_3$], 125.8 [q, J=5.4, C$_{ortho}$—CF$_3$,], 127.5 [q, J=32.8 Hz, C$_{ipso}$—CF$_3$,], 136.6/159.4 (s, arom.).

Example 48

1-O-(p-methoxybenzyl)-2-O-(m-trifluoromethylbenzyl)-D-erythritol compound (17r) (Reaction Scheme 4)

By following substantially the same procedures as for the synthesis of the compound (17g), the compound (16r) (302 mg, 0.69 mmol) was hydrolyzed with an aqueous acetic acid solution yielding the title compound (17r) quantitatively as an almost pure, colorless oily substance. This compound was used at the next step without purification.

[Chem. 66]

Compound (17r): colorless oily substance. $^1$H NMR (500 MHz, CDCl$_3$) δ: 2.18 (1H, br t-like, J=ca. 5.0, OH), 2.85 (1H, d, J=5.2, OH), 3.66-3.71 (5H, m, H-1a, H-1b, H-2, H-4a and H-4b), 3.81 (3H, s, OCH$_3$), 3.86 (1H, m, H-3), 4.47/4.51 (each 1H, d, J=11.5, CH$_2$Ar), 4.64/4.73 (each 1H, d, J=12.0, CH$_2$Ar), 6.88/7.24 (each 2H, d, J=8.6, arom.), 7.46 (1H, br dd, J=ca. 7.5, arom.), 7.50 (1H, br d, J=ca. 7.5, arom.), 7.55 (1H, br d, J=ca. 7.5, arom.), 7.57 (1H, br s, arom.). $^{13}$C NMR (125 MHz, CDCl$_3$) δ: 55.3 (OCH$_3$), 63.3 (C-4), 69.4 (C-1), 71.9/73.3 (CH$_2$Ph), 72.3 (C-3), 78.6 (C-2), 113.9/128.9/129.5/130.9 (d, arom.), 124.1 (q, J=271 Hz, CF$_3$), 124.3/127.6 (each q, J=3.6 Hz, C$_{ortho}$—CF$_3$), 130.6 (q, J=32.2 Hz, C$_{ipso}$—CF$_3$), 130.9/139.1/159.4 (s, arom.).

Example 49

1-O-(p-methoxybenzyl)-2-O-(p-trifluoromethylbenzyl)-D-erythritol compound (17s) (Reaction Scheme 4)

By following substantially the same procedures as for the synthesis of the compound (17g), the compound (16s) (280 mg, 0.64 mmol) was hydrolyzed with an aqueous acetic acid solution yielding the title compound (17s) quantitatively as an almost pure, colorless oily substance. This compound was used at the next step without purification.

[Chem. 67]

Compound (17s): colorless solid. $^1$H NMR (700 MHz, CDCl$_3$) δ: 2.21 (1H, t, J=6.0, OH), 2.86 (1H, d, J=5.2, OH), 3.65-3.71 (3H, m, H-1a, H-1b and H-2), 3.72 (1H, dd, J=11.0, 6.0, H-4a), 3.74 (1H, dd, J=11.0, 6.0, H-4b), 3.81 (3H, s, OCH$_3$), 3.84-3.88 (1H, m, H-3), 4.47/4.50 (each 1H, d, J=11.5, OCH$_2$Ar), 4.63/4.73 (each 1H, d, J=12.0, OCH$_2$Ar), 6.88/7.24 (each 2H, d-like, J=8.6, arom.), 7.42/7.59 (each 2H, br d-like, J=ca. 8.1, arom.). $^{13}$C NMR (175 MHz, CDCl$_3$) δ: 55.3 (OCH$_3$), 63.3 (C-4), 69.4 (C-1), 71.8/73.3 (OCH$_2$Ar), 72.3 (C-3), 78.6 (C-2), 113.9/127.6/129.5 (d, arom.), 124.2 (q, J=270, CF$_3$) 125.4 [q, J=3.4, C$_{ortho}$—CF$_3$], 130.0 [q, J=32.5, C$_{ipso}$—CF$_3$,], 129.5/142.1/159.5 (s, arom.).

Example 50

1-O-(p-methoxybenzyl)-2-O-(o-nitrobenzyl)-D-erythritol compound (17t) (Reaction Scheme 4)

By following substantially the same procedures as for the synthesis of the compound (17g), the compound (16t) (572 mg, 1.37 mmol) was hydrolyzed with an aqueous acetic acid solution yielding the title compound (17t) quantitatively as an almost pure, pale yellow oily substance. This compound was used at the next step without purification.

[Chem. 68]

Compound (17t): pale yellow oil. $^1$H NMR (500 MHz, CDCl$_3$) δ: 2.30/2.94 (each 1H, br s, OH), 3.68-3.78 (5H, m, H-1a, H-1b, H-2, H-4a and H-4b), 3.87-3.93 (1H, m, H-3), 3.80 (3H, s, OCH$_3$), 4.47/4.50 (each 1H, d, J=11.8, OCH$_2$Ar), 4.96/5.03 (each 11-1, d, J=14.0, OCH$_2$Ar), 6.87/7.24 (each 2H, d-like, J=8.6, arom.), 7.44 (1H, ddd, J=8.0, 7.8, 1.0, arom.), 7.61 (1H, ddd, J=8.0, 7.8, 1.2, arom.), 7.73 (1H, dd, J=8.0, 1.0, arom.), 8.03 (1H, dd, J=8.0, 1.2, arom.). $^{13}$C NMR (125 MHz, CDCl$_3$) δ: 55.3 (OCH$_3$), 63.3 (C-4), 68.9 (C-1), 69.1/73.3 (OCH$_2$Ar), 72.2 (C-3), 79.2 (C-2), 113.9/124.6/128.2/129.2/129.5/133.6 (d, arom.), 129.5/134.5/147.4/159.4 (s, arom.).

Example 51

1-O-(p-methoxybenzyl)-2-O-(m-nitrobenzyl)-D-erythritol compound (17u) (Reaction Scheme 4)

By following substantially the same procedures as for the synthesis of the compound (17g), the compound (16u) (620 mg, 1.48 mmol) was hydrolyzed with an aqueous acetic acid solution yielding the title compound (17t) quantitatively as an almost pure, pale yellow oily substance. This compound was used at the next step without purification.

[Chem. 69]

Compound (17u): pale yellow oil. $^1$H NMR (500 MHz, CDCl$_3$) δ: 2.23 (1H, br s-like, OH), 2.88 (1H, d, J=4.9, OH), 3.65-3.77 (5H, m, H-1a, H-1b, H-2, H-4a and H-4b), 3.81 (3H, s, OCH$_3$), 3.84-3.89 (1H, m, H-3), 4.47/4.51 (each 1H, d, J=11.5, OCH$_2$Ar), 4.69/4.77 (each 1H, d, J=12.0, OCH$_2$Ar), 6.88/7.24 (each 2H, d-like, J=8.6, arom.), 7.50 (1H, t, J=7.8, arom.), 7.64 (1H, br d-like, J=ca. 7.8, arom.), 8.14 (1H, br dd-like, J=7.8, 1.5, arom.), 8.19 (1H, br t-like, J=ca. 1.5, arom.). $^{13}$C NMR (125 MHz, CDCl$_3$) δ: 55.3 (OCH$_3$), 63.3 (C-4), 69.4 (C-1), 71.4/73.3 (OCH$_2$Ar), 72.2 (C-3), 78.8 (C-2), 114.0/122.3/122.7/129.3/129.5/133.4 (d, arom.), 129.4/140.4/148.3/159.5 (s, arom.).

Example 52

1-O-(p-methoxybenzyl)-2-O-(p-nitrobenzyl)-D-erythritol compound (17v) (Reaction Scheme 4)

By following substantially the same procedures as for the synthesis of the compound (17g), the compound (16v) (252 mg, 0.60 mmol) was hydrolyzed with an aqueous acetic acid solution yielding the title compound (17v) quantitatively as an almost pure, colorless oily substance. This compound was used at the next step without purification.
[Chem. 70]
Compound (17v): colorless solid. $^1$H NMR (700 MHz, CDCl$_3$) δ: 2.18/2.84 (each 1H, s, OH), 3.66-3.72 (3H, m, H-1a, H-1b and H-2), 3.73 (1H, dd, J=11.6, 5.0, H-4a), 3.74 (1H, dd, J=11.6, 4.0, H-4b), 3.81 (3H, s, OCH$_3$), 3.85-3.89 (1H, m, H-3), 4.47/4.50 (each 1H, d, J=11.6, OCH$_2$Ar), 4.70/4.78 (each 1H, d, J=12.8, OCH$_2$Ar), 6.88/7.24 (each 2H, d-like, J=8.6, arom.), 7.47/8.18 (each 2H, br d-like, J=ca. 8.8, arom.). $^{13}$C NMR (175 MHz, CDCl$_3$) δ: 55.3 (OCH$_3$), 63.3 (C-4), 69.4 (C-1), 71.4/73.4 (OCH$_2$Ar), 72.3 (C-3), 79.0 (C-2), 113.9/123.6/127.8/129.5 (d, arom.), 129.4/145.7/147.4/159.5 (s, arom.).

Example 53

1-O-(p-methoxybenzyl)-2-O-(p-(p-methoxybenzyloxymethyl)benzyl)-D-erythritol compound (17w) (Reaction Scheme 4)

By following substantially the same procedures as for the synthesis of the compound (17g), the compound (16w) (496 mg, 0.95 mmol) was hydrolyzed with an aqueous acetic acid solution yielding the title compound (17w) quantitatively as an almost pure, pale yellow oily substance. This compound was used at the next step without purification.
[Chem. 71]
Compound (17w): pale yellow oil. $^1$H NMR (500 MHz, CDCl$_3$) δ: 2.27 (1H, br s, OH), 2.88 (1H, d-like, J=ca 4.9, OH), 3.63-3.67 (3H, m, H-1a, H-1b and H-2), 3.67-3.72 (1H, br m, H-4a and H-4b), 3.80/3.81 (each 3H, s, OCH$_3$), 3.82 (1H, m, H-3), 4.47/4.49 (each 1H, d-like, J=11.5, OCH$_2$Ar), 4.48/4.52 (each 2H, s-like, OCH$_2$Ar), 4.56/4.67 (each 1H, d-like, J=11.5, OCH$_2$Ar), 6.86-6.91 (4H, m, arom.), 7.22-7.35 (8H, m, arom.). $^{13}$C NMR (125 MHz, CDCl$_3$) δ: 55.3 (OCH$_3$), 63.4 (C-4), 69.4 (C-1), 71.5/71.7/72.4/73.3 (OCH$_2$Ar), 72.3 (C-3), 78.2 (C-2), 113.8/113.9/127.9/128.0/128.3/129.39/129.42 (d, arom.), 129.6/130.3/137.3/138.1/159.2/159.4 (s, arom.).

Example 54

1-O-(p-methoxybenzyl)-2-O-(naphthalen-1-ylmethyl)-D-erythritol compound (17x) (Reaction Scheme 4)

By following substantially the same procedures as for the synthesis of the compound (17g), the compound (16x) (257 mg, 0.61 mmol) was hydrolyzed with an aqueous acetic acid solution yielding the title compound (17x) quantitatively as an almost pure, colorless oily substance. This compound was used at the next step without purification.
[Chem. 72]
Compound (17x): colorless solid. $^1$H NMR (500 MHz, CDCl$_3$) δ: 2.88 (2H, br s, OH), 3.64 (2H, d, J=4.3 Hz, H-4a and H-4b), 3.66 (1H, dd, J=10.0, 4.6 Hz, H-1a), 3.71 (1H, dd, J=10.0, 4.9 Hz, H-1b), 3.75 (1H, ddd, J=5.0, 4.9, 4.6 Hz, H-2), 3.80 (3H, s, OCH$_3$), 3.82 (1H, dt, J=5.0, 4.3 Hz, H-3), 4.47/4.49 (each 1H, d, J=11.8 Hz, OCH$_2$Ar), 4.98/5.16 (each 2H, d-like, J=8.6 Hz, OCH$_2$Ar), 7.39-8.13 (7H, m, arom.). $^{13}$C NMR (125 MHz, CDCl$_3$) δ: 55.3 (OCH$_3$), 63.3 (C-4), 69.4 (C-1), 71.0/73.3 (OCH$_2$Ar), 72.2 (C-3), 78.0 (C-2), 113.9/123.9/125.2/125.9/126.4/127.0/128.6/129.0/129.4 (d, arom.), 131.7/133.3/133.8/159.4 (s, arom.).

Example 55

1-O-(p-methoxybenzyl)-2-O-(naphthalen-2-ylmethyl)-D-erythritol compound (17y) (Reaction Scheme 4)

By following substantially the same procedures as for the synthesis of the compound (17g), the compound (16y) (270 mg, 0.63 mmol) was hydrolyzed with an aqueous acetic acid solution yielding the title compound (17y) quantitatively as an almost pure, colorless oily substance. This compound was used at the next step without purification.
[Chem. 73]
Compound (17y): colorless solid. $^1$H NMR (500 MHz, CDCl$_3$) δ: 2.34 (1H, br t-like, J=ca. 5.0, OH), 2.95 (1H, d, J=5.2 Hz, OH), 3.68 (1H, dd-like, J=ca. 11.0, 6.5 Hz, H-1a), 3.70 (1H, ddd-like, J=ca. 6.5, 5.2, 2.8 Hz, H-2), 3.71 (1H, dd-like, J=ca. 11.0, 2.8 Hz, H-1b), 3.73 (2H, br dd-like, J=ca. 5.0, 4.5 Hz, H-4a and H-4b), 3.80 (3H, s, OCH$_3$), 3.86 (1H, ddt-like, J=ca. 5.2, 5.2, 4.5 Hz, H-3), 4.47/4.50 (each 1H, d, J=11.5 Hz, OCH$_2$Ar), 4.73/4.83 (each 1H, d, J=12.0 Hz, OCH$_2$Ar), 6.87/7.24 (each 2H, d-like, J=8.6 Hz, arom.), 7.41-7.85 (7H, m, arom.). $^{13}$C NMR (125 MHz, CDCl$_3$). δ: 55.3 (OCH$_3$), 63.4 (C-4), 69.4 (C-1), 72.3 (C-3), 72.7/73.3 (OCH$_2$Ar), 78.1 (C-2), 113.9/125.8/126.0/126.2/126.7/127.7/127.9/128.3/129.4 (d, arom.), 129.6/133.0/133.2/135.3/159.4 (s, arom.).

Example 56

1-O-(p-methoxybenzyl)-2-O-(pyridin-3-ylmethyl)-D-erythritol compound (17z) (Reaction Scheme 4)

By following substantially the same procedures as for the synthesis of the compound (17g), the compound (16z) (517 mg, 1.38 mmol) was hydrolyzed with an aqueous acetic acid solution yielding the title compound (17z) quantitatively as an almost pure, pale yellow oily substance. This compound was used at the next step without purification.
[Chem. 74]
Compound (17z): pale yellow oil. $^1$H NMR (500 MHz, CDCl$_3$) δ: 2.60 (2H, br s, OH), 3.64-3.76 (5H, m, H-1a, H-1b, H-2, H-4a and H-4b), 3.81 (1H, s, OCH$_3$), 3.81-3.89 (1H, m, H-3), 4.47/4.50 (each 1H, d, J=11.8 Hz, CH$_2$Ar), 4.60/4.71 (each 1H, d, J=12.1 Hz, CH$_2$Ar), 6.88/7.24 (each 2H, d-like, J=8.9 Hz, arom.), 7.26 (1H, dd-like, J=7.7, 5.0 Hz, pyridine H-5), 7.66 (1H, dt-like, J=7.7, 2.0 Hz, pyridine H-4), 8.52 (1H, br d-like J=ca. 5.0 Hz, pyridine H-3), 8.54 (1H, br s, pyridine H-2). $^{13}$C NMR (125 MHz, CDCl$_3$) δ: 55.2 (OCH$_3$), 63.2 (C-4), 69.5 (C-1), 70.1/73.3 (CH$_2$Ar) 72.1 (C-3), 78.7 (C-2), 113.9/123.4/129.4/135.6/148.9 (d, arom.), 129.6/133.7/159.3 (s, arom.).

Example 57

1-O-(p-methoxybenzyl)-2-O-(pyridin-4-ylmethyl)-D-erythritol compound (17aa) (Reaction Scheme 4)

By following substantially the same procedures as for the synthesis of the compound (17g), the compound (16aa) (482 mg, 1.29 mmol) was hydrolyzed with an aqueous acetic acid solution yielding the title compound (17aa) quantitatively as an almost pure, pale yellow oily substance. This compound was used at the next step without purification.
[Chem. 75]
Compound (17aa): pale yellow oil. $^1$H NMR (500 MHz, CDCl$_3$) δ: 2.83 (2H, br s, OH), 3.65-3.74 (3H, m, H-1a, H-1b and H-2), 3.73 (1H, dd, J=11.5, 5.2 Hz, H-4a), 3.76 (1H, dd, J=11.5, 4.0 Hz, H-4b), 3.81 (3H, s, OCH$_3$), 3.87 (1H, ddd-like, J=ca. 5.2, 5.2, 4.0 Hz, H-3), 4.46/4.49 (each 1H, d, J=11.5 Hz, CH$_2$Ar), 4.61/4.71 (each 1H, d, J=13.2 Hz, CH$_2$Ar), 6.88/7.24 (each 2H, d-like, J=8.6 Hz, arom.), 7.22 (2H, br d-like, J=ca. 5.0 Hz, Pyridine H-3 and H-5), 8.54 (2H, br d-like, J=ca. 5.0 Hz, Pyridine H-2 and H-6). $^{13}$C NMR (125 MHz, CDCl$_3$) δ: 55.3 (OCH$_3$), 63.2 (C-4), 69.4 (C-1), 70.8/73.3 (CH$_2$Ar), 72.1 (C-3), 79.1 (C-2), 113.9/121.8/129.4/149.7 (d, arom.), 129.5/147.5159.4 (s, arom.).

Example 58

3,4-Anhydro-1-O-benzyl-2-O-methyl-D-erythritol compound (18a) (Reaction Scheme 4)

To a mixture of the compound (17a, 1.51 g, 6.7 mmol), triphenylphosphine (TPP, 2.1 g, 8.0 mmol) and toluene (10 ml) was dropwise added a 40% toluene (3.9 ml, 8.6 mmol) solution of diethyl azodicarboxylate (EDAD) at 80° C. The resulting reaction mixture was stirred at room temperature for 30 minutes and then heated under reflux for another 4 hours. After the solvent was removed, the residue was smashed in a diethylether-n-hexane (1:1) solution and the precipitated solid material was filtered off. The resulting filtrate was then concentrated, leaving a orange oily substance (2.61 g). This was then purified by column chromatography (hexane-AcOEt; 20:1→10:1) yielding the title compound (17a) (1.07 g, 77%) as a colorless oily substance.
[Chem. 76]
Compound (18a): colorless oily substance. $[α]_D^{24}$ +11.2 (c=1.08, CHCl$_3$). IR (neat): 1454, 1366, 1335, 1249, 1200, 1099 cm$^{-1}$. $^1$H NMR (500 MHz, CDCl$_3$) δ: 2.77 (1H, dd, J=5.2, 2.9 Hz, H-4a), 2.83 (1H, dd, J=5.2, 4.0 Hz, H-4b), 3.05 (1H, ddd, J=5.5, 4.0, 2.9 Hz, H-3), 3.26 (1H, ddd, J=5.5, 5.5, 4.0 Hz, H-2), 3.45 (3H, s, OCH$_3$), 3.61 (1H, dd, J=10.4, 5.5 Hz, H-1a), 3.66 (1H, dd, J=10.4, 4.0 Hz, H-1b), 4.59 (2H, s-like, OCH$_2$Ph), 7.26-7.36 (5H, m, arom.). $^{13}$C NMR (125 MHz, CDCl$_3$) δ: 45.5 (C-4), 50.9 (C-3), 58.4 (OCH$_3$), 70.2 (C-1), 73.5 (OCH$_2$Ph), 79.7 (C-2), 127.6/128.4 (d, arom.), 138.0 (s, arom.). FABMS (pos.) m/z: 231 [M+Na]$^+$.

Example 59

3,4-Anhydro-1-O-benzyl-2-O-ethyl-D-erythritol compound (18b) (Reaction Scheme 4) (Reaction Scheme 4)

By following substantially the same procedures as for the synthesis of the compound (18a), the compound (17b) (1.36 g, 5.7 mmol) was epoxidated with TPP and DEAD yielding the title compound (18b, 956 mg, 76%) as colorless oily substance.
[Chem. 77]
Compound (18b): colorless oily substance. $[α]_D^{24}$ +5.7 (c=1.20, CHCl$_3$). IR (neat): 1456, 1364, 1325, 1252, 1101 cm$^{-1}$. $^1$H NMR (700 MHz, CDCl$_3$) δ: 1.20 (3H, t, J=7.0 Hz, OCH$_2$CH$_3$), 2.77 (1H, dd, J=5.5, 2.8 Hz, H-4a), 2.81 (1H, dd, J=5.5, 4.0 Hz, H-4b), 3.06 (1H, ddd, J=5.4, 4.0, 2.8 Hz, H-3), 3.37 (1H, ddd, J=5.4, 5.4, 4.2 Hz, H-2), 3.59/3.65 (each 1H, dt, J=9.2, 7.0 Hz, OCH$_2$CH$_3$), 3.61 (1H, dd, J=10.2, 5.4 Hz, H-1a), 3.64 (1H, dd, J=10.2, 4.2 Hz, H-1b), 4.59 (2H, s-like, OCH$_2$Ph), 7.27-7.35 (5H, m, arom.). $^{13}$C NMR (175 MHz, CDCl$_3$) δ: 15.5 (OCH$_2$CH$_3$), 45.5 (C-4), 51.3 (C-3), 66.2 (OCH$_2$CH$_3$), 70.6 (C-1), 73.5 (OCH$_2$Ph), 78.0 (C-2), 127.6/128.3 (d, arom.), 138.2 (s, arom.). FABMS (pos.) m/z: 245 [M+Na]$^+$.

Example 60

3,4-Anhydro-1-O-benzyl-2-O-(1-pentyl)-D-erythritol compound (18c) (Reaction Scheme 4) (Reaction Scheme 4)

By following substantially the same procedures as for the synthesis of the compound (18a), the compound (17c) (600 mg, 2.12 mmol) was epoxidated with TPP and DEAD yielding the title compound (18c, 460 mg, 82%) as colorless oily substance.
[Chem. 78]
Compound (18c): colorless oily substance. $[α]_D^{22}$ +6.17 (c=1.02, CHCl$_3$). IR (neat): 1454, 1366, 1342, 1254, 1207, 1099, 1030 cm$^{-1}$. $^1$H NMR (500 MHz, CDCl$_3$) δ: 0.89 [3H, t, J=6.9 Hz, O(CH$_2$)$_4$CH$_3$], 1.27-1.36 [4H, m, O(CH$_2$)$_2$(CH$_2$)$_2$CH$_3$], 1.52-1.61 [2H, m, OCH$_2$CH$_2$(CH$_2$)$_2$CH$_3$], 2.77 (1H, dd, J=5.4, 2.6 Hz, H-4a), 2.80 (1H dd, J=5.4, 3.7 Hz, H-4b), 3.05 (1H, ddd, J=5.2, 3.7, 2.6 Hz, H-3), 3.36 (1H, ddd, J=5.5, 5.2, 4.3 Hz, H-2), 3.51/3.58 [each 1H, dt, J=9.2, 6.9 Hz, OCH$_2$(CH$_2$)$_3$CH$_3$], 3.61 (1H dd J=10.3, 5.5 Hz, H-1a), 3.64 (1H, dd, J=10.3, 4.3 Hz, H-1b), 4.59 (2H, s, OCH$_2$Ph), 7.25-7.36 (5H, m, arom.). $^{13}$C NMR (125 MHz, CDCl$_3$) δ. 14.0 [O(CH$_2$)$_4$CH$_3$], 22.5 [O(CH$_2$)$_3$CH$_2$CH$_3$], 28.2 [O(CH$_2$)$_2$CH$_2$CH$_2$CH$_3$], 29.7 [OCH$_2$CH$_2$(CH$_2$)$_2$CH$_3$], 45.4 (C-4), 51.3 (C-3), 70.6 (C-1), 71.0 [OCH$_2$(CH$_2$)$_3$CH$_3$], 73.4 (OCH$_2$Ph), 78.1 (C-2), 127.6/128.3 (d, arom.), 138.2 (s, arom). FABMS m/z: 287 [M+Na]$^+$.

Example 61

3,4-Anhydro-1-O-benzyl-2-O-(1-heptyl)-D-erythritol compound (18d) (Reaction Scheme 4)

By following substantially the same procedures as for the synthesis of the compound (18a), the compound (17d) (544 mg, 1.75 mmol) was epoxidated with TPP and DEAD yielding the title compound (18d, 435 mg, 85%) as colorless oily substance.
[Chem. 79]
Compound (18d): colorless oily substance. $[α]_D^{25}$ +4.2 (c=0.93, CHCl$_3$). IR (neat): 1454, 1366, 1254, 1099, 1030 cm$^{-1}$. $^1$H NMR (700 MHz, CDCl$_3$) δ: 0.88 (3H, t, J=6.9 Hz, O(CH$_2$)$_6$CH$_3$), 1.22-1.35 [8H, m O(CH$_2$)$_2$(CH$_2$)$_4$CH$_3$], 1.53-1.59 [2H, m OCH$_2$CH$_2$(CH$_2$)$_4$CH$_3$], 2.77 (1H dd J=5.4, 2.6 Hz H-4a), 2.81 (1H, dd, J=5.4, 4.0 Hz H-4b), 3.05 (1H, ddd, J=5.2, 4.0, 2.6 Hz, H-3), 3.36 (1H, ddd, J=5.4, 5.2, 4.2 Hz, H-2), 3.51/3.57 [each 1H, dt, J=9.2, 6.9 Hz, OCH$_2$(CH$_2$)$_5$CH$_3$], 3.61 (1H, dd J=10.2, 5.4 Hz, H-1a), 3.64 (1H, dd, J=10.2, 4.2 Hz, H-1b), 4.58 (2H, s-like, CH$_2$Ph), 7.26-7.36 (5H, in, arom.). $^{13}$C NMR (175 MHz, CDCl$_3$) δ: 14.1 [O(CH$_2$)$_6$CH$_3$], 22.6 [O(CH$_2$)$_5$CH$_2$CH$_3$], 26.0 [O(CH$_2$)$_2$CH$_2$(CH$_2$)$_3$CH$_3$], 29.1 [O(CH$_2$)$_3$CH$_2$CH$_2$CH$_3$], 30.0 [OCH$_2$CH$_2$(CH$_2$)$_4$CH$_3$], 31.8 [O(CH$_2$)$_4$CH$_2$CH$_2$CH$_3$], 45.4 (C-4), 51.4 (C-3), 70.6 (C-1), 71.0 [OCH$_2$(CH$_2$)$_5$CH$_3$], 73.5 (CH$_2$Ph), 78.1 (C-2), 127.6/128.4 (d, arom.), 138.2 (s, arom). FABMS m/z: 315 [M+Na]$^+$.

Example 62

3,4-Anhydro-1-O-benzyl-2-O-(1-tridecyl)-D-erythritol compound (18e) (Reaction Scheme 4)

By following substantially the same procedures as for the synthesis of the compound (18a), the compound (17e) (1.0 g, 2.5 mmol) was epoxidated with TPP and DEAD yielding the title compound (18e, 772 mg, 81%) as colorless oily substance.
[Chem. 80]

Compound (18e): colorless oily substance. [α]$_D^{24}$ +11.4 (c=0.94 CHCl$_3$). IR (neat): 1466, 1456, 1364, 1250, 1101, 1028 cm$^{-1}$. $^1$H NMR (700 MHz, CDCl$_3$) δ: 0.88 (3H, t, J=7.0 Hz, O(CH$_2$)$_{12}$CH$_3$], 1.22-1.34 [20H m O(CH$_2$)$_2$(CH$_2$)$_{10}$CH$_3$], 1.53-1.59 [2H, m OCH$_2$CH$_2$(CH$_2$)$_{10}$CH$_3$], 2.76 (1H, dd, J=5.4, 2.8 Hz, H-4a), 2.81 (1H, dd, J=5.4, 4.0 Hz, H-4b), 3.05 (1H, ddd, J=5.2, 4.0, 2.8 Hz, H-3), 3.36 (1H, ddd, J=5.4, 5.2, 4.2 Hz, H-2), 3.50/3.57 [each 1H, dt, J=9.2, 7.0 Hz, OCH$_2$(CH$_2$)$_{11}$CH$_3$], 3.61 (1H, dd, J=10.2, 5.4 Hz, H-1a), 3.64 (1H, dd, J=10.2, 4.2 Hz, H-1b), 4.59 (2H, s-like, OCH$_2$Ph), 7.26-7.36 (5H, m, arom.). $^{13}$C NMR (175 MHz, CDCl$_3$) δ: 14.1 [O(CH$_2$)$_{12}$CH$_3$], 22.7 [O(CH$_2$)$_{11}$CH$_2$CH$_3$], 26.0 [O(CH$_2$)$_2$CH$_2$(CH$_2$)$_9$CH$_3$], 29.3/29.5/29.60/29.63/29.65/29.67 [O(CH$_2$)$_3$(CH$_2$)$_7$(CH$_2$)$_2$CH$_3$], 30.0 [OCH$_2$CH$_2$(CH$_2$)$_{10}$CH$_3$], 31.9 [O(CH$_2$)$_{10}$CH$_2$CH$_2$CH$_3$], 45.4 (C-4), 51.4 (C-3), 70.6 (C-1), 71.0 [OCH$_2$(CH$_2$)$_{11}$CH$_3$], 73.5 (OCH$_2$Ph), 78.1 (C-2), 127.6/128.4 (d, arom.), 138.2 (s, arom.). FABMS m/z: 399 [M+Na]$^+$ Example 63

3,4-Anhydro-1-O-benzyl-2-O-neopentyl-D-erythritol compound (18f) (Reaction Scheme 4)

By following substantially the same procedures as for the synthesis of the compound (18a), the compound (17f) (110 mg, 0.39 mmol) was epoxidated with TPP and DEAD yielding the title compound (18f, 91 mg, 89%) as colorless oily substance.
[Chem. 81]

Compound (180: colorless oily substance. [α]$^{23}_D$ +11.2 (c=0.99, CHCl$_3$). IR (neat): 2955, 2866, 1454, 1362, 1258, 1099, 1026 cm$^{-1}$. $^1$HNMR (500 MHz, CDCl$_3$) δ: 0.90 [9H, s, OCH$_2$C(CH$_3$)$_3$], 2.79 (2H, d-like, J=3.4 Hz, H-4a and H-4b), 3.06 (1H, dt, J=4.9, 3.4 Hz H-3), 3.16 [each 1H, d, J=8.6 Hz, OCH$_2$C(CH$_3$)$_3$], 3.40 (1H, ddd, J=4.9, 4.9, 4.9 Hz, H-2), 3.61 (1H, dd, J=10.8; 4.9 Hz, H-1a), 3.64 (1H, dd, J=10.8, 4.9 Hz, H-1b), 4.59 [2H, s-like, OCH$_2$Ph], 7.25-7.36 (5H, m, arom.). $^{13}$C NMR (125 MHz, CDCl$_3$) δ. 26.7 [OCH$_2$C(CH$_3$)$_3$], 32.2 [OCH$_2$C(CH$_3$)$_3$], 45.0 (C-4), 51.7 (C-3), 70.7 (C-1), 73.4 (OCH$_2$Ph), 78.4 (C-2), 81.5 [OCH$_2$C(CH$_3$)$_3$], 127.5/127.6/128.4 (d, arom.), 138.3 (s, arom). FABMS m/z: 287 [M+Na]$^+$.

Example 64

3,4-Anhydro-2-O-benzyl-1-O-(p-methoxybenzyl)-D-erythritol compound (18g) (Reaction Scheme 4)

By following substantially the same procedures as for the synthesis of the compound (18a), the compound (17g) (200 mg, 0.6 mmol) was epoxidated with TPP and DEAD yielding the title compound (18 g, 210 mg, 90%) as colorless oily substance.
[Chem. 82]

Compound (18g): colorless oily substance. [α]$_D^{24}$ +9.7 (c=1.01, CHCl$_3$). IR (neat): 1613, 1514, 1456, 1365, 1302, 1248, 1175, 1094, 1034 cm$^{-1}$. $^1$H NMR (500 MHz, CDCl$_3$) δ: 2.71 (1H, dd, J=5.2, 2.6 Hz, H-4a), 2.77 (1H, dd, J=5.2, 4.0 Hz, H-4b), 3.08 (1H, ddd, J=5.2, 4.0, 2.6 Hz, H-3), 3.50 (1H, ddd-like, J=5.2, 5.2, 4.6 Hz, H-2), 3.62 (1H, dd, J=10.3, 5.2 Hz, H-1a), 3.64 (1H, dd, J=10.3, 4.6 Hz, H-1b), 3.81 (3H, s, OCH$_3$), 4.51 (2H, s-like, OCH$_2$Ar), 4.63/4.66 (each 1H, d, J=12.0 Hz, OCH$_2$Ar), 6.88 (2H, d-like, J=8.6 Hz, arom.), 7.25-7.35 (7H, m, arom.). $^{13}$C NMR (125 MHz, CDCl$_3$) δ: 45.4 (C-4), 51.4 (C-3), 55.3 (OCH$_3$), 70.4 (C-1), 72.6/73.1 (OCH$_2$Ar), 77.2 (C-2), 113.8/127.7/128.3/129.3 (d, arom.), 130.2/138.3/159.2 (s, arom.). FABMS (pos.) m/z: 337 [M+Na]$^+$.

Example 65

3,4-Anhydro-2-O-(o-methylbenzyl)-1-O-(p-methoxybenzyl)-D-erythritol compound (18h) (Reaction Scheme 4)

By following substantially the same procedures as for the synthesis of the compound (18a), the compound (17h) (125 mg, 0.36 mmol) was epoxidated with TPP and DEAD yielding the title compound (18h, 93 mg, 79%) as colorless oily substance.
[Chem. 83]

Compound (18h): colorless oily substance. [α]$_D^{26}$ +4.4 (c=0.84, CHCl$_3$). IR (neat): 1612, 1585, 1512, 1462, 1361, 1300, 1250, 1172, 1092, 1033 cm$^{-1}$. $^1$H NMR (500 MHz, CDCl$_3$) δ: 2.32 (3H, s, C$_6$H$_4$CH$_3$), 2.71 (1H, dd, J=5.2, 2.6, H-4a), 2.77 (1H, dd, J=5.2, 4.0, H-4b), 3.08 (1H, ddd, J=4.9, 4.0, 2.6, H-3), 3.51 (1H, ddd, J=5.4, 4.9, 4.3, H-2), 3.62 (1H, dd, J=10.3, 5.4, H-1a), 3.65 (1H, dd, J=10.3, 4.3, H-1b), 3.80 (3H, s, OCH$_3$), 4.52 (2H, s-like, OCH$_2$Ar), 4.62/4.65 (each 1H, d, J=11.7, OCH$_2$Ar), 6.87/7.26 (each 2H, d-like, J=8.6, arom.), 7.14-7.23 (3H, m, arom.), 7.29-7.32 (1H, m, arom). $^{13}$C NMR (125 MHz, CDCl$_3$) δ: 18.8 (C$_6$H$_4$CH$_3$), 45.3 (C-4), 51.4 (C-3), 55.3 (OCH$_3$), 70.5 (C-1), 71.2/73.1 (OCH$_2$Ar), 77.3 (C-2), 113.8/125.7/127.9/128.8/129.3/130.22 (d, arom.), 130.17/136.1/136.8/159.2 (s, arom.). FABMS (pos.) m/z: 351 [M+Na]$^+$.

Example 66

3,4-Anhydro-2-O-(m-methylbenzyl)-1-O-(p-methoxybenzyl)-D-erythritol compound (18i) (Reaction Scheme 4)

By following substantially the same procedures as for the synthesis of the compound (18a), the compound (17i) (150 mg, 0.433 mmol) was epoxidated with TPP and DEAD yielding the title compound (18i, 119 mg, 84%) as colorless oily substance.
[Chem. 84]

Compound (18i): colorless oily substance. [α]$_D^{23}$ +6.8 (c=1.38, CHCl$_3$). IR (neat): 1612, 1512, 1462, 1300, 1246, 1172, 1092, 1033 cm$^{-1}$. $^1$H NMR (500 MHz, CDCl$_3$) δ: 2.33 (3H, s, C$_6$H$_4$CH$_3$), 2.71 (1H, dd, J=5.4, 2.9, H-4a), 2.77 (1H, dd, J=5.4, 4.1, H-4b), 3.08 (1H, ddd, J=5.2, 4.1, 2.9, H-3), 3.49 (1H, ddd, J=5.2, 5.2, 4.9, H-2), 3.62 (1H, dd, J=10.3, 5.2, H-1a), 3.65 (1H, dd, J=10.3, 4.9, H-1b), 3.80 (3H, s, OCH$_3$), 4.51 (2H, s-like, OCH$_2$Ar), 4.59/4.61 (each 1H, d, J=11.8, OCH$_2$Ar), 6.87/7.26 (each 2H, d-like, J=8.6, arom.), 7.08/ 7.12 (each 1H, br d, J=7.5, arom.), 7.15 (1H, br s-like, arom.), 7.21 (1H, t, J=7.5, arom.). $^{13}$C NMR (125 MHz, CDCl$_3$) δ: 21.4 (C$_6$H$_4$CH$_3$), 45.4 (C-4), 51.4 (C-3), 55.3 (OCH$_3$), 70.4 (C-1), 72.6/73.1 (OCH$_2$Ar), 77.2 (C-2), 113.8/124.7/128.2/ 128.4/128.5/129.2 (d, arom.), 130.2/138.0/138.2/159.2 (s, arom.). FABMS (pos.) m/z: 351 [M+Na]$^+$.

Example 67

3,4-Anhydro-2-O-(p-methylbenzyl)-1-O-(p-methoxybenzyl)-D-erythritol compound (18j) (Reaction Scheme 4)

By following substantially the same procedures as for the synthesis of the compound (18a), the compound (17j) (150 mg, 0.43 mmol) was epoxidated with TPP and DEAD yielding the title compound (18j, 108 mg, 76%) as colorless oily substance.
[Chem. 85]
Compound (18j): colorless oily substance. [α]$_D^{24}$ +15.5 (c=0.56, CHCl$_3$). IR (neat): 1612, 1512, 1458, 1300, 1249, 1172, 1092, 1033 cm$^{-1}$. $^1$H NMR (500 MHz, CDCl$_3$) δ: 2.34 (3H, s, C$_6$H$_4$CH$_3$), 2.70 (1H, dd, J=5.2, 2.6, H-4a), 2.77 (1H, dd, J=5.2, 4.0, H-4b), 3.07 (1H, ddd, J=5.2, 4.0, 2.6, H-3), 3.48 (1H, ddd, J=5.2, 5.2, 4.6, H-2), 3.61 (1H, dd, J=10.3, 5.2, H-1a), 3.64 (1H, dd, J=10.3, 4.6, H-1b), 3.81 (3H, s, OCH$_3$), 4.50 (2H, s-like, OCH$_2$Ar), 4.59/4.62 (each 1H, d, J=11.8, OCH$_2$Ar), 6.88/7.26 (each 2H, d-like, J=8.6, arom.), 7.13/ 7.22 (each 2H, br d-like, J=7.8, arom.). $^{13}$C NMR (125 MHz, CDCl$_3$) δ: 21.2 (C$_6$H$_4$CH$_3$), 45.4 (C-4), 51.4 (C-3), 55.3 (OCH$_3$), 70.4 (C-1), 72.4/73.1 (OCH$_2$Ar), 77.3 (C-2), 113.8/ 127.8/129.0/129.3 (d, arom.), 130.2/135.2/137.4/159.2 (s, arom.). FABMS (pos.) m/z: 351 [M+Na]$^+$.

Example 68

3,4-Anhydro-2-O-(o-chlorobenzyl)-1-O-(p-methoxybenzyl)-D-erythritol compound (18k) (Reaction Scheme 4)

By following substantially the same procedures as for the synthesis of the compound (18a), the compound (17k) (120 mg, 0.33 mmol) was epoxidated with TPP and DEAD yielding the title compound (18k, 86 mg, 75%) as colorless oily substance.
[Chem. 86]
Compound (18k): colorless oily substance. [α]$_D^{26}$ +5.7 (c=1.15, CHCl$_3$). IR (neat): 1612, 1585, 1512, 1473, 1442, 1365, 1300, 1250, 1172, 1096, 1033 cm$^{-1}$. $^1$H NMR (500 MHz, CDCl$_3$) δ: 2.78 (1H, dd, J=5.2, 2.6, H-4a), 2.81 (1H, dd, J=5.2, 4.0, H-4b), 3.11 (1H, ddd, J=4.9, 4.0, 2.6, H-3), 3.55 (1H, ddd, J=5.2, 4.9, 4.6, H-2), 3.66 (1H, dd, J=10.3, 5.2, H-1a), 3.69 (1H, dd, J=10.3, 4.6, H-1b), 3.80 (3H, s, OCH$_3$), 4.52 (2H, s-like, OCH$_2$Ar), 4.73/4.76 (each 1H, d, J=12.9, OCH$_2$Ar), 6.87/7.27 (each 2H, d-like, J=8.6, arom.), 7.22 (1H, td, J=7.5, 2.0, arom.), 7.24 (1H, td, J=7.5, 2.0, arom.), 7.34 (1H, dd, J=7.5, 1.5, arom.), 7.51 (1H, dd, J=7.5, 2.0, arom.). $^{13}$C NMR (125 MHz, CDCl$_3$) δ: 45.4 (C-4), 51.3 (C-3), 55.3 (OCH$_3$), 69.6/73.2 (OCH$_2$Ar), 70.3 (C-1), 78.0 (C-2), 113.8/126.8/128.7/129.1/129.2/129.3 (d, arom.), 130.1/132.7/136.1/159.2 (s, arom.). FABMS (pos.) m/z: 371 [M+Na]$^+$.

Example 69

3,4-Anhydro-2-O-(m-chlorobenzyl)-1-O-(p-methoxybenzyl)-D-erythritol compound (18l) (Reaction Scheme 4)

By following substantially the same procedures as for the synthesis of the compound (18a), the compound (17l) (200 mg, 0.55 mmol) was epoxidated with TPP and DEAD yielding the title compound (18l, 146 mg, 77%) as colorless oily substance.
[Chem. 87]
Compound (18l): colorless oily substance. [α]$_D^{24}$ +5.2 (c=0.89, CHCl$_3$). IR (neat): 1612, 1582, 1512, 1465, 1435, 1361, 1300, 1250, 1207, 1172, 1099, 1034 cm$^{-1}$. $^1$H NMR (700 MHz, CDCl$_3$) δ: 2.74 (1H, dd, J=5.2, 2.6, H-4a), 2.79 (1H, dd, J=5.2, 4.0, H-4b), 3.08 (1H, ddd, J=4.8, 4.0, 2.6, H-3), 3.52 (1H, ddd, J=5.5, 4.8, 4.3, H-2), 3.62 (1H, dd, J=10.4, 5.5, H-1a), 3.65 (1H, dd, J=10.4, 4.3, H-1b), 3.81 (3H, s, OCH$_3$), 4.51 (2H, s-like, OCH$_2$Ar), 4.60/4.64 (each 1H, d, J=12.3, OCH$_2$Ar), 6.88/7.26 (each 2H, d-like, J=8.6, arom.), 7.18-7.21 (1H, m, arom.), 7.24-7.27 (2H, m, arom.), 7.35 (1H, br s-like, arom.). $^{13}$C NMR (175 MHz, CDCl$_3$) δ: 45.2 (C-4), 51.3 (C-3), 55.3 (OCH$_3$), 70.4 (C-1), 71.8/73.2 (OCH$_2$Ar), 77.5 (C-2), 113.8/125.5/127.6/127.7/129.3/129.6 (d, arom.), 130.1/134.3/149.5/159.3 (s, arom.). FABMS (pos.) m/z: 371 [M+Na]$^+$.

Example 70

3,4-Anhydro-2-O-(p-chlorobenzyl)-1-O-(p-methoxybenzyl)-D-erythritol compound (18m) (Reaction Scheme 4)

By following substantially the same procedures as for the synthesis of the compound (18a), the compound (17m) (170 mg, 0.46 mmol) was epoxidated with TPP and DEAD yielding the title compound (18m, 139 mg, 86%) as colorless oily substance.
[Chem. 88]
Compound (18m): colorless oily substance. [α]$^{26}_D$ +2.3 (c=1.08, CHCl$_3$). IR (neat): 1612, 1512, 1493, 1462, 1365, 1300, 1249, 1172, 1091, 1033, 1015 cm$^{-1}$. $^1$H NMR (500 MHz, CDCl$_3$) δ: 2.72 (1H, dd, J=5.2, 2.6, H-4a), 2.78 (1H, dd, J=5.2, 4.0, H-4b), 3.07 (1H, ddd, J=4.9, 4.0, 2.6, H-3), 3.52 (1H, ddd, J=5.5, 4.9, 4.9, H-2), 3.61 (1H, dd, J=10.3, 5.5, H-1a), 3.63 (1H, dd, J=10.3, 4.9, H-1b), 3.81 (3H, s, OCH$_3$), 4.50 (2H, s-like, OCH$_2$Ar), 4.59/4.70 (each 1H, d, J=12.0, OCH$_2$Ar), 6.88/7.29 (each 2H, d-like, J=8.6, arom.), 7.24-7.31 (4H, m, arom.). $^{13}$C NMR (125 MHz, CDCl$_3$) δ: 45.2 (C-4), 51.3 (C-3), 55.3 (OCH$_3$), 70.4 (C-1), 71.8/73.2 (OCH$_2$Ar), 77.2 (C-2), 113.8/128.5/129.0/129.3 (d, arom.), 130.0/133.4/136.9/159.2 (s, arom.). FABMS (pos.) m/z: 371 [M+Na]$^+$.

Example 71

3,4-Anhydro-2-O-(o-bromobenzyl)-1-O-(p-methoxybenzyl)-D-erythritol compound (18n) (Reaction Scheme 4)

By following substantially the same procedures as for the synthesis of the compound (18a), the compound (17n) (349 mg, 0.85 mmol) was epoxidated with TPP and DEAD yielding the title compound (18n, 287 mg, 86%) as colorless oily substance.

[Chem. 89]

Compound (18n): colorless oily substance. [α]$^{24}_D$ +9.8 (c=0.50, CHCl$_3$). IR (neat): 1612, 1512, 1466, 1443, 1300, 1250, 1173, 1096, 1030 cm$^{-1}$. $^1$H NMR (500 MHz, CDCl$_3$) δ: 2.79 (2H, dd, J=5.2, 2.6, H-4a), 2.81 (2H, dd, J=5.2, 3.9, H-4b), 3.11 (1H, ddd, J=4.9, 3.9, 2.6, H-3), 3.55 (1H, ddd, J=5.2, 4.9, 4.6, H-2), 3.67 (2H, dd, J=10.3, 5.2, H-1a), 3.70 (1H, dd, J=10.3, 4.6, H-1b), 3.81 (3H, s, OCH$_3$), 4.53 (2H, s-like, OCH$_2$Ar), 4.69/4.72 (each 2H, d, J=12.9, OCH$_2$Ar), 6.88/7.27 (each 2H, d-like, J=8.6, arom.), 7.14 (1H, dd, J=7.4, 1.4, arom.), 7.29 (1H, td, J=7.4, 1.2, arom.), 7.51 (1H, dd-like, J=ca. 7.7, 1.4, arom.), 7.52 (1H, dd-like, J=ca. 7.7, 1.2, arom.). $^{13}$C NMR (125 MHz, CDCl$_3$) δ: 45.4 (C-4), 51.3 (C-3), 55.3 (OCH$_3$), 70.3 (C-1), 71.8/73.2 (OCH$_2$Ar), 78.0 (C-2), 113.8/127.4/128.9/129.2/129.3/132.4 (d, arom.), 122.5/130.1/137.6/159.2 (s, arom.). FABMS (pos.) m/z: 415 and 417 [M+Na]$^+$.

Example 72

3,4-Anhydro-2-O-(m-bromobenzyl)-1-O-(p-methoxybenzyl)-D-erythritol compound (18o) (Reaction Scheme 4)

By following substantially the same procedures as for the synthesis of the compound (18a), the compound (17o) (337 mg, 0.82 mmol) was epoxidated with TPP and DEAD yielding the title compound (18o, 285 mg, 85%) as colorless oily substance.
[Chem. 90]

Compound (18o): colorless oily substance., [α]25$_D$ +8.5 (c=1.0, CHCl$_3$). IR (neat): 1612, 1574, 1512, 1469, 1427, 1393, 1362, 1300, 1246, 1207, 1173, 1096, 1034 cm$^{-1}$. $^1$H NMR (500 MHz, CDCl$_3$) δ: 2.73 (1H, dd, J=5.2, 2.6, H-4a), 2.79 (1H, dd, J=5.2, 4.0, H-4b), 3.08 (1H, ddd, J=4.9, 4.0, 2.6, H-3), 3.52 (1H, ddd, J=5.5, 4.9, 4.3, 11-2), 3.62 (1H, dd, J=10.3, 5.5, H-1a), 3.65 (1H, dd, J=10.3, 4.3, H-1b), 3.81 (3H, s, OCH$_3$), 4.51 (2H, s-like, OCH$_2$Ar), 4.59/4.63 (each 1H, d, J=12.3, OCH$_2$Ar), 6.88/7.26 (each 2H, d-like, J=8.6, arom), 7.19 (1H, t, J=7.8 Hz, arom.), 7.24 (1H, br, d-like, J=7.8 Hz, arom), 7.40 (1H, dt-like, J=7.8, 1.5, arom.), 7.50 (1H, t-like, J=1.5, arom.). $^{13}$C NMR (125 MHz, CDCl$_3$) δ: 45.2 (C-4), 51.3 (C-3), 55.3 (OCH$_3$), 70.3 (C-1), 71.7/73.2 (OCH$_2$Ar), 77.4 (C-2) 113.8/126.0/129.3/129.9/130.5/130.6 (d, arom.), 122.5/130.0/140.7/159.2 (s, arom.). FABMS (pos.) m/z: 415 and 417 [M+Na]$^+$.

Example 73

3,4-Anhydro-2-O-(p-bromobenzyl)-1-O-(p-methoxybenzyl)-D-erythritol compound (18p) (Reaction Scheme 4)

By following substantially the same procedures as for the synthesis of the compound (18a), the compound (17p) (361 mg, 0.88 mmol) was epoxidated with TPP and DEAD yielding the title compound (18p, 283 mg, 82%) as colorless oily substance.
[Chem. 91]

Compound (18p): colorless oily substance. [α]$^{24}_D$ +15.6 (c=0.5, CHCl$_3$). IR (neat): 1612, 1585, 1512, 1485, 1462, 1408, 1362, 1300, 1246, 1207, 1173, 1092, 1072, 1034, 1011 cm$^{-1}$. $^1$H NMR (500 MHz, CDCl$_3$) δ: 2.73 (1H, dd, J=5.5, 2.6, H-4a), 2.78 (1H, dd, J=5.2, 4.0, H-4b), 3.07 (1H, ddd, J=5.2, 4.0, 2.6, H-3), 3.52 (1H, ddd, J=5.5, 4.6, H-2), 3.61 (1H, dd, J=10.3, 5.5, H-1a), 3.63 (1H, dd, J=10.3, 4.6, H-1b), 3.81 (3H, s, OCH$_3$), 4.50 (2H, s-like, OCH$_2$Ar), 4.57/4.61 (each 1H, d, J=12.0, OCH$_2$Ar), 6.88/7.20/7.25/7.44 (each 2H, d-like, J=ca. 8.6, arom.). $^{13}$C NMR (125 MHz, CDCl$_3$) δ: 45.2 (C-4), 51.3 (C-3), 55.3 (OCH3), 70.4 (C-1), 71.8/73.2 (OCH$_2$Ar), 77.3 (C-2), 113.8/129.3/131.4 (d, arom.), 121.5/130.0/137.4/159.2 (s, arom.). FABMS (pos.) m/z: 415 and 417 [M+Na]$^+$.

Example 74

3,4-Anhydro-2-O-(p-methoxybenzyl)-1-O-(o-trifluoromethylbenzyl)-D-erythritol compound (18q) (Reaction Scheme 4)

By following substantially the same procedures as for the synthesis of the compound (18a), the compound (17q) (482 mg, 1.21 mmol) was epoxidated with TPP and DEAD yielding the title compound (18q, 405 mg, 88%) as colorless oily substance.
[Chem. 92]

Compound (18q): colorless oily substance. [α]$^{22}_D$ +2.0 (c=1.03, CHCl$_3$). IR (neat): 1612, 1585, 1512, 1458, 1366, 1315, 1249, 1165, 1118, 1038 cm$^{-1}$. $^1$H NMR (500 MHz, CDCl$_3$) δ: 2.76 (1H, dd, J=5.2, 2.6, H-4a), 2.81 (1H, dd, J=5.2, 4.0, H-4b), 3.10 (1H, ddd, J=5.2, 4.0, 2.6, H-3), 3.53 (1H, ddd, J=5.5, 5.2, 4.3, H-2), 3.67 (1H, dd, J=10.3, 5.5, H-1a), 3.69 (1H, dd, J=10.3, 4.3, H-1b), 3.80 (3H, s, OCH$_3$), 4.52/4.84 (each 2H, s, CH$_2$Ph), 6.88/7.27 (each 2H, d, J=8.6, arom.), 7.36/7.52 (each 1H, d, J=7.8, arom.), 7.62/7.74 (each 1H, d, J=7.8, arom.). $^{13}$C NMR (125 MHz, CDCl$_3$) δ: 45.4 (C-4), 51.1 (C-3), 55.2 (OCH$_3$), 68.3 [q, J=2.4, CH$_2$C$_6$H$_4$(o-CF$_3$)], (C-1), 70.3 (C-1), 73.2 [CH$_2$C$_6$H$_4$(p-OCH$_3$)], 78.2 (C-2), 113.8/127.32/129.0/129.2/131.9 (d, arom.), 124.3 [q, J=272, CF$_3$], 125.6 [q, J=5.4, C$_{ortho}$—CF$_3$,], 127.27 [q, J=29.8, C$_{ipso}$—CF$_3$], 130.1/137.1/159.2 (s, arom.). FABMS (pos.) m/z: 405 [M+Na]$^+$.

Example 75

3,4-Anhydro-2-O-(p-methoxybenzyl)-1-O-(m-trifluoromethylbenzyl)-D-erythritol compound (18r) (Reaction Scheme 4)

By following substantially the same procedures as for the synthesis of the compound (18a), the compound (17r) (268 mg, 0.67 mmol) was epoxidated with TPP and DEAD yielding the title compound (18r, 202 mg, 79%) as colorless oily substance.
[Chem. 93]

Compound (18r): colorless oily substance. [α]$^{22}_D$ +8.5 (c=3.6, CHCl$_3$). IR (neat): 1612, 1516, 1454, 1330, 1249, 1165, 1122, 1095, 1076, 1038 cm$^{-1}$. $^1$H NMR (500 MHz, CDCl$_3$) δ: 2.74 (1H, dd, J=5.5, 2.6, H-4a), 2.79 (1H, dd, J=5.5, 3.7, H-4b), 3.09 (1H, ddd, J=4.9, 3.7, 2.6, H-3), 3.55 (1H, ddd, J=5.5, 4.9, 4.3, H-2), 3.63 (1H, dd, J=10.3, 5.5, H-1a), 3.66 (1H, dd, J=10.3, 4.3, H-1b), 3.80 (3H, s, OCH$_3$), 4.51 (2H, s-like, OCH$_2$Ar), 4.67/4.71 (each 1H, d, J=12.3, OCH$_2$Ar), 6.88/7.26 (each 2H, d, J=8.6, arom.), 7.43 (1H, br dd, J=ca. 7.8, 7.8, arom.), 7.51/7.53 (each 1H, br d, J=ca. 7.8, arom.), 7.61 (1H, br s, arom.). $^{13}$C NMR (125 MHz, CDCl$_3$) δ: 45.1 (C-4), 51.3 (C-3), 55.2 (OCH$_3$), 70.3 (C-1), 71.8/73.1 (OCH$_2$Ar), 77.6 (C-2), 113.8/128.7/129.3/130.7 (d, arom.), 124.10 (q, J=271, CF$_3$), 124.11/124.4 (each, q, J=3.6, C$_{ortho}$—CF$_3$), 130.8 (q, J=32.2, C$_{ipso}$—CF$_3$), 130.0/139.4/159.2 (s, arom.). FABMS (pos.) m/z: 405 [M+Na]$^+$.

Example 76

3,4-Anhydro-2-O-(p-methoxybenzyl)-1-O-(p-trifluoromethylbenzyl)-D-erythritol compound (18s) (Reaction Scheme 4)

By following substantially the same procedures as for the synthesis of the compound (18a), the compound (17s) (250 mg, 0.65 mmol) was epoxidated with TPP and DEAD yielding the title compound (18s, 191 mg, 80%) as colorless oily substance.

[Chem. 94]

Compound (18s): colorless oily substance. $[\alpha]_D^{24}$ +6.5 (c=0.83, CHCl$_3$). IR (neat): 1612, 1516, 1466, 1327, 1250, 1165, 1123, 1034 cm$^{-1}$. $^1$H NMR (500 MHz, CDCl$_3$) δ: 2.76 (1H, dd, J=5.2, 2.6, H-4a), 2.79 (1H, dd, J=5.2, 4.0, H-4b), 3.09 (1H, ddd, J=4.6, 4.0, 2.6, H-3), 3.56 (1H, ddd, J=5.3, 4.6, 4.6, H-2), 3.63 (1H, dd, J=10.3, 5.3, H-1a), 3.66 (1H, dd, J=10.3, 4.6, H-1b), 3.81 (3H, s, OCH$_3$), 4.51 (2H, s-like, OCH$_2$Ar), 4.68/4.72 (each 1H, d, J=12.6, OCH$_2$Ar), 6.88/7.25 (each 1H, d-like, J=8.6, arom.), 7.44/7.58 (each 1H, br d-like, J=8.1, arom.). $^{13}$C NMR (125 MHz, CDCl$_3$) δ: 45.0 (C-4), 51.3 (C-3), 55.3 (OCH$_3$), 70.4 (C-1), 71.8/73.2 (OCH$_2$Ar), 77.7 (C-2), 113.5/127.5/129.3 (d, arom.), 124.0 (q, J=271, CF$_3$) 125.2 (q, J=3.6, C$_{ortho}$—CF$_3$), 129.7 (q, J=32.2, C$_{ipso}$—CF$_3$), 130.1/142.5/159.3 (s, arom.). FABMS (pos.) m/z: 405 [M+Na]$^+$.

Example 77

3,4-Anhydro-2-O-(p-methoxybenzyl)-1-O-(o-nitrobenzyl)-D-erythritol compound (18t) (Reaction Scheme 4)

By following substantially the same procedures as for the synthesis of the compound (18a), the compound (17t) (510 mg, 1.35 mmol) was epoxidated with TPP and DEAD yielding the title compound (18t, 408 mg, 84%) as colorless oily substance.

[Chem. 95]

Compound (18t): colorless oily substance. $[\alpha]_D^{25}$ +10.5 (c=4.20, CHCl$_3$). IR (neat): 1612, 1519, 1465, 1342, 1303, 1246, 1172, 1095, 1033 cm$^{-1}$. $^1$H NMR (500 MHz, CDCl$_3$) δ: 2.80 (1H, dd, J=5.2, 2.6, H-4a), 2.83 (1H, dd, J=5.2, 4.0, H-4b), 3.11 (1H, ddd, J=4.3, 4.0, 2.6, H-3), 3.59 (1H, ddd, J=5.2, 4.3, 4.3, H-2), 3.67 (1H, dd, J=10.3, 5.2, H-1a), 3.69 (1H, dd, J=10.3, 4.3, H-1b), 3.81 (3H, s, OCH$_3$), 4.51 (2H, s-like, OCH$_2$Ar), 5.00/5.05 (each 1H, d, J=14.9, OCH$_2$Ar), 6.88/7.26 (each 2H, d-like, J=8.6, arom.), 7.43 (1H, td, J=7.8, 0.9, arom.), 7.61 (1H, td, J=7.8, 1.2, arom.), 7.84 (1H, dd, J=7.8, 0.9, arom.), 8.05 (1H, dd, J=7.8, 1.2, arom.). $^{13}$C NMR (125 MHz, CDCl$_3$) δ: 45.2 (C-4), 51.1 (C-3), 55.3 (OCH$_3$), 69.0 (C-1), 70.1/73.2 (OCH$_2$Ar), 78.4 (C-2), 113.8/124.6/128.0/128.9/129.3/133.6 (d, arom.), 130.0/135.0/147.2/159.2 (s, arom.). FABMS (pos.) m/z: 382 [M+Na]$^+$.

Example 78

3,4-Anhydro-2-O-(p-methoxybenzyl)-1-O-(m-nitrobenzyl)-D-erythritol compound (18u) (Reaction Scheme 4) (Reaction Scheme 4)

By following substantially the same procedures as for the synthesis of the compound (18a), the compound (17u) (545 mg, 1.44 mmol) was epoxidated with TPP and DEAD yielding the title compound (18u, 424 mg, 82%) as colorless oily substance.

[Chem. 96]

Compound (18u): colorless oily substance. $[\alpha]_D^{25}$ +13.2 (c=0.95, CHCl$_3$). IR (neat): 1612, 1585, 1516, 1465, 1350, 1300, 1246, 1172, 1091, 1034 cm$^{-1}$. $^1$H NMR (500 MHz, CDCl$_3$) δ: 2.78 (1H, dd, J=5.2, 2.8, H-4a), 2.81 (1H, dd, J=5.2, 4.1, H-4b), 3.10 (1H, ddd, J=4.3, 4.1, 2.8, H-3), 3.62 (1H, ddd, J=4.8, 4.3, 4.0, H-2), 3.64 (1H, dd, J=10.0, 4.8, H-1a), 3.67 (1H, dd, J=10.0, 4.0, H-1b), 3.81 (3H, s, OCH$_3$), 4.51 (2H, s-like, OCH$_2$Ar), 4.71/4.76 (each 1H, d, J=12.6, OCH$_2$Ar), 6.88/7.26 (each 2H, d-like, J=8.6, arom.), 7.49 (1H, dd, J=8.0, 7.8, arom.), 7.65 (1H, br d-like, J=ca. 7.8, arom.), 8.13 (1H, br dd-like, J=ca. 8.0, 1.5, arom), 8.22 (1H, br t-like, J=ca. 1.5, arom.). $^{13}$C NMR (125 MHz, CDCl$_3$) δ: 45.0 (C-4), 51.3 (C-3), 55.3 (OCH$_3$), 70.3 (C-1), 71.4/73.2 (OCH$_2$Ar), 77.7 (C-2), 113.8/122.1/122.5/129.2/129.3/133.2 (d, arom.), 129.9/140.6/148.3/159.3 (s, arom.). FABMS (pos.) m/z: 382 [M+Na]$^+$.

Example 79

3,4-Anhydro-2-O-(p-methoxybenzyl)-1-O-(p-nitrobenzyl)-D-erythritol compound (18v) (Reaction Scheme 4)

By following substantially the same procedures as for the synthesis of the compound (18a), the compound (17v) (230 mg, 0.61 mmol) was epoxidated with TPP and DEAD yielding the title compound (18v, 184 mg, 85%) as colorless oily substance.

[Chem. 97]

Compound (18v): colorless oily substance. $[\alpha]_D^{24}$ −6.17 (c=1.50, CHCl$_3$). IR (neat): 1612, 1516, 1454, 1346, 1250, 1177, 1096 1034 cm$^{-1}$. $^1$H NMR (500 MHz, CDCl$_3$) δ: 2.78 (1H, dd, J=5.5, 2.9, H-4a), 2.80 (1H, dd, J=5.5, 4.1, H-4b), 3.10 (1H, ddd, J=4.1, 4.1, 2.9, H-3), 3.61 (1H, ddd, J=5.8, 4.3, 4.1, H-2), 3.660 (1H, dd, J=9.8, 5.8, H-1a), 3.663 (1H, dd, J=9.8, 4.3, H-1b), 3.81 (3H, s, OCH$_3$), 4.51 (2H, s-like, OCH$_2$Ar), 4.72/4.77 (each 1H, d, J=13.2, OCH$_2$Ar), 6.88/7.25 (each 1H, d-like, J=8.9, arom.), 7.49/8.17 (each 1H, d-like, J=8.9, arom.). $^{13}$C NMR (125 MHz, CDCl$_3$) δ: 44.8 (C-4), 51.3 (C-3), 55.3 (OCH$_3$), 70.3 (C-1), 71.5/73.2 (OCH$_2$Ar), 77.7 (C-2), 113.8/123.5/127.6/129.3 (d, arom.), 129.9/146.0/147.3/159.3 (s, arom.). FABMS (pos.) m/z: 382 [M+Na]$^+$.

Example 80

3,4-Anhydro-1-O-(p-hydroxymethylbenzyl)-2-O-(p-(p-methoxybenzyloxymethyl)benzyl)-D-erythritol compound (18w) (Reaction Scheme 4)

By following substantially the same procedures as for the synthesis of the compound (18a), the compound (17w) (450 mg, 0.93 mmol) was epoxidated with TPP and DEAD yielding the title compound (18w, 323 mg, 75%) as colorless oily substance.

[Chem. 98]

Compound (18w): colorless oily substance. $[\alpha]_D^{24}$ −6.17 (c=1.50, CHCl$_3$). IR (neat): 1612, 1516, 1454, 1346, 1250, 1177, 1096 1034 cm$^{-1}$. $^1$H NMR (500 MHz, CDCl$_3$) δ: 2.78 (1H, dd, J=5.5, 2.9, H-4a), 2.80 (1H, dd, J=5.5, 4.1, H-4b), 3.10 (1H, ddd, J=4.1, 4.1, 2.9, H-3), 3.61 (1H, ddd, J=5.8, 4.3, 4.1, H-2), 3.660 (1H, dd, J=9.8, 5.8, H-1a), 3.663 (1H, dd, J=9.8, 4.3, H-1b), 3.81 (3H, s, OCH$_3$), 4.51 (2H, s-like, OCH$_2$Ar), 4.72/4.77 (each 1H, d, J=13.2, OCH$_2$Ar), 6.88/7.25 (each 1H, d-like, J=8.9, arom.), 7.49/8.17 (each 1H, d-like, J=8.9, arom.). $^{13}$C NMR (125 MHz, CDCl$_3$) δ: 44.8

(C-4), 51.3 (C-3), 55.3 (OCH$_3$), 70.3 (C-1), 71.5/73.2 (OCH$_2$Ar), 77.7 (C-2), 113.8/123.5/127.6/129.3 (d, arom.), 129.9/146.0/147.3/159.3 (s, arom.). FABMS (pos.) m/z: 382 [M+Na]$^+$.

Example 81

3,4-Anhydro-1-O-(p-methoxybenzyl)-2-O-(naphthalen-1-ylmethyl)-D-erythritol compound (18x) (Reaction Scheme 4)

By following substantially the same procedures as for the synthesis of the compound (18a), the compound (17x) (185 mg, 0.48 mmol) was epoxidated with TPP and DEAD yielding the title compound (18x, 140 mg, 80%) as colorless oily substance.
[Chem. 99]
Compound (18x): colorless oily substance. $[\alpha]_D^{26}$ +9.5 (c=1.06, CHCl$_3$). IR (neat): 3360, 3047, 2997, 2862, 2353, 2059, 1732, 1612, 1512, 1300, 1249, 1172, 1095 cm$^{-1}$. $^1$H NMR (500 MHz, CDCl$_3$) δ: 2.67 (1H, dd, J=5.5, 2.9 Hz, H-4a), 2.72 (1H, dd, J=5.5, 4.0 Hz, H-4b), 3.09 (1H, ddd, J=5.2, 4.0, 2.9 Hz, H-3), 3.61 (1H, ddd, J=5.2, 5.2, 5.2 Hz H-2), 3.64 (1H, dd, J=5.2, 5.2 Hz, H-1a), 3.67 (1H, dd, J=5.2, 5.2 Hz, H-1b), 3.80 (3H, s, OCH$_3$), 4.50 (2H, s-like, OCH$_2$Ar), 5.09 (2H, s, OCH$_2$Ar), 6.86 (2H, d-like, J=8.9 Hz, arom.), 7.24 (2H, d-like, J=8.9 Hz, arom.), 7.41 (1H, dd, J=8.3, 7.2 Hz, arom.), 7.46-7.51 (3H, m, arom.), 7.80 (1H, d, J=8.3 Hz, arom.), 7.82-7.88 (1H, m, arom.), 8.12-8.18 (1H, m, arom.). $^{13}$C NMR (125 MHz, CHCl$_3$) δ: 45.3 (C-4), 51.5 (C-3), 55.3 (OCH$_3$), 70.5 (C-1), 71.4/73.2 (OCH$_2$Ar), 77.2 (C-2), 113.8/124.2/125.1/125.8/126.1/126.7/128.4/128.7/129.3 (d, arom.), 130.2/131.8/133.7/133.7/159.2 (s, arom.). FABMS (pos.) m/z: 387 [M+Na]$^+$.

Example 82

3,4-Anhydro-1-O-(p-methoxybenzyl)-2-O-(naphthalen-2-ylmethyl)-D-erythritol compound (18y) (Reaction Scheme 4)

By following substantially the same procedures as for the synthesis of the compound (18a), the compound (17y) (220 mg, 0.57 mmol) was epoxidated with TPP and DEAD yielding the title compound (18y, 157 mg, 75%) as colorless oily substance.
[Chem. 100]
Compound (18y): colorless oily substance. $[\alpha]_D^{23}$ +8.92 (c=1.20, CHCl$_3$). IR (neat): 2927, 2862, 1612, 1512, 1462, 1361, 1300, 1246, 1172, 1091, 1033 cm$^{-1}$. $^1$H NMR (700 MHz, CDCl$_3$) δ: 2.73 (1H, dd, J=5.4, 2.8 Hz, H-4a), 2.78 (1H, dd, J=5.4, 4.1 Hz, H-4b), 3.10 (1H, ddd, J=5.0, 4.1, 2.8 Hz, H-3), 3.56 (1H, ddd, J=5.3, 5.0, 4.4 Hz, H-2), 3.65 (1H, dd, J=10.2, 5.3 Hz, H-1a), 3.67 (1H, dd, J=10.2, 4.4 Hz, H-1b), 3.80 (3H, s, OCH$_3$), 4.51 (2H, s-like, OCH$_2$Ar), 4.79/4.83 (each 1H, d, J=12.0 Hz, OCH$_2$Ar), 6.87/7.26 (each 2H, d-like, J=8.6 Hz, arom.), 7.44-7.84 (7H, m, arom.). $^{13}$C NMR (175 MHz, CHCl$_3$) δ: 45.4 (C-4), 51.4 (C-3), 55.2 (OCH$_3$), 70.4 (C-1), 72.6/73.2 (OCH$_2$Ar), 77.2 (C-2), 113.8/125.7/125.9/126.1/126.4/127.7/127.9/128.1/129.3 (d, arom.), 130.2/133.0/133.2/135.8/159.2 (s, arom.). FABMS (pos.) m/z: 387 [M+Na]$^+$.

Example 83

3,4-Anhydro-1-O-(p-methoxybenzyl)-2-O-(pyridin-3-ylmethyl)-D-erythritol compound (18z) (Reaction Scheme 4)

By following substantially the same procedures as for the synthesis of the compound (18a), the compound (17z) (395 mg, 1.18 mmol) was epoxidated with TPP and DEAD yielding the title compound (18z, 214 mg, 52%) as pale yellow oily substance.
[Chem. 101]
Compound (18z): pale yellow oil. Analytical samples of 18z were obtained by means of column chromatography (hexane-ethyl acetate 5:1→1:1). $[\alpha]_D^{25}$ +5.21 (c=0.91, CHCl$_3$). IR (neat): 1728, 1612, 1582, 1516, 1466, 1450, 1427, 1366, 1300, 1250, 1177, 1092, 1030, cm$^{-1}$. $^1$H NMR (500 MHz, CDCl$_3$) δ: 2.75 (1H, dd, J=5.2, 2.6 Hz, H-4a), 2.79 (1H, dd, J=5.2, 4.0 Hz, H-4b), 3.08 (1H, ddd, J=4.3, 4.0, 2.9 Hz, H-3), 3.57 (1H, ddd, J=5.2, 4.3, 4.3 Hz, H-2), 3.62 (1H, dd, J=10.3, 5.2 Hz, H-1a), 3.65 (1H, dd, J=10.3, 4.3 Hz, H-1b), 3.81 (3H, s, OCH$_3$), 4.51 (2H, s-like, CH$_2$Ar), 4.65/4.69 (each 1H, d-like, J=12.3 Hz, CH$_2$Ar), 6.88/7.25 (each 2H, d-like, J=8.6 Hz, arom.), 7.27 (1H, dd-like, J=ca. 7.8, 5.0 Hz, Pyridine H-5), 7.69 (1H, dt-like, J=7.8, 2.0 Hz, Pyridine H-4) 8.53 (1H, d-like, J=5.0 Hz, Pyridine H-6), 8.56 (1H, br s, Pyridine H-2). $^{13}$C NMR (175 MHz, CDCl$_3$) δ: 45.0 (C-4), 51.3 (C-3), 55.3 (OCH$_3$), 70.2 (C-1), 70.3/73.2 (CH$_2$Ar), 77.5 (C-2), 113.8/123.3/129.3/135.4/148.9/149.0 (d, arom.), 129.9/133.8/159.2 (s, arom.). FABMS (pos.) m/z: 316 [M+H]$^+$.

Example 84

3,4-Anhydro-1-O-(p-methoxybenzyl)-2-O-(pyridin-4-ylmethyl)-D-erythritol compound (18aa) (Reaction Scheme 4)

By following substantially the same procedures as for the synthesis of the compound (18a), the compound (17aa) (420 mg, 1.26 mmol) was epoxidated with TPP and DEAD yielding the title compound (18aa, 204 mg, 51%) as colorless oily substance.
[Chem. 102]
Compound (18aa): colorless oily substance., $[\alpha]_D^{23}$ +7.3 (c=1.66, CHCl$_3$). IR (neat): 1609, 1512, 1458, 1416, 1361, 1300, 1250, 1172, 1096, 1034 cm$^{-1}$. $^1$H NMR (500 MHz, CDCl$_3$) δ: 2.78 (1H, dd, J=5.5, 2.9 Hz, H-4a), 2.80 (1H, dd, J=5.5, 4.3 Hz, H-4b), 3.09 (1H, ddd, J=4.3, 4.3, 2.9 Hz, H-3), 3.58 (1H, ddd, J=5.5, 4.3, 4.3 Hz, H-2), 3.64 (1H, dd, J=10.6, 5.5 Hz, H-1a), 3.67 (1H, dd, J=10.6, 4.3 Hz, H-1b), 3.81 (3H, s, OCH$_3$), 4.51 (2H, s-like, CH$_2$Ar), 4.64/4.69 (each 1H, d-like, J=13.8 Hz, CH$_2$Ar), 6.88/7.26 (each 2H, d-like, J=8.6 Hz, arom.), 7.25 (2H, d-like, J=6.1 Hz, pyridine H-2 and H-5), 8.55 (2H, d-like, J=6.1 Hz, pyridine H-2 and H-6). $^{13}$C NMR (175 MHz, CDCl$_a$) δ: 44.9 (C-4), 51.3 (C-3), 55.3 (OCH$_3$), 70.3 (C-1), 70.9/73.2 (CH$_2$Ar), 77.8 (C-2), 113.8/121.6/129.3/149.7 (d, arom.), 129.9/147.6/159.3 (s, arom.). FABMS (pos.) m/z: 316 [M+H]$^+$.

Example 85

2,3,5-tri-O-benzyl-1,4-[(R)-[1-O-benzyl-4-deoxy-2-O-methyl-D-erythritol-4-yl]episulfoniumylidene]-1,4-dideoxy-D-arabitol chloride (20a, X=Cl) (Reaction Scheme 5)

To a mixture of the epoxide compound (18a, 100 mg, 0.48 mmol), the thiosugar compound (19a) (168 mg, 0.4 mmol) and chloromethane (2 ml) was added tetrafluoroboric acid dimethyl ether complex (HBF$_4$.(CH$_3$)$_2$O, 63 μl, 0.52 mmol) at −60° C. The resulting reaction mixture was stirred for 3 hours and concentrated to dryness under reduced pressure. The residue was then purified with ion exchange resin IRA-400J (Cl$^-$ type) in 3 ml of methanol at room temperature, followed by filtering the resin off and concentrating the filtrate to yield an oily substance (290 mg). This substance was then purified with column chromatography (chloroform→chloroform/methanol; 100:1→50:1) yielding the title compound (20a, 234 mg, 88%).

[Chem. 103]

Compound (20a): colorless oily substance. $[\alpha]_D^{24}$ −7.3 (c=0.65, CHCl$_3$). IR (neat): 3174, 1454, 1404, 1365, 1261, 1095, 1072, 1030 cm$^{-1}$. $^1$H NMR (500 MHz, CDCl$_3$) δ: 3.41 (3H, s, OCH$_3$), 3.67 (1H, dd-like, J=ca. 11.5, 2.5 Hz, H-4'a), 3.68 (1H, ddd-like, J=ca. 6.0, 3.8, 2.5 Hz, H-3'), 3.76 (2H, d-like, J=8.0 Hz, H-5a and H-5b), 3.80 (1H, dd, J=11.5, 3.8 Hz, H-4'b), 4.10 (1H, dd, J=12.6, 3.7 Hz, H-1'a), 4.11-4.15 (1H, m, H-4), 4.13 (1H, dd-like, J=ca. 13.2, 2.5 Hz, H-1a), 4.16 (1H, dd-like, J=ca. 12.6, 7.8 Hz, H-1'b), 4.17 (1H, br d-like, J=ca. 1.5, 1.5 Hz, H-3), 4.31 (1H, dd, J=13.2, 3.8 Hz, H-1b), 4.34-4.39 (1H, m, H-2'), 4.39-4.41 (1H, m, H-2), 4.39 (1H, d, J=11.7 Hz, OCH$_2$Ph), 4.47-4.61 (7H, m, OCH$_2$Ph), 6.65 (1H, br s, OH), 7.13-7.37 (20H, m, arom.). $^{13}$C NMR (125 MHz, CDCl$_3$) δ: 48.4 (C-1), 51.9 (C-1'), 57.9 (OCH$_3$), 66.1 (C-4), 66.9 (C-5), 67.4 (C-4'), 68.1 (C-2'), 71.9/72.3/73.6 (2×C) (OCH$_2$Ph), 82.0 (C-3'), 82.3 (C-3), 82.4 (C-2), 127.7/127.8/127.96/127.99/128.2/128.3/128.4/128.5/128.56/128.6/128.7/128.8 (d, arom), 135.8/136.0/136.7/137.9 (arom). FABMS m/z: 629 [M-Cl]$^+$ (pos.).

Example 86

2,3,5-tri-O-benzyl-1,4-[(R)-[1-O-benzyl-4-deoxy-2-O-ethyl-D-erythritol-4-yl]episulfoniumylidene]-1,4-dideoxy-D-arabitol chloride (20b, X═Cl) (Reaction Scheme 5)

By following substantially the same procedure as used for the synthesis of the compound (20a), the epoxide compound (18b) was subjected to coupling reaction with the thiosugar compound (19a, 158 mg, 0.38 mmol), and the resulting reaction mixture was purified with ion exchange resin yielding the title compound (20b, 204 mg, 80%) as colorless oily substance.

[Chem. 104]

Compound (20b): colorless oily substance. $[\alpha]_D^{24}$ −8.8 (c=1.02, CHCl$_3$). IR (neat): 3186, 1497, 1454, 1400, 1366, 1327, 1257, 1207, 1099, 1072, 1026 cm$^{-1}$. $^1$H NMR (500 MHz, CDCl$_3$) δ: 1.15 (3H, t, J=7.0 Hz, OCH$_2$CH$_3$), 3.56/3.70 (each 1H, dq-like, J=9.2, 7.0 Hz, OCHHCH$_3$), 3.67 (1H, dd, J=10.6, 2.0 Hz, H-4'a), 3.74 (1H, dd, J=10.6, 2.6 Hz, H-4'b), 3.72-3.76 (1H, m, H-3'), 3.78 (2H, d, J=7.5 Hz, H-5a and H-5b), 4.07 (1H, br d-like, J=ca. 13.2 Hz, H-1a), 4.13 (1H, br dd-like, J=ca. 12.7, 3.5 Hz, H-1'a), 4.13-4.17 (1H, m, H-4), 4.17 (1H, dd-like, J=ca. 12.7, 7.8 Hz, H-1'b), 4.19 (1H, br dd-like, J=ca. 1.5, 1.5 Hz, H-3), 4.31 (1H, dd-like, J=ca. 13.2, 3.2 Hz, H-1b), 4.33-4.37 (1H, m, H-2'), 4.39 (1H, d, J=11.8 Hz, OCH$_2$Ph), 4.40-4.42 (1H, m, H-2), 4.43-4.62 (7H, m, OCH$_2$Ph), 6.57 (1H, br s, OH), 7.12-7.36 (20H, m, arom.). $^{13}$C NMR (125 MHz, CDCl$_3$) δ: 15.5 (OCH$_2$CH$_3$), 48.3 (C-1), 51.8 (C-1'), 65.8 (C-4), 66.0 (OCH$_2$CH$_3$), 67.0 (C-5), 68.0 (C-2'), 68.5 (C-4'), 71.9/72.2/73.5/73.6 (OCH$_2$Ph), 80.4 (C-3'), 82.4 (C-3), 82.5 (C-2), 127.6/127.8/127.9/128.1/128.2/128.3/128.4/128.47/128.54/128.68/128.72/128.83 (d, arom.), 135.9/136.0/136.7/137.9 (s, arom.). FABMS (pos.) m/z: 643 [MCl]$^+$.

Example 87

2,3,5-tri-O-benzyl-1,4-[(R)-[1-O-benzyl-4-deoxy-2-O-(1-pentyl)-D-erythritol-4-yl]episulfoniumylidene]-1,4-dideoxy-D-arabitol chloride (20c, X═Cl) (Reaction Scheme 5)

By following substantially the same procedure as used for the synthesis of the compound (20a), the epoxide compound (18c, 150 mg, 0.57 mmol) was subjected to coupling reaction with the thiosugar compound (19a, 200 mg, 0.48 mmol), and the resulting reaction mixture was purified with ion exchange resin yielding the title compound (20c, 281 mg, 82%) as colorless oily substance.

[Chem. 105]

Compound (20c): colorless oily substance. $[\alpha]^{23}_D$ −6.4 (c=0.96, CHCl$_3$). IR (neat): 3167, 1497, 1454, 1400, 1362, 1207, 1096, 1030 cm$^{-1}$. $^1$H NMR (700 MHz, CDCl$_3$) δ: 0.87 [3H, t, J=7.0 Hz, O(CH$_2$)$_4$CH$_3$], 1.23-1.32 [4H m O(CH$_2$)$_2$(CH$_2$)$_2$CH$_3$], 1.48-1.56 [2H, m, OCH$_2$CH$_2$(CH$_2$)$_2$CH$_3$], 3.48/3.61 [each 1H, dt, J=9.2, 7.0 Hz, OCH$_2$(CH$_2$)$_3$CH$_3$], 3.67 (1H dd, J=11.4, 3.9 Hz, H-4'a), 3.74 (1H, br dd-like, J=ca. 6.0, 3.9 Hz, H-3'), 3.75 (1H, br d-like, J=ca. 11.4 Hz, H-4'b), 3.77 (2H, d, J=7.4 Hz, H-5a and H-5b), 4.07 (1H, br d, J=13.2 Hz, H-1a), 4.13 (1H, dd J=13.0, 4.0 Hz, H-1'a), 4.14-4.18 (1H, m, H-4), 4.17 (1H, dd-like, J=ca, 13.0, 7.8 Hz, H-1'b), 4.19 (1H, br s-like, H-3), 4.31 (1H, dd, J=13.2, 3.4 Hz, H-1b), 4.34-4.38 (1H, m, H-2'), 4.38-4.40 (1H, br m, H-2), 4.38-4.61 (8H, m, CH$_2$Ph), 6.60 (1H, br s, OH), 7.23-7.36 (20H, m, arom.). $^{13}$C NMR (175 MHz, CDCl$_3$) δ: 14.0 [O(CH$_2$)$_4$CH$_3$], 22.4 [O(CH$_2$)$_3$CH$_2$CH$_3$], 28.1 [O(CH$_2$)$_2$CH$_2$CH$_2$CH$_3$], 29.6 [OCH$_2$CH$_2$(CH$_2$)$_2$CH$_3$], 48.2 (C-1), 51.9 (C-1'), 65.9 (C-4), 67.0 (C-5), 68.1 (C-2'), 68.4 (C-4'), 70.8 [OCH$_2$(CH$_2$)$_3$CH$_3$], 71.9/72.3/73.6/73.6 (CH$_2$Ph), 80.7 (C-3'), 82.4 (C-3), 82.5 (C-2), 127.7/127.8/127.9/128.0/128.2/128.3/128.4/128.49/128.54/128.6/128.7/128.8 (d, arom.), 135.9/136.0/136.7/138.0 (s, arom). FABMS (pos.) m/z: 685 [MC1]$^+$.

Example 88

2,3,5-tri-O-benzyl-1,4-[(R)-[1-O-benzyl-4-deoxy-2-O-(1-heptyl)-D-erythritol-4-yl]episulfoniumylidene]-1,4-dideoxy-D-arabitol chloride (20d, X═Cl) (Reaction Scheme 5)

By following substantially the same procedure as used for the synthesis of the compound (20a), the epoxide compound (18d, 130 mg, 0.45 mmol) was subjected to coupling reaction with the thiosugar compound (19a, 156 mg, 0.37 mmol), and the resulting reaction mixture was purified with ion exchange resin yielding the title compound (20d, 231 mg, 83%) as colorless oily substance.

[Chem. 106]

Compound (20d): colorless oily substance. $[\alpha]^{23}_D$ −15.0 (c=1.32, CHCl$_3$). IR (neat): 3167, 1454, 1404, 1362, 1207, 1096, 1030 cm$^{-1}$. H NMR (700 MHz, CDCl$_3$) δ: 0.87 (3H, t, J=7.0 Hz, O(CH$_2$)$_6$CH$_3$), 1.21-1.31 [8H, m O(CH$_2$)$_2$(CH$_2$)$_4$CH$_3$], 1.47-1.55 [2H, m OCH$_2$CH$_2$(CH$_2$)$_4$CH$_3$], 3.49/3.60 [each 1H, dt, J=9.2, 7.0, OCH$_2$(CH$_2$)$_5$CH$_3$], 3.67 (1H, dd, J=11.0, 3.8 Hz, H-4'a), 3.72-3.76 (1H, m, H-3'), 3.75 (1H dd, J=11.0, 3.5 Hz, H-4'b), 3.77 (2H, d-like, J=7.4 Hz, H-5a and H-5b), 4.07 (1H, br d, J=ca. 13.2 Hz, H-1a), 4.13 (1H, dd, J=13.5, 3.8 Hz, H-1'a), 4.15-4.18 (1H, m, H-4), 4.16 (1H, dd, J=13.5, 7.5 Hz, H-1'b), 4.19 (1H, br s-like, H-3), 4.30 (1H, dd, J=13.2, 3.2 Hz, H-1b), 4.34-4.37 (1H, m, H-2'), 4.38 (1H, m. H-2), 4.38/4.47 (each 1H, d, J=11.6 Hz, CH$_2$Ph), 4.48-4.61

(6H, m, CH$_2$Ph), 6.58 (1H d, J=7.2 Hz, OH), 7.13-7.36 (20H, m, arom.). $^{13}$C NMR (175 MHz, CDCl$_3$) δ. 14.1 [O(CH$_2$)$_6$CH$_3$], 22.6 [O(CH$_2$)$_5$CH$_2$CH$_3$], 26.0 [O(CH$_2$)$_2$CH$_2$(CH$_2$)$_3$CH$_3$], 29.1 [O(CH$_2$)$_3$CH$_2$CH$_2$CH$_3$], 30.0 [OCH$_2$CH$_2$(CH$_2$)$_4$CH$_3$], 31.8 [O(CH$_2$)$_4$CH$_2$CH$_2$CH$_3$], 48.2 (C-1), 51.9 (C-1'), 65.9 (C-4), 67.0 (C-5), 68.1 (C-2'), 68.5 (C-4'), 70.9 [OCH$_2$(CH$_2$)$_5$CH$_3$], 71.9/72.3/73.58/73.63 (CH$_2$Ph), 80.7 (C-3'), 82.45 (C-3), 82.51 (C-2), 127.7/127.8/127.9/128.0/128.2/128.3/128.4/128.50/128.54/128.6/128.7/128.8 (d, arom.), 135.9/136.0/136.7/138.0 (s, arom). FABMS (pos.) m/z: 713 [M-Cl]$^+$.

Example 89

2,3,5-tri-O-benzyl-1,4-[(R)-[1-O-benzyl-4-deoxy-2-O-(1-tridecyl)-D-erythritol-4-yl]episulfoniumylidene]-1,4-dideoxy-D-arabitol chloride (20e, X=Cl) (Reaction Scheme 5)

By following substantially the same procedure as used for the synthesis of the compound (20a), the epoxide compound (18e, 100 mg, 0.27 mmol) was subjected to coupling reaction with the thiosugar compound (19a, 93 mg, 0.22 mmol), and the resulting reaction mixture was purified with ion exchange resin yielding the title compound (20e, 154 mg, 81%) as colorless oily substance.
[Chem. 107]
Compound (20e): colorless oily substance. [α]$_D^{24}$ −3.9 (c=0.96 CHCl$_3$). IR (neat): 3333, 2924, 2855, 1456, 1361, 1096, 1074, 1028 cm$^{-1}$. $^1$H NMR (700 MHz, CDCl$_3$) δ: 0.88 [3H, t, J=7.0 Hz, O(CH$_2$)$_{12}$CH$_3$], 1.21-1.31 [20H, m, O(CH$_2$)$_2$(CH$_2$)$_{10}$CH$_3$], 1.47-1.53 [2H, m, OCH$_2$CH$_2$(CH$_2$)$_{10}$CH$_3$], 3.48/3.60 [each 1H, dt, J=9.2, 7.0 Hz, OCH$_2$CH$_2$(CH$_2$)$_{10}$CH$_3$], 3.66 (1H, dd, J=10.6, 2.8 Hz, H-4'a), 3.72-3.76 (1H, m, H-3'), 3.74 (1H, dd, J=10.6, 2.8 Hz, H-4'b), 3.77 (2H, d, J=7.6 Hz, H-5a and H-5b), 4.07 (1H, dd, J=13.2, 1.8 Hz, H-1a), 4.13 (1H, dd, J=12.5, 4.0 Hz, H-1'a), 4.14-4.18 (1H, m, H-4), 4.17 (1H, dd, J=12.5, 9.0 Hz, H-1'b), 4.19 (1H, br dd-like, J=ca. 1.5, 1.5 Hz, H-3), 4.29 (1H, dd, J=13.2, 3.8 Hz, H-1b), 4.34-4.38 (1H, m, H-2'), 4.38-4.40 (1H, m, H-2), 4.39 (1H, d, J=11.8 Hz, OCH$_2$Ph), 4.44-4.60 (8H, m, OCH$_2$Ph), 6.60 (1H, br s, OH), 7.14-7.35 (20H, m, arom). $^{13}$C NMR (175 MHz, CDCl$_3$) δ: 14.1 [O(CH$_2$)$_{12}$CH$_3$], 22.6 [O(CH$_2$)$_{11}$CH$_2$CH$_3$], 26.1 [O(CH$_2$)$_2$CH$_2$(CH$_2$)$_9$CH$_3$], 29.3/29.5/29.6/29.7 [O(CH$_2$)$_3$(CH$_2$)$_7$(CH$_2$)$_2$CH$_3$], 30.0 [OCH$_2$CH$_2$(CH$_2$)$_{10}$CH$_3$], 31.9 [O(CH$_2$)$_{10}$CH$_2$CH$_2$CH$_3$], 48.2 (C-1), 51.9 (C-1'), 65.8 (C-4), 67.0 (C-5), 68.1 (C-2'), 68.4 (C-4'), 70.9 [OCH$_2$(CH$_2$)$_{11}$CH$_3$], 71.9/72.3/73.56/73.61 (OCH$_2$Ph), 80.7 (C-3'), 82.4 (C-3), 82.5 (C-2), 127.6/127.8/127.9/128.0/128.18/128.25/128.4/128.48/128.53/128.6/128.7/128.8 (d, arom), 135.9/136.0/136.7/138.0 (4C, s, arom). FABMS (pos.) m/z: 797 [M-Cl]$^+$.

Example 90

2,3,5-tri-O-benzyl-1,4-[(R)-[1-O-benzyl-4-deoxy-2-O-neopentyl-D-erythritol-4-yl]episulfoniumylidene]-1,4-dideoxy-D-arabitol chloride (20f, X=Cl) (Reaction Scheme 5)

By following substantially the same procedure as used for the synthesis of the compound (20a), the epoxide compound (18f, 60 mg, 0.23 mmol) was subjected to coupling reaction with the thiosugar compound (19a, 69 mg, 0.16 mmol), and the resulting reaction mixture was purified with ion exchange resin yielding the title compound (20f, 98 mg, 83%) as colorless oily substance.

[Chem. 108]
Compound (20f): colorless oily substance. [α]$_D^{20}$ −11.8 (c=1.05, CHCl$_3$). IR (neat): 3167, 2951, 2866, 1605, 1454, 1404, 1361, 1327, 1254, 1211, 1095, 1061, 1026 cm$^{-1}$. $^1$H NMR (500 MHz, CDCl$_3$) δ: 0.85 [9H, s, OCH$_2$C(CH$_3$)$_3$], 3.13/3.31 [each 1H, d, J=8.9 Hz, OCH$_2$C(CH$_3$)$_3$], 3.68 (1H, dd, J=10.4, 3.5 Hz, H-4'a), 3.69-3.73 (1H, m, H-3'), 3.73 (1H dd J=10.8, 8.9 Hz H-5a), 3.77 (1H, dd, J=10.8, 7.2 Hz, H-5b), 3.78 (1H, dd, J=10.4, 2.3 Hz, H-4'b), 4.08 (1H, dd, J=12.3, 3.4 Hz, H-1'a), 4.148 (1H, dd-like, J=ca. 12.3, 8.0 Hz, H-1'b), 4.15 (1H, br s-like, H-3), 4.16 (1H, dd-like, J=13.2, 2.3 Hz, H-1a), 4.14-4.18 (1H, m, H-4), 4.30 (1H, dd, J=13.2, 3.7 Hz, H-1b), 4.34-4.40 (1H, m, H-2'), 4.40 (1H, m, H-2), 4.44 (1H, d, J=11.8 Hz, CH$_2$Ph), 4.47-4.61 (7H, m, CH$_2$Ph), 7.14-7.36 (20H, m, arom.). $^{13}$C NMR (125 MHz, CDCl$_3$) δ. 26.7 [OCH$_2$C(CH$_3$)$_3$], 32.1 [OCH$_2$C(CH$_3$)$_3$], 48.0 (C-1), 51.8 (C-1'), 66.2 (C-4), 67.1 (C-5), 68.1 (C-2'), 68.5 (C-4'), 71.9/72.4/73.5/73.7 (CH$_2$Ph), 81.0 [OCH$_2$C(CH$_3$)$_3$], 81.3 (C-3'), 82.3 (C-2), 82.5 (C-3), 127.6/127.7/127.97/127.99/128.2/128.3/128.4/128.5/128.6/128.76/128.81 (d, arom.), 135.8/136.0/136.2/138.2 (s, arom). FABMS (pos.) m/z: 685 [M-Cl]$^+$.

Example 91

1,4-[(R)-[2-O-benzyl-4-deoxy-1-O-(p-methoxybenzyl)-D-erythritol-4-yl]episulfoniumylidene]-1,4-dideoxy-2,3,5-tri-O-(p-methoxybenzyl)-D-arabitol tetrafluoroborate (20g, X=BF$_4$) (Reaction Scheme 5)

To a mixture of the epoxide compound (18 g, 100 mg, 0.32 mmol), the thiosugar (19b, 136 mg, 0.27 mmol) and dichloromethane (2 ml) was added tetrafluoroboric acid dimethylether complex (HBF$_4$.(CH$_3$)$_2$, 63 μl, 0.52 mmol) at −60° C. The resulting reaction mixture was stirred at −60° C. for another 3 hours. After adding sodium acetate at −60° C. and quenching, the reaction, the resulting suspension was filtered, and the resulting inorganic substance was washed with dichloromethane. The filtrate was combined with the washings, and the mixture was concentrated under reduced pressure, leaving a pale yellow oily substance (284 mg). The residue was then treated with ion exchange resin IRA-400J (Cl$^-$ type) in 3 ml of methanol at room temperature, followed by purification with column chromatography (chloroform/methanol; 50:1→10:1) yielding the title compound (20 g, 185 mg, 76%) as colorless oily substance.
[Chem. 109]
Compound (20g): colorless oily substance. [α]$_D^{23}$ −8.87 (c=1.02, CHCl$_3$). IR (neat): 3499, 1612, 1516, 1454, 1303, 1250, 1176, 1072, 1030 cm$^{-1}$. $^1$H NMR (700 MHz, CDCl$_3$) δ: 3.59 (1H, dd, J=10.6, 3.6, H-4'a), 3.63 (1H, dd, J=10.2, 8.8, H-5a), 3.64 (1H, dd, J=13.2, 3.0, H-1a), 3.67 (1H, dd, J=10.6, 3.6, H-4'b), 3.680 (1H, dd, J=10.2, 6.7, H-5b), 3.682 (1H, dd, J=13.2, 2.0, H-1b), 3.72 (1H, ddd, J=5.5, 3.6, 3.6, H-3'), 3.76 (1H, dd-like, J=ca. 13.5, 7.1, H-1'a), 3.767/3.774/3.78/3.81 (each 3H, s, OCH$_3$), 3.80 (1H, dd-like, J=ca. 13.5, 3.6, H-1'b), 3.99 (1H, br dd-like, J=ca. 8.8. 6.7, H-4), 4.12 (1H, dd-like, J=ca. 2.0, 1.2, H-3), 4.27 (1H, ddd-like, J=ca. 3.0 2.0, 2.0, H-2), 4.23/4.30 (each 1H, d, J=11.4, OCH$_2$Ar), 4.29-4.32 (1H, m, H-2'), 4.37-4.47 (6H, m, CH$_2$Ar), 4.57/4.32 (each 1H, d, J=11.4, OCH$_2$Ar), 6.81-6.87 (8H, m, arom.), 7.02-7.30 (12H, m, arom.). $^{13}$C NMR (125 MHz, CDCl$_3$) δ: 48.1 (C-1), 50.8 (C-1'), 55.2 (C×4, OCH$_3$), 66.2 (C-4), 66.4 (C-5), 68.4 (C-4'), 68.6 (C-2'), 71.4/71.7/72.9/73.1/73.2 (CH$_2$Ar), 79.4 (C-3'), 81.9 (C-3), 82.1 (C-2), 113.8/113.9/114.0/114.1/128.00/128.3/128.5/129.55/129.63 (C×2)/130.0 (d, arom.), 127.9/128.03/128.9/137.6/159.3/159.5/159.71/159.74 (s, arom.). FABMS (pos.) m/z: 825 [M-BF$_4$]$^+$.

Example 92

1,4-Dideoxy-1,4-[(R)-[4-deoxy-1-O-(p-methoxybenzyl)-2-O-(o-methylbenzyl)-D-erythritol-4-yl]-episulfoniumylidene]-2,3,5-tri-O-(p-methoxybenzyl)-D-arabitol tetrafluoroborate (20h, X═BF$_4$) (Reaction Scheme 5)

By following substantially the same procedure as used for the synthesis of the compound (20g), the epoxide compound (18h, 33 mg, 0.24 mmol) and the thiosugar compound (19b, 102 mg, 0.20 mmol) were treated with tetrafluoroboric acid dimethylether complex (33 μl, 0.27 mmol), and the resulting reaction mixture was purified with ion exchange resin yielding the title compound (20h, 96 mg, 52%) as colorless oily substance.
[Chem. 110]
Compound (20h): colorless oily substance. $[\alpha]^{25}_D$ −8.96 (c=1.15, CHCl$_3$). IR (neat): 3499, 1612, 1585, 1516, 1451, 1396, 1361, 1250, 1176, 1080, 1034 cm$^{-1}$. $^1$H NMR (500 MHz, CDCl$_3$) δ: 2.30 (3H, s, C$_6$H$_4$CH$_3$), 3.58 (1H, dd, J=13.2, 2.0, H-1a), 3.60 (1H, dd, J=10.9, 3.5, H-4'a), 3.61 (1H, dd, J=10.3, 8.0, H-5a), 3.64 (1H, d, J=13.2, 3.8, H-1b), 3.66 (1H, dd, J=10.3, 6.9, H-5b), 3.70 (1H, dd, J=10.9, 4.1, H-4'b), 3.73 (1H, dd, J=14.0, 7.5, H-1'a), 3.74-3.77 (1H, m, H-3'), 3.77/3.78/3.79/3.82 (each 3H, s, OCH$_3$), 3.82 (1H, dd, J=14.0, 3.8, H-1'b), 3.97 (1H, br dd-like, J=ca. 8.0, 6.9, H-4), 4.11 (1H, br dd-like, J=ca. 2.0, 1.2, H-3), 4.23 (1H, ddd-like, J=ca. 3.8, 2.0, 2.0, H-2), 4.21/4.28 (each 1H, d, J=11.5 Hz, OCH$_2$Ar), 4.23 (1H, br dd-like, J=ca. 7.5, 3.8, H-2'), 4.36-4.47 (6H, m, OCH$_2$Ar), 4.57/4.66 (each 1H, d, J=11.2, OCH$_2$Ar), 6.81-6.88 (8H, m, arom.), 7.02-7.27 (12H, m, arom.). $^{13}$C NMR (125 MHz, CDCl$_1$) δ: 18.8 (C$_6$H$_4$CH$_3$), 48.1 (C-1), 51.1 (C-1'), 55.5 (OCH$_3$), 66.2 (C-4), 66.4 (C-5), 68.4 (C-4'), 68.7 (C-2'), 71.2/71.4/71.7/73.1/73.3 (OCH$_2$Ar), 79.6 (C-3'), 82.0 (C-3), 82.1 (C-2), 113.85/113.93/114.0/114.1/125.9/128.3/129.4/129.6/130.0/130.3 (d, arom.), 127.9/128.0/128.9/135.6/137.1/159.3/159.5/159.7/159.8 (s, arom.). FABMS (pos.) m/z: 839 [M-BF$_4$]$^+$.

Example 93

1,4-Dideoxy-1,4-[(R)-[4-deoxy-1-O-(p-methoxybenzyl)-2-O-(m-methylbenzyl)-D-erythritol-4-yl]-episulfoniumylidene]-2,3,5-tri-O-(p-methoxybenzyl)-D-arabitol tetrafluoroborate (20i, X═BF$_4$) (Reaction Scheme 5)

By following substantially the same procedure as used for the synthesis of the compound (20g), the epoxide compound (18i, 77 mg, 0.24 mmol) and the thiosugar compound (19b, 100 mg, 0.20 mmol) were treated with tetrafluoroboric acid dimethylether complex (33 μl, 0.27 mmol), and the resulting reaction mixture was purified with ion exchange resin yielding the title compound (20i, 94 mg, 52%) as colorless oily substance.
[Chem. 111]
Compound (20i): colorless oily substance. $[\alpha]^{24}_D$ −3.25 (c=0.84, CHCl$_3$). IR (neat): 3499, 1612, 1585, 1512, 1462, 1304, 1250, 1177, 1069, 1030 cm$^{-1}$. $^1$H NMR (500 MHz, CDCl$_3$) δ: 2.30 (3H, s, C$_6$H$_4$CH$_3$), 3.59 (1H, dd, J=10.6, 3.5, H-4'a), 3.640 (1H, dd-like, J=ca. 13.0, 3.0, H-1a), 3.65 (1H, dd-like, J=ca. 10.5, 8.0, 11-5a), 3.668 (1H, dd-like, J=ca. 13.0, 4.2, H-1b), 3.676 (1H, dd-like, J=ca. 10.6, 4.2 Hz, H-4'b), 3.69 (1H, dd-like, J=ca. 10.5, 6.2, H-5b), 3.73 (1H, ddd-like, J=ca. 5.5, 4.2, 3.5, H-3'), 3.77 (1H, dd, J=13.2, 7.5, H-1'a), 3.77/3.78/3.79/3.81 (each 3H, s, OCH$_3$), 3.83 (1H, dd, J=13.2, 3.4, H-1'b), 4.00 (1H, br dd-like, J=ca. 8.0, 6.2, H-4), 4.12 (1H, br dd-like, J=ca. 2.0, 1.2, H-3), 4.23/4.30 (each 1H, d, J=11.8, OCH$_2$Ar), 4.25 (1H, ddd-like, J=ca. 4.2, 3.0, 2.0, H-2), 4.29-4.33 (1H, m, H-2'), 4.37-4.48 (6H, m, OCH$_2$Ar), 4.54/4.60 (each 1H, d, J=11.2, CH$_2$Ar), 6.81-6.88 (8H, m, arom.), 7.02-7.23 (12H, m, arom.). $^{13}$C NMR (125 MHz, CDCl$_3$) δ: 21.3 (C$_6$H$_4$CH$_3$), 48.2 (C-1), 51.0 (C-1'), 66.4 (C-5), 68.4 (C-4'), 68.7 (C-2'), 71.4/71.7/72.9/73.1/73.2 (CH$_2$Ar), 79.4 (C-3'), 81.9 (C-3), 82.1 (C-2), 113.85/113.93/114.0/114.1/125.4/128.4/128.76/129.1/129.5/129.6/130.0 (d, arom.), 127.8/128.0/128.84/137.5/138.2/159.3/159.5/159.7/159.8 (s, arom.). FABMS (pos.) m/z: 839 [M-BF$_4$]$^+$.

Example 94

1,4-Dideoxy-1,4-[(R)-[4-deoxy-1-O-(p-methoxybenzyl)-2-O-(p-methylbenzyl)-D-erythritol-4-yl]-episulfoniumylidene]-2,3,5-tri-O-(p-methoxybenzyl)-D-arabitol tetrafluoroborate (20j, X═BF$_4$) (Reaction Scheme 5)

By following substantially the same procedure as used for the synthesis of the compound (20g), the epoxide compound (18j, 72 mg, 0.22 mmol) and the thiosugar compound (19b, 94 mg, 0.18 mmol) were treated with tetrafluoroboric acid dimethylether complex (30 μl, 0.25 mmol), and the resulting reaction mixture was purified with ion exchange resin yielding the title compound (20j, 85 mg, 50%) as colorless oily substance.
[Chem. 112]
Compound (20j): colorless oily substance. $[\alpha]^{23}_D$ −2.18 (c=0.85, CHCl$_3$). IR (neat): 3499, 1612, 1516, 1462, 1304, 1250, 1177, 1072, 1034 cm$^{-1}$. $^1$H NMR (500 MHz, CDCl$_3$) δ: 2.28 (3H, s, C$_6$H$_4$CH$_3$), 3.58 (1H, dd, J=10.6, 3.5, H-4'a), 3.638 (1H, dd-like, J=ca. 13.2, 3.0, H-1a), 3.642 (1H, dd-like, J=ca. 10.6, 7.8, H-5a), 3.66 (1H, dd-like, J=ca. 10.6, 4.2, H-4'b), 3.666 (1H, dd-like, J=ca. 13.2, 3.0, H-1b), 3.68 (1H, dd-like, J=ca. 10.6, 7.0, H-5b), 3.72 (1H, ddd, J=5.5, 4.2, 3.5, H-3'), 3.76 (1H, dd, J=13.2, 6.6, H-1'a), 3.77/3.78/3.79/3.81 (each 3H, s, OCH$_3$), 3.82 (1H, dd, J=13.2, 3.8 Hz, H-1'b), 3.99 (1H, br dd-like, J=ca. 7.8, 7.0, H-4), 4.13 (1H, br dd-like, J=ca. 2.0, 1.2, H-3), 4.22/4.29 (each 1H, d, J=11.5, OCH$_2$Ar), 4.25 (1H, ddd-like, J=ca. 3.0, 3.0, 2.0, H-2), 4.28-4.33 (1H, m, H-2'), 4.37-4.48 (6H, m, OCH$_2$Ar), 4.53/4.59 (each 1H, d, J=11.2, OCH$_2$Ar), 6.81-6.88 (8H, m, arom.), 7.01-7.22 (12H, m, arom.). $^{13}$C NMR (125 MHz, CDCl$_3$) δ: 21.1 (C$_6$H$_4$CH$_3$), 48.1 (C-1), 51.0 (C-1'), 55.2 (OCH$_3$), 66.1 (C-4), 66.4 (C-5), 68.4 (C-4'), 68.7 (C-2'), 71.4/71.7/72.8/73.1/73.2 (OCH$_2$Ar), 79.2 (C-3'), 82.0 (C-3), 82.1 (C-2), 113.85/113.93/114.0/114.1/128.5/129.2/129.55/129.63/130.0 (d, arom.), 127.9/128.0/128.9/134.5/137.8/159.3/159.5/159.7/159.8 (s, arom.). FABMS (pos.) m/z: 839 [M-BF$_4$]$^+$.

Example 95

1,4-[(R)-[2-O-(o-chlorobenzyl)-4-deoxy-1-O-(p-methoxybenzyl)-D-erythritol-4-yl]episulfoniumylidene]-1,4-dideoxy-2,3,5-tri-O-(p-methoxybenzyl)-D-arabitol tetrafluoroborate (20k, X═BF$_4$) (Reaction Scheme 5)

By following substantially the same procedure as used for the synthesis of the compound (20g), the epoxide compound (18k, 69 mg, 0.20 mmol) and the thiosugar compound (19b, 84 mg, 0.16 mmol) were treated with tetrafluoroboric acid dimethylether complex (27 μl, 0.22 mmol), and the resulting reaction mixture was purified with ion exchange resin yielding the title compound (20k, 76 mg, 49%) as colorless oily substance.
[Chem. 113]

Compound (20k): colorless oily substance. $[\alpha]^{23}{}_D$ −3.57 (c=1.26, CHCl$_3$). IR (neat): 3499, 1612, 1512, 1458, 1304, 1250, 1176, 1072, 1030 cm$^{-1}$. $^1$H NMR (500 MHz, CDCl$_3$) δ: 3.636 (1H, dd, J=10.3, 8.9, H-5a), 3.644 (1H, dd, J=10.3, 3.8, H-4'a), 3.68 (1H, dd, J=10.3, 6.9, H-5b), 3.71 (1H, dd, J=13.0, 3.0, H-1a), 3.72 (1H, dd, J=10.3, 3.8, H-4'b), 3.74 (1H, ddd-like, J=ca. 4.5, 3.8, 3.8, H-3'), 3.77 (3H, s, OCH$_3$), 3.78 (1H, dd, J=13.2, 7.0, H-1'a), 3.79 (6H, s, OCH$_3$), 3.81 (1H, dd-like, J=ca. 13.0, 4.0, H-1b), 3.81 (3H, s, OCH$_3$), 3.87 (1H, dd, J=13.2, 3.4, H-1'b), 4.00 (1H, br dd-like, J=ca. 8.9, 6.9, H-4), 4.12 (1H, br dd-like, J=ca. 2.0, 1.2, H-3), 4.27/4.35 (each 1H, d, J=11.5, OCH$_2$Ar), 4.30 (1H, ddd-like, J=ca. 4.0, 3.0, 2.0, H-2), 4.30-4.35 (1H, m, H-2'), 4.38-4.48 (6H, m, OCH$_2$Ar), 4.66/4.73 (each 1H, d, J=11.7, OCH$_2$Ar), 6.81-6.88 (8H, m, arom.), 7.03-7.43 (12H, m, arom.). $^{13}$C NMR (125 MHz, CDCl$_3$) δ: 48.1 (C-1), 50.8 (C-1'), 55.26/55.29 (C×3) (OCH$_3$), 66.35 (C-4), 66.44 (C-5), 68.3 (C-4'), 68.6 (C-2'), 70.0/71.5/71.8/73.2/73.3 (OCH$_2$Ar), 79.7 (C-3'), 81.9 (C-3), 82.1 (C-2), 113.9/114.0/114.08/114.13/127.1/129.4/129.5/129.6/129.65/129.70/130.0/130.7 (d, arom.), 127.8/128.0/128.8/133.6/135.1/159.3/159.6/159.77/159.80 (s, arom.). FABMS (pos.) m/z: 859 [M-BF$_4$]$^+$.

Example 96

1,4-[(R)-[2-O-(m-chlorobenzyl)-4-deoxy-1-O-(p-methoxybenzyl)-D-erythritol-4-yl]episulfoniumylidene]-1,4-dideoxy-2,3,5-tri-O-(p-methoxybenzyl)-D-arabitol tetrafluoroborate (20l, X=BF$_4$)
(Reaction Scheme 5)

By following substantially the same procedure as used for the synthesis of the compound (20g), the epoxide compound (18l, 82 mg, 0.24 mmol) and the thiosugar compound (19b, 100 mg, 0.20 mmol) were treated with tetrafluoroboric acid dimethylether complex (27 μl, 0.22 mmol), and the resulting reaction mixture was purified with ion exchange resin yielding the title compound (20l, 103 mg, 56%) as colorless oily substance.
[Chem. 114]

Compound (20l): colorless oily substance. $[\alpha]^{24}{}_D$ −12.3 (c=0.75, CHCl$_3$). IR (neat): 3499, 1612, 1512, 1466, 1304, 1250, 1177, 1072, 1030 cm$^{-1}$. $^1$H NMR (500 MHz, CDCl$_3$) δ: 3.59 (1H, dd, J=10.6, 3.8, H-4'a), 3.64 (1H, dd, J=10.3, 8.9, H-5a), 3.67 (1H, dd, J=10.6, 4.0, H-4'b), 3.68 (1H, dd, J=10.3, 6.3, H-5b), 3.70 (1H, dd, J=13.2, 3.7, H-1a), 3.74 (1H, ddd-like, J=ca. 5.0, 4.0, 3.8, H-3'), 3.776 (1H, dd-like, J=ca. 13.2, 4.5, H-1b), 3.77/3.78/3.79/3.81 (each 3H, s, OCH$_3$), 3.76-3.79 (1H, m, H-1'a), 3.83 (1H, dd, J=13.2, 4.6, H-1'b), 4.00 (1H, br dd-like, J=ca. 8.9, 6.3, H-4), 4.11 (1H, dd-like, J=ca. 2.0, 1.2, H-3), 4.26/4.34 (each 1H, d, J=11.5, OCH$_2$Ar), 4.29 (1H, ddd-like, J=ca. 4.0, 3.7, 2.0, H-2), 4.30-4.35 (1H, m, H-2'), 4.37-4.48 (6H, m, OCH$_2$Ar), 4.57/4.59 (each 1H, d, J=11.7, OCH$_2$Ar), 6.81-6.88 (8H, m, arom.), 7.03-7.31 (12H, m, arom.). $^{13}$C NMR (125 MHz, CDCl$_3$) δ: 48.2 (C-1), 50.8 (C-1'), 55.26/55.3 (OCH$_3$), 66.3 (C-4), 66.5 (C-5), 68.3 (C-4'), 68.6 (C-2'), 71.5/71.8/72.0/73.2/73.3 (OCH$_2$Ar), 79.9 (C-3'), 81.9 (C-3), 82.1 (C-2), 113.9/114.0/114.08/114.13/126.3/128.01/129.56/129.59/129.66/129.68/129.8/130.0 (d, arom.), 127.8/127.96/128.8/159.4/159.6/159.77/159.80 (s, arom.). FABMS (pos.) m/z: 859 [M-BF$_4$]$^+$.

Example 97

1,4-[(R)-[2-O-(p-chlorobenzyl)-4-deoxy-1-O-(p-methoxybenzyl)-D-erythritol-4-yl]episulfoniumylidene]-1,4-dideoxy-2,3,5-tri-O-(p-methoxybenzyl)-D-arabitol tetrafluoroborate (20m, X=BF$_4$)
(Reaction Scheme 5)

By following substantially the same procedure as used for the synthesis of the compound (20g), the epoxide compound (18m, 69 mg, 0.20 mmol) and the thiosugar compound (19b, 84 mg, 0.16 mmol) were treated with tetrafluoroboric acid dimethylether complex (27 μl, 0.22 mmol), and the resulting reaction mixture was purified with ion exchange resin yielding the title compound (20m, 68 mg, 44%) as colorless oily substance.
[Chem. 115]

Compound (20m): colorless oily substance. $[\alpha]^{24}{}_D$ −7.61 (c=1.38, CHCl$_3$). IR (neat): 3498, 1612, 1516, 1454, 1303, 1250, 1176, 1069, 1030 cm$^{-1}$. $^1$H NMR (500 MHz, CDCl$_3$) δ: 3.58 (1H, dd, J=10.6, 3.8, H-4'a), 3.640 (1H, dd, J=10.3, 8.0, H-5a), 3.644 (1H, dd, J=10.6, 4.0, H-4'b), 3.68 (1H, dd, J=10.3, 6.6, H-5b), 3.70 (1H, dd, J=13.4, 3.5, H-1a), 3.74 (1H, ddd-like, J=ca. 5.2, 4.0, 3.8, H-3'), 3.73-3.77 (1H, m, H-1b), 3.77/3.779/3.780/3.810 (each 3H, s. OCH$_3$), 3.78 (1H, dd-like, J=ca. 13.2, 7.0, H-1'a), 3.806 (1H, dd-like, J=ca. 13.2, 4.0, H-1'b), 3.99 (1H, br dd-like, J=ca. 8.0, 6.6, H-4), 4.12 (1H, br dd-like, J=ca. 2.0, 1.2, H-3), 4.26/4.34 (each 1H, d, J=11.5, OCH$_2$Ar), 4.29 (1H, br m, H-2), 4.30-4.33 (1H, m, H-2'), 4.34-4.47 (6H, m, OCH$_2$A), 4.26/4.34 (each 1H, d, J=11.8, OCH$_2$Ar), 6.81-6.87 (8H, m, arom.), 7.02-7.27 (12H, m, arom.). $^{13}$C NMR (125 MHz, CDCl$_3$) δ: 48.2 (C-1), 50.7 (C-1'), 55.2 (C×3)/55.3 (OCH$_3$), 66.2 (C-4), 66.5 (C-5), 68.4 (C-4'), 68.6 (C-2'), 71.5/71.8/72.1/73.16/73.20 (OCH$_2$Ar), 79.7 (C-3'), 81.9 (C-3), 82.1 (C-2), 113.8/113.9/114.06/114.10/128.6/129.55/129.59/129.62/129.7/130.0 (d, arom.), 127.9/128.0/128.8/133.7/136.3/159.4/159.6/159.7/159.8 (s, arom.). FABMS (pos.) m/z: 859 [M-BF$_4$]$^+$.

Example 98

1,4-[(R)-[2-O-(o-bromobenzyl)-4-deoxy-1-O-(p-methoxybenzyl)-D-erythritol-4-yl]episulfoniumylidene]-1,4-dideoxy-2,3,5-tri-O-(p-methoxybenzyl)-D-arabitol tetrafluoroborate (20n, X=BF$_4$)
(Reaction Scheme 5)

By following substantially the same procedure as used for the synthesis of the compound (20g), the epoxide compound (18n, 102 mg, 0.28 mmol) and the thiosugar compound (19b, 112 mg, 0.22 mmol) were treated with tetrafluoroboric acid dimethylether complex (390, 0.28 mmol), and the resulting reaction mixture was purified with ion exchange resin yielding the title compound (20n, 89 mg, 41%) as colorless oily substance.
[Chem. 116]

Compound (20n): colorless oily substance. $[\alpha]_D{}^{24}$ −4.47 (c=0.50, CHCl$_3$). IR (neat): 3499, 1612, 1516, 1469, 1361, 1250, 1178, 1072, 1030 cm$^{-1}$. $^1$H NMR (500 MHz, CDCl$_3$) δ: 3.63 (1H, dd, J=10.1, 9.2, H-5a), 3.64 (1H, dd, J=10.6, 3.8, H-4'a), 3.68 (1H, dd, J=10.1, 6.6, H-5b), 3.71 (1H, dd, J=13.2, 4.0, H-1a), 3.72 (1H, dd, J=10.6, 3.8, H-4'b), 3.75 (1H, dd, J=13.2, 3.8, H-1'a), 3.72-3.76 (1H, m, H-3'), 3.77/3.780/3.782/3.81 (each 3H, s, OCH$_3$), 3.80 (1H, br dd-like, J=ca.

13.2, 4.0, H-1b), 3.86 (1H, dd, J=13.2, 3.5, H-1'b), 3.99 (1H, br dd-like, J=ca. 9.2, 6.6, H-4), 4.13 (1H, br, s-like, H-3), 4.31 (1H, m, H-2), 4.30-4.33 (1H, m, H-2'), 4.27/4.44 (each 1H, d, J=12.8, OCH$_2$Ar), 4.38-4.46 (6H, m, OCH$_2$Ar), 4.63/4.70 (each 2H, d, J=11.8, arom.), 6.81-6.89 (8H, m, arom.), 7.03-7.52 (12H, m, arom.). $^{13}$C NMR (125 MHz, CDCl$_3$) δ: 48.1 (C-1), 50.8 (C-1'), 55.2/55.3 (OCH$_3$), 66.38 (C-5), 66.43 (C-4), 68.3 (C-4'), 68.5 (C-2'), 71.5/71.8/72.1/73.1/73.3 (OCH$_2$Ar), 79.7 (C-3'), 81.9 (C-3), 82.1 (C-2), 113.8/113.9/114.0/114.1/127.7/129.58/129.64/129.66/129.69/130.8 (d, arom.), 127.9/128.0/128.8/136.7/159.3/159.5/159.7/159.8 (s, arom.). FABMS (pos.) m/z: 903 and 905 [M-BF$_4$]$^+$.

Example 99

1,4-[(R)-[2-O-(m-bromobenzyl)-4-deoxy-1-O-(p-methoxybenzyl)-D-erythritol-4-yl]episulfoniumylidene]-1,4-dideoxy-2,3,5-tri-O-(p-methoxybenzyl)-D-arabitol tetrafluoroborate (20o, X=BF$_4$)
(Reaction Scheme 5)

By following substantially the same procedure as used for the synthesis of the compound (20g), the epoxide compound (18o, 102 mg, 0.26 mmol) and the thiosugar compound (19b, 110 mg, 0.21 mmol) were treated with tetrafluoroboric acid dimethylether complex (39 μl, 0.28 mmol), and the resulting reaction mixture was purified with ion exchange resin yielding the title compound (20o, 85 mg, 40%) as colorless oily substance.
[Chem. 117]
Compound (20o): colorless oily substance. [α]$^{24}_D$ +2.5 (c=0.36, CHCl$_3$). IR (neat): 3491, 1612, 1585, 1512, 1462, 1408, 1361, 1304, 1246, 1211, 1176, 1072, 1029 cm$^{-1}$. $^1$H NMR (500 MHz, CDCl$_3$) δ: 3.59 (1H, dd, J=10.6, 3.7, H-4'a), 3.64 (1H, dd, J=10.6, 8.6, H-5a), 3.65 (1H, dd, J=10.6, 3.7, H-4'b), 3.67 (1H, dd, J=10.6, 10.0, H-5b), 3.69 (1H, dd, J=13.2, 3.7, H-1a), 3.74 (1H, dd, J=13.2, 3.7, H-1b), 3.71-3.75 (1H, m, H-3'), 3.776/3.786/3.788/3.82 (each 3H, s, OCH$_3$), 3.73-3.80 (1H, m, H-1'a), 3.82 (1H, dd, J=13.5, 2.6, H-1'b), 4.00 (1H, br dd-like, J=10.0, 8.6, H-4), 4.11 (1H, br dd-like, J=ca 2.0, 2.0, H-3), 4.26/4.34 (each 1H, d, J=11.8, OCH$_2$Ar), 4.28 (1H, br ddd-like, J=3.7, 3.7, 2.0, H-2), 4.27-4.34 (1H, m, H-2'), 4.37-4.47 (6H, m, OCH$_2$Ar), 4.56/4.59 (each, 1H, d, J=11.8 Hz, OCH$_2$Ar), 6.81-7.48 (20H, m, arom.). $^{13}$C NMR (125 MHz, CDCl$_3$) δ: 48.2 (C-1), 50.8 (C-1'), 55.3 (OCH$_3$), 66.3 (C-4), 66.4 (C-5), 68.3 (C-4'), 68.6 (C-2'), 71.5/71.8/72.0/73.19/73.24 (OCH$_2$Ar), 79.8 (C-3'), 81.9 (C-3), 82.0 (C-2), 113.9/114.0/114.07/114.11/126.8/129.6/129.68/129.69/130.0/130.1/130.9 (d, arom.), 122.4/127.8/127.9/128.8/129.5/140.1/159.4/159.6/159.76/159.79 (s, arom.). FABMS (pos.) m/z: 903 and 905 [M-BF$_4$]$^+$.

Example 100)

1,4-[(R)-[2-O-(p-bromobenzyl)-4-deoxy-1-O-(p-methoxybenzyl)-D-erythritol-4-yl]episulfoniumylidene]-1,4-dideoxy-2,3,5-tri-O-(p-methoxybenzyl)-D-arabitol tetrafluoroborate (20p, X=BF$_4$)
(Reaction Scheme 5)

By following substantially the same procedure as used for the synthesis of the compound (20g), the epoxide compound (18p, 106 mg, 0.27 mmol) and the thiosugar compound (19b, 115 mg, 0.23 mmol) were treated with tetrafluoroboric acid dimethylether complex (41 μl, 0.29 mmol), and the resulting reaction mixture was purified with ion exchange resin yielding the title compound (20p, 98 mg, 46%) as colorless oily substance.
[Chem. 118]
Compound (20p): colorless oily substance. [α]$^{24}_D$ +1.7 (c=0.41, CHCl$_3$). IR (neat): 3503, 1612, 1585, 1512, 1462, 1404, 1362, 1304, 1254, 1215, 1177, 1072, 1030 cm$^{-1}$. $^1$H NMR (500 MHz, CDCl$_3$) δ: 3.58 (1H, dd, J=10.6, 3.8, H-4'a), 3.638 (1H, dd, J=10.6, 3.8, H-4'b), 3.642 (1H, dd, J=10.6, 8.6, H-5a), 3.675 (1H, dd, J=10.6, 7.0, H-5b), 3.682 (1H, dd, J=13.4, 3.8, H-1a), 3.73 (1H, ddd, J=5.5, 3.8, 3.8, H-3'), 3.76 (1H, dd-like, J=ca. 13.4, 2.0, H-1b), 3.76-3.80 (2H, m, H-1'a and H-1'b), 3.77/3.78/3.79/3.81 (each 3H, s, OCH$_3$), 3.99 (1H, br dd-like, J=8.6, 7.0, H-4), 4.12 (1H, br s-like, H-3), 4.28-4.32 (1H, m, H-2'), 4.29 (1H, m, H-2), 4.26/4.34 (each 1H, d, J=11.5, OCH$_2$Ar), 4.34-4.47 (6H, m, OCH$_2$Ar), 4.53/4.56 (each 1H, d, J=11.8, OCH$_2$Ar), 6.82-6.87 (8H, m, arom), 7.05/7.12/7.16/7.18/7.19/7.40 (each 2H, d-like, J=ca. 8.6 Hz, arom.). $^{13}$C NMR (125 MHz, CDCl$_3$) δ: 48.2 (C-1), 50.7 (C-1'), 55.2 (OCH$_3$), 66.2 (C-4), 66.5 (C-5), 68.3 (C-4'), 68.6 (C-2'), 71.5/71.8/72.1/73.17/73.21 (OCH$_2$Ar), 79.7 (C-3'), 81.9 (C-3), 82.0 (C-2), 113.86/113.94/114.08/114.10/129.57/129.64/129.7/129.9/130.0/131.5 (d, arom), 121.8/127.8/127.9/128.8/129.5/136.7/159.4/159.6/159.7/159.8 (s, arom). FABMS (pos.) m/z: 903 and 905 [M-BF$_4$]$^+$.

Example 101

1,4-Dideoxy-1,4-[(R)-[4-deoxy-1-O-(p-methoxybenzyl)-2-O-(o-trifluoromethylbenzyl)-D-erythritol-4-yl]episulfoniumylidene]-2,3,5-tri-O-(p-methoxybenzyl)-D-arabitol tetrafluoroborate (20q, X=BF$_4$)
(Reaction Scheme 5)

By following substantially the same procedure as used for the synthesis of the compound (20g), the epoxide compound (18q, 101 mg, 0.26 mmol) and the thiosugar compound (19b, 111 mg, 0.22 mmol) were treated with tetrafluoroboric acid dimethylether complex (39 μl, 0.28 mmol), and the resulting reaction mixture was purified with ion exchange resin yielding the title compound (20q, 120 mg, 56%) as colorless oily substance.
[Chem. 119]
Compound (20q): colorless oily substance. [α]$^{24}_D$ −8.1 (c=0.98, CHCl$_3$). IR (neat): 3406, 2936, 2873, 1612, 1585, 1516, 1458, 1408, 1362, 1315, 1250, 1177, 1115, 1083, 1034 cm$^{-1}$. $^1$H NMR (500 MHz, CDCl$_3$) δ: 3.62 (1H, dd, J=10.9, 3.7, H-4'a), 3.64 (1H, dd, J=10.6, 9.0, H-5a), 3.69 (1H, dd, J=10.6, 6.9, H-5b), 3.71 (1H, dd, J=10.9, 4.5, H-4'b), 3.72 (1H, dd, J=13.0, 3.8, H-1a), 3.75-3.83 (3H, m, H-1b, H-1'a and H-3'), 3.85 (1H, dd, J=13.2, 3.7, H-1'b), 3.76/3.77/3.78/3.80 (each 3H, s, OCH$_3$), 4.01 (1H, br dd-like, J=ca. 9.0, 6.9, H-4), 4.13 (1H, br s-like, H-3), 4.26/4.34 (each 1H, d, J=11.5, OCH$_2$Ar), 4.30 (1H, br m, H-2), 4.32-4.34 (1H, m, H-2'), 4.37-4.47 (6H, m, OCH$_2$Ar), 4.74/4.82 (each 1H, d, J=12.4, OCH$_2$Ar), 6.80-7.63 (20H, m, arom.). $^{13}$C NMR (125 MHz, CDCl$_3$) δ: 48.1 (C-1), 50.7 (C-1'), 55.2/55.3 (OCH$_3$), 66.3 (C-4), 66.4 (C-5), 68.2 (C-4'), 68.5 (C-2'), 68.8/71.5/71.7/73.1/73.2 (OCH$_2$Ar), 80.2 (C-3'), 81.9 (C-3), 82.1 (C-2), 113.8/113.9/114.0/114.1/127.9/129.57/129.61/129.7/129.9/130.7/132.2 (d, arom.), 124.3 [q, J=272 Hz, CF$_3$,], 125.8 [q, J=5.0 Hz, C$_{ortho}$—CF$_3$,], 128.0 [q, J=31.0 Hz, C$_{ipso}$—CF$_3$,], 128.8/135.9/159.3/159.5/159.71/159.74 [C$_{ipso}$—OCH$_3$]. FABMS (pos.) m/z: 893 [M-BF$_4$]$^+$.

Example 102

1,4-Dideoxy-1,4-[(R)-[4-deoxy-1-O-(p-methoxybenzyl)-2-O-(m-trifluoromethylbenzyl)-D-erythritol-4-yl]episulfoniumylidene]-2,3,5-tri-O-(p-methoxybenzyl)-D-arabitol tetrafluoroborate (20r, X=BF$_4$) (Reaction Scheme 5)

By following substantially the same procedure as used for the synthesis of the compound (20g), the epoxide compound (18r, 129 mg, 0.34 mmol) and the thiosugar compound (19b, 144 mg, 0.282 mmol) were treated with tetrafluoroboric acid dimethylether complex (50 μl, 0.37 mmol), and the resulting reaction mixture was purified with ion exchange resin yielding the title compound (20r, 134 mg, 48%) as colorless oily substance.

[Chem. 120]

Compound (20r): colorless oily substance. [α]$_D^{24}$ −2.2 (c=0.4, CHCl$_3$). IR (neat): 3499, 2920, 1612, 1585, 1516, 1465, 1362, 1330, 1304, 1253, 1177, 1072, 1033 cm$^{-1}$. $^1$H NMR (500 MHz, CDCl$_3$) δ: 3.59 (1H, dd, J=10.9, 3.7, H-4'a), 3.63 (1H, dd, J=10.3, 9.0, H-5a), 3.671 (1H, dd, J=10.9, 5.0, H-4'b), 3.673 (1H, dd, J=10.3, 6.3, H-5b), 3.69 (1H, dd, J=13.2, 4.8, H-1a), 3.72-3.81 (4H, m, H-1b, H-1'a, H-1'b and H-3'), 3.76/3.77/3.78/3.80 (each 3H, s, OCH$_3$), 4.00 (1H, br dd-like, J=9.0, 6.3, H-4), 4.11 (1H, br s-like, H-3), 4.24 (1H, d, J=11.5, OCH$_2$Ar), 4.30 (1H, br m, H-2), 4.32-4.35 (1H, m, H-2'), 4.25/4.34 (each 1H, d, J=11.5, OCH$_2$Ar), 4.37-4.46 (6H, m, OCH$_2$Ar), 4.65 (2H, s-like, OCH$_2$Ar), 6.80-6.86 (8H, m, arom.), 7.02-7.22 (8H, m, arom.), 7.41 (1H, dd, J=7.8, 7.8, arom.), 7.50 (1H, br d-like, J=ca. 7.8, arom.), 7.51 (1H, br d-like, J=ca. 7.8, arom.). $^{13}$C NMR (125 MHz, CDCl$_3$) δ: 48.2 (C-1), 50.6 (C-1'), 55.2/55.3 (OCH$_3$), 66.3 (C-4), 66.4 (C-5), 68.2 (C-4'), 68.6 (C-2'), 71.5/71.7/72.0/73.1/73.2 (OCH$_2$Ar), 80.0 (C-3'), 81.8 (C-3), 82.0 (C-2), 113.8/113.9/114.0/114.1/129.0/129.57/129.63/129.7/130.0/131.4 (d, arom.), 124.1 (q, J=271, CF$_3$), 124.4/124.5 (each q, J=3.6, C$_{ortho}$—CF$_3$), 130.6 [q, J=32.2, C$_{ipso}$—CF$_3$], 127.8/127.9/128.8/129.5/138.9/159.3/159.5/159.7/159.8 (s, arom.). FABMS (pos.) m/z: 893 [M-BF$_4$]$^+$.

Example 103

1,4-Dideoxy-1,4-[(R)-[4-deoxy-1-O-(p-methoxybenzyl)-2-O-(p-trifluoromethylbenzyl)-D-erythritol-4-yl]episulfoniumylidene]-2,3,5-tri-O-(p-methoxybenzyl)-D-arabitol tetrafluoroborate (20s, X=BF$_4$) (Reaction Scheme 5)

By following substantially the same procedure as used for the synthesis of the compound (20g), the epoxide compound (18s, 80 mg, 0.16 mmol) and the thiosugar compound (19b, 92 mg, 0.18 mmol) were treated with tetrafluoroboric acid dimethylether complex (31 μl, 0.25 mmol), and the resulting reaction mixture was purified with ion exchange resin yielding the title compound (20s, 92 mg, 52%) as colorless oily substance.

[Chem. 121]

Compound (20s): colorless oily substance. [α]$_D^{24}$ −3.65 (c=0.90, CHCl$_3$). IR (neat): 3498, 1612, 1516, 1466, 1327, 1249, 1176, 1065 cm$^{-1}$. $^1$H NMR (700 MHz, CDCl$_3$) δ: 3.60 (1H, dd, J=10.8, 3.6, H-4'a), 3.65 (1H, dd-like, J=ca. 10.8, 5.0, H-4'b), 3.64 (1H, dd, J=10.4, 9.0, H-5a), 3.68 (1H, dd, J=10.4, 6.8, H-5b), 3.71 (1H, dd, J=13.2, 3.6, H-1a), 3.75-3.79 (1H, m, H-3'), 3.772/3.776/3.780/3.81 (each 3H, s, OCH$_3$), 3.80 (2H, d-like, J=ca. 5.6, H-1'a and H-1'b), 3.83 (1H, br d-like, J=ca. 13.2, H-1b), 3.99 (1H, br dd-like, J=ca. 9.0, 6.8, H-4), 4.05 (1H, d, J=6.4, OH), 4.11 (1H, br s-like, H-3), 4.27 (1H, d, J=11.5, OCH$_2$Ar), 4.30 (1H, m, H-2), 4.30-4.34 (1H, m, H-2'), 4.34-4.47 (8H, m, OCH$_2$Ar), 6.81-6.87 (8H, m, arom.), 7.04/7.12/7.17/7.19 (each 2H, d-like, J=ca. 8.6, arom.) 7.40/7.53 (each 1H, d-like, J=8.0, arom.). $^{13}$C NMR (125 MHz, CDCl$_3$) δ: 48.1 (C-1), 50.6 (C-1'), 55.2/55.3 (OCH$_3$), 66.4 (C-4), 66.5 (C-5), 68.3 (C-4'), 68.7 (C-2'), 71.6/71.8/72.0/73.3 (OCH$_2$Ar), 80.0 (C-3'), 81.9 (C-3), 82.0 (C-2), 113.9/114.0/114.10/114.13 (d, arom.), 124.0 (q, J=275, CF$_3$) 125.4 (q, J=3.6, C$_{ortho}$—CF$_3$), 129.8 (q, J=32.2, C$_{ipso}$—CF$_3$), 127.7/127.9/128.7/129.5 (s, arom.). 128.1/129.60/129.66/129.71/130.0 (d, arom.), 141.9/159.4/159.6/159.81/159.84 (s, arom.). FABMS (pos.) m/z: 893 [M-BF$_4$]$^+$.

Example 104

1,4-Dideoxy-1,4-[(R)-[4-deoxy-1-O-(p-methoxybenzyl)-2-O-(o-nitrobenzyl)-D-erythritol-4-yl]-episulfoniumylidene]-2,3,5-tri-O-(p-methoxybenzyl)-D-arabitol tetrafluoroborate (20t, X=BF$_4$) (Reaction Scheme 5)

By following substantially the same procedure as used for the synthesis of the compound (20g), the epoxide compound (18t, 100 mg, 0.28 mmol) and the thiosugar compound (19b, 118 mg, 0.23 mmol) were treated with tetrafluoroboric acid dimethylether complex (41 μl, 0.28 mmol), and the resulting reaction mixture was purified with ion exchange resin yielding the title compound (20t, 110 mg, 50%) as colorless oily substance.

[Chem. 122]

Compound (20t): colorless oily substance. [α]$_D^{25}$ −13.8 (c=0.94, CHCl$_3$). IR (neat): 3503, 1612, 1585, 1516, 1465, 1346, 1303, 1250, 1177, 1072, 1033 cm$^{-1}$. $^1$H NMR (500 MHz, CDCl$_3$) δ: 3.61 (1H, dd, J=10.9, 4.0, H-4'a), 3.674 (1H, dd, J=10.3, 9.2, H-5a), 3.678 (1H, dd, J=10.9, 4.0, H-4'b), 3.72 (1H, dd, J=13.8, 3.7, H-1a), 3.73 (1H, dd, J=10.3, 7.2, H-5b), 3.70-3.74 (1H, m, H-3'), 3.76 (1H, dd, J=13.0, 6.3, H-1'a), 3.77/3.81 (each 3H, s, OCH$_3$), 3.78 (6H, s, OCH$_3$), 3.81 (1H, dd, J=13.0, 3.0, H-1'b), 3.94 (1H, dd, J=13.8, 1.7, H-1b), 4.11 (1H, br dd-like, J=9.2, 7.2, H-4), 4.16 (1H, br dd-like, J=ca. 2.0, 1.2, H-3), 4.29-4.33 (1H, m, H-2'), 4.31/4.39 (each 1H, d, J=11.5, 8H, m, OCH$_2$Ar), 4.34 (1H, ddd-like, J=ca. 3.7, 2.0, 1.7, H-2), 4.37-4.49 (6H, m, OCH$_2$Ar), 4.90/4.95 (each 1H, J=12.9, OCH$_2$Ar), 6.80-6.88 (8H, m, arom.), 7.05-7.24 (8H, m, arom.), 7.43 (1H, ddd, J=7.8, 7.5, 1.4, arom.), 7.58 (1H, ddd, J=8.3, 7.8, 1.2, arom.), 7.63 (1H, dd, J=7.5, 1.4, arom.), 7.93 (1H, dd, J=8.3, 1.2, arom.). $^{13}$C NMR (125 MHz, CDCl$_3$) δ: 48.1 (C-1), 50.4 (C-1'), 55.2/55.3 (OCH$_3$), 66.2 (C-4), 66.4 (C-5), 68.1 (C-4'), 68.4 (C-2'), 69.5/71.5/71.7/73.1/73.2 (OCH$_2$Ar), 80.3 (C-3'), 81.9 (C-3), 82.2 (C-2), 113.8/113.9/114.05/114.07/124.5/128.7/129.6/129.65/129.72/129.7/130.0/133.7 (d, arom.), 127.9/128.0/128.9/133.1/148.0/159.3/159.5/159.7 (s, arom.). FABMS (pos.) m/z: 870 [M-BF$_4$]$^+$.

Example 105

1,4-Dideoxy-1,4-[(R)-[4-deoxy-1-O-(p-methoxybenzyl)-2-O-(m-nitrobenzyl)-D-erythritol-4-yl]-episulfoniumylidene]-2,3,5-tri-O-(p-methoxybenzyl)-D-arabitol tetrafluoroborate (20u, X=BF$_4$) (Reaction Scheme 5)

By following substantially the same procedure as used for the synthesis of the compound (20g), the epoxide compound (18u, 100 mg, 0.29 mmol) and the thiosugar compound (19b, 118 mg, 0.23 mmol) were treated with tetrafluoroboric acid dimethylether complex (44 μl, 0.32 mmol), and the resulting reaction mixture was purified with ion exchange resin yielding the title compound (20u, 110 mg, 50%) as colorless oily substance.
[Chem. 123]

Compound (20u): colorless oily substance. $[\alpha]_D^{24}$ −7.78 (c=1.4, CHCl$_3$). IR (neat): 3498, 1612, 1585, 1516, 1454, 1350, 1303, 1246, 1176, 1068, 1029 cm$^{-1}$. $^1$H NMR (500 MHz, CDCl$_3$) δ: 3.61 (1H, dd, J=10.9, 3.7, H-4'a), 3.66 (1H, dd, J=10.3, 9.2, H-5a), 3.69 (1H, dd, J=10.9, 4.0, H-4'b), 3.70 (1H, dd, J=10.3, 6.3, H-5b), 3.77 (6H, s, OCH$_3$), 3.78/3.80 (each 3H, s, OCH$_3$), 3.79-3.82 (2H, m, H-1a and H-3'), 3.82-3.88 (2H, m, H-1'a and H-1'b), 4.02 (1H, br dd, J=9.2, 6.3, H-4), 4.12 (1H, s-like, H-3), 4.28/4.37 (each 1H, J=11.5, OCH$_2$Ar), 4.31-4.37 (1H, m, H-2'), 4.35 (1H, br m, H-2), 4.38-4.47 (6H, m, OCH$_2$Ar), 4.69 (2H, s-lke, OCH$_2$Ar), 6.80-7.22 (16H, m, arom.), 7.45 (1H, dd, J=8.0, 7.8, arom.), 7.63 (1H, br d, J=ca. 7.8, arom.), 8.07 (1H, br dd, J=ca. 8.0, 1.5, arom.), 8.13 (1H, br t-like, J=1.5, arom.). $^{13}$C NMR (125 MHz, CDCl$_3$) δ: 48.3 (C-1), 50.6 (C-1'), 55.20/55.24 (OCH$_3$), 66.3 (C-4), 66.5 (C-5), 68.2 (C-4'), 68.4 (C-2'), 71.3/71.5/71.7/73.17/73.1782 (OCH$_2$Ar), 80.3 (C-3'), 81.8 (C-3), 82.0 (C-2), 113.8/113.9/114.0/122.3/122.6/129.4/129.56/129.61/129.7/129.9 (d, arom.), 127.8/127.9/128.7/129.5/159.3/159.5/159.7 (s, arom.). FABMS (pos.) m/z: 870 [M-BF$_4$]$^+$.

Example 106

1,4-Dideoxy-1,4-[(R)-[4-deoxy-1-O-(p-methoxybenzyl)-2-O-(p-nitrobenzyl)-D-erythritol-4-yl]-episulfoniumylidene]-2,3,5-tri-O-(p-methoxybenzyl)-D-arabitol tetrafluoroborate (20v, X=BF$_4$) (Reaction Scheme 5)

By following substantially the same procedure as used for the synthesis of the compound (20g), the epoxide compound (18v, 90 mg, 0.25 mmol) and the thiosugar compound (19b, 106 mg, 0.21 mmol) were treated with tetrafluoroboric acid dimethylether complex (37 μl, 0.27 mmol), and the resulting reaction mixture was purified with ion exchange resin yielding the title compound (20v, 105 mg, 65%) as colorless oily substance.
[Chem. 124]

Compound (20v): colorless oily substance. $[\alpha]_D^{24}$ −39.4 (c=0.26, CHCl$_3$). IR (neat): 3518, 1612, 1516, 1466, 1346, 1303, 1249, 1177, 1087 1033 cm$^{-1}$. $^1$H NMR (500 MHz, CDCl$_3$) δ: 3.60 (1H, dd, J=10.6, 3.7 Hz, H-4'a), 3.65 (1H, dd-like, J=ca. 10.6, 8.9 Hz, H-5a), 3.66 (1H, dd-like, J=ca. 10.6, 3.1 Hz, H-4'b), 3.70 (1H, dd, J=10.6, 6.6 Hz, H-5b), 3.73 (1H, dd, J=13.5, 3.1 Hz, H-1a), 3.76-3.79 (1H, m, H-3'), 3.79-3:85 (2H, m, H-1'a and H-1'b), 3.768 (6H, s, OCH$_3$), 3.774/3.80 (each 3H, s, OCH$_3$), 3.90 (1H, br d-like, J=ca. 13.5 Hz, H-1b), 4.02 (1H, br dd-like, J=ca. 8.9, 6.6 Hz, H-4), 4.13 (1H, s-like, H-3), 4.30 (1H, d, J=11.5 Hz, OCH$_2$Ar), 4.30-4.34 (1H, m, H-2'), 4.36 (1H, m, H-2), 4.34-4.47 (5H, m, OCH$_2$Ar), 4.67/4.70 (each 1H, d, J=12.9 Hz, OCH$_2$Ar), 6.81-6.89 (8H, m, arom.), 7.03-7.21 (8H, m, arom.), 7.42/8.10 (each 1H, d-like, J=8.9, arom.). $^{13}$C NMR (125 MHz, CDCl$_3$) δ: 48.2 (C-1), 50.3 (C-1'), 55.2/55.3 (OCH$_3$), 66.4 (C-4), 66.5 (C-5), 68.2 (C-4'), 68.7 (C-2'), 71.4/71.6/71.8/73.21/73.24 (OCH$_2$Ar), 80.2 (C-3'), 81.9 (C-3), 82.0 (C-2), 113.9/114.0/114.08/114.10/123.5/128.2/129.58/129.62/129.7/129.9 (d, arom.), 127.8/127.9/128.7/129.5/145.4/147.3/159.4/159.6/159.78/159.81 (s, arom.). FABMS (pos.) m/z: 870 [M-BF$_4$]$^+$.

Example 107

1,4-Dideoxy-1,4-[(R)-[4-deoxy-1-O-(p-methoxybenzyl)-2-O-(p-(p-methoxybenzyloxymethyl)benzyl)-D-erythritol-4-yl]episulfoniumylidene]-2,3,5-tri-O-(p-methoxybenzyl)-D-arabitol tetrafluoroborate (20w, X=BF$_4$) (Reaction Scheme 5)

By following substantially the same procedure as used for the synthesis of the compound (20g), the epoxide compound (18w, 109 mg, 0.24 mmol) and the thiosugar compound (19b, 100 mg, 0.31 mmol) were treated with tetrafluoroboric acid dimethylether complex (42 μl, 0.27 mmol), and the resulting reaction mixture was purified with ion exchange resin yielding the title compound (20w, 120 mg, 57%) as colorless oily substance.
[Chem. 125]

Compound (20w): colorless oily substance. $[\alpha]^{23}_D$ −6.02 (c=0.73, CHCl$_3$). IR (neat): 3503, 1612, 1585, 1512, 1462, 1420, 1396, 1362, 1304, 1250, 1177, 1076, 1034 cm$^{-1}$. $^1$H NMR (700 MHz, CDCl$_3$) δ: 3.59 (1H, dd, J=10.6, 3.4, H-4'a), 3.63 (1H, dd, J=10.3, 8.6, H-5a), 3.65 (1H, dd-like, J=ca. 13.2, 3.0, H-1a), 3.666 (1H, dd-like, J=ca. 10.6, 4.0, H-4'b), 3.670 (1H, dd, J=10.6, 6.5, H-5b), 3.70 (1H, dd, J=13.2, 1.6, H-1b), 3.73 (1H, ddd-like, J=ca. 5.5, 4.0, 3.4, H-3'), 3.74 (1H, dd, J=13.5, 7.2, H-1'a), 3.77/3.776/3.779/3.780/3.803 (each 3H, s, OCH$_3$), 3.80 (1H, dd-like, J=ca. 13.5, 3.8, H-1'b), 3.99 (1H, br dd-like, J=ca. 8.6, 6.5, H-4), 4.11 (1H, br s-like, H-3), 4.14 (br s, OH), 4.21/4.29 (each 1H, d, J=11.4, OCH$_2$Ar), 4.24 (1H, m, Hz, H-2), 4.28-4.32 (1H, m, H-2'), 4.38-4.47 (10H, m, OCH$_2$Ar), 4.57/4.66 (each 1H, d, J=11.4, OCH$_2$Ar), 6.81-6.88 (10H, m, arom.), 7.01-7.31 (14H, m, arom.). $^{13}$C NMR (175 MHz, CDCl$_3$) δ: 48.1 (C-1), 50.9 (C-1'), 55.3 (OCH$_3$), 66.2 (C-4), 66.4 (C-5), 68.4 (C-4'), 68.7 (C-2'), 71.45/71.49/71.7/72.7/73.2/73.3 (OCH$_2$Ar), 79.4 (C-3'), 81.9 (C-3), 82.1 (C-2), 113.8/113.9/114.00/114.07/114.12/127.9/128.4/129.4/129.6/129.7/130.0 (d, arom.), 128.0/128.9/130.2/136.9/138.3/159.2/159.4/159.6/159.75/159.79 (s, arom.). FABMS (pos.) m/z: 975 [M-BE$_t$]$^+$.

Example 108

1,4-Dideoxy-1,4-[(R)-[4-deoxy-1-O-(p-methoxybenzyl)-2-O-(naphthalen-1-ylmethyl)-D-erythritol-4-yl]episulfoniumylidene]-2,3,5-tri-O-(p-methoxybenzyl)-D-arabitol tetrafluoroborate (20×, X=BF$_4$) (Reaction Scheme 5)

By following substantially the same procedure as used for the synthesis of the compound (20g), the epoxide compound (18x, 94 mg, 0.26 mmol) and the thiosugar compound (19b, 110 mg, 0.22 mmol) were treated with tetrafluoroboric acid dimethylether complex (39 μl, 0.28 mmol), and the resulting reaction mixture was treated with ion exchange resin yielding the title compound (20x, 68 mg, 33%) as colorless oily substance.
[Chem. 126]

Compound (20×): colorless oily substance. $[\alpha]_D^{26}$ +6.8 (c=1.40, CHCl$_3$). IR (neat): 3499, 2935, 2870, 1612, 1585, 1516, 1465, 1392, 1304, 1249, 1177, 1072, 1030 cm$^{-1}$. $^1$H NMR (500 MHz, CDCl$_3$) δ: 3.25 (1H, dd, J=13.2, 1.5 Hz, H-1a), 3.37 (1H, dd, J=13.2, 3.7 Hz, H-1b), 3.50 (1H, dd, J=10.5, 8.5 Hz, H-5a), 3.51 (1H, dd, J=13.2, 7.5 Hz, H-1'a), 3.53 (1H, dd, J=10.5, 7.0 Hz, H-5b), 3.63 (1H, dd, J=10.3, 2.9

Hz, H-4'a), 3.69 (1H, dd, J=13.2, 3.5 Hz, H-1'b), 3.76 (1H, dd-like, J=ca. 10.3, 3.7 Hz, H-4'b), 3.76-3.80 (1H, m, H-3'), 3.767/3.774/3.78/3.81 (each 3H, s, OCH$_3$), 3.82 (1H, br J=ca. 8.5, 7.0 Hz, H-4), 4.02 (1H, dd-like, J=ca. 2.0, 1.2 Hz, H-3), 4.10/4.18 (2H, d, J=11.5 Hz, OCH$_2$Ar), 4.11 (1H, ddd-like, J=ca. 3.7, 2.0, 1.5 Hz, H-2), 4.28-4.33 (1H, m, H-2'), 4.29-4.40 (4H, m, OCH$_2$Ar), 4.43/4.46/4.93/5.18 (each 1H, d, J=11.5 Hz, OCH$_2$Ar), 6.78-6.86 (8H, m, arom.), 6.98-8.14 (15H, m, arom.). $^{13}$C NMR (125 MHz, CHCl$_3$) δ: 47.7 (C-1), 50.8 (C-1'), 55.25/55.29 (OCH$_3$), 66.1 (C-4), 66.3 (C-5), 68.4 (C-2'), 68.5 (C-4'), 71.0/71.3/71.6/73.1/73.3 (OCH$_2$Ar), 78.9 (C-3'), 81.8 (C-3), 81.9 (C-2), 113.88/113.92/114.0/114.1/124.4/125.4/126.0/126.6/127.9/128.6/129.1/129.56/129.73/130.0 (d, arom.), 127.9/128.0/128.9/129.7/131.9/133.0/133.8/159.3/159.5/159.7 (C×2) (s, arom.). FABMS (pos.) m/z: 875 [M-BF$_4$]

Example 109

1,4-Dideoxy-1,4-[(R)-[4-deoxy-1-O-(p-methoxybenzyl)-2-O-(naphthalen-2-ylmethyl)-D-erythritol-4-yl] episulfoniumylidene]-2,3,5-tri-O-(p-methoxybenzyl)-D-arabitol tetrafluoroborate (20y, X=BF$_4$)
(Reaction Scheme 5)

By following substantially the same procedure as used for the synthesis of the compound (20g), the epoxide compound (18y, 74 mg, 0.20 mmol) and the thiosugar compound (19b, 86 mg, 0.17 mmol) were treated with tetrafluoroboric acid dimethylether complex (32 µl, 0.23 mmol), and the resulting reaction mixture was purified with ion exchange resin yielding the title compound (20y, 91 mg, 56%) as colorless oily substance.
[Chem. 127]

Compound (20y): colorless oily substance. $[\alpha]_D^{24}$ −4.01 (c=1.32, CHCl$_3$). IR (neat): 3499, 2931, 2839, 1612, 1585, 1516, 1465, 1454, 1361, 1303, 1250, 1177, 1072, 1034 cm$^{-1}$. $^1$H NMR (500 MHz, CDCl$_3$) δ: 3.59 (1H, dd-like, J=ca. 13.2, 2.5 Hz, H-1a), 3.610 (1H, dd-like, J=ca. 10.5, 8.5 Hz, H-5a), 3.614 (1H, dd-like, J=10.6, 3.5 Hz, H-4'a), 3.63 (1H, dd-like, J=ca. 13.2, 3.5 Hz, H-1b), 3.64 (1H, dd-like, J=ca. 10.5, 7.0 Hz, H-5b), 3.70 (1H, dd, J=10.6, 4.0 Hz, H-4'b), 3.753/3.764/3.78/3.81 (each 3H, s, OCH$_3$), 3.77 (1H, dd-like, J=ca. 13.4, 6.8 Hz, H-1'a), 3.77-3.81 (1H, m, H-3'), 3.84 (1H, dd, J=13.4, 3.7 Hz, H-1'b), 3.98 (1H, br dd-like, J=8.5, 7.0 Hz, H-4), 4.07 (1H, dd-like, J=ca. 2.0, 1.2 Hz, H-3), 4.10/4.18 (each 1H, d, J=11.8 Hz, OCH$_2$Ar), 4.19 (1H, ddd-like, J=3.5, 2.5, 2.0 Hz, H-2), 4.32-4.40 (1H, m, H-2'), 4.34-4.46 (4H, m, OCH$_2$Ar), 4.74/4.79 (2H, d, J=11.5 Hz, OCH$_2$Ar), 6.77-6.87 (8H, m, arom.), 6.94-7.83 (15H, m, arom.). $^{13}$C NMR (125 MHz, CHCl$_3$) δ: 48.2 (C-1), 50.9 (C-1'), 55.2/55.3 (OCH$_3$), 66.2 (C-4), 66.4 (C-5), 68.5 (C-4'), 68.7 (C-2'), 71.3/71.6/73.1/73.3 (OCH$_2$Ar), 79.5 (C-3'), 81.9 (C-3), 82.0 (C-2), 113.85/113.92/114.0/114.1/126.2/126.3/127.3/127.7/128.0/128.3/129.58/129.61/129.64/130.0 (d, arom.), 127.8/128.9/129.6/133.0/133.2/135.0/159.3/159.5/159.67/159.73 (s, arom.). FABMS (pos.) m/z: 875 [M-BF$_4$]$^+$.

Example 110

1,4-Dideoxy-1,4-[(R)-[4-deoxy-1-O-(p-methoxybenzyl)-2-O-(pyridin-3-ylmethyl)-D-erythritol-4-yl] episulfoniumylidene]-2,3,5-tri-O-(p-methoxybenzyl)-D-arabitol tetrafluoroborate (20z, X=BF$_4$)
(Reaction Scheme 5)

By following substantially the same procedure as used for the synthesis of the compound (20g), the epoxide compound (18z, 154 mg, 0.49 mmol) and the thiosugar compound (19b, 200 mg, 0.39 mmol) were treated with tetrafluoroboric acid dimethylether complex (144 µl, 1.05 mmol), and the resulting reaction mixture was purified with ion exchange resin yielding the title compound (20z, 125 mg, 35%) as colorless oily substance.
[Chem. 128]

Compound (20z): colorless oily substance. $[\alpha]_D^{25}$ −4.95 (c=1.67, CHCl$_3$). IR (neat): 3499, 1612, 1585, 1516, 1466, 1427, 1396, 1362, 1304, 1250, 1177, 1072, 1030 cm$^{-1}$. $^1$H NMR (500 MHz, CDCl$_3$) δ: 3.60 (1H, dd, J=10.6, 3.8 Hz, H-4'a), 3.64 (1H, dd, J=10.6, 9.2 Hz, H-5a), 3.68 (1H, dd, J=10.6, 6.6 Hz, H-5b), 3.69 (1H, dd, J=10.6, 2.6 Hz, H-4'b), 3.73 (1H, dd, J=13.2, 3.6 Hz, H-1a), 3.74-3.78 (1H, m, H-3'), 3.75-3.84 (2H, m, H-1'a and H-1'b), 3.766/3.775/3.776/3.80 (each 3H, s, OCH$_3$), 3.84 (1H, dd, J=13.2, 1.4 Hz, H-1b), 4.03 (1H, br dd-like, J=ca. 9.2, 6.6 Hz, H-4), 4.12 (1H, br s-like, H-3), 4.27/4.35 (each 1H, d, J=11.5 4.38-4.43 (1H, m, CH$_2$Ar), 4.29-4.33 (1H, m, H-2'), 4.33 (1H, m, H-2), 4.36-4.47 (6H, m, CH$_2$Ar), 4.60/4.64 (each 1H, d, J=11.8 Hz, CH$_2$Ar), 6.80-6.86 (8H, m, arom.), 7.05/7.13/7.17/7.20 (each 2H, d-like, J=8.6 Hz, arom.), 7.22 (1H, dd-like, J=ca. 7.8, 5.0 Hz, Pyridine H-5), 7.66 (1H, d-like, J=7.8 Hz, Pyridine H-4) 8.48 (1H, br s, Pyridine H-6), 8.52 (1H, br s, Pyridine H-2). $^{13}$C NMR (125 MHz, CDCl$_d$) δ: 48.2 (C-1), 50.6 (C-1'), 55.2/55.3 (OCH$_3$), 66.2 (C-4), 66.5 (C-5), 68.3 (C-4'), 68.5 (C-2'), 70.2/71.5/71.7/73.16/73.21 (CH$_2$Ar), 80.0 (C-3'), 81.9 (C-3), 82.1 (C-2), 113.85/113.93/114.0/114.1/123.6/129.57/129.63/129.7/130.0//136.1/149.1/149.3 (d, arom.), 127.9/128.0/128.8/133.4/159.3/159.5/159.7/159.8 (s, arom.). FABMS (pos.) m/z: 826 [M-BF$_4$]$^+$.

Example 111

1,4-Dideoxy-1,4-[(R)-[4-deoxy-1-O-(p-methoxybenzyl)-2-O-(pyridin-4-ylmethyl)-D-erythritol-4-yl] episulfoniumylidene]-2,3,5-tri-O-(p-methoxybenzyl)-D-arabitol tetrafluoroborate (20aa, X=BF$_4$)
(Reaction Scheme 5)

By following substantially the same procedure as used for the synthesis of the compound (20g), the epoxide compound (18aa, 100 mg, 0.32 mmol) and the thiosugar compound (19b, 115 mg, 0.23 mmol) were treated with tetrafluoroboric acid dimethylether complex (78 µl, 0.57 mmol), and the resulting reaction mixture was purified with ion exchange resin yielding the title compound (20aa, 94 mg, 46%) as colorless oily substance.
[Chem. 129]

Compound (20aa): colorless oily substance., $[\alpha]_D^{23}$ −6.3 (c=1.15, CHCl$_3$). IR (neat): 3495, 1612, 1585, 1516, 1462, 1416, 1362, 1304, 1250, 1177, 1069, 1034 cm$^{-1}$. $^1$H NMR (500 MHz, CDCl$_3$) δ: 3.61 (1H, dd, J=10.6, 3.8 Hz, H-4'a), 3.65 (1H, dd, J=10.0, 8.9 Hz, H-5a), 3.69 (1H, dd, J=10.6, 4.0 Hz, H-4'b), 3.70 (1H, dd, J=10.0, 6.0 Hz, H-5b), 3.76 (1H, dd-like, J=ca. 13.2, 3.4 Hz, H-1a), 3.75-3.80 (1H, m, H-3'), 3.77/3.776/3.780/3.81 (each 3H, s. OCH$_3$), 3.83 (1H, m, H-1'a), 3.86 (1H, m, H-1'b), 3.90 (1H, br d-like, J=ca. 13.2 Hz, H-1b), 4.03 (1H, br dd-like, J=ca. 8.9, 6.0 Hz, H-4), 4.12 (1H, br s-like, H-3), 4.29 (1H, d, J=11.5 Hz, CH$_2$Ar), 4.32-4.36 (1H, m, H-2'), 4.34 (1H, br m, H-2), 4.36-4.48 (7H, m, CH$_2$Ar), 4.43 (2H, s-like, CH$_2$Ar), 6.81-6.87 (8H, m, arom.), 7.06/7.13/7.18/7.19 (each 2H, d-like, J=ca. 8.6 Hz, arom.), 7.18-7.22 (2H, m, Pyridine H-3 and H-5), 8.52 (2H, br s, Pyridine H-2 and H-6). $^{13}$C NMR (125 MHz, CDCl$_3$) δ: 48.2 (C-1), 50.6 (C-1'), 55.3 (OCH$_3$), 66.3 (C-4), 66.5 (C-5), 68.2 (C-4'), 68.5 (C-2'), 71.0/71.6/71.8/73.2/73.3 (CH$_2$Ar), 80.5

(C-3'), 81.9 (C-3), 82.0 (C-2), 113.9/114.0/114.09/114.13/ 122.1/129.57/129.65/129.71/130.0/149.7 (d, arom.), 127.8/ 127.9/128.7/129.5/147.1/159.4/159.6/159.78/159.81 (s, arom.). FABMS (pos.) m/z: 826 [M-BF$_4$]$^+$.

Example 112

1,4-Dideoxy-1,4-[(R)-[4-deoxy-2-O-methyl-D-erythritol-4-yl]episulfoniumylidene]-D-arabitol chloride (Ia) (Reaction Scheme 5)

A suspension of 10% palladium-carbon (100 mg) in 80% acetic acid aqueous solution (2 ml) was prereduced with hydrogen, and 80% acetic acid aqueous solution (3 ml) of the compound 20a (160 mg, 0.24 mmol) was added to the resulting suspension, and the resulting mixture was then hydrogenated at 50-60° C. for 12 hours. The catalyst was then filtered off, and the filtrate was concentrated leaving a colorless oily substance (78 mg). In the resulting oily substance, it was found that a partially acetylated product was formed together. The resulting oily substance was then treated with a mixture of 0.1 ml of 10% hydrochloric acid with 1 ml of methanol at room temperature for 3 hours, and the solvent was then removed off under reduced pressure yielding a colorless oily substance (74 mg) which was in turn purified by clcm using a chloroform-methanol (10:1) mixture and then a chloroform-methanol-water mixture (6:4:1) to yield the title compound (1a) (53 mg, 72%).
[Chem. 130]

Compound (Ia): colorless oily substance. $[\alpha]^{26}_D$ +2.1 (c=1.97, CH$_3$OH). IR (neat): 3333, 1651, 1408, 1261, 1084, 1053, 1026 cm$^{-1}$. $^1$H NMR (500 MHz, CD$_3$OD) δ: 3.29 (1H, ddd-like, J=ca. 6.0, 4.0, 4.0 Hz, H-3'), 3.47 (3H, s, OCH$_3$), 3.66 (1H, dd, J=12.3, 4.0 Hz, H-4'a), 3.73 (1H, dd, J=12.9, 9.2 Hz, H-1'a), 3.80 (1H, dd, J=12.3, 4.0 Hz, H-4'b), 3.82 (1H, dd, J=12.9, 3.4 Hz, H-1'b), 3.85 (2H, d-like, J=ca. 2.3 Hz, H-1a and H-1b), 3.92 (1H, dd, J=10.9, 9.5 Hz, H-5a), 3.99 (1H, br dd-like, J=ca. 9.5, 4.9 Hz, H-4), 4.05 (1H, dd, J=10.9, 4.9 Hz, H-5b), 4.20 (1H, ddd, J=9.2, 6.0, 3.4 Hz, H-2'), 4.36 (1H, dd, J=2.3, 1.1 Hz, H-3), 4.62 (1H, dt, J=2.3, 2.3 Hz, H-2). $^{13}$C NMR (125 MHz, CD$_3$OD) δ: 51.8 (C-1'), 52.1 (C-1), 58.5 (OCH$_3$), 60.0 (C-4'), 61.0 (C-5), 68.6 (C-2'), 73.7 (C-4), 79.4 (C-2), 79.5 (C-3), 85.1 (C-3'). FAB-MS m/z: 269 [M-Cl]$^+$ (pos.), FAB-HRMS m/z: 269.1059 (C$_{10}$H$_{21}$O$_6$S requires 269.1059).

Example 113

1,4-Dideoxy-1,4-[(R)-[4-deoxy-2-O-ethyl-D-erythritol-4-yl]episulfoniumylidene]-D-arabitol chloride (Ib) (Reaction Scheme 5)

By following substantially the same procedure as used for the synthesis of the compound (1a), the compound (20b, 110 mg, 0.16 mmol) was hydrogenated yielding the title compound (1b, 41 mg, 79%) as colorless oily substance.
[Chem. 131]

Compound (Ib): colorless oily substance. $[\alpha]_D^{24}$ +3.3 (c=0.68, CH$_3$OH). IR (neat): 3333, 1647, 1408, 1261, 1173, 1084, 1030 cm$^{-1}$. $^1$H NMR (700 MHz, CD$_3$OD) δ: 1.21 (3H, t, J=7.0 Hz, OCH$_2$CH$_3$), 3.39 (1H, dd, J=5.8, 4.2, 4.0 Hz, H-3'), 3.59/3.75 (each 1H, dq, J=9.4, 7.0 Hz, OCH$_2$CH$_3$), 3.65 (1H, dd, J=12.1, 4.0 Hz, H-4'a), 3.74 (1H, dd, J=13.2, 9.0 Hz, H-1'a), 3.76 (1H, dd, J=12.1, 4.2 Hz, H-4'b), 3.83 (1H, dd, J=13.2, 3.4 Hz, H-1'b), 3.86 (2H, d-like, J=ca. 2.6 Hz, H-1a and H-1b), 3.92 (1H, dd, J=11.4, 9.6 Hz, H-5a), 3.99 (1H, br dd-like, J=ca. 9.6, 5.2 Hz, H-4), 4.05 (1H, dd, J=11.4, 5.2 Hz, H-5b), 4.19 (1H, ddd, J=9.0, 5.8, 3.4 Hz, H-2'), 4.37 (1H, dd, J=2.4, 1.2 Hz, H-3), 4.62 (1H, td, J=2.6, 2.4 Hz, H-2). $^{13}$C NMR (175 MHz, CD$_3$OD) δ: 15.8 (OCH$_2$CH$_3$), 51.8 (C-1'), 52.1 (C-1), 60.8 (C-4'), 61.1 (C-5), 67.2 (OCH$_2$CH$_3$), 68.7 (C-2'), 73.7 (C-4), 79.4 (C-2), 79.5 (C-3), 83.5 (C-3'). FABMS m/z: 283 [M-Cl]$^+$ (pos.), FABHRMS m/z: 283.1212 (C$_{11}$H$_{23}$O$_6$S requires 283.1215).

Example 114

1,4-Dideoxy-1,4-[(R)-[4-deoxy-2-O-(1-pentyl)-D-erythritol-4-yl]episulfoniumylidene]-D-arabitol chloride (Ic) (Reaction Scheme 5)

By following substantially the same procedure as used for the synthesis of the compound (Ia), the compound (20c, 80 mg, 0.11 mmol) was hydrogenated yielding the title compound (Ic, 32.5 mg, 81%) as colorless oily substance.
[Chem. 132]

Compound (Ic): colorless oily substance. $[\alpha]^{23}_D$ +20.4 (c=1.27, CH$_3$OH). IR (neat): 3032, 1454, 1404, 1373, 1254, 1215, 1157, 1072 cm$^{-1}$. $^1$H NMR (500 MHz, CD$_3$OD) δ: 0.92 [3H, t, J=6.9 Hz, O(CH$_2$)$_4$CH$_3$], 1.31-1.38 [4H m O(CH$_2$)$_2$(CH$_2$)$_2$CH$_3$], 1.54-1.64 [2H, m, OCH$_2$CH$_2$(CH$_2$)$_2$CH$_3$], 3.38 (1H, ddd, J=5.7, 4.3, 4.1 Hz, H-3'), 3.52/3.69 [each 1H, dt, J=9.2, 6.9 Hz, OCH$_2$(CH$_2$)$_3$CH$_3$], 3.66 (1H, dd, J=12.0, 4.1 Hz, H-4'a), 3.74 (1H, dd, J=13.2, 9.2 Hz, H-1'a), 3.76 (1H, dd, J=12.0, 4.3 Hz, H-4'b), 3.83 (1H, dd, J=13.2, 3.5 Hz, H-1'b), 3.85 (1H, d-like, J=2.6 Hz, H-1a and H-1b), 3.92 (1H, dd, J=10.6, 9.8 Hz, H-5a), 3.98 (1H, br dd-like, J=ca. 9.8, 4.3 Hz, H-4), 4.05 (1H, dd, J=10.6, 4.3 Hz, H-5b), 4.20 (1H, ddd, J=9.2, 5.7, 3.5 Hz, H-2'), 4.37 (1H, dd, J=2.6, 1.1 Hz, H-3), 4.62 (1H, dt, J=2.6, 2.6 Hz, H-2). $^{13}$C NMR (125 MHz, CD$_3$OD) δ: 14.3 [O(CH$_2$)$_4$CH$_3$], 23.6 [O(CH$_2$)$_3$CH$_2$CH$_3$], 29.4 [O(CH$_2$)$_2$CH$_2$CH$_2$CH$_3$], 30.7 [OCH$_2$CH$_2$(CH$_2$)$_2$CH$_3$], 51.8 (C-1'), 52.2 (C-1), 60.7 (C-4'), 61.0 (C-5), 68.7 (C-2'), 71.9 [OCH$_2$(CH$_2$)$_3$CH$_3$], 73.8 (C-4), 79.46 (C-2), 79.52 (C-3), 83.7 (C-3'). FABMS m/z: 325 [M-Cl]$^+$ (pos.), FAB-HRMS m/z: 325.1639 (C$_{14}$H$_{29}$O$_6$S requires 325.1685).

Example 115

1,4-Dideoxy-1,4-[(R)-[4-deoxy-2-O-(1-heptyl)-D-erythritol-4-yl]episulfoniumylidene]-D-arabitol chloride (Id) (Reaction Scheme 5)

By following substantially the same procedure as used for the synthesis of the compound (Ia), the compound (20d, 120 mg, 0.16 mmol) was hydrogenated yielding the title compound (Id, 52 mg, 83%) as colorless oily substance.
[Chem. 133]

Compound (Id): colorless oily substance. $[\alpha]^{23}_D$ +10.0 (c=0.96, CH$_3$OH). IR (neat): 3287, 1454, 1404, 1315, 1261, 1215, 1173, 1088, 1022 cm$^{-1}$. $^1$H NMR (500 MHz, CD$_3$OD) δ: 0.90 (3H, t, J=6.9 Hz, O(CH$_2$)$_5$CH$_3$], 1.26-1.40 [8H, m O(CH$_2$)$_2$(CH$_2$)$_4$CH$_3$], 1.55-1.63 [2H, m OCH$_2$CH$_2$(CH$_2$)$_4$CH$_3$], 3.38 (1H, ddd, J=5.7, 4.6, 4.0 Hz, H-3'), 3.53/3.69 [each 1H, dt, J=9.2, 6.9 Hz, OCH$_2$(CH$_2$)$_5$CH$_3$], 3.66 (1H, dd, J=12.0, 4.0 Hz, H-4'a), 3.74 (1H, dd, J=13.2, 8.9 Hz, H-1'a), 3.77 (1H, dd, J=12.0, 4.6 Hz, H-4'b), 3.83 (1H, dd, J=13.2, 3.4 Hz, H-1'b), 3.85 (2H, d-like, J=2.6 Hz, H-1a and H-1b), 3.93 (1H, dd, J=10.3, 9.5 Hz, H-5a), 3.97 (1H, br dd-like, J=ca. 9.5, 4.3 Hz, H-4), 4.05 (1H, dd, J=10.3, 4.3 Hz, H-5b), 4.20 (1H, ddd, J=8.9, 5.7, 3.4 Hz, H-2'), 4.37 (1H, dd, J=2.3, 1.2 Hz, H-3), 4.62 (1H, td, J=2.6, 2.3 Hz, H-2). $^{13}$C NMR (125 MHz, CD$_3$OD) δ: 14.4 [O(CH$_2$)$_6$CH$_3$], 23.7 [O(CH$_2$)$_5$CH$_2$CH$_3$], 27.2 [O(CH$_2$)$_2$CH$_2$(CH$_2$)$_3$CH$_3$], 30.3 [O(CH$_2$)$_3$ $CH_2CH_2CH_3$], 31.1 [$OCH_2CH_2(CH_2)_4CH_3$], 33.0 [$O(CH_2)_4CH_2CH_2CH_3$], 51.8 (C-1'), 52.2 (C-1), 60.7 (C-4'), 61.1 (C-5), 68.7 (C-2'), 72.0 [$OCH_2(CH_2)_5CH_3$], 73.8 (C-4), 79.48 (C-2), 79.52 (C-3), 83.7 (C-3'). FABMS m/z: 353 [M-Cl]$^+$ (pos.), FABHRMS m/z: 353.2024 ($C_{14}H_{29}O_6S$ requires 325.1998).

Example 116

1,4-Dideoxy-1,4-[(R)-[4-deoxy-2-O-(1-tridecyl)-D-erythritol-4-yl]episulfoniumylidene]-D-arabitol chloride (Ie) (Reaction Scheme 5)

By following substantially the same procedure as used for the synthesis of the compound (Ia), the compound (20e, 83 mg, 0.10 mmol) was hydrogenated yielding the title compound (Ie, 37.2 mg, 79%) as colorless oily substance.
[Chem. 134]

Compound (Ie): colorless oily substance. $[\alpha]_D^{26}$ +11.0 (c=0.51, $CH_3OH$). IR (neat): 3433, 1645, 1506, 1408, 1262, 1086, 1053, 1026 cm$^{-1}$. $^1$H NMR (700 MHz, $CDCl_3$) δ: 0.89 [3H, t, J=7.0 Hz, $O(CH_2)_{12}CH_3$], 1.25-1.34 [20H, m, O$(CH_2)_2(CH_2)_{10}CH_3$], 1.54-1.63 [2H, m, $OCH_2CH_2(CH_2)_{10}CH_3$], 3.37 (1H, ddd, J=5.6, 4.4, 4.0 Hz, H-3'), 3.52/3.68 [each 1H, dt, J=9.2, 7.0 Hz, $OCH_2(CH_2)_{11}CH_3$], 3.66 (1H, dd, J=12.0, 4.0 Hz, H-4'a), 3.74 (1H, dd, J=13.2, 9.0 Hz, H-1'a), 3.76 (1H, dd, J=12.0, 4.4 Hz, H-4'b), 3.82 (1H, dd, J=13.2, 3.4 Hz, H-1'b), 3.85 (2H, d-like, J=ca. 2.8 Hz, H-1a and H-1b), 3.92 (1H, dd, J=11.0, 9.8 Hz, H-5a), 3.97 (1H, dd-like, J=ca. 9.8, 4.8 Hz, H-4), 4.04 (1H, dd, J=11.0, 4.8 Hz, H-5b), 4.20 (1H, ddd, J=9.0, 5.6, 3.4 Hz, H-2'), 4.37 (1H, dd, J=2.2, 1.2 Hz, H-3), 4.62 (1H, td-like, J=2.8, 2.2 Hz, H-2). $^{13}$C NMR (175 MHz, $CDCl_3$) δ: 14.4 [$O(CH_2)_{12}CH_3$], 23.7 [$O(CH_2)_{11}CH_2CH_3$], 27.2 [$O(CH_2)_2CH_2(CH_2)_9CH_3$], 30.4/30.6/30.7 [$O(CH_2)_3(CH_2)_7(CH_2)_2CH_3$], 31.1 [$OCH_2CH_2(CH_2)_{10}CH_3$], 33.0 [$O(CH_2)_{10}CH_2CH_2CH_3$], 51.8 (C-1'), 52.2 (C-1), 60.8 (C-4'), 61.1 (C-5), 68.8 (C-2'), 72.0 [$OCH_2(CH_2)_{12}CH_3$], 73.8 (C-4), 79.5 (C-2), 79.6 (C-3), 83.7 (C-3'). FABMS (pos.) m/z: 437 [M-Cl]$^+$, FABHRMS m/z: 437.2949 ($C_{22}H_{45}O_6S$ requires 437.2937).

Example 117

1,4-Dideoxy-1,4-[(R)-[4-deoxy-2-O-neopentyl-D-erythritol-4-yl]episulfoniumylidene]-D-arabitol chloride (If) (Reaction, Scheme 5)

By following substantially the same procedure as used for the synthesis of the compound (Ia), the compound (20f, 60 mg, 0.08 mmol) was hydrogenated yielding the title compound (If, 24 mg, 80%) as colorless oily substance.
[Chem. 135]

Compound (If): colorless oily substance. $[\alpha]_D^{24}$ +12.7 (c=0.66, $CH_3OH$). IR (neat): 3267, 1632, 1408, 1361, 1323, 1265, 1219, 1172, 1087, 1023 cm$^{-1}$. $^1$H NMR (500 MHz, $CD_3OD$) δ: 0.92 [9H, s, $C(CH_3)_3$], 3.20/3.37 [each 1H, d, J=8.6 Hz, $OCH_2C(CH_3)_3$], 3.35 (1H, ddd, J=6.0, 4.3, 4.0 Hz, H-3'), 3.68 (1H, dd, J=12.0, 4.0 Hz, H-4'a), 3.75 (1H, dd, J=13.0, 9.5 Hz, H-1'a), 3.76 (1H, dd, J=12.0, 4.3 Hz, H-4'b), 3.83 (1H, dd, J=12.6, 3.5 Hz, H-1a), 3.86 (1H, dd, J=13.0, 3.5 Hz, H-1'b), 3.87 (1H, dd, J=12.6, 1.7 Hz, H-1b), 3.92 (1H, dd, J=10.6, 9.8 Hz, H-5a), 3.97 (1H, br dd-like, J=ca. 9.8, 4.3 Hz, H-4), 4.05 (1H, dd, J=10.6, 4.3 Hz, H-5b), 4.23 (1H, ddd, J=9.5, 6.0, 3.5 Hz, H-2'), 4.38 (1H, br d-like, J=ca. 1.5 Hz, H-3), 4.62 (1H, ddd, J=3.5, 1.7, 1.5 Hz, H-2). $^{13}$C NMR (125 MHz, $CD_3OD$) δ: 27.1 [$C(CH_3)_3$], 33.1 [$C(CH_3)_3$], 51.9 (C-1'), 52.3 (C-1), 60.8 (C-4'), 61.0 (C-5), 68.9 (C-2'), 73.8 (C-4), 79.5 (C-2 and C-3), 82.2 [$OCH_2C(CH_3)_3$], 84.2 (C-3'). FABMS (pos.) m/z: 325 [M-Cl]$^+$, FABHRMS m/z: 325.1678 ($C_{22}H_{45}O_6S$ requires 325.1685).

Example 118

1,4-Dideoxy-1,4-[(R)-[2-O-benzyl-4-deoxy-D-erythritol-4-yl]episulfoniumylidene]-D-arabitol chloride (Ig) (Reaction Scheme 5)

The compound (20 g, 100 mg, 0.11 mmol) was treated in a mixture of 80% TFA aqueous solution (6 ml) and chloroform (3 ml) at room temperature for 2 hours. The reaction mixture was then concentrated to dryness under reduced pressure, and the resulting residue was washed with chloroform yielding 1,4-dideoxy-1,4-[(R)-[2-O-benzyl-4-deoxy-D-erythritol-4-yl]episulfoniumylidene]-D-arabitol tetrafluoroborate (Ig, X=$BF_4$) quantitatively. This compound was stirred with ion exchange resin IRA400J (2g) in methanol (2 ml) for 4 hours, and the resin was then filtered off and washed with methanol. The filtrate and the washings were combined and concentrated yielding a colorless oily substance which was in turn purified with clcm (chloroform→chloroform-methanol (50:1)→chloroform-methanol (10:1) yielding the title compound (Ig) (X=Cl, 34 mg, 85%) as colorless oily substance.
[Chem. 136]

Compound (Ig): colorless oily substance. (41 mg), which on column chromatography ($CHCl_3$→$CHCl_3$-MeOH, 50:1→$CHCl_3$-MeOH, 10:1) gave title sulfonium salts Ig (X=Cl, 34 mg, 85%) as colorless oily substance. $[\alpha]_D^{28}$ +3.5 (c=0.48, $CH_3OH$). IR (neat): 3364, 1651, 1496, 1454, 1396, 1361, 1338, 1316, 1261, 1119, 1076, 1026 cm$^{-1}$. $^1$H NMR (700 MHz, $CD_3OD$) δ: 3.53 (1H, ddd, J=5.8, 4.2, 3.8, H-3'), 3.69 (1H, dd, J=13.2, 8.8, H-1'a), 3.70 (1H, dd, J=12.0, 3.8, H-4'a), 3.71 (1H, dd, J=12.9, 1.6, H-1a), 3.77 (1H, dd, J=12.9, 3.4, H-1b), 3.82 (1H, dd, J=13.2, 3.4, H-1'b), 3.84 (1H, dd, J=12.0, 4.2, H-4'b), 3.90 (1H, dd, J=11.2, 9.6, H-5a), 3.95 (1H, br dd-like, J=ca. 9.6, 5.0, H-4), 4.02 (1H, dd, J=11.2, 5.0, H-5b), 4.24 (1H, ddd, J=8.8, 5.8, 3.4, H-2'), 4.35 (1H, br s-like, H-3), 4.58 (1H, ddd-like, J=3.4, 1.6, 1.2, H-2), 4.62/4.76 (each 1H, d, J=11.6, $OCH_2Ar$), 7.27-7.41 (5H, m, arom.). $^{13}$C NMR (175 MHz, $CD_3OD$) δ: 51.9 (C-1'), 52.1 (C-1), 60.8 (C-4'), 61.0 (C-5), 68.7 (C-2'), 73.5 ($OCH_2Ar$), 73.7 (C-4), 79.4 (C-2), 79.6 (C-3), 82.9 (C-3'), 129.0/129.4/129.5 (d, arom.), 139.4 (s, arom.). FABMS m/z: 345 [M-Cl]$^+$ (pos.). FABHRMS m/z: 345.1346 ($C_{16}H_{25}O_6S$ requires 345.1372).

Example 119

1,4-Dideoxy-1,4-[(R)-[4-deoxy-2-O-(o-methylbenzyl)-D-erythritol-4-yl]episulfoniumylidene]-D-arabitol chloride (Ih) (Reaction Scheme 5)

By following substantially the same procedures as used for the synthesis of the compound (Ig) above, the compound (20h 78 mg, 0.084 mol) was de-p-methoxybenzylated to give the corresponding sulfonium tetrafluoroboric acid salt, which was then subjected to ion exchange reaction yielding the title compound (Ih, 26.0 mg, 78%) as colorless oily substance.
[Chem. 137]

Compound (Ih): colorless oily substance. $[\alpha]_D^{24}$ +11.9 (c=1.40, $CH_3OH$). IR (neat): 3302, 1632, 1605, 1462, 1404, 1315, 1258, 1219, 1173, 1076 cm$^{-1}$. $^1$H NMR (500 MHz, $CD_3OD$) δ: 2.37 (3H, s, $CH_3$), 3.56 (1H, dt, J=5.5, 4.3, H-3'), 3.67 (1H, dd, J=13.2, 8.9, H-1'a), 3.69 (1H, br J=ca. 12.6, H-1a), 3.72 (1H, dd, J=11.7, 4.3 Hz, H-4'a), 3.75 (1H, dd, J=12.6, 3.4, H-1b), 3.79 (1H, dd, J=13.2, 3.5, H-1'b), 3.84 (1H, dd, J=11.7, 4.3, H-4'b), 3.89 (1H, dd, J=10.1, 9.8, H-5a), 3.93 (1H, br dd-like, J=ca. 9.8, 3.8, H-4), 4.02 (1H, dd, J=10.1, 3.8, H-5b), 4.25 (1H, ddd, J=8.9, 5.5, 3.5, H-2'), 4.34 (1H, br d-like, J=ca. 1.5, H-3), 4.57 (1H, br dd-like, J=ca. 3.4, 1.5, H-2), 4.63/4.82 (each 1H, d, J=11.5, OCH$_2$Ar), 7.13-7.22 (3H, m, arom.), 7.35 (1H, d, J=7.2, arom.). $^{13}$C NMR (125 MHz, CD$_3$OD) δ: 19.1 (CH$_3$), 51.8 (C-1'), 52.2 (C-1), 60.9 (C-4'), 61.0 (C-5), 68.8 (C-2'), 71.9 (OCH$_2$Ar), 73.7 (C-4), 79.4 (C-2), 79.6 (C-3), 83.0 (C-3'), 126.9/129.2/130.4/131.3 (d, arom.), 137.2/138.2 (s, arom.). FABMS m/z: 359 [M-Cl]$^+$ (pos.). FABHRMS m/z: 359.1560 (C$_{17}$H$_{27}$O$_6$S requires 359.1528).

Example 120

1,4-Dideoxy-1,4-[(R)-[4-deoxy-2-O-(m-methylbenzyl)-D-erythritol-4-yl]episulfoniumylidene]-D-arabitol chloride (Ii) (Reaction Scheme 5)

By following substantially the same procedures as used for the synthesis of the compound (Ig) above, the compound (20l, 65 mg, 0.070 mmol) was de-p-methoxybenzylated to give the corresponding sulfonium tetrafluoroborate, which was then subjected to ion exchange reaction yielding the title compound (Ii, 22.4 mg, 81%) as colorless oily substance.
[Chem. 138]
Compound (Ii): colorless oily substance. $[α]^{25}_D$ +0.6 (c=1.19, CHCl$_3$). IR (neat): 3306, 1632, 1605, 1470, 1415, 1404, 1203, 1134, 1080 cm$^{-1}$. $^1$H NMR (500 MHz, CD$_3$OD) δ: 2.33 (3H, s, CH$_3$), 3.51 (1H, ddd, J=5.8, 4.3, 4.0, H-3'), 3.66 (1H, dd, J=13.2, 8.6, H-1'a), 3.69 (1H, br d-like, J=ca. 13.2, H-1a), 3.70 (1H, dd, J=12.0, 4.0, H-4'a), 3.76 (1H, dd, J=13.2, 3.5, H-1b), 3.80 (1H, dd, J=13.2, 3.5, H-1'b), 3.83 (1H, dd, J=12.0, 4.3, H-4'b), 3.89 (1H, dd, J=9.8, 9.8, H-5a), 3.93 (1H, br dd-like, J=ca. 9.8, 3.7, H-4), 4.01 (1H, dd, J=9.8, 3.7, H-5b), 4.23 (1H, ddd, J=8.6, 5.8, 3.5, H-2'), 4.34 (1H, br d-like, J=ca. 1.7, H-3), 4.56 (1H, br dd-like, J=ca. 3.5, 1.7, H-2), 4.57/4.72 (each 1H, d, J=11.2, OCH$_2$Ar), 7.11/7.17 (each 1H, br d, J=7.5, arom.), 7.21 (1H, br s-like, arom.), 7.22 (1H, t, J=7.5, arom.). $^{13}$C NMR (125 MHz, CD$_3$OD) δ: 21.4 (CH$_3$), 51.9 (C-1'), 52.1 (C-1), 60.7 (C-4'), 61.0 (C-5), 68.7 (C-2'), 73.6 (OCH$_2$Ar), 73.8 (C-4), 79.4 (C-2), 79.6 (C-3), 82.7 (C-3'), 126.5/129.4/129.7/130.1 (d, arom.), 139.2/139.3 (s, arom.). FABMS m/z: 359 [M-Cl]$^+$ (pos.). FABHRMS m/z: 359.1509 (C$_{17}$H$_{27}$O$_6$S requires 359.1528).

Example 121

1,4-Dideoxy-1,4-[(R)-[4-deoxy-2-O-(p-methylbenzyl)-D-erythritol-4-yl]episulfoniumylidene]-D-arabitol chloride (Ij) (Reaction Scheme 5)

By following substantially the same procedures as used for the synthesis of the compound (Ig) above, the compound (20j, 65 mg, 0.070 mmol) was de-p-methoxybenzylated to give the corresponding sulfonium tetrafluoroborate, which was then subjected to ion exchange reaction yielding the title compound (Ij, 21.8 mg, 78%) as colorless oily substance.
[Chem. 139]
Compound (Ij): colorless oily substance. $[α]^{23}_D$ +4.86 (c=1.05, CH$_3$OH). IR (neat): 3287, 1632, 1601, 1578, 1470, 1431, 1416, 1319, 1261, 1207, 1180, 1076, 1022 cm$^{-1}$. $^1$H NMR (700 MHz, CD$_3$OD) δ: 2.32 (3H, s, CH$_3$), 3.51 (1H, ddd, J=5.8, 4.2, 3.6, H-3'), 3.66 (1H, dd, J=13.2, 8.6, H-1'a), 3.69 (1H, dd, J=12.0, 3.6, H-4'a), 3.71 (1H, dd, J=12.8, 1.6, H-1a), 3.76 (1H, dd, J=12.8, 3.6, H-1b), 3.79 (1H, dd, J=13.2, 3.4, H-1'b), 3.82 (1H, dd, J=12.0, 4.2, H-4'b), 3.89 (1H, dd, J=11.0, 9.6, H-5a), 3.94 (1H, br dd-like, J=ca. 9.6, 4.8, H-4), 4.01 (1H, dd, J=11.0, 4.8, H-5b), 4.22 (1H, ddd, J=8.6, 5.8, 3.4, H-2'), 4.34 (1H, br s, H-3), 4.56/4.71 (each 1H, d, J=11.4, OCH$_2$Ar), 4.57 (1H, br m, H-2), 7.16/7.27 (each 2H, d-like, J=8.0, arom.). $^{13}$C NMR (175 MHz, CD$_3$OD) δ: 21.2 (CH$_3$), 51.9 (C-1'), 52.1 (C-1), 60.8 (C-4'), 61.0 (C-5), 68.7 (C-2'), 73.4 (OCH$_2$Ar), 73.7 (C-4), 79.4 (C-2), 79.6 (C-3), 82.6 (C-3'), 129.6/130.1 (d, arom.), 136.3/138.9 (s, arom.). FABMS m/z: 359 [M-Cl]$^+$ (pos.). FABHRMS m/z: 359.1490 (C$_{17}$H$_{22}$O$_6$S requires 359.1528).

Example 122

1,4-Dideoxy-1,4-[(R)-[2-O-(o-chlorobenzyl)-4-deoxy-D-erythritol-4-yl]episulfoniumylidene]-D-arabitol chloride (Ik) (Reaction Scheme 5)

By following substantially the same procedures as used for the synthesis of the compound (Ig) above, the compound (20k, 70 mg, 0.074 mmol) was de-p-methoxybenzylated to give the corresponding sulfonium tetrafluoroborate, which was then subjected to ion exchange reaction yielding the title compound (Ik, 24.3 mg, 79%) as colorless oily substance.
[Chem. 140]
Compound (Ik): colorless oily substance. $[α]^{21}_D$ +12.6 (c=1.00, CH$_3$OH). IR (neat): 3302, 1620, 1597, 1443, 1404, 1319, 1261, 1207, 1173, 1084, 1049 cm$^{-1}$. $^1$H NMR (500 MHz, CD$_3$OD) δ: 3.58 (1H, ddd, J=5.8, 4.0, 4.0, H-3'), 3.74 (1H, dd, J=12.9, 9.2, H-1'a), 3.75 (1H, dd, J=12.0, 4.0, H-4'a), 3.78 (1H, dd, J=12.9, 2.0, H-1a), 3.81 (1H, dd, J=12.9, 3.2, H-1b), 3.87 (1H, dd, J=12.9, 3.5, H-1'b), 3.88 (1H, dd, J=12.0, 4.0, H-4'b), 3.90 (1H, dd, J=10.9, 9.2 Hz, H-5a), 3.97 (1H, br dd-like, J=9.2, 4.9, H-4), 4.03 (1H, dd, J=10.9, 4.9, H-5b), 4.28 (1H, ddd, J=9.2, 5.8, 3.5, H-2'), 4.36 (1H, br d-like, J=ca. 1.2, H-3), 4.60 (1H, ddd-like, J=ca. 3.2, 2.0, 1.2, H-2), 4.75/4.85 (each 1H, d, J=12.3, OCH$_2$Ar), 7.29 (1H, td, J=7.5, 2.3, arom.), 7.31 (1H, td, J=7.5, 2.3, arom.), 7.39 (1H, dd-like, J=7.5, 2.3, arom.), 7.57 (1H, dd-like, J=7.5, 2.3, arom.). $^{13}$C NMR (125 MHz, CD$_3$OD) δ: 51.8 (C-1'), 52.2 (C-1), 60.8 (C-4'), 61.0 (C-5), 68.7 (C-2'), 70.7 (OCH$_2$Ar), 73.8 (C-4), 79.4 (C-2), 79.6 (C-3), 83.5 (C-3'), 128.2/130.41/130.45/131.4 (d, arom.), 134.4/137.0 (s, arom.). FABMS m/z: 379 [M-Cl]$^+$ (pos.). FABHRMS m/z: 379.0989 (C$_{16}$H$_{24}$ClO$_6$S requires 379.0982).

Example 123

1,4-Dideoxy-1,4-[(R)-[2-O-(m-chlorobenzyl)-4-deoxy-D-erythritol-4-yl]episulfoniumylidene]-D-arabitol chloride (Il) (Reaction Scheme 5)

By following substantially the same procedures as used for the synthesis of the compound (Ig) above, the compound (20l, 75 mg, 0.079 mmol) was de-p-methoxybenzylated to give the corresponding sulfonium tetrafluoroborate, which was then subjected to ion exchange reaction yielding the title compound (Il, 29.6 mg, 82%) as colorless oily substance.
[Chem. 141]
Compound (Il): colorless oily substance. $[α]^{24}_D$ +6.38 (c=0.95, CH$_3$OH). IR (neat): 3580, 1647, 1601, 1578, 1470, 1431, 1416, 1319, 1261, 1207, 1173, 1080, 1022 cm$^{-1}$. $^1$H NMR (500 MHz, CD$_3$OD) δ: 3.56 (1H, ddd, J=5.7, 4.3, 4.1 Hz, H-3'), 3.71 (1H, dd, J=12.3, 4.1 Hz, H-4'a), 3.74 (1H, dd, J=13.2, 9.2 Hz, H-1'a), 3.87 (1H, dd, J=13.0, 1.7 Hz, H-1a), 3.81 (1H, dd, J=13.0, 3.5 Hz, H-1b), 3.83 (1H, dd, J=12.3, 4.3 Hz, H-4'b), 3.85 (1H, dd, J=13.2, 3.5 Hz, H-1'b), 3.91 (1H, dd, J=10.9, 9.4 Hz, H-5a), 3.98 (1H, br dd-like, J=ca. 9.4, 4.9 Hz, H-4), 4.03 (1H, dd, J=10.9, 4.9 Hz, H-5b), 4.27 (1H, ddd, J=9.2, 5.4, 3.5 Hz, H-2'), 4.36 (1H, br d-like, J=ca. 1.2 Hz, H-3), 4.60 (1H, ddd-like, J=ca. 3.5, 1.7, 1.2 Hz, H-2), 4.63/4.76 (each 1H, d, J=11.8 Hz, OCH$_2$Ar), 7.26-7.35 (3H, m, arom.), 7.44 (1H, br s-like, arom.). $^{13}$C NMR (125 MHz, CD$_3$OD) δ: 51.7 (C-1'), 52.2 (C-1), 60.8 (C-4'), 61.0 (C-5), 68.7 (C-2'), 72.7 (OCH$_2$Ar), 73.7 (C-4), 79.4 (C-2), 79.6 (C-3), 83.4 (C-3'), 127.4/128.9/129.0/131.0 (d, arom.), 135.3/141.9 (s, arom.). FABMS m/z: 379 [M-Cl]+ (pos.). FAB-HRMS m/z: 379.0967 (C$_{16}$H$_{24}$ClO$_6$S requires 379.0982).

Example 124

1,4-Dideoxy-1,4-[(R)-[2-O-(p-chlorobenzyl)-4-deoxy-D-erythritol-4-yl]episulfoniumylidene]-D-arabitol chloride (Im) (Reaction Scheme 5)

By following substantially the same procedures as used for the synthesis of the compound (Ig) above, the compound (20m, 60 mg, 0.063 mmol) was de-p-methoxybenzylated to give the corresponding sulfonium tetrafluoroborate, which was then subjected to ion exchange reaction yielding the title compound (Im, 21.3 mg, 81%) as colorless oily substance.
[Chem. 142]
Compound (Im): colorless oily substance. $[\alpha]_D^{25}$ +6.51 (c=0.83, CH$_3$OH). IR (neat): 3287, 1651, 1601, 1578, 1493, 1454, 1416, 1412, 1315, 1258, 1207, 1173, 1088, 1018 cm$^{-1}$. $^1$H NMR (500 MHz, CD$_3$OD) δ: 3.53 (1H, ddd, J=5.8, 4.3, 4.0, H-3'), 3.70 (1H, dd, J=12.0, 4.0, H-4'a), 3.72 (1H, dd, J=12.6, 9.2, H-1'a), 3.76 (1H, dd, J=12.6, 1.7, H-1a), 3.81 (1H, dd, J=12.6, 3.4, H-1b), 3.83 (1H, dd, J=12.0, 4.3, H-4'b), 3.84 (1H, dd, J=12.6, 3.5, H-1'b), 3.91 (1H, dd, J=10.9, 9.5, H-5a), 3.97 (1H, br dd-like, J=ca. 9.5, 4.9, H-4), 4.03 (1H, dd, J=10.9, 4.9, H-5b), 4.25 (1H, ddd, J=9.2, 5.8, 3.5, H-2'), 4.36 (1H, br d-like, J=ca. 1.2, H-3), 4.59 (1H, ddd-like, J=3.4, 1.7, 1.2, H-2), 4.61/4.75 (each 1H, d, J=11.8, OCH$_2$Ar), 7.34/7.39 (each 2H, d-like, J=8.6, arom.). $^{13}$C NMR (125 MHz, CD$_3$OD) δ: 51.8 (C-1'), 52.2 (C-1), 60.8 (C-4'), 61.0 (C-5), 68.7 (C-2'), 72.7 (OCH$_2$Ar), 73.7 (C-4), 79.4 (C-2), 79.6 (C-3), 83.3 (C-3'), 129.5/130.8 (d, arom.), 134.6/138.3 (s, arom.). FABMS m/z: 379 [M-Cl]$^+$ (pos.). FABHRMS m/z: 379.0998 (C$_{16}$H$_{24}$ClO$_6$S requires 379.0982).

Example 125

1,4-Dideoxy-1,4-[(R)-[2-O-(o-bromobenzyl)-4-deoxy-D-erythritol-4-yl]episulfoniumylidene]-D-arabitol chloride (In) (Reaction Scheme 5)

By following substantially the same procedures as used for the synthesis of the compound (Ig) above, the compound (20n, 55 mg, 0.055 mmol) was de-p-methoxybenzylated to give the corresponding sulfonium tetrafluoroborate, which was then subjected to ion exchange reaction yielding the title compound (Im, 19.1 mg, 83%) as colorless oily substance.
[Chem. 143]
Compound (In): colorless oily substance. $[\alpha]_D^{23}$ +14.1 (c=0.27, CH$_3$OH). IR (neat): 3236, 1454, 1400, 1362, 1312, 1285, 1207, 1088, 1072, 1029 cm$^{-1}$. $^1$H NMR (500 MHz, CD$_3$OD) δ: 3.58 (1H, dt, J=6.0, 4.0, H-3'), 3.750 (1H, dd, J=12.1, 4.0, H-4'a), 3.754 (1H, dd, J=12.9, 9.2, H-1'a), 3.78 (1H, dd, J=12.6, 2.3, H-1a), 3.81 (1H, dd, J=12.6, 3.2, H-1b), 3.886 (1H, dd, J=12.1, 4.0, H-4'b), 3.890 (1H, dd, J=12.9, 3.8, H-1'b), 3.90 (1H, dd, J=10.7, 9.5, H-5a), 3.97 (1H, br dd-like, J=9.5, 4.9, H-4), 4.03 (1H, dd, J=10.7, 4.9, H-5b), 4.28 (1H, ddd, J=9.2, 6.0, 3.8, H-2'), 4.35 (1H, br dd-like, J=1.2, 1.2, H-3), 4.59 (1H, ddd-like, J=3.2, 2.3, 1.2, H-2), 4.72/4.83 (each 1H, d, J=12.3, OCH$_2$Ar), 7.22 (1H, td-like, J=ca. 7.3, 1.7, arom) 7.36 (1H, td-like, J=ca. 7.3, 1.2, arom), 7.56 (1H, dd, J=7.3, 1.7, arom.), 7.58 (1H, dd, J=7.3, 1.2, arom.). $^{13}$C NMR (125 MHz, CD$_3$OD) δ: 51.9 (C-1'), 52.3 (C-1), 60.7 (C-4'), 61.0 (C-5), 68.6 (C-2'), 72.9 (ArCH$_2$), 73.8 (C-4), 79.4 (C-2), 79.5 (C-3), 83.5 (C-3'), 124.2/138.6 (s, arom), 128.8/130.7/131.5/133.8 (d, arom). FABMS (pos.) m/z: 423 and 425 [M-Cl]$^+$, FABHRMS m/z: 423.0461 (C$_{16}$H$_{24}$O$_6$S$^{79}$Br requires 423.0477).

Example 126

1,4-Dideoxy-1,4-[(R)-[2-O-(m-bromobenzyl)-4-deoxy-D-erythritol-4-yl]episulfoniumylidene]-D-arabitol chloride (Io) (Reaction Scheme 5)

By following substantially the same procedures as used for the synthesis of the compound (Ig) above, the compound (20o, 53 mg, 0.053 mmol) was de-p-methoxybenzylated to give the corresponding sulfonium tetrafluoroborate, which was then subjected to ion exchange reaction yielding the title compound (Io, 19.2 mg, 78%) as colorless oily substance.
[Chem. 144]
Compound (Io): colorless oily substance. $[\alpha]_D^{24}$ +6.0 (c=0.55, CH$_3$OH). IR (neat): 3271, 1678, 1593, 1470, 1454, 1415, 1315, 1203, 1130, 1080, 1045 cm$^{-1}$. $^1$H NMR (500 MHz, CD$_3$OD) δ: 3.54 (1H, ddd, J=5.5, 4.3, 4.0, H-3'), 3.71 (1H, dd, J=11.7, 4.0, H-4'a), 3.73 (1H, dd, J=13.2, 8.9, H-1'a), 3.77 (1H, dd, J=13.2, 1.8, H-1a), 3.81 (1H, dd, J=13.2, 3.5, H-1'b), 3.83 (1H, dd, J=11.7, 4.3, H-4'b), 3.84 (1H, dd, J=13.2, 3.2, H-1b), 3.91 (1H, dd, J=10.9, 9.5, H-5a), 3.97 (1H, br dd, J=9.5, 4.6, H-4), 4.03 (1H, dd, J=10.9, 4.6, H-5b), 4.26 (1H, ddd, J=8.9, 5.5, 3.5, H-2'), 4.35 (1H, br dd-like, J=ca. 1.8, 1.2, H-3), 4.59 (1H, ddd-like, J=ca. 3.2, 1.8, 1.8, H-2), 4.62/4.75 (each 1H, d, J=12.0, OCH$_2$Ar), 7.26 (1H, t, J=7.7, arom.), 7.36 (1H, br, ddd-like, J=ca. 7.7, 1.5, 1.2, arom.), 7.44 (1H, ddd-like, J=ca. 7.7, 2.0, 1.2, arom.), 7.60 (1H, dd-like, J=ca. 2.0, 1.5, arom). $^{13}$C NMR (125 MHz, CD$_3$OD) δ: 51.7 (C-1'), 52.2 (C-1), 60.8 (C-4'), 61.0 (C-5), 68.7 (C-2'), 72.6 (ArCH$_2$), 73.7 (C-4), 79.5 (C-2), 79.6 (C-3), 83.4 (C-3'), 127.8/131.3/131.9/132.0 (d, arom), 123.4/142.2 (s, arom). FABMS (pos.) m/z: 423 and 425 [M-Cl]$^+$, FABHRMS m/z: 423.0455 (C$_{16}$H$_{24}$O$_6$S$^{79}$Br requires 423.0477).

Example 127

1,4-Dideoxy-1,4-[(R)-[2-O-(p-bromobenzyl)-4-deoxy-D-erythritol-4-yl]episulfoniumylidene]-D-arabitol chloride (Ip) (Reaction Scheme 5)

By following substantially the same procedures as used for the synthesis of the compound (Ig) above, the compound (20p, 65 mg, 0.065 mmol) was de-p-methoxybenzylated to give the corresponding sulfonium tetrafluoroborate, which was then subjected to ion exchange reaction yielding the title compound (Ip, 23.1 mg, 77%) as colorless oily substance.
[Chem. 145]
Compound (Ip): colorless oily substance. $[\alpha]_D^{26}$ +10.2 (c=1.25, MeOH). IR (neat): 3313, 1593, 1489, 1458, 1408, 1335, 1254, 1200, 1072, 1015 cm$^{-1}$. $^1$H NMR (500 MHz, CD$_3$OD) δ: 3.53 (1H, dt, J=5.7, 4.0, H-3'), 3.70 (1H, dd, J=12.0, 4.0, H-4'a), 3.72 (1H, dd, J=13.0, 9.2, H-1'a), 3.76 (1H, dd, J=13.0, 1.7, H-1a), 3.80 (1H, dd, J=13.0, 3.5, H-1'b), 3.83 (1H, dd, J=12.0, 4.0, H-4'b and 1H, dd, J=13.0, 3.6, H-1b), 3.90 (1H, dd, J=10.6, 10.0, H-5a), 3.96 (1H, br dd-like, J=10.0, 4.6, H-4), 4.03 (1H, dd, J=10.6, 4.6, H-5b), 4.25 (1H, ddd, J=9.2, 5.7, 3.5, H-2'), 4.35 (1H, br d-like, J=1.7, H-3), 4.58 (1H, br ddd-like, J=3.6, 1.7, 1.7, H-2), 4.59/4.73 (each 1H, d, J=11.8, OCH$_2$Ar), 7.32/7.49 (each 2H, d-like, J=8.6, arom.). $^{13}$C NMR (125 MHz, CDCl$_3$) δ: 51.8 (C-1'), 52.2 (C-1), 60.7 (C-4'), 61.0 (C-5), 68.7 (C-2'), 72.7 (OCH$_2$Ar), 73.8 (C-4), 79.5 (C-2), 79.6 (C-3), 83.3 (C-3'), 131.1/132.6 (d, arom), 122.5/138.8 (s, arom). FABMS (pos.) m/z: 423 and 425 FABHRMS m/z: 423.0479 (C$_{16}$H$_{24}$O$_6$S$^{79}$Br requires 423.0477).

Example 128

1,4-Dideoxy-1,4-[(R)-[4-deoxy-2-O-(o-trifluoromethylbenzyl)-D-erythritol-4-yl]episulfoniumylidene]-D-arabitol chloride (Iq) (Reaction Scheme 5)

By following substantially the same procedures as used for the synthesis of the compound (Ig) above, the compound (20q, 80 mg, 0.082 mmol) was de-p-methoxybenzylated to give the corresponding sulfonium tetrafluoroborate, which was then subjected to ion exchange reaction yielding the title compound (Iq, 30.0 mg, 82%) as colorless oily substance.
[Chem. 146]

Compound (Iq): colorless oily substance. $[α]_D^{24}$ +12.3 (c=2.0, CH$_3$OH). IR (neat): 3286, 1612, 1454, 1415, 1315, 1165, 1115, 1057, 1037 cm$^{-1}$. $^1$H NMR (500 MHz, CD$_3$OD) δ: 3.62 (1H, ddd, J=5.4, 4.3, 4.0, H-3'), 3.74 (1H, dd, J=12.1, 4.0, H-4'a), 3.78 (1H, dd, J=12.9, 9.0, H-1'a), 3.79 (1H, dd, J=12.6, 2.0, H-1a), 3.82 (1H, dd, J=12.6, 2.9, H-1b), 3.85 (1H, dd, J=12.1, 4.3, H-4'b), 3.88 (1H, dd, J=12.9, 3.4, H-1'b), 3.91 (1H, dd, J=10.9, 9.5, H-5a), 3.98 (1H, br dd, J=9.5, 4.9, H-4), 4.04 (1H, dd, J=10.9, 4.9, H-5b), 4.31 (1H, ddd, J=9.0, 5.4, 3.4, H-2'), 4.36 (1H, dd-like, J=ca. 2.0, 1.2, H-3), 4.60 (1H, ddd-like, J=2.9, 2.0, 2.0, H-2), 4.86/4.96 (each 1H, d, J=12.9, OCH$_2$Ar), 7.46/7.63 (each 1H, br t, J=ca. 7.8, arom.), 7.67/7.82 (each 1H, br d, J=ca. 7.8, arom.). $^{13}$C NMR (125 MHz, CD$_3$OD) δ: 51.6 (C-1'), 52.3 (C-1), 60.8 (C-4'), 61.0 (C-5), 68.8 (C-2'), 69.7 [q, J=2.4 Hz, CH$_2$C$_6$H$_4$-(o-CF$_3$)], 73.7 (C-4), 79.46 (C-2), 79.53 (C-3), 84.0 (C-3'), 125.8 [q, J=272 Hz, CF$_3$,], 126.7 [q, J=5.0 Hz, C$_{ortho}$—CF$_3$], 128.5 [q, J=31.0 Hz, C$_{ipso}$—CF$_3$,], 129.0/131.1/133.4 (d, arom.), 138.0 (s, arom.). FABMS (pos.) m/z: 413 [M-Cl]$^+$, FABHRMS m/z: 413.1220 (C$_{17}$H$_{24}$O$_6$F$_3$S requires 413.1246).

Example 129

1,4-Dideoxy-1,4-[(R)-[4-deoxy-2-O-(m-trifluoromethylbenzyl)-D-erythritol-4-yl]episulfoniumylidene]-D-arabitol chloride (Ir) (Reaction Scheme 5)

By following substantially the same procedures as used for the synthesis of the compound (Ig) above, the compound (20r, 72 mg, 0.073 mmol) was de-p-methoxybenzylated to give the corresponding sulfonium tetrafluoroborate, which was then subjected to ion exchange reaction yielding the title compound (Ir, 26.7 mg, 81%) as colorless oily substance.
[Chem. 147]

Compound (Ir): colorless oily substance. $[α]_D^{24}$ +7.9 (c=1.46, CH$_3$OH). IR (neat): 3286, 2926, 1612, 1454, 1396, 1330, 1199, 1165, 1122, 1072 cm$^{-1}$. $^1$H NMR (500 MHz, CD$_3$OD) δ: 3.58 (1H, dt, J=5.5, 4.3, H-3'), 3.73 (1H, dd, J=12.4, 4.3, H-4'a), 3.78 (1H, dd, J=12.6, 1.7, H-1a), 3.79 (1H, dd, J=13.0, 8.9, H-1'a), 3.82 (1H, dd, J=12.6, 3.2, H-1b), 3.85 (1H, dd, J=12.4, 4.3, H-4'b), 3.86 (1H, dd, J=13.0, 3.5, H-1'b), 3.91 (1H, dd, J=10.9, 9.5, H-5a), 3.98 (1H, br dd-like, J=ca. 9.5, 4.9, 14-4), 4.03 (1H, dd, J=10.9, 4.9, H-5b), 4.28 (1H, ddd, J=8.9, 5.5, 3.5, H-2'), 4.35 (1H, br d, J=ca. 1.2, H-3), 4.59 (1H, ddd-like, J=3.2, 1.7, 1.2, H-2), 4.72/4.85 (each 1H, d, J=12.0, OCH$_2$Ar), 7.54 (1H, br t, J=ca. 8.0, arom), 7.59 (1H, br d, J=ca. 8.0, arom.), 7.66 (1H, br d, J=ca. 8.0, arom.), 7.73 (1H, br s, arom.). $^{13}$C NMR (125 MHz, CD$_3$OD) δ: 51.7 (C-1'), 52.3 (C-1), 60.9 (C-4'), 61.0 (C-5), 68.8 (C-2'), 72.7 (ArCH$_2$), 73.7 (C-4), 79.5 (C-2), 79.6 (C-3), 83.7 (C-3'), 125.7 (q, J=269 Hz, CF$_3$), 125.4/124.6 [each q, J=3.6 Hz, C$_{ortho}$—CF$_3$,], 130.2/132.7 (d, arom.), 131.7 (q, J=32.2 Hz, C$_{ipso}$—CF$_3$), 141.0 (s, arom.). FABMS (pos.) m/z: 413 [M-Cl]$^+$, FABHRMS m/z: 413.1267 (C$_{17}$H$_{24}$O$_6$F$_3$S requires 413.1246).

Example 130

1,4-Dideoxy-1,4-[(R)-[4-deoxy-2-O-(p-trifluoromethylbenzyl)-D-erythritol-4-yl]episulfoniumylidene]-D-arabitol chloride (Is) (Reaction Scheme 5)

By following substantially the same procedures as used for the synthesis of the compound (Ig) above, the compound (20s, 90 mg, 0.092 mmol) was de-p-methoxybenzylated to give the corresponding sulfonium tetrafluoroborate, which was then subjected to ion exchange reaction yielding the title compound (Is, 33.3 mg, 81%) as colorless oily substance.
[Chem. 148]

Compound (Is): colorless oily substance. $[α]_D^{24}$ +14.9 (c=0.45, CH$_3$OH). IR (neat): 3183, 1620, 1392, 1327, 1169, 1126, 1065, 1015 cm$^{-1}$. $^1$H NMR (500 MHz, CD$_3$OD) δ: 3.57 (1H, dt, J=5.5, 4.3 Hz, H-3'), 3.72 (1H, dd, J=12.3, 4.3, H-4'a), 3.76 (1H, dd, J=12.9, 9.2, H-1'a), 3.79 (1H, dd, J=12.6, 2.0, H-1a), 3.82 (1H, dd, J=12.6, 3.2, H-1b), 3.85 (1H, dd, J=12.3, 4.3, H-4'b), 3.86 (1H, dd, J=12.9, 3.5, H-1'b), 3.91 (1H, dd, J=10.6, 9.5, H-5a), 3.98 (1H, br dd-like, J=ca. 9.5, 4.9, H-4), 4.03 (1H, dd, J=10.6, 4.9, H-5b), 4.28 (1H, ddd, J=9.2, 5.5, 3.5, H-2'), 4.35 (1H, dd-like, J=ca. 2.0, 1.5, H-3), 4.59 (1H, ddd-like, J=3.2, 2.0, 2.0, H-2), 4.72/4.86 (each 1H, d, J=12.3, OCH$_2$Ar), 7.59/7.64 (each 1H, d, J=8.3, arom). $^{13}$C NMR (125 MHz, CD$_3$OD) δ: 51.7 (C-1'), 52.2 (C-1), 60.8 (C-4'), 61.0 (C-5), 68.8 (C-2'), 72.6 (OCH$_2$Ar), 73.7 (C-4), 79.5 (C-2), 79.6 (C-3), 83.7 (C-3'), 125.5 (CF$_3$, J=280) 126.3 (C$_{ortho}$—CF$_3$, J=3.59), 129.3 (d, arom), 130.8 (C$_{ipso}$—CF$_3$, J=32.2), 144.2 (s, arom). FABMS (pos.) m/z: 413 [M-Cl]$^+$, FABHRMS m/z: 413.1256 (C$_{17}$H$_{24}$O$_6$F$_3$S requires 413.1246).

Example 131

1,4-Dideoxy-1,4-[(R)-[4-deoxy-2-O-(o-nitrobenzyl)-D-erythritol-4-yl]episulfoniumylidene]-D-arabitol chloride (It) (Reaction Scheme 5)

By following substantially the same procedures as used for the synthesis of the compound (Ig) above, the compound (20t, 88 mg, 0.092 mmol) was de-p-methoxybenzylated to give the corresponding sulfonium tetrafluoroborate, which was then subjected to ion exchange reaction yielding the title compound (It, 31.3 mg, 80%) as colorless oily substance.
[Chem. 149]

Compound (It): colorless oily substance. $[α]^{25}_D$ +2.1 (c=1.12, CHCl$_3$). IR (neat): 3287, 1612, 1578, 1524, 1404, 1346, 1308, 1261, 1200, 1173, 1076, 1026 cm$^{-1}$. $^1$H NMR (500 MHz, CD$_3$OD) δ: 3.60 (1H, ddd-like, J=5.8, 4.0, 4.0, H-3'), 3.74 (1H, dd, J=12.3, 4.0, H-4'a), 3.75 (1H, dd, J=12.9, 9.2, H-1'a), 3.82 (1H, dd, J=12.9, 3.0, H-1a), 3.848 (1H, dd-like, J=12.9, 1.7, H-1b), 3.852 (1H, dd-like, J=12.9, 3.2, H-1'b), 3.87 (1H, dd, J=12.3, 4.0, H-4'b), 3.92 (1H, dd, J=10.1, 8.4, H-5a), 4.01 (1H, br dd-like, J=8.4, 5.2, H-4), 4.04

(1H, dd, J=10.1, 5.2, H-5b), 4.29 (1H, ddd, J=9.2, 5.8, 3.2, H-2'), 4.37 (1H, br d-like, J=ca. 1.5, H-3), 4.61 (1H, ddd-like, J=ca. 3.0, 1.7, 1.5, H-2), 5.01/5.08 (each 1H, d, J=11.5, OCH$_2$Ar), 7.53 (1H, ddd, J=8.3, 7.8, 1.2, arom.), 7.69 (1H, td, J=7.8, 1.2, arom.), 7.81 (1H, dd, J=7.8, 1.2, arom.), 8.01 (1H, dd, J=8.3, 1.2, arom.). $^{13}$C NMR (125 MHz, CD$_3$OD) δ: 51.6 (C-1'), 52.2 (C-1), 60.7 (C-4'), 61.0 (C-5), 68.7 (C-2'), 70.3 (OCH$_2$Ar), 73.6 (C-4), 79.4 (C-2), 79.6 (C-3), 84.1 (C-3'), 125.6/129.8/131.1/134.6 (d, arom.), 135.0/149.4 (s, arom.). FABMS m/z: 390, [M-Cl]$^+$ (pos.), HRFABMS m/z: 390.1214, (C$_{16}$H$_{24}$O$_8$NS requires 390.1223).

Example 132

1,4-Dideoxy-1,4-[(R)-[4-deoxy-2-O-(m-nitrobenzyl)-D-erythritol-4-yl]episulfoniumylidene]-D-arabitol chloride (Iu) (Reaction Scheme 5)

By following substantially the same procedures as used for the synthesis of the compound (Ig) above, the compound (20u, 88 mg, 0.092 mmol) was de-p-methoxybenzylated to give the corresponding sulfonium tetrafluoroborate, which was then subjected to ion exchange reaction yielding the title compound (Iu, 18.7 mg, 81%) as colorless oily substance.
[Chem. 150]
Compound (Iu): colorless oily substance. [α]$^{22}_D$ +13.3 (c=0.6, CH$_3$OH). IR (neat): 3305, 1593, 1513, 1454, 1415, 1350, 1257, 1211, 1172, 1080 cm$^{-1}$. $^1$H NMR (500 MHz, CDCl$_3$) δ: 3.60 (1H, ddd, J=5.2, 4.0, 4.0, H-3'), 3.73 (1H, dd, J=12.0, 4.0, H-4'a), 3.77 (1H, dd, J=12.9, 8.9, H-1'a), 3.79 (1H, dd, J=12.9, 2.0, H-1a), 3.83 (1H, dd, J=12.9, 3.5, H-1'b), 3.86 (1H, dd, J=12.0, 4.0, H-4'b), 3.87 (1H, dd, J=12.9, 3.5, H-1b), 3.91 (1H, dd, J=10.6, 9.5, H-5a), 3.98 (1H, br dd, J=9.5, 4.9, H-4), 4.03 (1H, dd, J=10.6, 4.9, H-5b), 4.29 (1H, ddd, J=8.9, 5.2, 3.5, H-2'), 4.35 (1H, br d-like, J=1.5, m, H-3), 4.59 (1H, ddd-like, J=3.5, 2.0, 1.5, H-2), 4.77/4.90 (each 1H, d, J=12.3, OCH$_2$Ar), 7.59 (1H, dd, J=8.0, 7.8, arom.), 7.80 (1H, br d, J=ca. 7.8, arom.), 8.16 (1H, br dd, J=ca. 8.0, 1.5, arom.), 8.31 (1H, br t, J=ca. 1.5, arom.). $^{13}$C NMR (125 MHz, CDCl$_3$) δ: 51.7 (C-1'), 52.3 (C-1), 60.9 (C-4'), 61.0 (C-5), 68.8 (C-2'), 72.3 (OCH$_2$Ar), 73.7 (C-4), 79.4. (C-2), 79.6 (C-3), 83.9 (C-3'), 123.5/123.6/130.7/135.0 (d, arom.), 142.0 (s, arom.). FABMS (pos.) m/z: 390 [M-Cl]$^+$, FABHRMS m/z: 390.1248 (C$_{16}$H$_{24}$O$_8$NS requires 390.1223).

Example 133

1,4-Dideoxy-1,4-[(R)[4-deoxy-2-O-(p-nitrobenzyl)-D-erythritol-4-yl]episulfoniumylidene]-D-arabitol chloride (Iv) (Reaction Scheme 5)

By following substantially the same procedures as used for the synthesis of the compound (Ig) above, the compound (20v, 95 mg, 0.099 mmol) was de-p-methoxybenzylated to give the corresponding sulfonium tetrafluoroborate, which was then subjected to ion exchange reaction yielding the title compound (Iv, 34.6 mg, 82%) as colorless oily substance.
[Chem. 151]
Compound (Iv): colorless oily substance. [α]$_D^{24}$ +4.4 (c=0.78, CH$_3$OH). IR (neat): 3264, 1605, 1516, 1346, 1207, 1180, 1084, 1057, 1015 cm$^{-1}$. $^1$H NMR (500 MHz, CD$_3$OD) δ: 3.58 (1H, ddd, J=5.5, 4.3, 4.0 Hz, H-3'), 3.72 (1H, dd, J=12.3, 4.3 Hz, H-4'a), 3.76 (1H, dd, J=12.9, 9.2 Hz, H-1'a), 3.78 (1H, dd, J=12.9, 2.0 Hz, H-1a), 3.81 (1H, dd, J=12.9, 3.2 Hz, H-1b), 3.85 (1H, dd, J=12.3, 4.0 Hz, H-4'b), 3.87 (1H, dd, J=12.9, 3.2 Hz, H-1'b), 3.90 (1H, dd, J=10.9, 9.5 Hz, H-5a), 3.98 (1H, br dd-like, J=ca. 9.5, 4.9 Hz, H-4), 4.02 (1H, dd, J=10.9, 4.9 Hz, H-5b), 4.28 (1H, ddd, J=9.2, 5.5, 3.2 Hz, H-2'), 4.35 (1H, dd-like, J=ca. 2.0, 1.5, H-3), 4.59 (1H, ddd-like, J=ca. 3.2, 2.0, 2.0, H-2), 4.76/4.89 (each 1H, d, J=12.9 Hz, OCH$_2$Ar), 7.63/8.20 (each 1H, d, J=8.9 Hz, arom). $^{13}$C NMR (125 MHz, CD$_3$OD) δ: 51.7 (C-1'), 52.2 (C-1), 60.8 (C-4'), 61.0 (C-5), 68.7 (C-2'), 72.3 (OCH$_2$Ar), 73.7 (C-4), 79.4 (C-2), 79.5 (C-3), 84.6 (C-3'), 124.4/129.4 (d, arom), 147.4/148.8 (s, arom). FABMS (pos.) m/z: 390 [M-Cl]$^+$, FABHRMS m/z: 390.1243 (C$_{16}$H$_{24}$O$_8$NS requires 390.1223).

Example 134

1,4-Dideoxy-1,4-[(R)-[4-deoxy-2-O-(p-hydroxymethyl)benzyl)-D-erythritol-4-yl]episulfoniumylidene]-D-arabitol chloride (Iw) (Reaction Scheme 5)

By following substantially the same procedures as used for the synthesis of the compound (Ig) above, the compound (20w, 101 mg, 0.095 mmol) was de-p-methoxybenzylated to give the corresponding sulfonium tetrafluoroborate, which was then subjected to ion exchange reaction yielding the title compound (Iw, 30.4 mg, 78%) as colorless oily substance.
[Chem. 152]
Compound (Iw): colorless oily substance. [α]$^{24}_D$ +11.4 (c=1.76, CH$_3$OH,). IR (neat): 3360, 1632, 1466, 1454, 1416, 1315, 1261, 1177, 1080, 1049, 1022 cm$^{-1}$. $^1$H NMR (700 MHz, CD$_3$OD) δ: 3.53 (1H, ddd, J=5.8, 4.2, 3.8, H-3'), 3.66 (1H, dd, J=13.2, 8.8, H-1'a), 3.70 (1H, dd, J=12.0, 3.8, H-4'a), 3.71 (1H, dd, J=12.7, 1.4, H-1a), 3.76 (1H, dd, J=12.7, 3.4, H-1b), 3.80 (1H, dd, J=13.2, 3.4, H-1'b), 3.83 (1H, dd, J=12.0, 4.2, H-4'b), 3.89 (1H, dd, J=11.3, 9.8, H-5a), 3.95 (1H, br dd-like, J=9.8, 5.0, H-4), 4.02 (1H, dd, J=11.3, 5.0, H-5b), 4.23 (1H, ddd, J=8.8, 5.8, 3.4, H-2'), 4.35 (1H, br s-like, H-3), 4.57-4.59 (1H, br m, H-2), 4.59 (2H, s, C$_6$H$_4$CH$_2$OH), 4.61/4.75 (each 1H, d, J=11.6, OCH$_2$Ar), 7.35/7.38 (each 2H, d, J=8.0, arom.). $^{13}$C NMR (175 MHz, CD$_3$OD) δ: 51.9 (C-1'), 52.1 (C-1), 60.8 (C-4'), 61.0 (C-5), 64.9 (ArCH$_2$OH), 68.7 (C-2'), 73.3 (OCH$_2$Ar), 73.7 (C-4), 79.4 (C-2), 79.6 (C-3), 82.8 (C-3'), 128.2/129.5 (d, arom.), 138.4/142.5 (s, arom.). FABMS m/z: 375, [M-Cl]$^+$ (pos.), HRFABMS m/z: 375.1500, (C$_{17}$H$_{27}$O$_7$S requires 375.1478).

Example 135

1,4-Dideoxy-1,4-[(R)-[4-deoxy-2-O-(naphthalen-1-ylmethyl)benzyl)-D-erythritol-4-yl]-episulfoniumylidene]-D-arabitol chloride (Ix) (Reaction Scheme 5)

By following substantially the same procedures as used for the synthesis of the compound (Ig) above, the compound (20x, 64 mg, 0.066 mmol) was de-p-methoxybenzylated to give the corresponding sulfonium tetrafluoroborate, which was then subjected to ion exchange reaction yielding the title compound (Ix, 22.0 mg, 77%) as colorless oily substance.
[Chem. 153]
Compound (Ix): colorless oily substance. [α]$^{25}_D$ +2.58 (c=0.34, CH$_3$OH). IR (neat): 3332, 1631, 1512, 1454, 1416, 1338, 1168, 1072 cm$^{-1}$. $^1$H NMR (700 MHz, CD$_3$OD) δ: 3.41 (1H, dd, J=12.6, 1.0 Hz, H-1a), 3.43 (1H, dd, J=13.0, 8.8 Hz, H-1'a), 3.48 (1H, dd, J=12.6, 3.4 Hz, H-1b), 3.58 (1H, ddd, J=6.4, 4.0, 3.8 Hz, H-3'), 3.66 (1H, dd, J=13.0, 3.4 Hz, H-1'b), 3.74 (1H, dd, J=12.0, 3.8 Hz, H-4'a), 3.80 (1H, br dd-like, J=ca. 11.6, 9.6 Hz, H-4), 3.82 (1H, dd, J=11.6, 9.6 Hz, H-5a), 3.92 (1H, dd-like, J=ca. 11.6, 11.6 Hz, H-5b), 3.93 (1H, dd, J=12.0, 4.0 Hz, H-4'b), 4.23 (1H, ddd, J=8.8, 6.4, 3.4 Hz, H-2'), 4.27 (1H, br d-like, J=ca. 2.2 Hz, H-3), 4.46 (1H, ddd-like, J=3.4, 2.2, 1.0 Hz, H-2), 5.01/5.289 (each 1H, d, J=11.8 Hz, OCH$_2$Ar), 7.44-8.23 (7H, m, arom.). $^{13}$C NMR (175 MHz, CD$_3$OD) δ: 51.75 (C-1'), 51.81 (C-1), 60.7 (C-4'), 60.9 (C-5), 68.5 (C-2'), 71.6 (OCH$_2$Ar), 73.6 (C-4), 79.3 (C-2), 79.5 (C-3), 82.2 (C-3'), 125.4/126.4/127.0/127.6/128.7/129.8/130.2 (d, arom.), 133.3/134.7/135.4 (s, arom.). FABMS m/z: 395 [M-Cl]$^+$ (pos.). FABHRMS m/z: 395.1540 (C$_{20}$H$_{27}$O$_6$S requires 395.1528).

Example 136

1,4-Dideoxy-1,4-[(R)-[4-deoxy-2-O-(naphthalen-2-ylmethyl)benzyl)-D-erythritol-4-yl]-episulfoniumylidene]-D-arabitol chloride (Iy) (Reaction Scheme 5)

By following substantially the same procedures as, used for the synthesis of the compound (Ig) above, the compound (20y, 56 mg, 0.058 mmol) was de-p-methoxybenzylated to give the corresponding sulfonium tetrafluoroborate, which was then subjected to ion exchange reaction yielding the title compound (Iy, 19.1 mg, 76%) as colorless oily substance.
[Chem. 154]
Compound (Iy): colorless oily substance. $[\alpha]^{25}_D$ +4.38 (c=0.57, CH$_3$OH). IR (neat): 3305, 1631, 1504, 1469, 1454, 1246, 1172, 1076 cm$^{-1}$. $^1$H NMR (700 MHz, CD$_3$OD) δ: 3.59 (1H, ddd, J=5.8, 4.2, 4.0 Hz, H-3'), 3.70 (1H, dd, J=12.8, 1.4 Hz, H-1a), 3.72 (1H, dd, J=13.2, 8.6 Hz, H-1'a), 3.74 (1H, dd, J=12.0, 4.0 Hz, H-4'a), 3.76 (1H, dd, J=12.8, 3.6 Hz, H-1b), 3.86 (1H, dd, J=13.2, 3.2 Hz, H-1'b), 3.88 (1H, dd, J=12.0, 4.2 Hz, H-4'b), 3.89 (1H, dd, J=11.2, 9.6 Hz, H-5a), 3.96 (1H, br dd-like, J=ca. 9.6, 5.0 Hz, H-4), 4.01 (1H, dd, J=11.2, 5.0 Hz, H-5b), 4.28 (1H, ddd, J=8.6, 5.8, 3.2 Hz, H-2'), 4.33 (1H, br s-like, H-3), 4.46 (1H, ddd-like, J=3.6, 2.0, 1.4 Hz, H-2), 4.79/4.93 (each 1H, d, J=11.6 Hz, OCH$_2$Ar), 7.45-7.87 (7H, m, arom.). $^{13}$C NMR (175 MHz, CD$_3$OD) δ: 51.9 (C-1'), 52.1 (C-1), 60.8 (C-4'), 61.0 (C-5), 68.8 (C-2'), 73.6 (OCH$_2$Ar), 73.7 (C-4), 79.4 (C-2), 79.6 (C-3), 83.0 (C-3'), 127.1/127.25/127.27/128.0/128.7/129.0/129.2 (d, arom.), 134.6/134.8/136.9 (s, arom.). FABMS m/z: 395 [M-Cl]$^+$ (pos.). FABHRMS m/z: 395.1544 (C$_{20}$H$_{27}$O$_6$S requires 395.1528).

Example 137

1,4-Dideoxy-1,4-[(R)-[4-deoxy-2-O-(pyridin-3-ylmethyl)-D-erythritol-4-yl]episulfoniumylidene]-D-arabitol chloride (Iz) (Reaction Scheme 5)

By following substantially the same procedures as used for the synthesis of the compound (Ig) above, the compound (20z, 98 mg, 0.107 mmol) was de-p-methoxybenzylated to give the corresponding sulfonium tetrafluoroborate, which was then subjected to ion exchange reaction yielding the title compound (Iz, 37.0 mg, 82%) as colorless oily substance.
[Chem. 155]
Compound (Iz): colorless oily substance., $[\alpha]^{24}_D$ +14.1 (c=2.20, CH$_3$OH). IR (neat): 3264, 2550, 1678, 1632, 1612, 1558, 1470, 1408, 1327, 1254, 1200, 1177, 1084, 1030 cm$^{-1}$. $^1$H NMR (500 MHz, CD$_3$OD) δ: 3.65 (1H, ddd, J=5.2, 5.2, 4.6 Hz, H-3'), 3.74 (1H, dd, J=12.4, 4.6 Hz, H-4'a), 3.80 (1H, dd, J=12.9, 9.5 Hz, H-1'a), 3.85 (2H, d-like, J=ca. 2.3 Hz, H-1a and H-1b), 3.85 (1H, dd, J=12.3, 8.3 Hz, H-5a), 3.91 (1H, dd, J=12.9, 3.5 Hz, H-1'b), 3.92 (1H, dd, J=12.3, 6.6 Hz, H-5b), 4.03-4.07 (1H, m, H-4), 4.06 (2H, dd, J=12.4, 5.2 Hz, H-4'b), 4.30 (1H, ddd, J=9.5, 5.2, 3.5 Hz, H-2'), 4.37 (1H, br d-like, J=ca. 1.5 Hz, H-3), 4.63 (1H, td-like, J=ca. 2.3, 1.5 Hz, H-2), 4.84/4.94 (each 1H, d, J=12.9 Hz, CH$_2$Ar), 7.79 (2H, br s, pyridine H-5), 8.30 (1H, br d, J=8.0 Hz, pyridine H-6), 8.71 (1H, br s, pyridine H-4), 8.84 (1H, br s, pyridine H-2). $^{13}$C NMR (125 MHz, CD$_3$OD) δ: 51.5 (C-1'), 52.2 (C-1), 60.89/60.99 (C-4' and C-5), 68.7 (C-2'), 70.2 (CH$_2$Ar), 73.5 (C-4), 79.4 (C-2), 79.5 (C-3), 84.2 (C-3'), 126.8/142.1/145.5 (d, arom.), 138.5 (s, arom.). m/z: 346 [M–H-2Cl]$^+$, FABHRMS m/z: 346.1352 (C$_{15}$H$_{24}$O$_6$NS requires 346.1342).

Example 138

1,4-Dideoxy-1,4-[(R)-[4-deoxy-2-O-(pyridin-4-ylmethyl)-D-erythritol-4-yl]episulfoniumylidene]-D-arabitol chloride (Iaa) (Reaction Scheme 5)

By following substantially the same procedures as used for the synthesis of the compound (Ig) above, the compound (20aa, 90 mg, 0.098 mmol) was de-p-methoxybenzylated to give the corresponding sulfonium tetrafluoroborate, which was then subjected to ion exchange reaction yielding the title compound (Iaa, 33.2 mg, 81%) as colorless oily substance.
[Chem. 156]
Compound (Iaa): colorless oily substance., $[\alpha]^{24}_D$ +14.3 (c=1.76, CH$_3$OH,). IR (neat): 3271, 2550, 1678, 1643, 1612, 1508, 1416, 1315, 1254, 1200, 1177, 1126, 1084, 1065, 1026 cm$^{-1}$. $^1$H NMR (500 MHz, CD$_3$OD) δ: 3.69 (1H, ddd, J=5.2, 5.2, 4.6 Hz, H-3'), 3.77 (1H, dd, J=12.3, 4.6 Hz, H-4'a), 3.85 (1H, dd, J=13.2, 9.8 Hz, H-1'a), 3.87 (2H, d-like, J=ca. 2.3 Hz, H-1a and H-1b), 3.90 (1H, dd, J=12.9, 8.5 Hz, H-5a), 3.94 (1H, dd, J=12.9, 7.0 Hz, H-5b), 3.95 (1H, dd, J=13.2, 3.5 Hz, H-1'b), 4.06 (1H, dd-like, J=ca. 12.3, 5.2 Hz, H-4'b), 4.09 (1H, br dd-like, J=ca. 8.5, 7.0 Hz, H-4), 4.34 (1H, ddd, J=9.8, 5.2, 3.5 Hz, H-2'), 4.39 (1H, br d-like, J=ca. 2.0 Hz, H-3), 4.64 (1H, td-like, J=ca. 2.3, 2.0 Hz, H-2), 4.96/5.05 (each 1H, d, J=15.5 Hz, CH$_2$Ar), 7.98 (2H, br s, pyridine H-3 and H-5), 8.77 (2H, br s, pyridine H-2 and H-6). $^{13}$C NMR (125 MHz, CD$_3$OD) δ: 51.5 (C-1'), 52.2 (C-1), 60.97/61.01 (C-4' and C-5), 68.7 (C-2'), 71.3 (CH$_2$Ar), 73.5 (C-4), 79.5 (C-2), 79.6 (C-3), 84.7 (C-3'), 125.6/144.7 (d, arom.), 158.5 (s, arom.). m/z: 346 [M–H-2Cl]$^+$, FABHRMS m/z: 346.1355 (C$_{15}$H$_{24}$O$_6$NS requires 346.1342).

Example 139

Brush border membrane follicles of rat's small intestine were prepared in accordance with the literature (Kessler, M. et al., Biochem. Biophys. Act, 1978, 506, 136), and a suspension of the follicles in 0.1M maleate buffer (pH6.0) was used as an intraintestinal α-glucosidase (maltase, sucrose and isomaltase).

A compound to be tested was dissolved in methylsulfoxide (DMSO) and the resulting solution was diluted with 0.1M maleate buffer to prepare a solution of the testing compound (DMSO concentration: 10%). A solution of a substrate (sucrose (74 mM), maltose (74 mM) or isomaltose (74 mM, 501.11) in the maleate buffer, a solution (25 μl) of the testing compound and the enzyme solution (25 μl) were mixed and the resulting solution was incubated at 37° C. for 30 minutes. Immediately after incubation, the resulting solution was heated by boiling water to terminate the reaction and mixed with water (150 μl). The concentration of glucose was measured by glucose oxidase method. The final concentration of DMSO in the testing solution was set to 2.5%, and no influence of DMSO on an inhibitory activity was detected. A 50% inhibitory concentration (IC$_{50}$) was computed from the measured values.

TABLE 1

| Testing Compounds | α-glucosidase (IC$_{50}$ = μg/ml) | | |
|---|---|---|---|
| | Maltase | Sucrase | Isomaltase |
| Salacinol | 5.2 | 1.6 | 1.3 |
| Compound (Ia) | 5.3 | 0.46 | 0.39 |
| Compound (Ib) | 1.66 | 0.12 | 0.27 |
| Compound (Ic) | 1.52 | 0.5 | 0.47 |
| Compound (Id) | 0.8 | 0.24 | 0.25 |
| Compound (Ie) | 1.04 | 1.29 | 0.95 |
| Compound (If) | 0.3 | 0.09 | 0.28 |
| Compound (Ig) (X = BF$_4$) | 0.44 | 0.32 | 0.12 |
| Compound (Ig) (X = Cl) | 0.58 | 0.55 | 0.2 |
| Compound (Ih) | 0.66 | 0.41 | 0.48 |
| Compound (Ii) | 0.84 | 1.3 | 0.35 |
| Compound (Ij) | 0.86 | 1.1 | 0.68 |
| Compound (Ik) | 0.31 | 0.09 | 0.26 |
| Compound (Il) | 0.53 | 0.8 | 0.31 |
| Compound (Im) | 0.89 | 0.72 | 0.68 |
| Compound (Is) | 0.98 | 0.56 | 0.38 |
| Compound (Iv) | 0.68 | 0.38 | 0.23 |
| Compound (Iw) | 1 | 0.8 | 0.3 |
| voglibose | 1.2 | 0.22 | 2.1 |
| acalbose | 1.7 | 2 | 646 |

The result of Table 1 reveals that compounds (Ia-Id) according to the present invention Show remarkable glucosidase inhibitory effects.

INDUSTRIAL APPLICABILITY

The novel cyclic sulfonium salt compounds or isomers, solvates thereof or their pharmaceutically acceptable salts thereof have α-glucosidase inhibitory activities so that they are useful as medicine or health food for prevernting or treating diseases such as diabetes and so on as well as they are highly industrially valuable.

The invention claimed is:

1. A cyclic sulfonium salt compound as represented by general formula (I):

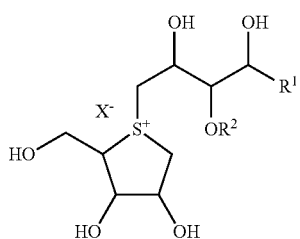

(I)

wherein

R$^1$ is hydrogen atom or —(CH(OH))n-CH$_2$OH (wherein n is 0 or an integer of 1 or 2);

R$^2$ is a benzyl group, an o-, m-, or p-halobenzyl group, an o-, m-, or p-nitrobenzyl group, an o-, m-, or p-methylbenzyl group, an o-, m-, or p-trifluoromethylbenzyl group, a hydroxymethylbenzyl group, a naphthylmethyl group, or a pyridylmethyl group and X$^-$ is a conjugated basic ion of halogen or BF$_4$ or an isomer or a solvate thereof or a pharmaceutically acceptable salt thereof.

2. A cyclic sulfonium salt compound as represented by general formula (II):

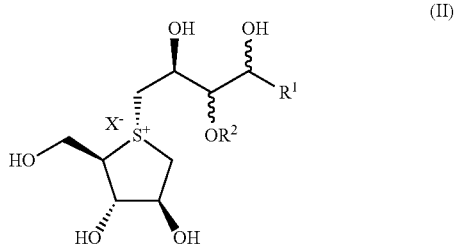

(II)

wherein

R$^1$ is hydrogen atom or —(CH(OH))n-CH$_2$OH (wherein n is 0 or an integer of 1 - 3);

R$^2$ is a benzyl group, an o-, m-, or p-halobenzyl group, an o-, m-, or p-nitrobenzyl group, an o-, m-, or p-methylbenzyl group, an o-, m-, or p-trifluoromethylbenzyl group, a hydroxymethylbenzyl group, a naphthylmethyl group, or a pyridylmethyl group and X$^-$ is a conjugated basic ion of halogen or BF$_4$ or an isomer or a solvate thereof or a pharmaceutically acceptable salt thereof.

3. The cyclic sulfonium salt compound or the isomer or the solvate thereof or the pharmaceutically acceptable salt thereof as claimed in claim 1 or 2, wherein R$^1$ is hydrogen atom or —CH$_2$OH or —(CH$_2$)$_2$—CH$_2$OH).

4. The cyclic sulfonium salt compound or the isomer or the solvate thereof or the pharmaceutically acceptable salt thereof as claimed in claim 1 or 2, wherein X$^-$ is Cl$^-$ or BF4$^-$.

* * * * *